United States Patent
Webber et al.

(10) Patent No.: US 10,227,344 B2
(45) Date of Patent: Mar. 12, 2019

(54) CK2 INHIBITORS, COMPOSITIONS AND METHODS THEREOF

(71) Applicant: Polaris Pharmaceuticals, Inc., San Diego, CA (US)

(72) Inventors: Stephen E. Webber, San Diego, CA (US); Xueliang Tao, San Diego, CA (US); Elena Brin, San Diego, CA (US)

(73) Assignee: Polaris Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 15/631,501

(22) Filed: Jun. 23, 2017

(65) Prior Publication Data

US 2017/0369489 A1    Dec. 28, 2017

Related U.S. Application Data

(60) Provisional application No. 62/354,308, filed on Jun. 24, 2016.

(51) Int. Cl.

| | |
|---|---|
| *C07D 487/04* | (2006.01) |
| *A61K 31/519* | (2006.01) |
| *C07D 471/04* | (2006.01) |
| *A61K 31/136* | (2006.01) |
| *A61K 31/275* | (2006.01) |
| *A61P 35/00* | (2006.01) |

(52) U.S. Cl.
CPC .......... *C07D 471/04* (2013.01); *A61K 31/136* (2013.01); *A61K 31/275* (2013.01); *A61K 31/519* (2013.01); *C07D 487/04* (2013.01); *A61P 35/00* (2018.01)

(58) Field of Classification Search
CPC ............................. C07D 487/04; A61K 31/519
USPC ........................................ 544/281; 514/259.1
See application file for complete search history.

(56) References Cited

U.S. PATENT DOCUMENTS

| | | |
|---|---|---|
| 2008/0039455 A1 | 2/2008 | Ince et al. |
| 2011/0152240 A1 | 6/2011 | Haddach et al. |

FOREIGN PATENT DOCUMENTS

| | | |
|---|---|---|
| WO | 2008143759 A1 | 2/2008 |
| WO | 2013144532 A1 | 10/2013 |

OTHER PUBLICATIONS

Cecil Textbook of Medicine, edited by Bennet, J.C., and Plum F., 20th edition,vol. 1, 1004-101 O, 1996.*
Freshney et al.,Culture of Animal Cells, A Manual of Basic Technique, Alan R. Liss, Inc., 1983, New York, p. 4.*
Dermeret al., Bio/Technology, 1994, 12:320.*
Golub et al., Science, 286, 531-537, 1999.*
Sep. 29, 2017 International Search Report and Written Opinion issued in PCT International Application No. PCT/US17/38976.

* cited by examiner

*Primary Examiner* — Venkataraman Balasubramanian
(74) *Attorney, Agent, or Firm* — Mintz Levin Cohn Ferris Glovsky and Popeo, P.C.

(57) ABSTRACT

The present invention provides synthesis, pharmaceutically acceptable formulations and uses of compounds in accordance with Formula (I), or a stereoisomer, a tautomer or a pharmaceutically acceptable salt thereof.

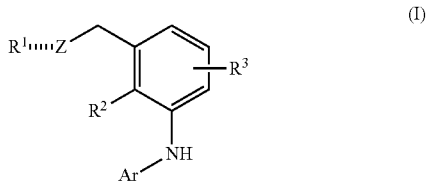

For Formula (I) compounds $R^1$, $R^2$, $R^3$, Ar and Z are as defined in the specification. The inventive Formula (I) compounds are inhibitors of CK2 and find utility in any number of therapeutic applications, including but not limited to treatment of proliferative disorders such as cancer, inflammation and immunological disorders.

13 Claims, No Drawings

CK2 INHIBITORS, COMPOSITIONS AND METHODS THEREOF

CROSS-REFERENCE

This application claims the benefit of U.S. provisional patent application Ser. No. 62/354,308, filed Jun. 24, 2016, which is herein incorporated by reference in its entirety.

FIELD

The present invention generally relates to compounds having activity as inhibitors of casein kinase 2 (CK2), as well as to related compositions and methods for utilizing the inventive compounds as therapeutic agents for treatment of CK2 dependent diseases, including the treatment of cancers.

BACKGROUND

Protein kinase CK2 or casein kinase 2 (CK2) is a highly conserved and ubiquitously expressed serine/threonine protein kinase, which exists as a tetrameric complex of two catalytic (α or α') and two regulatory (β) subunits. CK2 has broad function, which includes controlling cell growth, proliferation, and evasion of apoptosis by phosphorylation of a range of substrates in critical cellular signaling pathways including P13K (phosphatidylinositol 3-kinase)/AKT (protein kinase B), NFκB (nuclear factor kappa-light-chain-enhancer of activated B cells) and Wnt (wingless type MMTV integration site family. See, e.g. Ruzzene et al. *Biochim. Biophys Acta* (2010) 1804: 499-504; Di Maira et al. *Cell. Mol. Life Sci.* (2009) 66: 3363-3373; Dominguez, I. et al. *Cell. Mol. Life Sci.* (2009) 66: 1850-1857.

Elevated CK2 activity caused by overexpression of the enzyme (notably but not necessarily limited to the CK2 α and α' subunits) has been shown to correlate with tumor aggressiveness and tumor growth. In particular, CK2 overexpression has been demonstrated in hematological malignancies, including chronic lymphocytic leukemia, chronic myeloid leukemia, acute lymphoblastic leukemia, acute myeloid leukemia, and multiple myeloma. Elevated CK2 activity promotes tumorigenesis via the regulation of the activity of various oncogenes and tumor suppressor proteins. Hence, not until recently, CK2 is considered as a possible target in cancer chemotherapy. CK2 has also been demonstrated to increase a cell's oncogenic potential by sensitizing a cell to transformation by other oncogenic proteins. See, Landesman-Bollag et al. *Oncogene* (2001) 20: 3247-3257.

Although CK2 is generally regarded as a constitutively active kinase, more recent evidence suggests that the enzyme can regulate and be regulated by growth factors such as IL-6 and epidermal growth factor (EGF). Additionally, a variety of ATP-competitive, small-molecule inhibitors of CK2 have been identified. These include various polyhydroxylodated aromatic compounds (such as emodin and quercetin), polyhalogenated compounds (such as DRB (5,6-dichlororibofuranosylbenzimidazole) and TBB (4,5,6,7-tetrabromo-1H-benzotriazole), as well as the indolo-[1,2-a]quinazoline derative IQA. Inhibitors of CK2 that are useful for treating certain types of cancers are described in International Patent Application Nos. PCT/US2007/077464, PCT/US2008/074820, PCT/US2009/35609 and PCT/US2010/56712.

Through the use of small molecules, dominant negative over-expression of kinase inactive mutants, anti-sense methods, and small interfering RNA molecules (siRNA), complete eradication of the PC3 human prostate cancer tumor in tumor-bearing mice has been demonstrated.

Many of the existing CK2 inhibitors, including emodin, coumarins, TBB, quinazolines, DRB and quercetin, while useful for laboratory studies, lack the potency, physiochemical and pharmacological properties required to be a clinically useful chemotherapeutic agent. Therefore, a significant need remains for compounds that effectively and specifically inhibit CK2 activity in a clinical setting, as well as for associated compositions and methods. The present invention satisfies this need and provides further related advantages.

SUMMARY

The present invention is directed to compounds that inhibit or modulate the activity of CK2, as well as stereoisomers, tautomers and pharmaceutically acceptable salts of such compounds. The present invention is also directed to pharmaceutically acceptable compositions containing such compounds and associated methods for treating conditions that would benefit from CK2 inhibition, such as cancers, inflammatory conditions, infectious disorders, pain, immunological disorders, neurodegenerative disorders (such as Alzheimer's disease, Parkinson's disease), as well as other kinase-associated conditions etc.

In one embodiment the invention is directed to compounds according to Formula (I):

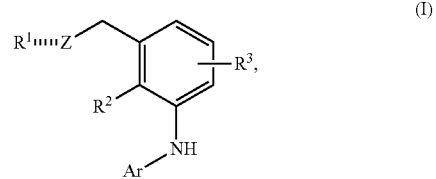

or a stereoisomer, a tautomer or a pharmaceutically acceptable salt thereof, wherein:

⁞⁞⁞⁞⁞ is ——, ▬ or ⁞⁞⁞⁞⁞ ;

Z is S(O), $SO_2$ or $S(O)NR^4$, $R^1$ is OH, alkyl, alkenyl, alkynyl, cycloalkyl, heterocyclyl, aryl or heteroaryl;

$R^2$ is H, $(C_1-C_8)$alkyl or halogen;

$R^3$ groups each independently are H, halogen, CN, $OR^5$, $(C_1-C_8)$alkyl, $(C_2-C_8)$alkenyl, $(C_2-C_8)$alkynyl, $NHR^5$, $NR^5R^5$, $[(C_1-C_8)$alkylene]$NHR^5$, $[(C_1-C_8)$alkylene]$NR^5R^5$, $N(C_1-C_8)$alkyl$[(C_1-C_8)$alkylene]$NHR^5$, $N(C_1-C_8)$alkyl$[(C_1-C_8)$alkylene]$NR^5R^5$, $C(O)NHR^5$, $C(O)NR^5R^5$, $SO_2NHR^5$, $SO_2NR^5R^5$, $S(O)R^5$, $SO_2R^5$, $NR^5C(O)R^5$, $NR^5SO_2R^5$, cycloalkyl, heterocyclyl, aryl or heteroaryl;

$R^4$ is H, CN, $CO_2(C_1-C_8)$alkyl, $CO_2$cycloalkyl, $CO_2$heterocyclyl, $CO_2$aryl, $CO_2$heteroaryl, $CO_2[(C_1-C_8)$alkylene]cycloalkyl, $CO_2[(C_1-C_8)$alkylene]heterocyclyl, $CO_2[(C_1-C_8)$alkylene]aryl or $CO_2[(C_1-C_8)$alkylene]heteroaryl;

$R^5$ is H, $(C_1-C_8)$alkyl, $(C_1-C_8)$haloalkyl, cycloalkyl, heterocyclyl, aryl, heteroaryl, $[(C_1-C_8)$alkylene]cycloalkyl, $[(C_1-C_8)$alkylene]heterocyclyl, $[(C_1-C_8)$alkylene]aryl or $[(C_1-C_8)$alkylene]heteroaryl, or $R^5$ and $R^5$ taken together with the nitrogen atom to which they are attached form a heterocyclyl;

Ar is

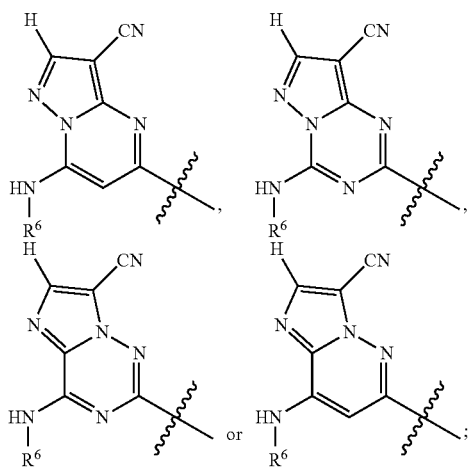

wherein

R⁶ is H, alkyl, haloalkyl, cycloalkyl, heterocyclyl, aryl, heteroaryl, [(C₁-C₈)alkylene]cycloalkyl or [(C₁-C₈)alkylene]heterocyclyl; and wherein any alkyl, alkenyl, alkynyl, haloalkyl, alkylene, cycloalkyl, heterocyclyl, aryl or heteroaryl is optionally substituted with 1, 2 or 3 groups selected from OH, CN, NH₂, NO₂, halogen, cycloalkyl, —(C₁-C₃ alkylene)NH₂ and —(C₁-C₃ alkylene)N(C₁-C₃ alkyl)₂.

The present invention also provides a pharmaceutical composition comprising (i) a therapeutically effective amount of at least one compound according to Formula (I) or a stereoisomer, a tautomer or a pharmaceutically acceptable salt thereof; (ii) in combination with a pharmaceutically acceptable carrier, diluent or excipient.

Also provided by the present invention is a method for attenuating or inhibiting the activity of CK2 in at least one cell overexpressing CK2, comprising contacting the at least one cell with a compound according to Formula (I) or a stereoisomer, tautomer or pharmaceutically acceptable salt thereof.

According to the inventive method at least one cell is a colon cancer cell, a gastric cancer cell, a thyroid cancer cell, a lung cancer cell, a liver cancer cell a leukemia cell, a B-cell lymphoma, a T-cell lymphoma, a hairy cell lymphoma, Hodgkins lymphoma cell, non-Hodgkins lymphoma cell, Burkitt's lymphoma cell, a pancreatic cancer cell, a melanoma cell, a multiple melanoma cell, a brain cancer cell, a CNS cancer cell, a renal cancer cell, a prostate cancer cell, an ovarian cancer cell, or a breast cancer cell.

According to yet another embodiment the invention provides a method for treating a CK2 dependent condition in a mammal in need thereof comprising administering to the mammal (i) a therapeutically effective amount of at least one compound according to Formula (I) or a stereoisomer, tautomer or pharmaceutically acceptable salt thereof, or (ii) a pharmaceutical composition in accordance with the invention.

Compounds and pharmaceutically acceptable formulations in accordance with the invention are useful for treating a CK2 dependent condition such as a cell proliferative condition. In certain embodiments the cell proliferative condition is a tumor-associated cancer (including a solid or circulating tumor). The tumor-associated cancer sometimes is cancer of the breast, prostate, pancreas, lung, colorecturm, skin, kidney, liver, thyroid gland or ovary. In some embodiments, the cell proliferative condition is a non-tumor cancer, such as a hematopoietic cancer or a myeloproliferative disorder. Exemplary myeloproliferative disorders include acute myelogenous (granulocytic) leukemia (AML), chronic myelogenous leukemia (CML), acute lymphocytic (lymphoblastic) leukemia (ALL), chronic lymphocytic leukemia (CLL), chronic idiopathic myelofibrosis, polycythemia vera, essential thrombocythemia, myeloid metaplasia, acute erythroblastic leukemia, Hodgkin's lymphoma, non-Hodgkin's lymphoma, hairy cell lymphoma, Burkitt's lymphoma, B-cell lymphoma, acute T-cell leukemia and T-cell lymphoma.

In one embodiment the compounds and pharmaceutically acceptable formulation in accordance with the invention are useful for treating a CK2 dependent condition wherein the condition is prostate cancer, ovarian cancer, pancreatic cancer, colon cancer, non-small cell lung cancer (NSCLC), cancer, breast cancer, renal cancer, melanoma cancer, multiple myeloma, glioblastoma, Burkitt's lymphoma or leukemia.

The above embodiments and other aspects of the invention are readily apparent in the detailed description that follows. To this end, various references are set forth herein which describe in more detail certain background information, procedures, compounds and/or compositions, and are each hereby incorporated by reference in their entireties.

DETAILED DESCRIPTION

In the following description certain specific details are set forth in order to provide a thorough understanding of various embodiments of the invention. However, one skilled in the art will understand that the invention may be practiced without these details. Unless the context requires otherwise, throughout the present specification and claims, the word "comprise" and variations thereof, such as, "comprises" and "comprising" are to be construed in an open, inclusive sense (i.e., as "including, but not limited to").

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

As used herein, and unless noted to the contrary, the following terms and phrases have the meaning noted below.

"Amino" refers to the —NH₂ substituent.

"Aminocarbonyl" refers to the —C(O)NH₂ substituent.

"Carboxyl" refers to the —CO₂H substituent.

"Carbonyl" refers to a —C(O)— or —C(═O)— group. Both notations are used interchangeably within the specification.

"Cyano" refers to the —C≡N substituent.

"Cyanoalkylene" refers to the -(alkylene)C≡N substituent.

"Acetyl" refers to the —C(O)CH₃ substituent.

"Hydroxy" or "hydroxyl" refers to the —OH substituent.

"Hydroxyalkylene" refers to the -(alkylene)OH substituent.

"Oxo" refers to a =O substituent.

"Thio" or "thiol" refer to a —SH substituent.

"Alkyl" refers to a saturated, straight or branched hydrocarbon chain radical consisting solely of carbon and hydrogen atoms, having from one to twelve carbon atoms ($C_1$-$C_{12}$ alkyl), from one to eight carbon atoms ($C_1$-$C_8$ alkyl) or from one to six carbon atoms ($C_1$-$C_6$ alkyl), and which is attached to the rest of the molecule by a single bond. Exemplary alkyl groups include methyl, ethyl, n-propyl, 1-methylethyl (isopropyl), n-butyl, n-pentyl, 1,1-dimethylethyl (t-butyl), 3-methylhexyl, 2-methylhexyl, and the like. Moieties with which the alkyl group can be substituted with are selected from but not necessarily limited to the group consisting of hydroxyl, amino, alkylamino, arylamino, alkoxy, thioalkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis", John Wiley and Sons, Second Edition, 1991.

"Lower alkyl" has the same meaning as alkyl defined above but having from one to three carbon atoms ($C_1$-$C_3$ alkyl).

"Alkenyl" refers to an unsaturated alkyl group having at least one double bond and from two to twelve carbon atoms ($C_2$-$C_{12}$ alkenyl), from two to eight carbon atoms ($C_2$-$C_8$ alkenyl) or from two to six carbon atoms ($C_2$-$C_6$ alkenyl), and which is attached to the rest of the molecule by a single bond, e.g., ethenyl, propenyl, butenyl, pentenyl, hexenyl, and the like.

"Alkynyl" refers to an unsaturated alkyl group having at least one triple bond and from two to twelve carbon atoms ($C_2$-$C_{12}$ alkynyl), from two to ten carbon atoms ($C_2$-$C_{10}$ alkynyl) from two to eight carbon atoms ($C_2$-$C_8$ alkynyl) or from two to six carbon atoms ($C_2$-$C_6$ alkynyl), and which is attached to the rest of the molecule by a single bond, e.g., ethynyl, propynyl, butynyl, pentynyl, hexynyl, and the like.

"Alkylene" or "alkylene chain" refers to a straight or branched divalent hydrocarbon (alkyl) chain linking the rest of the molecule to a radical group, consisting solely of carbon and hydrogen, respectively. Alkylenes can have from one to twelve carbon atoms, e.g., methylene, ethylene, propylene, n-butylene, and the like. The alkylene chain is attached to the rest of the molecule through a single or double bond. The points of attachment of the alkylene chain to the rest of the molecule can be through one carbon or any two carbons within the chain. "Optionally substituted alkylene" refers to alkylene or substituted alkylene.

"Alkenylene" refers to divalent alkene. Examples of alkenylene include without limitation, ethenylene (—CH=CH—) and all stereoisomeric and conformational isomeric forms thereof. "Substituted alkenylene" refers to divalent substituted alkene. "Optionally substituted alkenylene" refers to alkenylene or substituted alkenylene.

"Alkynylene" refers to divalent alkyne. Examples of alkynylene include without limitation, ethynylene, propynylene. "Substituted alkynylene" refers to divalent substituted alkyne.

"Alkoxy" refers to a radical of the formula —$OR_a$ where $R_a$ is an alkyl having the indicated number of carbon atoms as defined above. Examples of alkoxy groups include without limitation —O-methyl (methoxy), —O-ethyl (ethoxy), —O-propyl (propoxy), —O-isopropyl (iso propoxy) and the like.

"Aryl" refers to a hydrocarbon ring system radical comprising hydrogen, 6 to 18 carbon atoms and at least one aromatic ring. Exemplary aryls are hydrocarbon ring system radical comprising hydrogen and 6 to 9 carbon atoms and at least one aromatic ring; hydrocarbon ring system radical comprising hydrogen and 9 to 12 carbon atoms and at least one aromatic ring; hydrocarbon ring system radical comprising hydrogen and 12 to 15 carbon atoms and at least one aromatic ring; or hydrocarbon ring system radical comprising hydrogen and 15 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. "Optionally substituted aryl" refers to an aryl group or a substituted aryl group. The aryl group can be substituted with, but not necessarily limited to, one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis", John Wiley and Sons, Second Edition, 1991.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, three to nine carbon atoms, three to eight carbon atoms, three to seven carbon atoms, three to six carbon atoms, three to five carbon atoms, a ring with four carbon atoms, or a ring with three carbon atoms. The cycloalkyl ring may be saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo (bromine), chloro (chlorine), fluoro (fluorine), or iodo (iodine).

"Haloalkyl" refers to an alkyl radical having the indicated number of carbon atoms, as defined herein, wherein one or more hydrogen atoms of the alkyl group are substituted with a halogen (halo radicals), as defined above. The halogen atoms can be the same or different. Exemplary haloalkyls are trifluoromethyl, difluoromethyl, trichloromethyl, 2,2,2-trifluoroethyl, 1,2-difluoroethyl, 3-bromo-2-fluoropropyl, 1,2-dibromoethyl, and the like.

"Heterocyclyl", heterocycle", or "heterocyclic ring" refers to a stable 3- to 18-membered saturated or unsaturated radical which consists of two to twelve carbon atoms and from one to six heteroatoms, for example, one to five heteroatoms, one to four heteroatoms, one to three heteroatoms, or one to two heteroatoms selected from the group consisting of nitrogen, oxygen and sulfur. Exemplary heterocycles include without limitation stable 3-15 membered saturated or unsaturated radicals, stable 3-12 membered saturated or unsaturated radicals, stable 3-9 membered saturated or unsaturated radicals, stable 8-membered saturated or unsaturated radicals, stable 7-membered saturated or unsaturated radicals, stable 6-membered saturated or unsaturated radicals, or stable 5-membered saturated or unsaturated radicals.

Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of non-aromatic heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, thietanyl, trithianyl, tetrahydropyranyl, thiomorpholinyl, thiamorpholinyl, 1-oxo-thiomorpholinyl, and 1,1-dioxo-thiomorpholinyl. Heterocyclyls include heteroaryls as defined herein, and examples of aromatic heterocyclyls are listed in the definition of heteroaryls below.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a stable 5-12 membered ring, a stable 5-10 membered ring, a stable 5-9 membered ring, a stable 5-8 membered ring, a stable 5-7 membered ring, or a stable 6 membered ring that comprises at least 1 heteroatom, at least 2 heteroatoms, at least 3 heteroatoms, at least 4 heteroatoms, at least 5 heteroatoms or at least 6 heteroatoms. Heteroaryls may be a monocyclic, bicyclic, tricyclic or tetracyclic ring system, which may include fused or bridged ring systems; and the nitrogen, 2 carbon or sulfur atoms in the heteroaryl radical may be optionally oxidized; the nitrogen atom may be optionally quaternized. The heteroatom may be a member of an aromatic or non-aromatic ring, provided at least one ring in the heteroaryl is aromatic. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl).

"Thione" refers to a =S group attached to a carbon atom of a saturated or unsaturated $(C_3-C_8)$cyclic or a $(C_1-C_8)$ acyclic moiety.

"Sulfoxide" refers to a —S(O)— group in which the sulfur atom is covalently attached to two carbon atoms.

"Sulfone" refers to a —S(O)$_2$— group in which a hexavalent sulfur is attached to each of the two oxygen atoms through double bonds and is further attached to two carbon atoms through single covalent bonds.

The term "compound" refers to a chemical entity, whether in the solid, liquid or gaseous phase, and whether in a crude mixture or purified and isolated. The compound of the invention can exist in various isomeric forms, as well as in one or more tautomeric forms, including both single tautomers and mixtures of tautomers. The term "isomer" is intended to encompass all isomeric forms of a compound of this invention, including tautomeric forms of the compound.

Some compounds described here can have asymmetric centers and therefore exist in different enantiomeric and diastereomeric forms. A compound of the invention can be in the form of an optical isomer or a diastereomer. Accordingly, the invention encompasses compounds of the invention and their uses as described herein in the form of their optical isomers, diastereoisomers and mixtures thereof, including a racemic mixture. Optical isomers of the compounds of the invention can be obtained by known techniques such as asymmetric synthesis, chiral chromatography, or via chemical separation of stereoisomers through the employment of optically active resolving agents.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

In this description, a "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease. In the context of the present invention the terms "treat", "treating" and "treatment" also refer to:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The terms "modulate", "modulation" and the like refer to the ability of a compound to increase or decrease the function, or activity of, for example, protein kinase CK2 or casein kinase 2 (CK2). "Modulation", in its various forms, is intended to encompass inhibition, antagonism, partial antagonism, activation, agonism and/or partial agonism of the activity associated with CK2. CK2 inhibitors are compounds that bind to, partially or totally block stimulation, decrease, prevent, delay activation, inactivate, desensitize, or down regulate signal transduction. The ability of a compound to modulate CK2 activity can be demonstrated in a suitable enzymatic assay or a suitable cell-based assay.

A "patient" or "subject" includes an animal, such as a human, cow, horse, sheep, lamb, pig, chicken, turkey, quail, cat, dog, mouse, rat, rabbit or guinea pig. The animal can be a mammal such as a non-primate and a primate (e.g., monkey and human). In one embodiment, a patient is a human, such as a human infant, child, adolescent or adult.

The term "prodrug" refers to a precursor of a drug, a compound which upon administration to a patient, must undergo chemical conversion by metabolic processes before becoming an active pharmacological agent. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. Exemplary prodrugs of compounds in accordance with Formula (I) are esters, acetamides, and amides.

Compounds of the Invention

The present invention generally is directed to compounds encompassed by the genus of Formula (I):

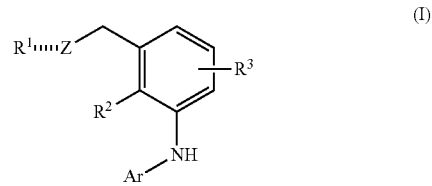

(I)

or stereoisomers, tautomers or pharmaceutically acceptable salts thereof.

In one embodiment $R^1$ is alkyl. In another embodiment $R^1$ is methyl.

In one embodiment $R^2$ is H.

In one embodiment Z is S(O). In another embodiment Z is $SO_2$.

In one embodiment the $R^3$ groups are independently H, halogen, $OR^5$, $NR^5R^5$, $[(C_1-C_8)alkylene]NR^5R^5$, cycloalkyl, heterocyclyl, $N(C_1-C_8)alkyl[(C_1-C_8)alkylene]NHR^5$ or $N(C_1-C_8)alkyl[(C_1-C_8)alkylene]NR^5R^5$, In another embodiment the $R^3$ groups are independently H, Cl, F, CN, $OR^5$, $NR^5R^5$, $[(C_1-C_8)alkylene]NR^5R^5$, cycloalkyl or heterocyclyl.

In another embodiment the $R^3$ groups are independently H, Cl, F, CN, $OR^5$, $NR^5R^5$, $[(C_1-C_8)alkylene]NR^5R^5$, cyclopropane or piperazine.

In one embodiment $R^4$ is H.

In one embodiment Ar is

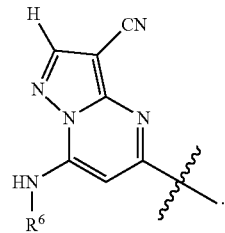

In one embodiment $R^5$ is $(C_1-C_8)$alkyl or $(C_1-C_8)$alkylene cycloalkyl. In another embodiment $R^5$ is $CH_3$, $CHF_2$, $CH_2CH_2NH_2$ or methylcyclopropane.

In one embodiment $R^6$ is cycloalkyl. In another embodiment $R^6$ is cyclopropane.

In one embodiment the compounds according to Formula (I) are selected from (±)-5-((4-chloro-3-((methylsulfinyl)methyl)phenyl)amino)-7-(cyclopropylamino)pyrazolo[1,5-a]pyrimidine-3-carbonitrile, 5-((4-chloro-3-((methylsulfonyl)methyl)phenyl)amino)-7-(cyclopropylamino)pyrazolo[1,5-a]pyrimidine-3-carbonitrile, (S)(+)-5-((4-chloro-3-((methylsulfinyl)methyl)phenyl)amino)-7-(cyclopropylamino)pyrazolo[1,5-a]pyrimidine-3-carbonitrile, (R)(−)-5-((4-chloro-3-((methylsulfinyl)methyl)phenyl)amino)-7-(cyclopropylamino)pyrazolo[1,5-a]pyrimidine-3-carbonitrile, (±)-7-(cyclopropylamino)-5-((4-fluoro-3-((methylsulfinyl)methyl)phenyl)amino)pyrazolo[1,5-a]pyrimidine-3-carbonitrile, (±)-5-((4-cyano-3-((methylsulfinyl)methyl)phenyl)amino)-7-(cyclopropylamino)pyrazolo[1,5-a]pyrimidine-3-carbonitrile, (±)-5-((4-((2-aminoethyl)(methyl)amino)-3-((methylsulfinyl)methyl)phenyl)amino)-7-(cyclopropylamino)pyrazolo[1,5-a]pyrimidine-3-carbonitrile mono trifluoroacetic acid salt, (±)-5-((4-(2-aminoethyl)-3-((methylsulfinyl)methyl)phenyl)amino)-7-(cyclopropylamino)pyrazolo[1,5-a]pyrimidine-3-carbonitrile mono trifluoroacetic acid salt, 5-((4-cyano-3-((methylsulfonyl)methyl)phenyl)amino)-7-(cyclopropylamino)pyrazolo[1,5-a]pyrimidine-3-carbonitrile, 5-((4-((2-aminoethyl)(methyl)amino)-3-((methylsulfonyl)methyl)phenyl)amino)-7-(cyclopropylamino)pyrazolo[1,5-a]pyrimidine-3-carbonitrile mono trifluoroacetic acid salt, 5-((4-(2-aminoethyl)-3-((methylsulfonyl)methyl)phenyl)amino)-7-(cyclopropylamino)pyrazolo[1,5-a]pyrimidine-3-carbonitrile mono trifluoroacetic acid salt, (±)-5-((4-chloro-3-((S-methylsulfonimidoyl)methyl)phenyl)amino)-7-(cyclopropylamino)pyrazolo[1,5-a]pyrimidine-3-carbonitrile, (±)-5-((4-cyclopropyl-3-((methylsulfinyl)methyl)phenyl)amino)-7-(cyclopropylamino)pyrazolo[1,5-a]pyrimidine-3-carbonitrile, (±)-7-(cyclopropylamino)-5-((3-((methylsulfinyl)methyl)-4-(piperazin-1-yl)phenyl)amino)pyrazolo[1,5-a]pyrimidine-3-carbonitrile mono trifluoroacetic acid salt, (±)-5-((4-(aminomethyl)-3-((methylsulfinyl)methyl)phenyl)amino)-7-(cyclopropylamino)pyrazolo[1,5-a]pyrimidine-3-carbonitrile mono trifluoroacetic acid salt, (±)-7-(cyclopropylamino)-5-((4-((cyclopropylmethyl)(methyl)amino)-3-((methylsulfinyl)methyl)phenyl)amino)pyrazolo[1,5-a]pyrimidine-3-carbonitrile, (±)-7-(cyclopropylamino)-5-((4-methoxy-3-((methylsulfinyl)methyl)phenyl)amino)pyrazolo[1,5-a]pyrimidine-3-carbonitrile, 7-(cyclopropylamino)-5-((4-methoxy-3-((methylsulfonyl)methyl)phenyl)amino)pyrazolo[1,5-a]pyrimidine-3-carbonitrile, (±)-7-(cyclopropylamino)-5-((4-(difluoromethoxy)-3-((methylsulfinyl)methyl)phenyl)amino)pyrazolo[1,5-a]pyrimidine-3-carbonitrile, 7-(cyclopropylamino)-5-((4-(difluoromethoxy)-3-((methylsulfonyl)methyl)phenyl)amino)pyrazolo[1,5-a]pyrimidine-3-carbonitrile, (±)-7-(cyclopropylamino)-5-((4-(methyl(2-(methylamino)ethyl)amino)-3-((methylsulfinyl)methyl)phenyl)amino)pyrazolo[1,5-a]pyrimidine-3-carbonitrile mono trifluoroacetic acid salt, 5-((4-((R)-3-aminopyrrolidin-1-yl)-3-(((R,S)-methylsulfinyl)methyl)phenyl)amino)-7-(cyclopropylamino)pyrazolo[1,5-a]pyrimidine-3-carbonitrile mono trifluoroacetic acid salt, 5-((4-((S)-3-aminopyrrolidin-1-yl)-3-(((R,S)-methylsulfinyl)methyl)phenyl)amino)-7-(cyclopropylamino)pyrazolo[1,5-a]pyrimidine-3-carbonitrile mono trifluoroacetic acid salt, 5-((4-((R)-3-aminopiperidin-1-yl)-3-(((R,S)-methylsulfinyl)methyl)phenyl)amino)-7-(cyclopropylamino)pyrazolo[1,5-a]pyrimidine-3-carbonitrile mono trifluoroacetic acid salt, 5-((4-((S)-3-aminopiperidin-1-yl)-3-(((R,S)-methylsulfinyl)methyl)phenyl)amino)-7-(cyclopropylamino)pyrazolo[1,5-a]pyrimidine-3-carbonitrile mono trifluoroacetic acid salt, 5-((4-(2-aminoethoxy)-3-((methylsulfonyl)methyl)phenyl)amino)-7-(cyclopropylamino)pyrazolo[1,5-a]pyrimidine-3-carbonitrile hydrochloric acid salt, (±)-7-(cyclopropylamino)-5-((4-(3-hydroxyazetidin-1-yl)-3-((methylsulfinyl)methyl)phenyl)amino)pyrazolo[1,5-a]pyrimidine-3-carbonitrile, (±)-5-((4-((1-aminocyclopropyl)methoxy)-3-((methylsulfinyl)methyl)phenyl)amino)-7-(cyclopropylamino)pyrazolo[1,5-a]pyrimidine-3-carbonitrile mono trifluoroacetic acid salt, (S)-5-((4-(3-aminopyrrolidin-1-yl)-3-((methylsulfonyl)methyl)phenyl)amino)-7-(cyclopropylamino)pyrazolo[1,5-a]pyrimidine-3-carbonitrile mono trifluoroacetic acid salt, (±)-5-((4-(2-amino-2-methylpropoxy)-3-((methylsulfinyl)methyl)phenyl)amino)-7-(cyclopropylamino)pyrazolo[1,5-a]pyrimidine-3-carbonitrile mono trifluoroacetic acid salt, (±)-5-((4-(2-aminoethoxy)-3-((methylsulfinyl)methyl)phenyl)amino)-7-(cyclopropylamino)pyrazolo[1,5-a]pyrimidine-3-carbonitrile, 5-((4-(azetidin-1-yl)-3-((methylsulfonyl)methyl)phenyl)amino)-7-(cyclopropylamino)pyrazolo[1,5-a]pyrimidine-3-carbonitrile, (±)-7-(cyclopropylamino)-5-((4-(dimethylamino)-3-((methylsulfinyl)methyl)phenyl)amino)pyrazolo[1,5-a]pyrimidine-3-carbonitrile, 7-(cyclopropylamino)-5-((4-(dimethylamino)-3-((methylsulfonyl)methyl)phenyl)amino)pyrazolo[1,5-a]pyrimidine-3-carbonitrile, (±)-7-(cyclopropylamino)-5-((3-((methylsulfinyl)methyl)-4-(1H-pyrazol-4-yl)phenyl)amino)pyrazolo[1,5-a]pyrimidine-3-carbonitrile, (±)-5-((4-(cyclopropyl(methyl)amino)-3-((methylsulfinyl)methyl)phenyl)amino)-7-(cyclopropylamino)pyrazolo[1,5-a]pyrimidine-3-carbonitrile, (±)-5-((4-(azetidin-1-yl)-3-((methylsulfinyl)methyl)phenyl)amino)-7-(cyclopropylamino)pyrazolo[1,5-a]pyrimidine-3-carbonitrile, (±)-5-((4-(1-(aminomethyl)cyclopropyl)-3-((methylsulfinyl)methyl)phenyl)amino)-7-(cyclopropylamino)pyrazolo[1,5-a]pyrimidine-3-carbonitrile, 5-((4-(1-(aminomethyl)cyclopropyl)-3-((methylsulfonyl)methyl)phenyl)amino)-7-(cyclopropylamino)pyrazolo[1,5-a]pyrimidine-3-carbonitrile mono trifluoroacetic acid salt, (±)-5-((4-(3-aminoazetidin-1-yl)-3-((methylsulfinyl)methyl)phenyl)amino)-7-(cyclopropylamino)pyrazolo[1,5-a]pyrimidine-3-carbonitrile, 5-((4-(3-aminoazetidin-1-yl)-3-((methylsulfonyl)methyl)phenyl)amino)-7-(cyclopropylamino)pyrazolo[1,5-a]pyrimidine-3-carbonitrile, (±)-5-((4-(3-(aminomethyl)azetidin-1-yl)-3-((methylsulfinyl)methyl)phenyl)amino)-7-(cyclopropylamino)pyrazolo[1,5-a]pyrimidine-3-carbonitrile, 5-((4-(3-(aminomethyl)azetidin-1-yl)-3-((methylsulfonyl)methyl)phenyl)amino)-7-(cyclopropylamino)pyrazolo[1,5-a]pyrimidine-3-carbonitrile, (±)-5-((4-(azetidin-3-yl(methyl)amino)-3-((methylsulfinyl)methyl)phenyl)amino)-7-(cyclopropylamino)pyrazolo[1,5-a]pyrimidine-3-carbonitrile, 5-((4-(azetidin-3-yl(methyl)amino)-3-((methylsulfonyl)methyl)phenyl)amino)-7-(cyclopropylamino)pyrazolo[1,5-a]pyrimidine-3-carbonitrile, (±)-7-(cyclopropylamino)-5-((3-((methylsulfinyl)methyl)-4-(pyrrolidin-1-yl)phenyl)amino)pyrazolo[1,5-a]pyrimidine-3-carbonitrile, (±)-6-((4-((2-aminoethyl)(methyl)amino)-3-((methylsulfinyl)methyl)phenyl)amino)-8-(cyclopropylamino)imidazo[1,2-b]pyridazine-3-carbonitrile mono trifluoroacetic acid salt, 6-((4-((2-aminoethyl)(methyl)amino)-3-((methylsulfonyl)methyl)phenyl)amino)-8-(cyclopropylamino)imidazo[1,2-b]pyridazine-3-carbonitrile mono trifluoroacetic acid salt, (±)-2-((4-((2-aminoethyl)(methyl)amino)-3-((methylsulfinyl)methyl)phenyl)amino)-4-(cyclopropylamino)imidazo[2,1-f][1,2,4]triazine-7-carbonitrile mono trifluoroacetic acid salt, 2-((4-((2-aminoethyl)(methyl)amino)-3-((methylsulfonyl)methyl)phenyl)amino)-4-(cyclopropylamino)imidazo[2,1-f][1,2,4]triazine-7-carbonitrile mono trifluoroacetic acid salt, (±)-2-((4-((2-aminoethyl)(methyl)amino)-3-((methylsulfinyl)methyl)phenyl)amino)-4-(cyclopropylamino)pyrazolo[1,5-a][1,3,5]triazine-8-carbonitrile mono trifluoroacetic acid salt, 2-((4-((2-aminoethyl)(methyl)amino)-3-((methylsulfonyl)methyl)phenyl)amino)-4-(cyclopropylamino)pyrazolo[1,5-a][1,3,5]triazine-8-carbonitrile mono trifluoroacetic acid salt, (±)-7-(cyclopropylamino)-5-((3-((methylsulfinyl)methyl)-4-(1,2,5,6-tetrahydropyridin-3-yl)phenyl)amino)pyrazolo[1,5-a]pyrimidine-3-carbonitrile mono trifluoroacetic acid salt, (±)-5-((4-cyclopropyl-3-((methylsulfinyl)methyl)phenyl)amino)-7-(pyridin-2-ylamino)pyrazolo[1,5-a]pyrimidine-3-carbonitrile, (±)-5-((4-cyclopropyl-3-((methylsulfinyl)methyl)phenyl)amino)-7-(pyridin-3-ylamino)pyrazolo[1,5-a]pyrimidine-3-carbonitrile, (±)-7-((6-aminopyridin-3-yl)amino)-5-((4-cyclopropyl-3-((methylsulfinyl)methyl)phenyl)amino)pyrazolo[1,5-a]pyrimidine-3-carbonitrile, (±)-7-((5-aminopyridin-2-yl)amino)-5-((4-cyclopropyl-3-((methylsulfinyl)methyl)phenyl)amino)pyrazolo[1,5-a]pyrimidine-3-carbonitrile, (±)-5-((4-((R,S)-1-aminoethyl)-3-((methylsulfinyl)methyl)phenyl)amino)-7-(cyclopropylamino)pyrazolo[1,5-a]pyrimidine-3-carbonitrile mono trifluoroacetic acid salt, (±)-5-((4-(1-aminocyclopropyl)-3-((methylsulfinyl)methyl)phenyl)amino)-7-(cyclopropylamino)pyrazolo[1,5-a]pyrimidine-3-carbonitrile mono trifluoroacetic acid salt, (±)-(E)-5-((4-(4-aminobut-2-en-2-yl)-3-((methylsulfinyl)methyl)phenyl)amino)-7-(cyclopropylamino)pyrazolo[1,5-a]pyrimidine-3-carbonitrile mono trifluoroacetic acid salt, (±)-7-(cyclopropylamino)-5-((3-((methylsulfinyl)methyl)-4-((R,S)-piperidin-3-yl)phenyl)amino)pyrazolo[1,5-a]pyrimidine-3-carbonitrile mono trifluoroacetic acid salt, (±)-7-(cyclopropylamino)-5-((4-(2,5-dihydro-1H-pyrrol-3-yl)-3-((methylsulfinyl)methyl)phenyl)amino)pyrazolo[1,5-a]pyrimidine-3-carbonitrile mono trifluoroacetic acid salt, (±)-7-(cyclopropylamino)-5-((3-((methylsulfinyl)methyl)-4-((R,S)-pyrrolidin-3-yl)phenyl)amino)pyrazolo[1,5-a]pyrimidine-3-carbonitrile mono trifluoroacetic acid salt, (±)-5-((4-((R,S)-4-aminobutan-2-yl)-3-((methylsulfinyl)methyl)phenyl)amino)-7-(cyclopropylamino)pyrazolo[1,5-a]pyrimidine-3-carbonitrile mono trifluoroacetic acid salt, (±)-5-((4-(((1-aminocyclopropyl)methyl)(methyl)amino)-3-((methylsulfinyl)methyl)phenyl)amino)-7-(cyclopropylamino)pyrazolo[1,5-a]pyrimidine-3-carbonitrile mono trifluoroacetic acid salt, 5-((4-(((1-aminocyclopropyl)methyl)(methyl)amino)-3-((methylsulfonyl)methyl)phenyl)amino)-7-(cyclopropylamino)pyrazolo[1,5-a]pyrimidine-3-carbonitrile mono trifluoroacetic acid salt, (±)-5-((4-((2-amino-2-methylpropyl)(methyl)amino)-3-((methylsulfinyl)methyl)phenyl)amino)-7-(cyclopropylamino)pyrazolo[1,5-a]pyrimidine-3-carbonitrile mono trifluoroacetic acid salt, (±)-7-((5-aminopyridin-2-yl)amino)-5-((4-((S)-3-aminopyrrolidin-1-yl)-3-((methylsulfinyl)methyl)phenyl)amino)pyrazolo[1,5-a]pyrimidine-3-carbonitrile, (±)-5-((4-cyclopropyl-3-((methylsulfinyl)methyl)phenyl)amino)-7-((5-((dimethylamino)methyl)pyridin-2-yl)amino)pyrazolo[1,5-a]pyrimidine-3-carbonitrile, (±)-7-((5-(aminomethyl)pyridin-2-yl)amino)-5-((4-cyclopropyl-3-((methylsulfinyl)methyl)phenyl)amino)pyrazolo[1,5-a]pyrimidine-3-carbonitrile, (±)-5-((4-chloro-3-((methylsulfinyl)methyl)phenyl)amino)-7-((5-((dimethylamino)methyl)pyridin-2-yl)amino)pyrazolo[1,5-a]pyrimidine-3-carbonitrile, (±)-7-((5-((dimethylamino)methyl)pyridin-2-yl)amino)-5-((3-((methylsulfinyl)methyl)-4-(pyrrolidin-1-yl)phenyl)amino)pyrazolo[1,5-a]pyrimidine-3-carbonitrile, (R,S)-5-((4-(4-aminobutan-2-yl)-3-((methylsulfonyl)methyl)phenyl)amino)-7-(cyclopropylamino)pyrazolo[1,5-a]pyrimidine-3-carbonitrile mono trifluoroacetic acid salt, (±)-5-((4-(2-aminocyclopropyl)-3-((methylsulfinyl)methyl)phenyl)amino)-7-(cyclopropylamino)pyrazolo[1,5-a]pyrimidine-3-carbonitrile mono trifluoroacetic acid salt, (±)-5-((4-(2-(aminomethyl)cyclopropyl)-3-((methylsulfinyl)methyl)phenyl)amino)-7-(cyclopropylamino)pyrazolo[1,5-a]pyrimidine-3-carbonitrile mono trifluoroacetic acid salt, (±)-5-((4-(2-(2-aminoethyl)cyclopropyl)-3-((methylsulfinyl)methyl)phenyl)amino)-7-(cyclopropylamino)pyrazolo[1,5-a]pyrimidine-3-carbonitrile mono trifluoroacetic acid salt, (±)-2-amino-N-(4-((3-cyano-7-(cyclopropylamino)pyrazolo[1,5-a]pyrimidin-5-yl)amino)-2-((methylsulfinyl)methyl)phenyl)-N-methylacetamide mono trifluoroacetic acid salt 7-(cyclopropylamino)-5-((4-fluoro-3-((methylsulfonyl)methyl)phenyl)amino)pyrazolo[1,5-a]pyrimidine-3-carbonitrile, 5-((4-cyclopropyl-3-((methylsulfonyl)methyl)phenyl)amino)-7-(cyclopropylamino)pyrazolo[1,5-a]pyrimidine-3-carbonitrile, 7-(cyclopropylamino)-5-((3-((methylsulfonyl)methyl)-4-(piperazin-1-yl)phenyl)amino)pyrazolo[1,5-a]pyrimidine-3-carbonitrile mono trifluoroacetic acid salt, 5-((4-(aminomethyl)-3-((methylsulfonyl)methyl)phenyl)amino)-7-(cyclopropylamino)pyrazolo[1,5-a]pyrimidine-3-carbonitrile mono trifluoroacetic acid salt, 7-(cyclopropylamino)-5-((4-((cyclopropylmethyl)(methyl)amino)-3-((methylsulfonyl)methyl)phenyl)amino)pyrazolo[1,5-a]pyrimidine-3-carbonitrile, 7-(cyclopropylamino)-5-((4-(methyl(2-(methylamino)ethyl)amino)-3-((methylsulfonyl)methyl)phenyl)amino)pyrazolo[1,5-a]pyrimidine-3-carbonitrile mono trifluoroacetic acid salt, (R)-5-((4-(3-aminopyrrolidin-1-yl)-3-((methylsulfonyl)methyl)phenyl)amino)-7-(cyclopropylamino)pyrazolo[1,5-a]pyrimidine-3-carbonitrile mono trifluoroacetic acid salt, (R)-5-((4-(3-aminopiperidin-1-yl)-3-((methylsulfonyl)methyl)phenyl)amino)-7-(cyclopropylamino)pyrazolo[1,5-a]pyrimidine-3-carbonitrile mono trifluoroacetic acid salt, (S)-5-((4-(3-aminopiperidin-1-yl)-3-((methylsulfonyl)methyl)phenyl)amino)-7-(cyclopropylamino)pyrazolo[1,5-a]pyrimidine-3-carbonitrile mono trifluoroacetic acid salt, 7-(cyclopropylamino)-5-((4-(3-hydroxyazetidin-1-yl)-3-((methylsulfonyl)methyl)phenyl)amino)pyrazolo[1,5-a]pyrimidine-3-carbonitrile, 5-((4-((1-aminocyclopropyl)methoxy)-3-((methylsulfonyl)methyl)phenyl)amino)-7-(cyclopropylamino)pyrazolo[1,5-a]pyrimidine-3-carbonitrile mono trifluoroacetic acid salt, 5-((4-(2-amino-2-methylpropoxy)-3-((methylsulfonyl)methyl)phenyl)amino)-7-(cyclopropylamino)pyrazolo[1,5-a]pyrimidine-3-carbonitrile mono trifluoroacetic acid salt, 7-(cyclopropylamino)-5-((3-((methylsulfonyl)methyl)-4-(1H-pyrazol-4-yl)phenyl)amino)pyrazolo[1,5-a]pyrimidine-3-carbonitrile, 5-((4-(cyclopropyl(methyl)amino)-3-((methylsulfonyl)methyl)phenyl)amino)-7-(cyclopropylamino)pyrazolo[1,5-a]pyrimidine-3-carbonitrile, 7-(cyclopropylamino)-5-((3-((methylsulfonyl)methyl)-4-(pyrrolidin-1-yl)phenyl)amino)pyrazolo[1,5-a]pyrimidine-3-carbonitrile, 7-(cyclopropylamino)-5-((3-((methylsulfonyl)methyl)-4-(1,2,5,6-tetrahydropyridin-3-yl)phenyl)amino)pyrazolo[1,5-a]pyrimidine-3-carbonitrile mono trifluoroacetic acid salt, 5-((4-cyclopropyl-3-((methylsulfonyl)methyl)phenyl)amino)-7-(pyridin-2-ylamino)pyrazolo[1,5-a]pyrimidine-3-carbonitrile, 5-((4-cyclopropyl-3-((methylsulfonyl)methyl)phenyl)amino)-7-(pyridin-3-ylamino)pyrazolo[1,5-a]pyrimidine-3-carbonitrile, 7-((6-aminopyridin-3-yl)amino)-5-((4-cyclopropyl-3-((methylsulfonyl)methyl)phenyl)amino)pyrazolo[1,5-a]pyrimidine-3-carbonitrile, 7-((5-aminopyridin-2-yl)amino)-5-((4-cyclopropyl-3-((methylsulfonyl)methyl)phenyl)amino)pyrazolo[1,5-a]pyrimidine-3-carbonitrile, (R,S)-5-((4-(1-aminoethyl)-3-((methylsulfonyl)methyl)phenyl)amino)-7-(cyclopropylamino)pyrazolo[1,5-a]pyrimidine-3-carbonitrile mono trifluoroacetic acid salt, 5-((4-(1-aminocyclopropyl)-3-((methylsulfonyl)methyl)phenyl)amino)-7-(cyclopropylamino)pyrazolo[1,5-a]pyrimidine-3-carbonitrile mono trifluoroacetic acid salt, (E)-5-((4-(4-aminobut-2-en-2-yl)-3-((methylsulfonyl)methyl)phenyl)amino)-7-(cyclopropylamino)pyrazolo[1,5-a]pyrimidine-3-carbonitrile mono trifluoroacetic acid salt, (R,S)-7-(cyclopropylamino)-5-((3-((methylsulfonyl)methyl)-4-(piperidin-3-yl)phenyl)amino)pyrazolo[1,5-a]pyrimidine-3-carbonitrile mono trifluoroacetic acid salt, 7-(cyclopropylamino)-5-((4-(2,5-dihydro-1H-pyrrol-3-yl)-3-((methylsulfonyl)methyl)phenyl)amino)pyrazolo[1,5-a]pyrimidine-3-carbonitrile mono trifluoroacetic acid salt, (R,S)-7-(cyclopropylamino)-5-((3-((methylsulfonyl)methyl)-4-(pyrrolidin-3-yl)phenyl)amino)pyrazolo[1,5-a]pyrimidine-3-carbonitrile mono trifluoroacetic acid salt, 5-((4-((2-amino-2-methylpropyl)(methyl)amino)-3-((methylsulfonyl)methyl)phenyl)amino)-7-(cyclopropylamino)pyrazolo[1,5-a]pyrimidine-3-carbonitrile mono trifluoroacetic acid salt, (S)-7-((5-aminopyridin-2-yl)amino)-5-((4-(3-aminopyrrolidin-1-yl)-3-((methylsulfonyl)methyl)phenyl)amino)pyrazolo[1,5-a]pyrimidine-3-carbonitrile, 5-((4-cyclopropyl-3-((methylsulfonyl)methyl)phenyl)amino)-7-((5-((dimethylamino)methyl)pyridin-2-yl)amino)pyrazolo[1,5-a]pyrimidine-3-carbonitrile, 7-((5-(aminomethyl)pyridin-2-yl)amino)-5-((4-cyclopropyl-3-((methylsulfonyl)methyl)phenyl)amino)pyrazolo[1,5-a]pyrimidine-3-carbonitrile, 5-((4-chloro-3-((methylsulfonyl)methyl)phenyl)amino)-7-((5-((dimethylamino)methyl)pyridin-2-yl)amino)pyrazolo[1,5-a]pyrimidine-3-carbonitrile, 7-((5-((dimethylamino)methyl)pyridin-2-yl)amino)-5-((3-((methylsulfonyl)methyl)-4-(pyrrolidin-1-yl)phenyl)amino)pyrazolo[1,5-a]pyrimidine-3-carbonitrile, 5-((4-(2-aminocyclopropyl)-3-((methylsulfonyl)methyl)phenyl)amino)-7-(cyclopropylamino)pyrazolo[1,5-a]pyrimidine-3-carbonitrile mono trifluoroacetic acid salt, 5-((4-(2-(aminomethyl)cyclopropyl)-3-((methylsulfonyl)methyl)phenyl)amino)-7-(cyclopropylamino)pyrazolo[1,5-a]pyrimidine-3-carbonitrile mono trifluoroacetic acid salt, 5-((4-(2-(2-aminoethyl)cyclopropyl)-3-((methylsulfonyl)methyl)phenyl)amino)-7-(cyclopropylamino)pyrazolo[1,5-a]pyrimidine-3-carbonitrile mono trifluoroacetic acid salt, and 2-amino-N-(4-((3-cyano-7-(cyclopropylamino)pyrazolo[1,5-a]pyrimidin-5-yl)amino)-2-((methylsulfonyl)methyl)phenyl)-N-methylacetamide mono trifluoroacetic acid salt, or a stereoisomer, a tautomer or a pharmaceutically acceptable salt thereof.

The inventive compounds according to Formula (I) may be isotopically-labeled by having one or more atoms replaced by an atom having a different atomic mass or mass number. Examples of isotopes that can be incorporated into compounds of according to Formula (I) include isotopes of hydrogen, carbon, nitrogen, oxygen, phosphorous, fluorine, chlorine, or iodine. Illustrative of such isotopes are $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabeled compounds can be used to measure the biodistribution, tissue concentration and the kinetics of transport and excretion from biological tissues including a subject to which such a labeled compound is administered. Labeled compounds are also used to determine therapeutic effectiveness, the site or mode of action, and the binding affinity of a candidate therapeutic to a pharmacologically important target. Certain radioactive-labeled compounds according to Formula (I), therefore, are useful in drug and/or tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, affords certain therapeutic advantages resulting from the greater metabolic stability, for example, increased in vivo half-life of compounds containing deuterium. Substitution of hydrogen with deuterium may reduce dose required for therapeutic effect, and hence may be preferred in a discovery or clinical setting.

Substitution with positron emitting isotopes, such as $^{11}$C, $^{18}$F, $^{15}$O and $^{13}$N, provides labeled analogs of the inventive compounds that are useful in Positron Emission Tomography (PET) studies, e.g., for examining substrate receptor occupancy. Isotopically-labeled compounds according to Formula (I) can generally be prepared by conventional techniques known to those skilled in the art or by processes analogous to those described in the Preparations and Examples section as set out below using an appropriate isotopic-labeling reagent.

Embodiments of the invention disclosed herein are also meant to encompass the in vivo metabolic products of compounds according to Formula (I). Such products may result from, for example, the oxidation, reduction, hydrolysis, amidation, esterification, and like processes primarily due to enzymatic activity upon administration of a compound of the invention. Accordingly, the invention includes compounds that are produced as by-products of enzymatic or non-enzymatic activity on an inventive compound following the administration of such a compound to a mammal for a period of time sufficient to yield a metabolic product. Metabolic products, particularly pharmaceutically active metabolites are typically identified by administering a radiolabeled compound of the invention in a detectable dose to a subject, such as rat, mouse, guinea pig, monkey, or human, for a sufficient period of time during which metabolism occurs, and isolating the metabolic products from urine, blood or other biological samples that are obtained from the subject receiving the radiolabeled compound.

The invention also provides pharmaceutically acceptable salt forms of Formula (I) compounds. Encompassed within the scope of the invention are both acid and base addition salts that are formed by contacting a pharmaceutically suitable acid or a pharmaceutically suitable base with a compound of the invention.

To this end, a "pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

Similarly, a "pharmaceutically acceptable base addition salt" refers to those salts which retain the biological effectiveness and properties of the free acids, which are not biologically or otherwise undesirable. These salts are prepared by addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

Compounds of the invention or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)-for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

The term "tautomer" refers to a proton shift from one atom of a molecule to another atom of the same molecule.

The inventive compounds are synthesized using conventional synthetic methods, and more specifically using the general methods noted below.

Pharmaceutical Formulations

In one embodiment, a compounds according to Formula (I) are formulated as pharmaceutically acceptable compositions that contain a Formula (I) compound in an amount effective to treat a particular disease or condition of interest upon administration of the pharmaceutical composition to a mammal. Pharmaceutical compositions in accordance with the present invention can comprise a Formula (I) compound in combination with a pharmaceutically acceptable carrier, diluent or excipient.

In this regard, a "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Further, a "mammal" includes humans and both domestic animals such as laboratory animals and household pets (e.g., cats, dogs, swine, cattle, sheep, goats, horses, rabbits), and non-domestic animals such as wildlife and the like.

The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient (s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by any methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

In certain embodiments a pharmaceutical composition comprising a compound of Formula (I) is administered to a mammal in an amount sufficient to inhibit CK2 activity upon administration, and preferably with acceptable toxicity to the same. CK2 activity of Formula (I) compounds can be determined by one skilled in the art, for example, as described in the Examples below. Appropriate concentrations and dosages can be readily determined by one skilled in the art.

Therapeutic Use

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

"Effective amount" or "therapeutically effective amount" refers to that amount of a compound of the invention which, when administered to a mammal, preferably a human, is sufficient to effect treatment, as defined below, of a CK2 related condition or disease in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

Compounds of the invention or pharmaceutically acceptable salt thereof may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

In certain embodiments the disclosed compounds are useful for inhibiting the activity of CK2 and/or can be useful in analyzing CK2 signaling activity in model systems and/or for preventing, treating, or ameliorating a symptom associated with a disease, disorder, or pathological condition involving CK2, preferably one afflicting humans. A compound which inhibits the activity of CK2 will be useful in preventing, treating, ameliorating, or reducing the symptoms or progression of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by CK2, such as, for example, hematological tumors, solid tumors, circulating tumors and/or metastases thereof, including myeloproliferative disorders, leukemias and myelodysplastic syndrome, malignant lymphomas, for example, acute myelogenous (granulocytic) leukemia (AML), chronic myelogenous leukemia (CML), acute lymphocytic (lymphoblastic) leukemia (ALL), chronic lymphocytic leukemia (CLL), chronic idiopathic myelofibrosis, polycythemia vera, essential thrombocythemia, myeloid metaplasia, acute erythroblastic leukemia, Hodgkin's lymphoma, non-Hodgkin's lymphoma, hairy cell lymphoma, Burkitt's lymphoma, B-cell lymphoma, acute T-cell leukemia and T-cell lymphoma, head and neck tumors including brain tumors and brain metastases, tumors of the thorax including non-small cell and small cell lung tumors, gastrointestinal tumors, endocrine tumors, mammary and other gynecological tumors, urological tumors including renal, bladder and prostate tumors, skin tumors, and sarcomas, and/or metastases thereof.

Furthermore, the inventive compounds and their pharmaceutical compositions are candidate therapeutics for the prophylaxis and/or therapy of cytokine related diseases, such as inflammatory diseases, pain, allergies, or other conditions associated with proinflammatory cytokines. Exemplary conditions associated with inflammation and pain include without limitation, acid reflux, heartburn, acne, celiac disease, chronic pain, dementia, chronic or acute inflammation, diabetes, dry eyes, edema, emphysema, inflammation of the joints such as chronic inflammatory arthritis, rheumatoid arthritis, psoriatic arthritis, osteoarthritis, juvenile rheumatoid arthritis, Reiter's syndrome, rheumatoid traumatic arthritis, rubella arthritis, acute synovitis and gouty arthritis; inflammatory skin diseases such as sunburn, psoriasis, erythrodermic psoriasis, pustular psoriasis, eczema, dermatitis, acute or chronic graft formation, atopic dermatitis, contact dermatitis, urticaria and scleroderma; inflammation of the gastrointestinal tract such as inflammatory bowel disease, Crohn's disease and related conditions, ulcerative colitis, colitis, and diverticulitis; nephritis, urethritis, salpingitis, oophoritis, endomyometritis, spondylitis, systemic lupus erythematosus and related disorders, multiple sclerosis, asthma, meningitis, myelitis, encephalomyelitis, encephalitis, phlebitis, thrombophlebitis, respiratory diseases such as asthma, bronchitis, chronic obstructive pulmonary disease (COPD), septic shock, inflammatory lung disease and adult respiratory distress syndrome, and allergic rhinitis; endocarditis, osteomyelitis, rheumatic fever, rheumatic pericarditis, rheumatic endocarditis, rheumatic myocarditis, rheumatic mitral valve disease, rheumatic aortic valve disease, prostatitis, prostatocystitis, spondoarthropathies ankylosing spondylitis, synovitis, tenosynovotis, myositis, pharyngitis, polymyalgia rheumatica, shoulder tendonitis or bursitis, gout, pseudo gout, vasculitides, inflammatory diseases of the thyroid selected from granulomatous thyroiditis, lymphocytic thyroiditis, invasive fibrous thyroiditis, acute thyroiditis; Hashimoto's thyroiditis, Kawasaki's disease, Raynaud's phenomenon, Sjogren's syndrome, neuroinflammatory disease, sepsis, conjunctivitis, keratitis, iridocyclitis, optic neuritis, otitis, lymphoadenitis, nasopaharingitis, sinusitis, pharyngitis, tonsillitis, laryngitis, epiglottitis, bronchitis, pneumonitis, stomatitis, gingivitis. oesophagitis, gastritis, peritonitis, hepatitis, cholelithiasis, cholecystitis, glomerulonephritis, goodpasture's disease, crescentic glomerulonephritis, pancreatitis, endomyometritis, myometritis, metritis, cervicitis, endocervicitis, exocervicitis, parametritis, tuberculosis, vaginitis, vulvitis, silicosis, sarcoidosis, pneumoconiosis, pyresis, inflammatory polyarthropathies, psoriatric arthropathies, intestinal fibrosis, bronchiectasis and enteropathic arthropathies, gastroenteritis, hepatitis, high blood pressure, interstitial cystitis, metabolic syndrome (syndrome X), obesity, osteopenia, juvenile cystic kidney disease, and type I nephronophthisis (NPHP), osteoporosis, Guam-Parkinson dementia, supranuclear palsy, Kufs disease, and Pick's disease, as well as memory impairment, brain ischemia, schizophrenia, periodontal disease, polyarteritis, polychondritis, spastic colon, systemic candidiasis, urinary track infections, inflammatory cancer (e.g., inflammatory breast cancer) and the like.

Although inflammation is the unifying pathogenic process of these diseases, current therapies only treat the symptoms of the disease and not the underlying cause of inflammation. The compositions of the present invention are useful for the treatment and/or prophylaxis of inflammatory diseases and related complications and disorders.

Accordingly, certain embodiments are directed to a method for treating a CK2 dependent condition in a mammal in need thereof, the method comprising administering an effective amount of a pharmaceutical composition as described above (i.e., a pharmaceutical composition comprising any one or more compounds of Formula (I) to a mammal.

As described above deregulation of protein synthesis is a common event in human cancers. A key regulator of cell growth, proliferation, and apoptosis is CK2 whose activity is a key determinant of tumorigenicity. Inhibitors of CK2 are suitable candidate therapeutics for treating cell proliferative disorders such as cancer. A wide variety of cancers, including solid tumors, lymphomas and leukemias, are amenable to the compositions and methods disclosed herein. Types of cancer that may be treated include, but are not limited to: adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell). Additional types of cancers that may be treated include: histiocytic disorders; leukemia; histiocytosis malignant; Hodgkin's disease; immunoproliferative small; non-Hodgkin's lymphoma; T-cell lymphoma, B-cell lymphoma, hairy cell lymphoma, Burkitt's lymphoma, plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor.

Other cancers that can be treated using the inventive compounds include without limitation adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin.

In one embodiment the inventive compounds are candidate therapeutic agents for the treatment of cancers such as angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

In a particular embodiment the present disclosure provides methods for treating colon cancer, gastric cancer, thyroid cancer, lung cancer, leukemia, pancreatic cancer, melanoma, multiple melanoma, brain cancer, CNS cancer, renal cancer, prostate cancer, ovarian cancer, or breast cancer. Illustrative of the category "brain cancer" are glioblastomas, astrocytomas, medulloblastoma, meningiomas and other disease conditions related to brain cancer metastases. According to such a method, a therapeutically effective amount of at least one compound according to Formula (I) or a stereoisomer, tautomer or pharmaceutically acceptable salt thereof can be administered to a subject who has been diagnosed with a cell proliferative disease, such as a cancer. Alternatively, a pharmaceutical composition comprising at least one compound according to Formula I or a stereoisomer, tautomer or pharmaceutically acceptable salt thereof can be administered to a subject who has been diagnosed with cancer.

In certain embodiments the compounds in accordance with the invention are administered to a subject with cancer in conjunction with other conventional cancer therapies such as radiation treatment or surgery. Radiation therapy is well-known in the art and includes X-ray therapies, such as gamma-irradiation, and radiopharmaceutical therapies.

In certain embodiments the inventive CK2 inhibitor compounds are used with at least one anti-cancer agent. Anti-cancer agents include chemotherapeutic drugs. A chemotherapeutic agent includes, but is not limited to, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor.

Administration of a combination of one or more of the CK2 inhibitor compounds provided herein and one or more additional chemotherapeutic agents is also contemplated. Administration of a combination can be sequential, wherein treatment with one agent is done before treatment with a second agent. Alternatively, administration can be concurrent where treatment with two or more agents occurs at the same time. Sequential administration can be done within a reasonable time after the completion of a first therapy before beginning a second therapy. Administration of multiple agents concurrently can be in the same daily dose or in separate doses.

In certain embodiments, the additional chemotherapeutic agent can comprise another compound, antibody, or protein that is an anti-cancer agent. Such anti-cancer agents include, but are not limited to, alkylating agents (including, but not limited to, cyclophosphamide, mechlorethamine, chlorambucil, melphalan), anthracyclines (including, but are not limited to, daunorubicin, doxorubicin, epirubicin, idarubicin, mitoxantrone, valrubicin), cytoskeletal disruptors (including, but are not limited to, taxanes such as paclitaxel and docetaxel), epothilones, histone deacetylase inhibitors (including, but not limited to, vorinostat, romidepsin), topoisomerase II inhibitors (including, but not limited to, etoposide, teniposide, tafluposide), kinase Inhibitors (including, but are not limited to, bortezomib, erlotinib, gefitinib, imatinib, vismodegib), monoclonal antibodies (including but not limited to bevacizumab, cetuximab, ipilimumab, ofatumumab, ocrelizumab, panitumab, rituximab), nucleotide analogs and precursor analogs (including, but are not limited to, azacytidine, azathioprine, capecitabine, cytarabine, doxifluridine, fluorouracil, gemcitabine, hydroxyurea, mercaptopurine, methotrexate, and thioguanine), peptide antibiotics (including, but not limited to, bleomycin, actinomycin), platinum-based agents (including, but not limited to, carboplatin, cisplatin, oxaliplatin), retinoids (tretinoin, alitretinoin, bexarotene) and vinca alkaloids and derivatives (including, but not limited to, vinblastine, vincristine, vindesine, and vinorelbine). In certain embodiments, the anti-cancer agents assessed in combination with the inventive CK2 inhibitor includes DNA damaging agents (including, but not limited to, 5-FU, fludarabine, gemcitabine, cisplatin, doxorubicin), kinase inhibitors (including, but not limited to, trametinib, erlotinib, sunitinib), tubulin inhibitors and stabilizer (including, but not limited to vinblastine and paclitaxel), mTOR inhibitor (including, but not limited, to rapamycins), and proteasome inhibitors (including, but not limited to bortezomib).

In certain embodiments, the additional chemotherapeutic agent can comprise another compound, antibody, or protein that potentiates and/or relieves the side effects of anti-cancer drugs. In certain embodiments, such additional chemotherapeutic agents thus include, but are not limited to, anti-angiogenesis, anti-nausea agents, and the like. In certain embodiments, such additional chemotherapeutic agents include, but are not limited to, agents such as erythropoietin and the like.

In certain embodiments a CK2 inhibitor in accordance with the present invention is used simultaneously, in the same formulation or in separate formulations, or sequentially with an additional agent(s) as part of a combination therapy regimen.

The inventive compounds their corresponding salts and pharmaceutically acceptable compositions are candidate therapeutics for treating brain related disorders which include without limitation autism, Fragile X-syndrome, Parkinson's disease and Alzheimer's disease. Treatment is effected by administering to a subject in need of treatment a Formula I compound, its pharmaceutically acceptable salt form, or a pharmaceutically acceptable composition of a Formula (I) compound or its salt.

The invention also supports the use of the inventive compounds or a pharmaceutically acceptable formulation of the inventive compound as an inhibitor of CK2 activity. Such inhibition is achieved by contacting a cell expressing CK2 with a compound or a pharmaceutically acceptable formulation, to lower or inhibit CK2 activity, to provide therapeutic efficacy for a CK2 dependent condition in a mammal in need thereof.

Therapeutically effective dosages of a compound according to Formula (I) or a composition of a Formula (I) compound will generally range from about 1 to 2000 mg/day, from about 10 to about 1000 mg/day, from about 10 to about 500 mg/day, from about 10 to about 250 mg/day, from about 10 to about 100 mg/day, or from about 10 to about 50 mg/day. The therapeutically effective dosages may be administered in one or multiple doses. It will be appreciated, however, that specific doses of the compounds of the invention for any particular patient will depend on a variety of factors such as age, sex, body weight, general health condition, diet, individual response of the patient to be treated, time of administration, severity of the disease to be treated, the activity of particular compound applied, dosage form, mode of application and concomitant medication. The therapeutically effective amount for a given situation will readily be determined by routine experimentation and is within the skills and judgment of the ordinary clinician or physician. In any case the compound or composition will be administered at dosages and in a manner which allows a therapeutically effective amount to be delivered based upon patient's unique condition.

CK2 has also been shown to play a role in the pathogenesis of atherosclerosis, and may prevent atherogenesis by maintaining laminar shear stress flow. CK2 plays a role in vascularization, and has been shown to mediate the hypoxia-induced activation of histone deacetylases (HDACs). CK2 is also involved in diseases relating to skeletal muscle and bone tissue, including, e.g., cardiomyocyte hypertrophy, heart failure, impaired insulin signaling and insulin resistance, hypophosphatemia and inadequate bone matrix mineralization.

Thus in one aspect, the invention provides methods to treat each of these conditions, comprising administering to a subject in need of such treatment an effect amount of a CK2 inhibitor, such as a compound of Formula (I) as described herein.

The invention also in part pertains to methods for modulating an immune response in a subject, and methods for treating a condition associated with an aberrant immune response in a subject. Thus, provided are methods for determining whether a compound herein modulates an immune response, which comprise contacting a system with a compound described herein in an amount effective for modulating (e.g., inhibiting) an immune response or a signal associated with an immune response. Signals associated with immunomodulatory activity include, e.g., stimulation of T-cell proliferation, suppression or induction of cytokines, including, e.g., interleukins, interferon-γ and TNF. Methods of assessing immunomodulatory activity are known in the art.

General Synthetic Scheme

Compounds of Formula (I) are prepared according to the method:

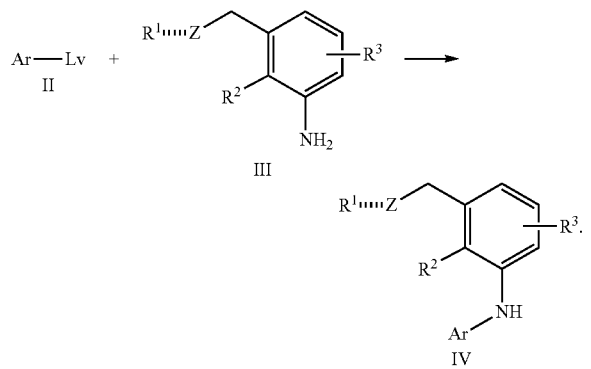

where Ar is as previously defined; Lv is a leaving group such as halogen, $S(O)_nR'$ and $OSO_2R''$; n=0, 1 or 2; R'=alkyl or aryl; R''=CH$_3$, Ph, CF$_3$; and R$^1$, R$^2$, R$^3$ and Z are as previously defined. Specifically, Intermediate (II) and Intermediate (III) are exposed under nucleophilic aromatic substitution (S$_N$Ar) or via a carbon-nitrogen metal catalyzed cross-catalyzed reaction most commonly performed with a homogenous Pd catalyst and phosphine ligand. Whenever necessary, product (IV) is further modified to produce a compound of Formula (I).

EXAMPLES

All synthetic chemistry was performed in standard laboratory glassware unless indicated otherwise in the examples. Commercial reagents were used as received. Microwave reactions were performed in a Biotage Initiator using the instrument software to control heating time and pressure. Analytical LC/MS was performed on a API 150EX with Shimadzu LC-10AD VP LC and Shimadzu SPD-10A UV-Vis detector or an Agilent 1200 system with a variable wavelength detector and Agilent 6140 single quadrupole mass spectrometer, alternating positive and negative ion scans. Retention times were determined from the extracted 220 nm UV chromatogram. Chiral HPLC was performed on a Knauer Smartline preparative HPLC system with a variable wavelength detector. Retention times were determined from the extracted 210 nm and 300 nm UV chromatograms. $^1$H NMR was performed on a Bruker Avance 300 at 300 MHz or 400 at 400 MHz or a Bruker Avance DRX-500 or AV-500 at 500 MHz. For complicated splitting patterns, the apparent splitting was tabulated. Analytical thin layer chromatography was performed on silica (Macherey-Nagel ALUGRAM Xtra SIL G, 0.2 mm, UV$_{254}$ indicator) and was visualized under UV light. Silica gel chromatography was performed manually, or with an Isco CombiFlash for gradient elution. Melting points were collected using a Büchi B-540 melting point apparatus.

Example 1

(±)-5-((4-Chloro-3-((methylsulfinyl)methyl)phenyl)amino)-7-(cyclopropylamino)pyrazolo[1,5-a]pyrimidine-3-carbonitrile (Cpd 1)

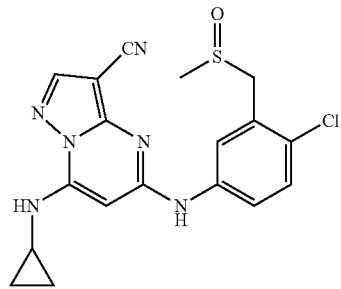

The aniline used to synthesize this example has been synthesized by two different methods as described below.

The preparation of 5-chloro-7-(cyclopropylamino)pyrazolo[1,5-a]pyrimidine-3-carbonitrile [1356564-11-8] has been described in the literature by Dowling et. al. (*ACS Med. Chem. Lett.* (2012) 3(4):278-283; ibid. (2013) 4(8):800-805) and WO2013/144532.

5,7-Dihydroxypyrazolo[1,5-a]pyrimidine-3-carbonitrile

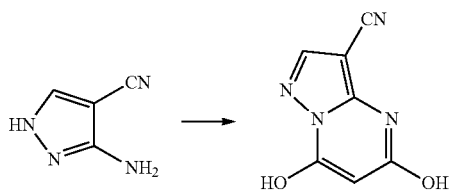 [SMILES: N#Cc1c[nH]nc1N ; N#Cc1cnn2c(O)cc(O)nc12]

To a mixture of 3-amino-1H-pyrazole-4-carbonitrile (16.5 g, 0.15 mol) and diethyl malonate (24.5 g, 0.153 mol) in ethanol (660 mL) under nitrogen atmosphere, was added sodium ethoxide (26 g, 0.382 mol). The reaction mixture was stirred at 100° C. for 3 days. After cooling to room temperature, the reaction mixture was acidified by aqueous HCl (12 N) to pH 2. The resulting whole mixture was concentrated under reduced pressure to provide a grey solid, which was washed with PE and was further dried in vacuum to give a crude title compound (48 g, contained NaCl etc.). The crude product was directly used in the next reaction.

5,7-Dichloropyrazolo[1,5-a]pyrimidine-3-carbonitrile

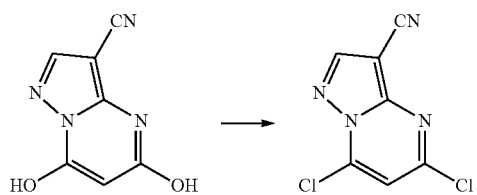 [SMILES: N#Cc1cnn2c(O)cc(O)nc12 ; N#Cc1cnn2c(Cl)cc(Cl)nc12]

To a mixture of 5,7-dihydroxypyrazolo[1,5-a]pyrimidine-3-carbonitrile (obtained in last step) in POCl$_3$ (250 g) cooling with ice bath, N,N-diethylaniline (24 g, 1.1 eq) was added slowly. The resulting mixture was stirred at room temperature for 30 minutes, then at 115° C. for overnight. After cooling to room temperature, the reaction mixture was concentrated to remove most of POCl$_3$. The residue was poured into ice-water (600 mL), extracted with EA (400 mL×3). The combined extracts were washed with brine, dried over Na$_2$SO$_4$, concentrated to give the crude product, which was purified on a silica gel column (eluting with PE:EA=10:1, 5:1, 3:1, 1:1) to give the title compound as a light yellow solid (16.5 g, 51.6% in two steps).

5-Chloro-7-(cyclopropylamino)pyrazolo[1,5-a]pyrimidine-3-carbonitrile

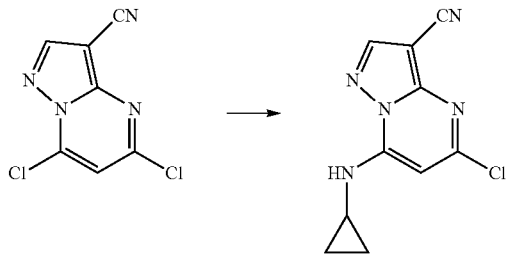 [SMILES: N#Cc1cnn2c(Cl)cc(Cl)nc12 ; N#Cc1cnn2c(NC3CC3)cc(Cl)nc12]

To a solution of 5,7-dichloropyrazolo[1,5-a]pyrimidine-3-carbonitrile (1000 mg, 4.69 mmol) in 50 mL of i-PrOH, were added Et$_3$N (950 mg, 9.4 mmol) and cyclopropanamine (540 mg, 9.4 mmol). The reaction mixture was stirred at r.t for 4 h. The mixture was concentrated to remove most of solvent and the residue was mixed with DCM (200 mL), washed with water (50 mL×2), brine, dried over Na$_2$SO$_4$, and was concentrated to give the crude product, which was purified on a silica gel column. The desired product obtained was further titrated with small amount of DCM to afford title compound as an off-white solid (878 mg, 80%).

Tert-butyl 5-chloro-3-cyanopyrazolo[1,5-a]pyrimidin-7-yl(cyclopropyl)carbamate

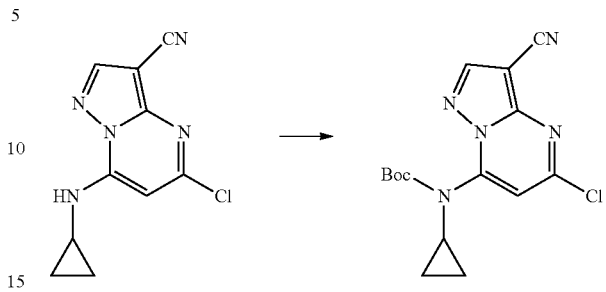

To a solution of 5-chloro-7-(cyclopropylamino)pyrazolo[1,5-a]pyrimidine-3-carbonitrile (549 mg, 2.35 mmol) in DCM (20 mL), were added (Boc)$_2$O (2.0 g, 9.4 mmol), Et$_3$N (0.7 g, 7.0 mmol), and DMAP (72 mg, 0.586 mmol). The reaction mixture was stirred at 35° C. for 2 h. TLC indicated completion of the reaction. The reaction mixture was diluted with DCM (100 mL), washed with water (50 mL), brine (50 mL), dried over Na$_2$SO$_4$, and concentrated to give a crude product, which was purified on a silica gel column (eluting with PE:EA=10:1 to 3:1) to afford the title compound as a white solid (614 mg, 78.5%). LCMS: 98%, $t_R$=1.771 min, m/z=234 [M+H-Boc]$^+$ $^1$H NMR (300 MHz, Chloroform-d) δ 8.34 (s, 1H), 6.92 (s, 1H), 3.24 (tt, J=7.0, 3.7 Hz, 1H), 1.41 (s, 9H), 0.95-0.85 (m, 2H), 0.66-0.57 (m, 2H).

(2-Chloro-5-nitrophenyl)methanol

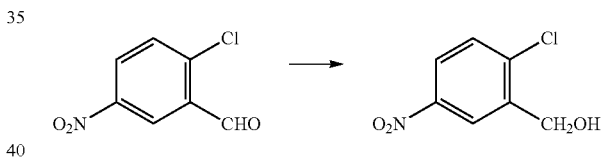

To a solution of 2-chloro-5-nitrobenzaldehyde (20 g, 108 mmol) in MeOH:THF (10:1, 220 mL) cooling with an ice-water bath, sodium borohydride (8.0 g, 216 mmol) was added in portions. After completion of addition, the resulting reaction mixture was stirred at room temperature for 1 hour. The solvents were removed by roto-vap and the residue was carefully mixed with water (150 mL). The aqueous mixture was extracted with EA (200 mL×2). The combined extracts were washed with brine (100 mL×2), dried over NaSO$_4$, and concentrated to provide the title compound (20.2 g, yield 100%) as a white solid, which was directly used in the next reaction.

2-(Bromomethyl)-1-chloro-4-nitrobenzene

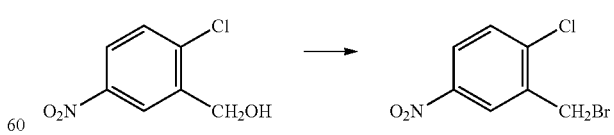

To a solution of (2-chloro-5-nitrophenyl)methanol (5.0 g, 26.93 mmol), and Ph$_3$P (10.58 g, 40.4 mmol, 1.5 eq.) in DCM (120 mL) at 0° C., NBS (9.58 g, 53.86 mmol, 2 eq.) was added slowly. The reaction mixture was stirred at 0° C. for 2 h. The reaction mixture was diluted with DCM (100 mL), washed with water (100 mL×2), brine, dried (Na$_2$SO$_4$), and concentrated to provide the crude product, which was then purified on a silica gel column (eluting with PE:EA=100:1 to 80:1) to get the title compound as a light yellow solid (6.5 g, yield=96%).

(2-Chloro-5-nitrobenzyl)(methyl)sulfane

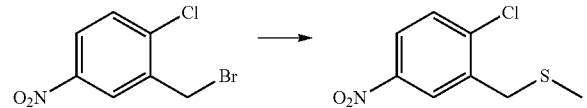

To a mixture of 2-(bromomethyl)-1-chloro-4-nitrobenzene (6.5 g, 25.94 mmol) in MeOH (100 mL) cooled with ice bath under Argon atmosphere, was added NaSMe (2.0 g, 28.5 mmol, 1.1 eq.) The reaction mixture was stirred at 0° C. to room temperature overnight. After removal of most of methanol by rotovap, the residue was dissolved in EtOAc (150 mL) and the resulting mixture was washed with water (50 mL×2), brine, dried over $Na_2SO_4$, and concentrated to afford the crude product, which was purified on a silica gel column (eluting with 100% hexanes to 5% EtOAc/95% hexanes) to give the title compound as a light yellow oil which solidified on stand (5.5 g, yield=95%).

(±)-1-Chloro-2-((methylsulfinyl)methyl)-4-nitrobenzene

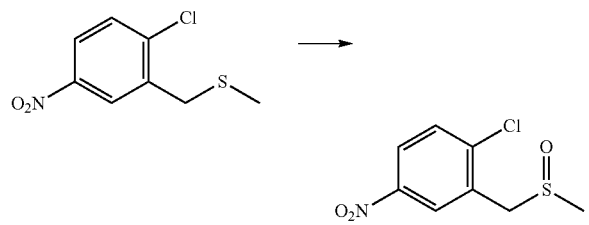

To a solution of (2-chloro-5-nitrobenzyl)(methyl)sulfane (2.17 g, 10 mmol) in DCM (20 mL) cooling with an ice bath, was added MCPBA (77%, 2.23 g, 10 mmol, 1.0 eq.). The reaction mixture was stirred at room temperature overnight. The mixture was diluted with EtOAc (80 mL), washed with 1N of NaOH aqueous solution (15 mL), water, brine, dried ($Na_2SO_4$), and evaporated to give a crude product, which was then purified on a silica gel column (eluting with hexanes/EtOAc 3/1 to 1/2) to get the title compound as a white solid (1.82 g, yield=78%).

(±)-4-Chloro-3-((methylsulfinyl)methyl)aniline

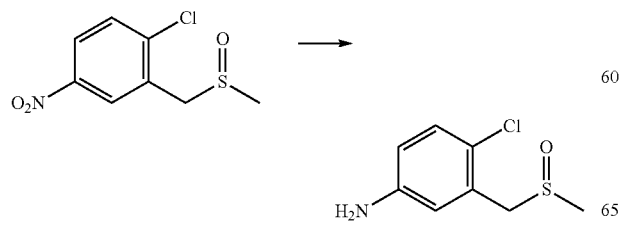

The reduction of the nitro group of (±)-1-chloro-2-((methylsulfinyl)methyl)-4-nitrobenzene was performed as described for (±)-4-fluoro-3-((methylsulfinyl)methyl)aniline used in the synthesis of Example 5.

(±)-5-(4-Chloro-3-(methylsulfinylmethyl)phenylamino)-7-(cyclopropylamino)pyrazolo[1,5-a]pyrimidine-3-carbonitrile (Cpd 1)

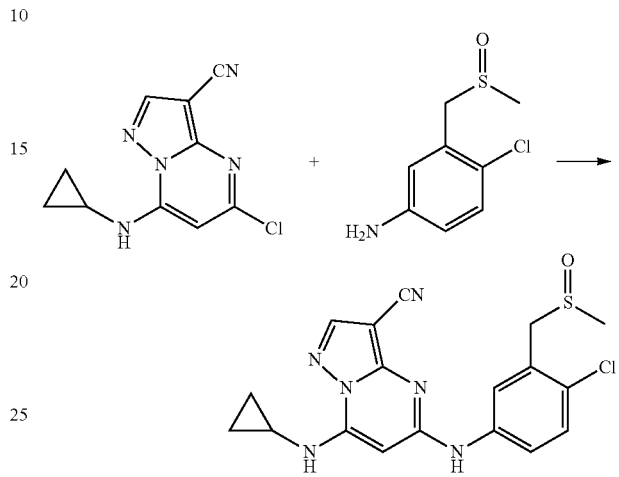

To a mixture of 5-chloro-7-(cyclopropylamino)pyrazolo[1,5-a]pyrimidine-3-carbonitrile (252 mg, 1.08 mmol), (±)-4-chloro-3-(methylsulfinylmethyl)aniline (220 mg, 1.08 mmol), $Cs_2CO_3$ (703 mg, 2.16 mmol) and BINAP (67 mg, 0.108 mmol) in dry NMP (8 mL) under nitrogen atmosphere, was added $Pd_2(dba)_3$ (51 mg, 0.065 mmol). The reaction mixture was stirred at 150° C. for 2.5 hours. After cooling down to room temperature, the reaction mixture was mixed with EtOAc (20 mL), washed with water, brine, dried ($Na_2SO_4$), and concentrated. The crude product was purified on a silica gel column (eluting with DCM:MeOH=20:1) to get the title compound as an off white solid (195 mg, 40% yield). ES+, m/z 401.3 [M+1]; $^1$H NMR (400 MHz, DMSO-$d_6$), δ 9.85 (s, 1H), 8.37 (s, 1H), 8.28 (s, 1H), 7.87 (dd, J=8.8, 2.4 Hz, 1H), 7.74 (d, J=2.4 Hz, 1H), 7.48 (d, J=8.8 Hz, 1H), 6.01 (s, 1H), 4.23 (d, J=12.8 Hz, 2H), 4.07 (d, J=12.8 Hz, 2H), 2.62 (s, 3H), 2.59-2.63 (m, 1H), 0.83-0.80 (m, 2H), 0.74-0.71 (m, 2H).

Example 2

5-((4-Chloro-3-((methylsulfonyl)methyl)phenyl)amino)-7-(cyclopropylamino)pyrazolo[1,5-a]pyrimidine-3-carbonitrile (Cpd 2)

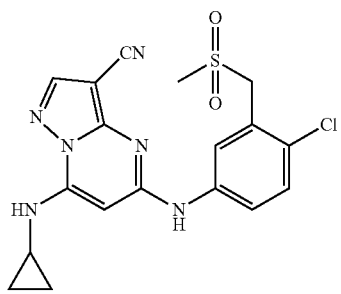 [SMILES: CS(=O)(=O)Cc1cc(Nc2cc(NC3CC3)n3ncc(C#N)c3n2)ccc1Cl]

33

Tert-butyl (4-chloro-3-((methylsulfonyl)methyl)phenyl)carbamate

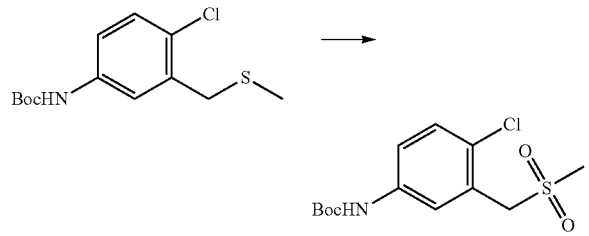

To a solution of tert-butyl (4-chloro-3-((methylthio)methyl)phenyl)carbamate (0.3 g, 0.99 mmol) in DCM (30 mL) at 0° C., was added 85% of MCPBA (0.4 g, 1.98 mmol) slowly. The reaction mixture was stirred at r.t for 1 hour. The reaction mixture diluted with DCM (50 mL) and the resulting mixture was washed with aqueous NaOH solution (1 N, 10 mL), water (50 mL), brine, dried over Na$_2$SO$_4$, and concentrated to give a crude product, which was purified on a silica gel column (eluting with DCM/EA=50/1) to provide the tile compound as a white solid (320 mg, 97% yield).

4-Chloro-3-((methylsulfonyl)methyl)aniline

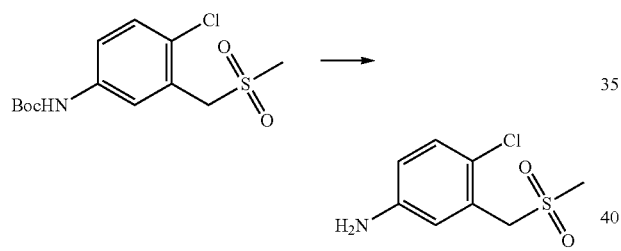

A mixture of tert-butyl (4-chloro-3-((methylsulfonyl)methyl)phenyl)carbamate (300 mg) in 20% of TFA in DCM (5 mL) was stirred at room temperature for 5 hours. The mixture was diluted with DCM (30 mL), washed with aqueous NaOH (1 N, 20 mL), water, brine, dried over Na$_2$SO$_4$, and concentrated to give the title compound as a light yellow solid (180 mg, 87% yield).

5-((4-Chloro-3-((methylsulfonyl)methyl)phenyl)amino)-7-(cyclopropylamino)pyrazolo[1,5-a]pyrimidine-3-carbonitrile (Cpd 2)

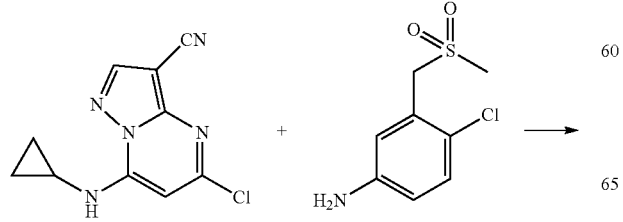

34

-continued

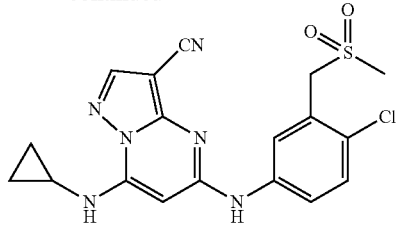

To a mixture of 5-chloro-7-(cyclopropylamino)pyrazolo[1,5-a]pyrimidine-3-carbonitrile (135 mg, 0.58 mmol, See Example 1), 4-chloro-3-((methylsulfonyl)methyl)aniline (127 mg, 0.58 mmol), Cs$_2$CO$_3$ (264 mg, 0.81 mmol) and BINAP (36 mg, 0.058 mmol) in NMP (6 mL) under nitrogen atmosphere, was added Pd$_2$(dba)$_3$ (45 mg, 0.058 mmol) The reaction mixture was stirred at 130° C. for 2 hours. The reaction mixture was diluted with ethyl acetate (100 mL), and the resulting mixture was washed with water, brine, dried over Na$_2$SO$_4$, and concentrated to give a dark residue, which was purified on silica gel column (eluting with DCM/MeOH=10/1) to provide the title compound as an off white solid (130 mg, yield 54%). ES+, m/z 417.1 [M+1]; $^1$H NMR (400 MHz, DMSO-d$_6$), δ 9.88 (s, 1H), 8.38 (s, 1H), 8.29 (s, 1H), 7.95 (dd, J=8.8, 2.4 Hz, 1H), 7.76 (d, J=2.4 Hz, 1H), 7.50 (d, J=8.8 Hz, 1H), 6.03 (s, 1H), 4.62 (s, 2H), 3.05 (s, 3H), 2.62 (m, 1H), 0.83-0.81 (m, 2H), 0.73-0.71 (m, 2H).

Example 3

(S)(+)-5-((4-Chloro-3-((methylsulfinyl)methyl)phenyl)amino)-7-(cyclopropylamino)pyrazolo[1,5-a]pyrimidine-3-carbonitrile (Cpd 3)

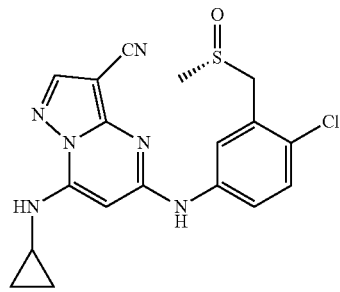 [SMILES: C[S@](=O)Cc1cc(Nc2cc(NC3CC3)n3ncc(C#N)c3n2)ccc1Cl]

Example 4

(R)(−)-5-((4-Chloro-3-((methylsulfinyl)methyl)phenyl)amino)-7-(cyclopropylamino)pyrazolo[1,5-a]pyrimidine-3-carbonitrile (Cpd 4)

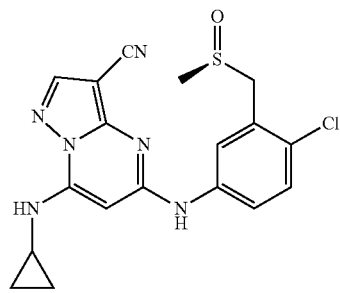

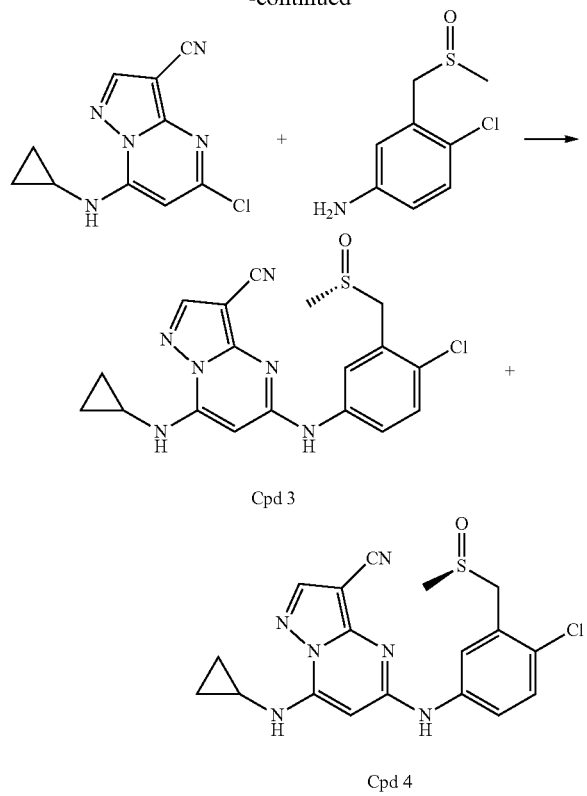

Cpd 3

Cpd 4

To a mixture of 5-chloro-7-(cyclopropylamino)pyrazolo[1,5-a]pyrimidine-3-carbonitrile (982 mg, 4.21 mmol, See Example 1), 4-chloro-3-(methylsulfinylmethyl)aniline (1.123 g, 5.53 mmol), cesium carbonate (3.132 g, 9.61 mmol) and 2,2'-bis(diphenylphosphino)-1,1'-binaphthyl (300 mg, 0.482 mmol) in dry N-methylpyrrolidinone (18 mL) was added tris(dibenzylideneacetone)dipalladium(0) (227 mg, 0.248 mmol) under nitrogen. The reaction mixture was stirred at 150° C. for 2.5 h. The reaction mixture was cooled to room temperature and diluted with water (36 mL). The precipitate was collected and washed with a mixture of water and N-methylpyrrolidinone (2:1 v/v, 6 mL). The solid was washed with water (2×6 mL) and ether (2×6 mL) and dried in air. The crude product was purified by gradient silica gel column chromatography eluting with dichloromethane:methanol (20:1→10:1) to give the racemic title compound as an off-white solid (1.19 g, 71%).

The enantiomers were separated by the following chiral preparative HPLC techniques:
Analytical LC/MS Method:
HPLC column: Kinetex, 2.6 µm, C18, 50×2.1 mm, maintained at 40° C.
HPLC Gradient: 1.0 mL/min, 95:5:0.1 water:acetonitrile:formic acid to 5:95:0.1 water:acetonitrile:formic acid in 2.0 min, maintaining for 0.5 min.
Analytical Chiral HPLC Method:
HPLC column: Daicel CHIRALPAK T101 column, 20 µm, 4.6×250 mm, maintained at ambient temperature.
HPLC Eluent: 0.5 mL/min, 95:5 methanol:acetonitrile.
Preparative Chiral HPLC Method:
HPLC column: Daicel CHIRALPAK T101 column, 20 µm, 50×500 mm, maintained at ambient temperature.
HPLC Eluent: 25 mL/min, 95:5 methanol:acetonitrile.

The fractions containing the S-enantiomer were evaporated and the residue was triturated with ethyl acetate (10 mL) to give (S)(+)-5-(4-chloro-3-(methylsulfinylmethyl)phenylamino)-7-(cyclopropylamino)pyrazolo[1,5-a]pyrimidine-3-carbonitrile or Cpd 3 (240 mg, 14%) as a tan solid. LCMS: 96%, $t_R$=1.514 min, m/z=401 [M+H]$^+$. $^1$H NMR (300 MHz, DMSO-d$_6$) δ 9.86 (s, 1H), 8.38 (s, 1H), 8.33-8.27 (m, 1H), 7.87 (dd, J=8.8, 2.6 Hz, 1H), 7.74 (d, J=2.6 Hz, 1H), 7.48 (d, J=8.8 Hz, 1H), 6.01 (s, 1H), 4.24 (d, J=12.9 Hz, 1H), 4.07 (d, J=12.8 Hz, 1H), 2.69-2.57 (m, 1H). 2.62 (s, 3H), 0.89-0.77 (m, 2H), 0.77-0.64 (m, 2H). Optical rotation: $[\alpha]_D^{25}$ +73° (c 0.1, DMF). ee: 100%

The fractions containing the R-enantiomer were evaporated and the residue was triturated with ethyl acetate (10 mL). The product was dissolved in refluxing acetic acid (2 mL) and to the solution was added charcoal (20 mg). The mixture was filtered and the solid was washed with acetic acid (2×100 µL). To the filtrate was carefully added water (2.2 mL). The precipitate was collected and washed with a mixture of acetic acid:water (1:1 v/v, 0.5 mL) and with water (3×3 mL). The product was dried in a desiccator at 70° C. for 16 h to give (R)(−)-5-(4-chloro-3-(methylsulfinylmethyl)phenylamino)-7-(cyclopropylamino)pyrazolo[1,5-a]pyrimidine-3-carbonitrile (153 mg, 9%) as a tan solid. LCMS: 99%, $t_R$=1.512 min, m/z=401 [M+H]$^+$ $^1$H NMR (500 MHz, DMSO-d$_6$) δ 9.85 (s, 1H), 8.38 (s, 1H), 8.30 (d, J=2.0 Hz, 1H), 7.86 (dd, J=8.8, 2.7 Hz, 1H), 7.74 (d, J=2.7 Hz, 1H), 7.48 (d, J=8.8 Hz, 1H), 6.01 (s, 1H), 4.24 (d, J=12.8 Hz, 1H), 4.07 (d, J=12.8 Hz, 1H), 2.65-2.58 (m, 1H), 2.62 (s, 3H), 0.87-0.79 (m, 2H), 0.75-0.69 (m, 2H). Optical rotation: $[\alpha]_D^{25}$ −70° (c 0.1, DMF). ee: 99.3%.

Example 5

(±)-7-(Cyclopropylamino)-5-((4-fluoro-3-((methylsulfinyl)methyl)phenyl)amino)pyrazolo[1,5-a]pyrimidine-3-carbonitrile (Cpd 5)

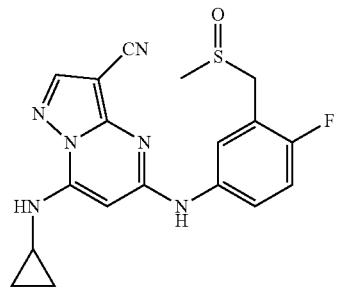 [SMILES: CS(=O)Cc1cc(Nc2cc(NC3CC3)n3ncc(C#N)c3n2)ccc1F]

(±)-4-Fluoro-3-((methylsulfinyl)methyl)aniline

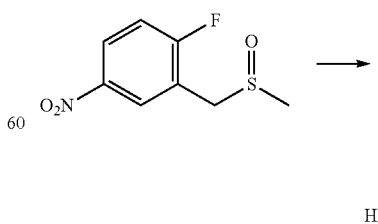

A mixture of (±)-1-fluoro-2-((methylsulfinyl)methyl)-4-nitrobenzene (0.71 g, 3.27 mmol), iron powder (0.915 g, 16.36 mmol, 5 eq. and ammonium chloride (0.875 g, 16.36 mmol, 5 eq) in 70% of aqueous ethanol (15 mL) was refluxed under argon for 5 hours. TLC indicated the disappearance of the starting material. The reaction was cooled down to room temperature. The solids were filtered off and the filtration was concentrated to dryness. The residue was loaded on a silica gel column eluting with DCM/MeOH (95/5 to 9/1) to give the title compound as a light yellow oil (543 mg, 88.8% yield).

(±)-7-(Cyclopropylamino)-5-((4-fluoro-3-((methylsulfinyl)methyl)phenyl)amino)pyrazolo[1,5-a]pyrimidine-3-carbonitrile (Cpd 5)

The synthesis of this compound was prepared as described in Example 1 from 5-chloro-7-(cyclopropylamino)pyrazolo[1,5-a]pyrimidine-3-carbonitrile and (±)-4-fluoro-3-((methylsulfinyl)methyl)aniline. ES+, m/z 385.4 [M+1], 407.3 [M+23]; $^1$H NMR (500 MHz, DMSO-d$_6$), δ 9.73 (s, 1H), 8.35 (s, 1H), 8.24 (s, 1H), 7.84-7.81 (m, 1H), 7.60 (dd, J=6.5, 2.5 Hz, 1H), 7.25 (dd, J=9.0, 9.5 Hz, 1H), 5.97 (s, 1H), 4.16 (d, J=13.0 Hz, 1H), 3.98 (d, J=13.0 Hz, 1H), 2.60 (m 1H), 2.57 (s, 3H), 0.83-0.80 (m, 2H), 0.73-0.70 (m, 2H).

Example 6

(±)-5-((4-Cyano-3-((methylsulfinyl)methyl)phenyl)amino)-7-(cyclopropylamino)pyrazolo[1,5-a]pyrimidine-3-carbonitrile 2-((methylthio)methyl)-4-nitrobenzonitrile (Cpd 6)

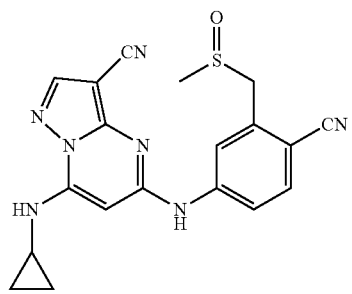 [SMILES: CS(=O)Cc1cc(Nc2cc(NC3CC3)n3ncc(C#N)c3n2)ccc1C#N]

2-((methylthio)methyl)-4-nitrobenzonitrile

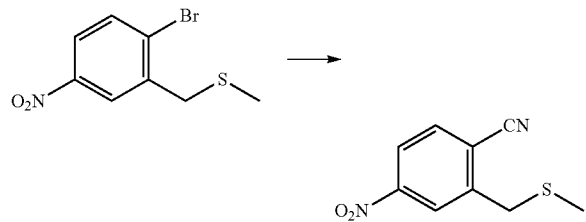

To a mixture of (2-bromo-5-nitrobenzyl)(methyl)sulfane (976 mg, 3.7 mmol), Zn(CN)$_2$ (875 mg, 7.4 mmol, 2 eq.) in dry NMP (10 mL) under argon atmosphere, was added Pd(Ph$_3$P)$_4$ (430 mg, 0.1 eq). The reaction mixture was stirred at 100° C. overnight. The reaction mixture was cooled to room temperature, diluted with EtOAc (100 mL). The solids were filtered off. The filtration was washed with water (30 mL×2), brine, dried (Na$_2$SO$_4$), and concentrated to get a dark oily residue, which was purified on a silica gel column [eluting with 100% hexanes to hexanes/EtOAc (95/5)] to provide the desired product (650 mg, 83.9% yield).

(±)-2-((Methylsulfinyl)methyl)-4-nitrobenzonitrile

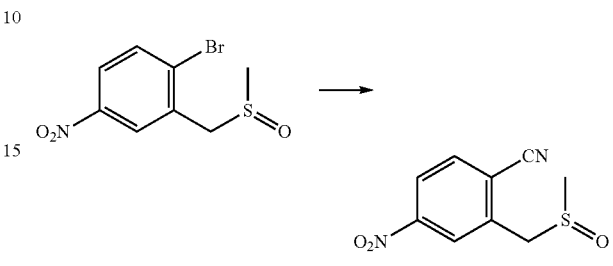

To a mixture of 1-bromo-2-((methylsulfinyl)methyl)-4-nitrobenzene (1.0 g, 3.6 mmol), Zn(CN)$_2$ (850 mg, 7.2 mmol, 2 eq.) in dry NMP (10 mL) under argon atmosphere, was added Pd(Ph$_3$P)$_4$ (400 mg, 0.1 eq). The reaction mixture was stirred at 100° C. overnight. After cooling to room temperature, the reaction mixture was diluted with EtOAc (100 mL) and the resulting mixture was filtered to get rid of solids. The filtration was washed with water (30 mL×2), brine, dried (Na$_2$SO$_4$), and concentrated to get a residue, which was purified on a silica gel column (eluting with hexanes/EtOAc (3/1) to 100% EtOAc) to provide the desired product as a brown solid (750 mg, 93% yield).

(±)-4-Amino-2-((methylsulfinyl)methyl)benzonitrile

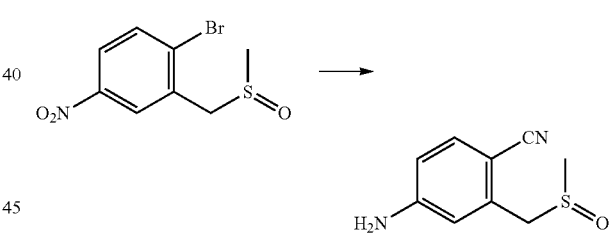

The reduction of (±)-2-((methylsulfinyl)methyl)-4-nitrobenzonitrile was performed as described for (±)-4-fluoro-3-((methylsulfinyl)methyl)aniline used in the synthesis of Example 5.

(±)-5-((4-cyano-3-((methylsulfinyl)methyl)phenyl)amino)-7-(cyclopropylamino)pyrazolo[1,5-a]pyrimidine-3-carbonitrile The synthesis of this compound was prepared as described in Example 1 from 5-chloro-7-(cyclopropylamino)pyrazolo[1,5-a]pyrimidine-3-carbonitrile and (±)-4-amino-2-((methylsulfinyl)methyl)benzonitrile. ES+, m/z 392.3 (M+1), 414.5 [M+23]; $^1$H NMR (500 MHz, DMSO-d$_6$), δ 10.23 (s, 1H), 8.46 (s, 1H), 8.43 (s, 1H), 8.08 (dd, J=9.0, 2.0 Hz, 1H), 7.84 (d, J=9.0 Hz, 1H), 7.83 (d, J=2.0 Hz, 1H), 6.10 (s, 1H), 4.31 (d, J=13.0 Hz, 1H), 4.08 (d, J=13.0 Hz, 1H), 2.63 (s, 3H), 2.64-2.62 (m, 1H), 0.86-0.82 (m, 2H), 0.75-0.72 (m, 2H).

Example 7

(±)-5-((4-((2-Aminoethyl)(methyl)amino)-3-((methylsulfinyl)methyl)phenyl)amino)-7-(cyclopropylamino)pyrazolo[1,5-a]pyrimidine-3-carbonitrile mono trifluoroacetic acid salt (Cpd 7)

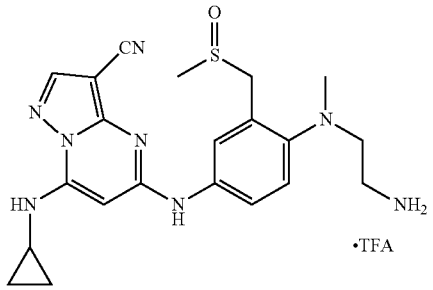 [SMILES: CN(CCN)c1ccc(Nc2cc(NC3CC3)n3ncc(C#N)c3n2)cc1CS(C)=O]

(±)-Tert-butyl (2-(methyl(2-((methylsulfinyl)methyl)-4-nitrophenyl)amino)ethyl)carbamate

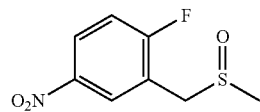

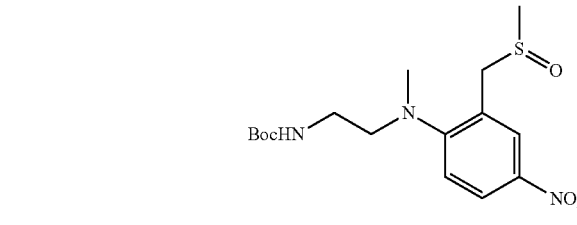

A mixture of (±)-1-fluoro-2-((methylsulfinyl)methyl)-4-nitrobenzene (742 mg, 2.83 mmol), tert-butyl (2-(methylamino)ethyl)carbamate (591 mg, 3.4 mmol, 1.2 eq), and potassium carbonate (586 mg, 4.25 mmol, 1.5 eq.) in DMF (6 mL) was heated at 95° C. overnight. The reaction mixture was cooled down to room temperature, diluted with EtOAc (100 mL). The mixture was washed with water (30 mL×2), brine, dried (Na$_2$SO$_4$), and concentrated. The crude product was purified on a silica gel column [eluting with DCM to 2% MeOH/DCM] to get the title compound as an oily product (1.0 g, 95% yield).

(±)-Tert-butyl (2-((4-amino-2-((methylsulfinyl)methyl)phenyl)(methyl)amino)ethyl)carbamate

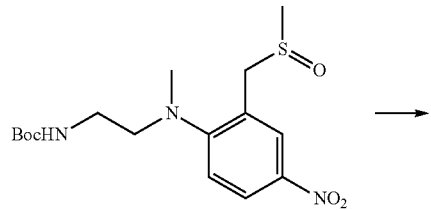

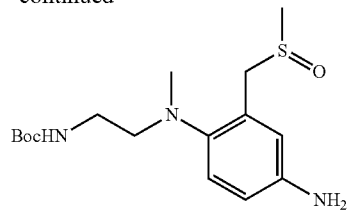

The reduction of the nitro group of (±)-tert-butyl (2-(methyl(2-((methylsulfinyl)methyl)-4-nitrophenyl)amino)ethyl)carbamate was performed as described for (±)-4-fluoro-3-((methylsulfinyl)methyl)aniline used in the synthesis of Example 5.

(±)-Tert-butyl (5-((4-((2-((tert-butoxycarbonyl)amino)ethyl)(methyl)amino)-3-((methylsulfinyl)methyl)phenyl)amino)-3-cyanopyrazolo[1,5-a]pyrimidin-7-yl)(cyclopropyl)carbamate

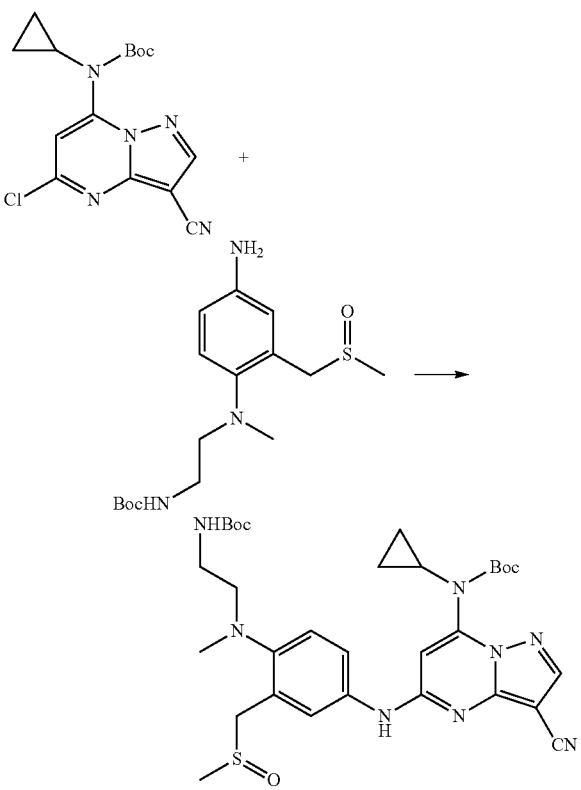

To a mixture of tert-butyl (5-chloro-3-cyanopyrazolo[1,5-a]pyrimidin-7-yl)(cyclopropyl)carbamate (490 mg, 1.47 mmol), (±)-tert-butyl (2-((4-amino-2-((methylsulfinyl)methyl)phenyl)(methyl)amino)ethyl)carbamate (500 mg, 1.46 mmol, 1 eq.), Cs$_2$CO$_3$ (960 mg, 2.94 mmol, 2 eq.) and BINAP (90 mg, 0.14 mmol, 0.1 eq) in dry NMP (12 mL) under Argon atmosphere, was added Pd$_2$(dba)$_3$ (135 mg, 0.14 mmol, 0.1 eq.). The reaction mixture was stirred at 135° C. for 4 hours. After cooling down to room temperature, the reaction mixture was mixed with EtOAc (100 mL), washed with water, brine, dried (Na$_2$SO$_4$), and concentrated. The crude product was purified on a silica gel column (eluting with DCM to 2% MeOH/DCM), and prep-TLC (5% MeOH/ EtOAc) to get the title compound as an off white solid (282 mg, 30.3% yield). ES+, m/z 639.5 [M+1].

(±)-5-((4-((2-aminoethyl)(methyl)amino)-3-((methylsulfinyl)methyl)phenyl)amino)-7-(cyclopropylamino)pyrazolo[1,5-a]pyrimidine-3-carbonitrile mono trifluoroacetic acid salt

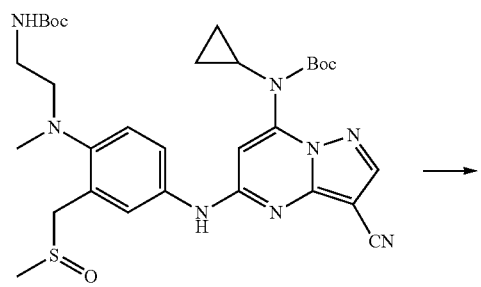

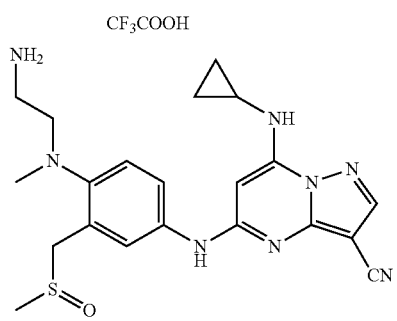

A mixture of (±)-tert-butyl (5-((4-((2-((tert-butoxycarbonyl)amino)ethyl)(methyl)amino)-3-((methylsulfinyl)methyl)phenyl)amino)-3-cyanopyrazolo[1,5-a]pyrimidin-7-yl)(cyclopropyl)carbamate (75 mg, 0.117 mmol) in 1.6 mL of 20% TFA/DCM (v/v) was stirred at 0° C. to r.t for three hours. The reaction mixture was concentrated under reduced pressure to get a residue, which was dissolved in 5 mL of methanol/EtOAc (1/10), and was evaporated again to dryness. The residue was dissolved in EtOAc only again and concentrated under reduced pressure. The final residue was treated with EtOAc/Hexanes (1/4). The solids were collected by filtration and dried in high vacuum overnight to give the title product as an off-white solid (43 mg, yield 66%). $^1$H NMR in DMSO-d$_6$ confirmed that the product was a mono TFA salt. ES+, m/z 439.7 [M+1]; $^1$H NMR (500 MHz, DMSO-d$_6$), δ 9.71 (s, 1H), 8.35 (s, 1H), 8.23 (s, 1H), 7.82 (dd, J=9.0, 2.5 Hz, 1H), 7.68 (brs, 3H), 7.63 (d, J=2.5 Hz, 1H), 7.31 (d, J=9.0 Hz, 1H), 5.98 (s, 1H), 4.24 (d, J=13.0 Hz, 1H), 4.20 (d, J=13.0 Hz, 1H), 3.15-3.12 (m, 1H), 3.10-3.08 (m, 1H), 2.95-2.93 (m, 1H), 2.89-2.86 (m, 1H), 2.71 (s, 3H), 2.60 (m, 1H), 2.56 (s, 3H), 0.82-0.80 (m, 2H), 0.73-0.70 (m, 1H).

Example 8

(±)-5-((4-(2-Aminoethyl)-3-((methylsulfinyl)methyl)phenyl)amino)-7-(cyclopropylamino)pyrazolo[1,5-a]pyrimidine-3-carbonitrile mono trifluoroacetic acid salt (Cpd 8)

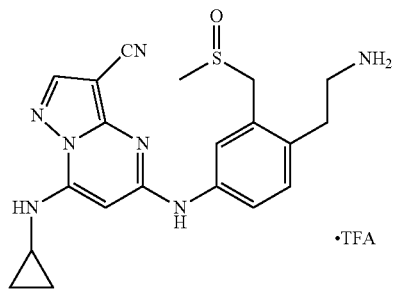 [SMILES: CS(=O)Cc1cc(Nc2cc(NC3CC3)n3ncc(C#N)c3n2)ccc1CCN]

Tert-butyl (2-((methylthio)methyl)-4-nitrophenethyl)carbamate

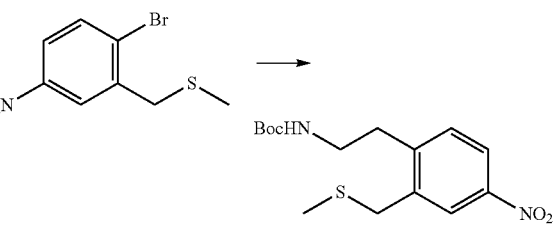

To a mixture (2-bromo-5-nitrobenzyl)(methyl)sulfane (1.0 g, 3.98 mmol), potassium tert-butyl N-[2-(trifluoroboranuidyl)ethyl]carbamate (950 mg, 3.62 mmol, 1.0 eq.), potassium carbonate (2.0 g, 14.5 mmol, 4.0 eq.) in toluene/water (18 mL/6 mL) under argon, was added PddppfCl$_2$ (180 mg, 0.245 mmol, 0.07 eq.). The resulting reaction mixture was stirred at 100° C. overnight. The reaction mixture was cooled to room temperature, diluted with EtOAc (120 mL), and the mixture was washed with water (30 mL×2), brine, dried (Na$_2$SO$_4$), and concentrated to get a residue, which was purified on a silica gel column [eluting with hexanes/ EtOAc (10/1 to 5/1)] to give the desired product as a light yellow solid (626 mg, 48% yield).

(±)-Tert-butyl (2-((methylsulfinyl)methyl)-4-nitrophenethyl)carbamate

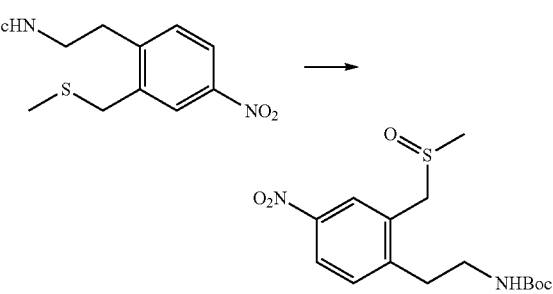

To a solution of tert-butyl (2-((methylthio)methyl)-4-nitrophenethyl)carbamate (626 mg, 1.92 mmol) in DCM (15 mL) at 0° C., was added MCPBA (77%, 350 mg, 1.05 eq.). The reaction mixture was stirred at 0° C. room temperature overnight. The mixture was diluted with DCM (100 mL), washed with 2 N of NaOH aqueous solution (10 mL), water (20 mL), brine, dried ($Na_2SO_4$), and concentrated. The residue was purified on a silica gel column (eluting with 100% EtOAc) to get the title compound as a foam solid (580 mg, 88% yield).

(±)-Tert-butyl (4-amino-2-((methylsulfinyl)methyl)phenethyl)carbamate

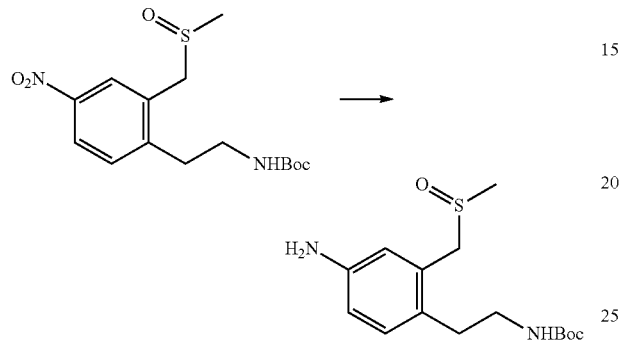

The reduction of the nitro group of was performed as described for (±)-4-fluoro-3-((methylsulfinyl)methyl)aniline used in the synthesis of Example 5.

(±)-5-((4-(2-Aminoethyl)-3-((methylsulfinyl)methyl)phenyl)amino)-7-(cyclopropylamino)pyrazolo[1,5-a]pyrimidine-3-carbonitrile mono trifluoroacetic acid salt This compound was prepared in two steps in a similar fashion as described in Example 7 from (±)-tert-butyl (4-amino-2-((methylsulfinyl)methyl)phenethyl)carbamate and tert-butyl (5-chloro-3-cyanopyrazolo[1,5-a]pyrimidin-7-yl)(cyclopropyl)carbamate. ES+, m/z 410.5 [M+1]; $^1$H NMR (500 MHz, DMSO-$d_6$), δ 9.75 (s, 1H), 8.36 (s, 1H), 8.25 (s, 1H), 7.85-7.75 (m, 4H), 7.61 (d, J=2.0 Hz, 1H), 7.26 (d, J=8.5 Hz, 1H), 6.00 (s, 1H), 4.19 (d, J=13.0 Hz, 1H), 4.05 (d, J=13.0 Hz, 1H), 3.05-2.95 (m, 2H), 2.92 (t, J=8.0 Hz, 2H), 2.65 (s, 3H), 2.60 (m, 1H), 0.82-0.80 (m, 2H), 0.73-0.70 (m, 2H).

Example 9

5-((4-Cyano-3-((methylsulfonyl)methyl)phenyl)amino)-7-(cyclopropylamino)pyrazolo[1,5-a]pyrimidine-3-carbonitrile (Cpd 9)

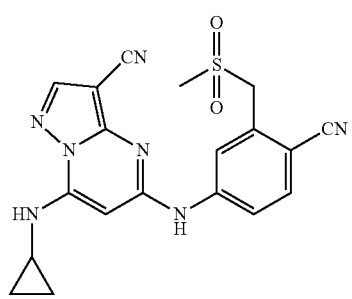 [SMILES: CS(=O)(=O)Cc1cc(Nc2cc(NC3CC3)n3ncc(C#N)c3n2)ccc1C#N]

This compound was prepared in a similar fashion as described in Example 6 from 5-chloro-7-(cyclopropylamino)pyrazolo[1,5-a]pyrimidine-3-carbonitrile and 4-amino-2-((methylsulfonyl)methyl)benzonitrile. ES-, m/z 407; $^1$H NMR (500 MHz, DMSO-$d_6$), δ 10.25 (s, 1H), 8.47 (s, 1H), 8.44 (s, 1H), 8.17 (dd, J=9.0, 2.0 Hz, 1H), 7.87 (d, J=9.0 Hz, 1H), 7.84 (d, J=9.0 Hz, 1H), 6.10 (s, 1H), 4.66 (s, 2H), 3.12 (s, 3H), 2.64 (m, 1H), 0.85-0.82 (m, 2H), 0.75-0.72 (m, 2H).

Example 10

5-((4-((2-Aminoethyl)(methyl)amino)-3-((methylsulfonyl)methyl)phenyl)amino)-7-(cyclopropylamino)pyrazolo[1,5-a]pyrimidine-3-carbonitrile mono trifluoroacetic acid salt (Cpd 10)

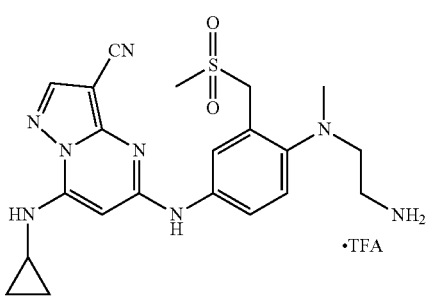 [SMILES: CN(CCN)c1ccc(Nc2cc(NC3CC3)n3ncc(C#N)c3n2)cc1CS(C)(=O)=O]

This compound was prepared as a mono TFA salt as described in Example 7 from (±)-tert-butyl (5-((4-((2-((tert-butoxycarbonyl)amino)ethyl)(methyl)amino)-3-((methylsulfonyl)methyl)phenyl)amino)-3-cyanopyrazolo[1,5-a]pyrimidin-7-yl)(cyclopropyl)carbamate in 20% TFA/DCM (v/v). ES+, m/z 455.4 [M+1]; $^1$H NMR (500 MHz, DMSO-$d_6$), δ 9.74 (s, 1H), 8.35 (s, 1H), 8.24 (s, 1H), 7.99 (dd, J=9.0, 2.0 Hz, 1H), 7.63 (brs, 3H), 7.60 (d, J=2.5 Hz, 1H), 7.36 (d, J=9.0 Hz, 1H), 6.01 (s, 1H), 4.65 (s, 2H), 3.09 (s, 3H), 3.11-3.08 (m, 2H), 2.98-2.94 (m, 2H), 2.62-2.59 (m, 1H), 2.56 (s, 3H), 0.82-0.79 (m, 2H), 0.73-0.70 (m, 2H).

Example 11

5-((4-(2-Aminoethyl)-3-((methylsulfonyl)methyl)phenyl)amino)-7-(cyclopropylamino)pyrazolo[1,5-a]pyrimidine-3-carbonitrile mono trifluoroacetic acid salt (Cpd 11)

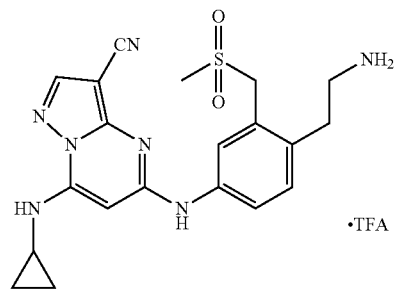 [SMILES: CS(=O)(=O)Cc1cc(Nc2cc(NC3CC3)n3ncc(C#N)c3n2)ccc1CCN]

This compound was prepared as a mono TFA salt as described in Example 8 with (±)-tert-butyl (4-amino-2-

((methylsulfonyl)methyl)phenethyl)carbamate and tert-butyl (5-chloro-3-cyanopyrazolo[1,5-a]pyrimidin-7-yl)(cyclopropyl)carbamate. ES+, m/z 426.6 [M+1]; $^1$H NMR (500 MHz, DMSO-d$_6$), δ 9.77 (s, 1H), 8.36 (s, 1H), 8.25 (s, 1H), 7.90 (dd, J=3.5, 2.0 Hz, 1H), 7.80 (brs, 3H), 7.62 (d, J=2.0 Hz, 1H), 7.30 (d, J=3.5 Hz, 1H), 6.01 (s, 1H), 4.56 (s, 2H), 3.07 (s, 3H), 3.01-2.95 (m, 2H), 2.98-2.94 (m, 2H), 2.61 (m, 1H), 0.82-0.80 (m, 2H), 0.73-0.70 (m, 2H).

Example 12

(±)-5-((4-Chloro-3-((S-methylsulfonimidoyl)methyl)phenyl)amino)-7-(cyclopropylamino)pyrazolo[1,5-a]pyrimidine-3-carbonitrile (Cpd 12)

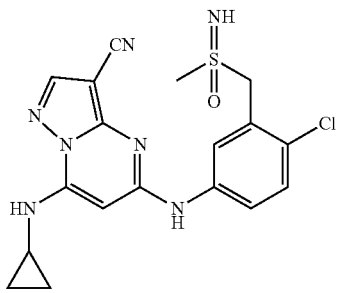 [SMILES: CS(=N)(=O)Cc1cc(Nc2cc(NC3CC3)n3ncc(C#N)c3n2)ccc1Cl]

(±)-Tert-butyl [(2-chloro-5-nitrobenzyl)(methyl)(oxo)-λ$^6$-sulfanylidene]carbamate

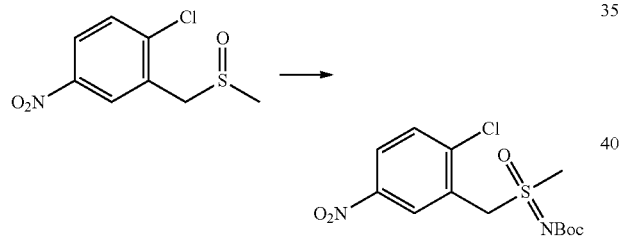

To a mixture of (±)-1-chloro-2-((methylsulfinyl)methyl)-4-nitrobenzene (502 mg, 2.15 mmol), tert-butyl carbamate (377 mg, 3.22 mmol, 1.5 eq.), MgO (346 mg, 8.6 mmol, 4.0 eg.), Rh$_2$(OAc)$_4$ (24 mg, 0.054 mmol, 0.025 eq.) in DCM (20 mL), was added PhI(OAc)$_2$ (1.04 g, 3.22 mmol, 1.5 eq.). The resulting reaction mixture was stirred at 40° C. overnight. The reaction mixture was filtered and the filtration was concentrated to give a residue, which was purified on silica gel column (eluting with hexanes/EtOAc 4/1 to 3/1) to provide the title compound as a white solid (700 mg, yield 93%).

(±)-Tert-butyl [(5-amino-2-chlorobenzyl)(methyl)(oxo)-16-sulfanylidene]carbamate

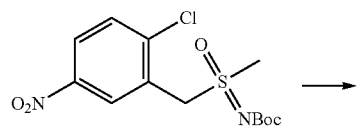

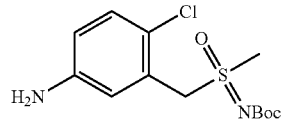

The reduction of the nitro group of (±)-tert-butyl [(2-chloro-5-nitrobenzyl)(methyl)(oxo)-λ$^6$-sulfanylidene]carbamate was performed as described for (±)-4-fluoro-3-((methylsulfinyl)methyl)aniline used in the synthesis of Example 5.

(±)-5-((4-chloro-3-((S-methylsulfonimidoyl)methyl)phenyl)amino)-7-(cyclopropylamino)pyrazolo[1,5-a]pyrimidine-3-carbonitrile (±)-5-((4-chloro-3-((S-methylsulfonimidoyl)methyl)phenyl)amino)-7-(cyclopropylamino)pyrazolo[1,5-a]pyrimidine-3-carbonitrile (Cpd 12) was prepared in a similar fashion as described in the last step of Example 2 as a free base, from (±)-tert-butyl [(5-amino-2-chlorobenzyl)(methyl)(oxo)-16-sulfanylidene]carbamate and 5-chloro-7-(cyclopropylamino)pyrazolo[1,5-a]pyrimidine-3-carbonitrile. ES+, m/z 416.1 [M+1]; $^1$H NMR (500 MHz, DMSO-d$_6$), δ 9.85 (s, 1H), 8.37 (s, 1H), 8.30 (s, 1H), 7.86 (dd, J=9.0, 2.5 Hz, 1H), 7.83 (d, J=2.5 Hz, 1H), 7.48 (d, J=9.0 Hz, 1H), 6.02 (s, 1H), 4.53 (d, J=14.0 Hz, 1H), 4.50 (d, J=14.0 Hz, 1H), 3.78 (s, 1H), 2.91 (s, 3H), 2.64-2.61 (m, 1H), 0.84-0.80 (m, 2H), 0.74-0.71 (m, 2H).

Example 13

(±)-5-((4-Cyclopropyl-3-((methylsulfinyl)methyl)phenyl)amino)-7-(cyclopropylamino)pyrazolo[1,5-a]pyrimidine-3-carbonitrile (Cpd 13)

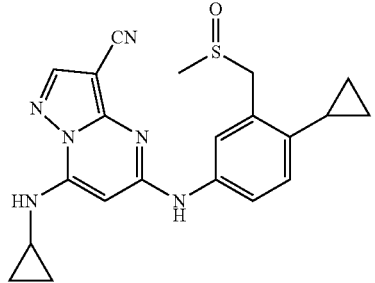 [SMILES: CS(=O)Cc1cc(Nc2cc(NC3CC3)n3ncc(C#N)c3n2)ccc1C1CC1]

(±)-1-Cyclopropyl-2-((methylsulfinyl)methyl)-4-nitrobenzene

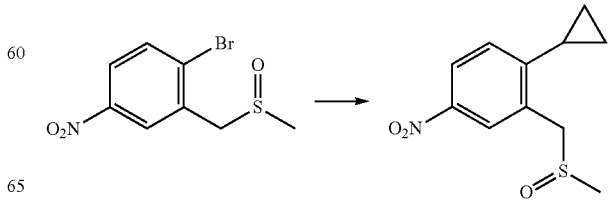

To a mixture of (±)-1-bromo-2-((methylsulfinyl)methyl)-4-nitrobenzene (503 mg, 1.81 mmol), cyclopropylboronic acid (186 mg, 2.16 mmol, 1.2 eq.), potassium carbonate (0.99 g, 4.0 eq.), in toluene/water (18 mL/6 mL) under argon, was added PddppfCl$_2$ (131.7 mg, 0.18 mmol, 0.1 eq.). The resulting reaction mixture was heated at 90° C. overnight. The reaction mixture was cooled to room temperature, diluted with EtOAc (100 mL), and the mixture was washed with water (30 mL×2), brine, dried (Na$_2$SO$_4$), and concentrated to get a residue, which was purified on a silica gel column [eluting with hexanes/EtOAc (1/1)] to give the desired product as a light brown solid (335 mg, 76% yield).

The nitro group was reduced to the corresponding amine with iron powder, ammonium chloride and ethanol as described in Example 5.

(±)-5-((4-Cyclopropyl-3-((methylsulfinyl)methyl)phenyl)amino)-7-(cyclopropylamino)pyrazolo[1,5-a]pyrimidine-3-carbonitrile)

This compound was prepared in accordance with the general synthetic scheme provided herein. ES+, m/z 407.6 [M+1]; $^1$H NMR (500 MHz, DMSO-d$_6$), δ 9.65 (s, 1H), 8.34 (s, 1H), 8.20 (s, 1H), 7.68 (dd, J=8.5, 1.5 Hz, 1H), 7.54 (d, J=2.5 Hz, 1H), 7.00 (d, J=8.5 Hz, 1H), 5.99 (s, 1H), 4.28 (d, J=13.0 Hz, 1H), 4.15 (d, J=13.0 Hz, 1H), 2.62 (s, 3H), 2.61-2.58 (m, 1H), 2.07-2.01 (m, 1H), 0.93-0.90 (m, 2H), 0.81-0.79 (m, 2H), 0.72-0.70 (m, 2H), 0.67-0.65 (m, 1H), 0.63-0.61 (m, 1H).

Example 14

(±)-7-(Cyclopropylamino)-5-((3-((methylsulfinyl)methyl)-4-(piperazin-1-yl)phenyl)amino)pyrazolo[1,5-a]pyrimidine-3-carbonitrile mono trifluoroacetic acid salt (Cpd 14)

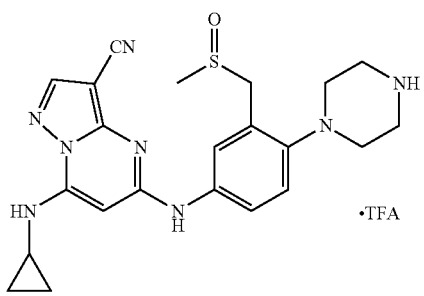 [SMILES: CS(=O)Cc1cc(Nc2cc(NC3CC3)n3ncc(C#N)c3n2)ccc1N1CCNCC1]

This compound was prepared in accordance with the general synthetic scheme provided herein. ES+, m/z 451.1 [M+1]; $^1$H NMR (500 MHz, DMSO-d$_6$), δ 9.72 (s, 1H), 8.72 (brs, 2H), 8.35 (s, 1H), 8.23 (s, 1H), 7.87 (dd, J=9.0, 2.5 Hz, 1H), 7.59 (d, J=2.5 Hz, 1H), 7.26 (d, J=8.5 Hz, 1H), 6.00 (s, 1H), 4.13 (d, J=12.5 Hz, 1H), 4.09 (d, J=12.5 Hz, 1H), 3.25-3.20 (m, 4H), 3.08-3.02 (m, 2H), 3.01-2.98 (m, 2H), 2.62-2.60 (m, 1H), 2.58 (s, 3H), 0.82-0.78 (m, 2H), 0.73-0.70 (m, 2H).

Example 15

(±)-5-((4-(Aminomethyl)-3-((methylsulfinyl)methyl)phenyl)amino)-7-(cyclopropylamino)pyrazolo[1,5-a]pyrimidine-3-carbonitrile mono trifluoroacetic acid salt (Cpd 15)

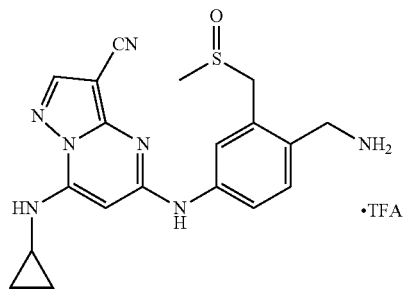 [SMILES: CS(=O)Cc1cc(Nc2cc(NC3CC3)n3ncc(C#N)c3n2)ccc1CN]

This compound was prepared in accordance with the general synthetic scheme provided herein. ES+, m/z 396.4 [M+1]; $^1$H NMR (500 MHz, DMSO-d$_6$), δ 9.88 (s, 1H), 8.38 (s, 1H), 8.31 (s, 1H), 7.95 (brs, 3H), 7.89 (dd, J=8.5, 2.0 Hz, 1H), 7.66 (d, J=2.0 Hz, 1H), 7.47 (d, J=8.5 Hz, 1H), 6.02 (s, 1H), 4.49 (d, J=14.0 Hz, 1H), 4.20 (d, J=14.0 Hz, 1H), 4.13-4.09 (m, 1H), 4.05-4.01 (m, 1H), 2.71 (s, 3H), 2.62 (m, 1H), 0.85-0.82 (m, 2H), 0.74-0.72 (m, 2H).

Example 16

(±)-7-(Cyclopropylamino)-5-((4-((cyclopropylmethyl)(methyl)amino)-3-((methylsulfinyl)methyl)phenyl)amino)pyrazolo[1,5-a]pyrimidine-3-carbonitrile (Cpd 16)

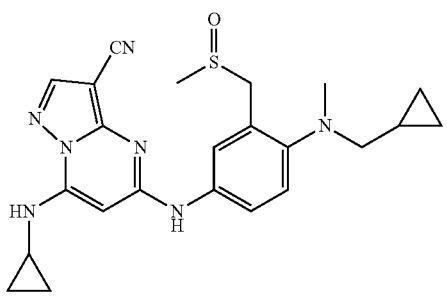 [SMILES: CN(CC1CC1)c1ccc(Nc2cc(NC3CC3)n3ncc(C#N)c3n2)cc1CS(C)=O]

This compound was prepared in accordance with the general synthetic scheme provided herein. ES+, m/z 450.3 [M+1]; $^1$H NMR (500 MHz, DMSO-d$_6$), δ 9.64 (s, 1H), 8.34 (s, 1H), 8.19 (s, 1H), 7.77 (d, J=8.5 Hz, 1H), 7.58 (d, J=2.5 Hz, 1H), 7.26 (d, J=8.5 Hz, 1H), 5.98 (s, 1H), 4.13 (d, J=12.5 Hz, 1H), 4.10 (d, J=12.5 Hz, 1H), 2.66 (s, 3H), 2.68-2.62 (m, 2H), 2.60 (m, 1H), 2.56 (s 3H), 0.87 (m, 1H), 0.82-0.79 (m, 2H), 0.72-0.70 (m, 2H), 0.44-0.42 (m, 2H), 0.10-0.08 (m, 2H).

Example 17

(±)-7-(Cyclopropylamino)-5-((4-methoxy-3-((methylsulfinyl)methyl)phenyl)amino)pyrazolo[1,5-a]pyrimidine-3-carbonitrile (Cpd 17)

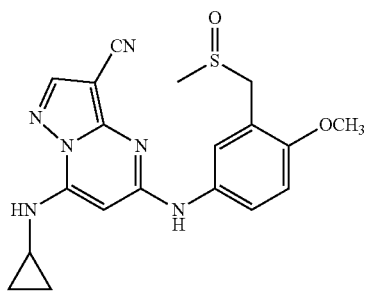 [SMILES: COc1ccc(Nc2cc(NC3CC3)n3ncc(C#N)c3n2)cc1CS(C)=O]

(±)-2-((methylsulfinyl)methyl)-4-nitrophenol

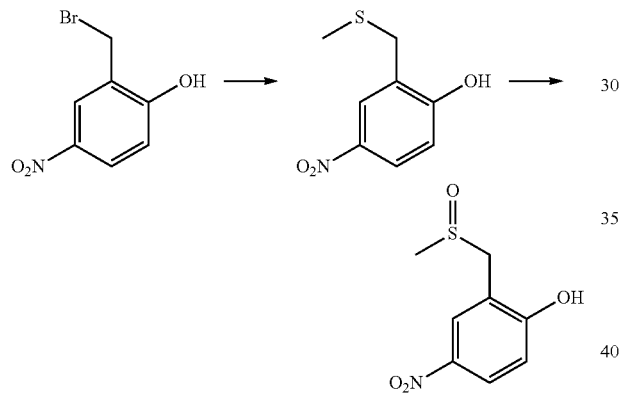

Step 1

2-((methylthio)methyl)-4-nitrophenol

To a solution of 2-(bromomethyl)-4-nitrophenol (12.61 g, 54.6 mmol) in N,N-dimethylformamide (250 mL) was added sodium thiomethoxide (21 wt % aqueous solution, 54.35 g, 163 mmol) at 0° C. The reaction mixture was stirred at room temperature for 3 h. The mixture was diluted with water (600 mL) and extracted with dichloromethane (2×100 mL). The combined organic layers were dried over sodium sulfate, filtered and evaporated. The residue was triturated with a 1:1 mixture of diethyl ether and petroleum ether (2×60 mL). The crude product was triturated with water (200 mL) to give the title compound (6.67 g, 33.5 mmol, 61%) as an orange solid. LCMS: 89%, $t_R$=1.370 min, m/z=200 [M+H]$^+$.

The combined diethyl ether-petroleum ether trituration mother liquors were evaporated. The residue was triturated with water (50 mL) to give a second crop of 2-((methylthiol)methyl)-4-nitrophenol (3.20 g, 16.1 mmol, 29%) as a yellow solid. LCMS: 98%, $t_R$=1.369 min, m/z=200 [M+H]$^+$.

Step 2

(±)-2-((methylsulfinyl)methyl)-4-nitrophenol

To a solution of (950 mg, 4.77 mmol) in dichloromethane (20 mL) was added 3-chloroperbenzoic acid (77%, 910 mg, 4.06 mmol) in portions at room temperature. The reaction mixture was stirred at room temperature for 1 h. The precipitate was collected and washed with dichloromethane (1×5 mL) to give (±)-2-((methylsulfinyl)methyl)-4-nitrophenol (700 mg, 3.26 mmol, 80%) as a pale yellow solid. LCMS: 98%, $t_R$=0.754 min, m/z=216 [M+H]$^+$.

(±)-7-(Cyclopropylamino)-5-((4-methoxy-3-((methylsulfinyl)methyl)phenyl)amino)pyrazolo[1,5-a]pyrimidine-3-carbonitrile This compound was prepared using the same general method as described in Example 18. (22% yield) as a pale yellow solid. LCMS: 94%, $t_R$=1.448 min, m/z=397 [M+H]$^+$. $^1$H NMR (500 MHz, DMSO-d$_6$), δ 9.54 (s, 1H), 8.32 (s, 1H), 8.15 (d, J=2.0 Hz, 2H), 7.77-7.71 (m, 1H), 7.47 (d, J=2.7 Hz, 1H), 7.06 (d, J=8.9 Hz, 1H), 5.93 (s, 1H), 4.04 (d, J=12.4 Hz, 1H), 3.95 (d, J=12.4 Hz, 1H), 3.81 (s, 3H), 2.61-2.56 (m, 1H), 2.52 (s, 3H), 0.83-0.77 (m, 2H), 0.72-0.68 (m, 2H). m.p.=227-229° C.

Example 18

7-(Cyclopropylamino)-5-((4-methoxy-3-((methylsulfonyl)methyl)phenyl)amino)pyrazolo[1,5-a]pyrimidine-3-carbonitrile (Cpd 18)

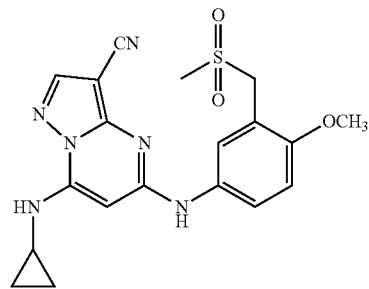 [SMILES: COc1ccc(Nc2cc(NC3CC3)n3ncc(C#N)c3n2)cc1CS(C)(=O)=O]

Step 1

2-((Methylsulfonyl)methyl)-4-nitrophenol

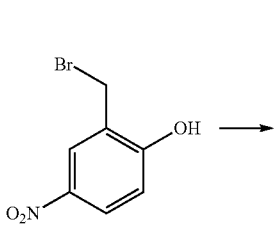

To a solution of 2-(bromomethyl)-4-nitrophenol (6.97 g, 30.2 mmol) in N,N-dimethylformamide (70 mL) was added sodium methanesulfinate (9.20 g, 90.1 mmol). The reaction mixture was stirred at room temperature for 30 min. The mixture was poured into 6 N hydrochloric acid (400 mL) at 0° C. and the mixture was stirred at 0° C. for 30 min.

The precipitate was collected and washed with water (50 mL). The solid was dried in a desiccator over phosphorus pentoxide to give the title compound (4.98 g, 21.6 mmol, 72%) as a pale yellow solid.

LCMS: 93%, $t_R$=1.247 min, m/z=230.1 [M–H]⁻.

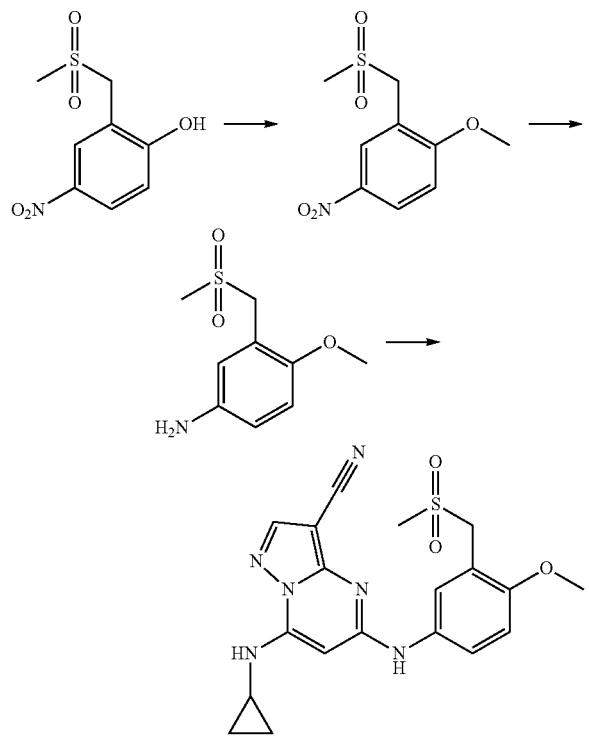

Step 2

1-Methoxy-2-((methylsulfonyl)methyl)-4-nitrobenzene

To a mixture of 2-((methylsulfonyl)methyl)-4-nitrophenol (200 mg, 0.87 mmol) and potassium carbonate (168 mg, 1.22 mmol) in tetrahydrofuran (4 mL) was added iodomethane (60 µL, 0.96 mmol) and the reaction mixture was stirred at room temperature for 1 h. To the reaction mixture was added N,N-dimethylformamide (1 mL) and iodomethane (30 µL, 0.48 mmol). The reaction mixture was stirred at 40° C. for 16 h. The mixture was diluted with ethyl acetate (50 mL). The mixture was washed with water (1×50 mL), dried over sodium sulfate and evaporated to give the title compound (120 mg, 0.49 mmol, 56%) as a white crystalline solid.

LCMS: 89%, $t_R$=1.085, m/z=263 [M+H+H₂O]⁺.

Step 3

4-Methoxy-3-((methylsulfonyl)methyl)aniline

To a stirred mixture of 1-methoxy-2-((methylsulfonyl)methyl)-4-nitrobenzene (30 mg, 0.12 mmol) and iron powder (34 mg, 0.61 mmol) in a mixture of methanol and tetrahydrofuran (1:1, 600 µL) was added saturated aqueous ammonium chloride solution (109 µL). The reaction mixture was stirred at 80° C. for 1 h.

In a separate reaction vessel, to a stirred mixture of 1-methoxy-2-(methylsulfonylmethyl)-4-nitrobenzene (80 mg, 0.33 mmol) and iron powder (91 mg, 1.63 mmol) in a mixture of methanol and tetrahydrofuran (1:1, 1.6 mL) was added saturated aqueous ammonium chloride solution (291 µL). The reaction mixture was stirred at 80° C. for 1 h.

The two reaction mixtures were combined. The mixture was diluted with ethyl acetate (10 mL) and washed with saturated sodium bicarbonate solution (1×5 mL). The aqueous layer was extracted with ethyl acetate (1×5 mL). The combined organic layers were dried over magnesium sulfate and evaporated to give the title compound (70 mg, 0.33 mmol, 72%) as a tan solid.

LCMS: 87%, $t_R$=0.751 min, m/z=216 [M+H]⁺. ¹H NMR (500 MHz, DMSO-d₆) δ 6.79 (d, J=8.4 Hz, 1H), 6.61–6.55 (m, 2H), 4.74 (s, 2H), 4.25 (s, 2H), 3.31 (s, 3H), 2.82 (s, 3H).

Step 4

7-(Cyclopropylamino)-5-[4-methoxy-3-(methylsulfonylmethyl)anilino]pyrazolo[1,5-a]pyrimidine-3-carbonitrile A mixture of 5-chloro-7-(cyclopropylamino)pyrazolo[1,5-a]pyrimidine-3-carbonitrile (54 mg, 0.23 mmol), 4-methoxy-3-(methylsulfonylmethyl)aniline (60 mg, 0.28 mmol), 2,2'-bis(diphenylphosphino)-1,1'-binaphthalene (BINAP, 14 mg, 0.023 mmol), tris(dibenzylideneacetone)dipalladium(0) (11 mg, 0.012 mmol) and cesium carbonate (175 mg, 0.53 mmol) in N-methyl-2-pyrrolidinone (1 mL) was stirred at 150° C. for 2.5 h. The reaction mixture was diluted with water (15 mL). The precipitate was collected, washed with water (5 mL) and dried in air. The crude product was purified by silica gel column chromatography eluting with chloroform. The product was triturated with ethanol (1 mL) to give the title compound (30 mg, 0.073 mmol, 32%) as a pale yellow crystalline solid.

LCMS: 98%, $t_R$=1.512 min, m/z=413.1 [M+H]⁺, ¹H NMR (500 MHz, DMSO-d₆) δ 9.57 (s, 1H), 8.32 (s, 1H), 8.16 (d, J=2.0 Hz, 1H), 7.88–7.81 (m, 1H), 7.49 (d, J=2.7 Hz, 1H), 7.10 (d, J=9.0 Hz, 1H), 5.95 (s, 1H), 4.41 (s, 2H), 3.82 (s, 3H), 2.92 (s, 3H), 2.62–2.56 (m, 1H), 0.83–0.77 (m, 2H), 0.73–0.68 (m, 2H). m.p.=233–235° C.

Example 19

(±)-7-(Cyclopropylamino)-5-((4-(difluoromethoxy)-3-((methylsulfinyl)methyl)phenyl)amino)pyrazolo[1,5-a]pyrimidine-3-carbonitrile (Cpd 19)

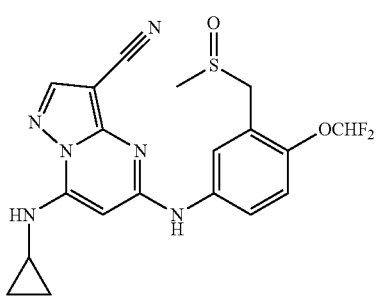 [SMILES: CS(=O)Cc1cc(Nc2cc(NC3CC3)n3ncc(C#N)c3n2)ccc1OC(F)F]

This compound was prepared using the same general method as described in Example 20.

(20% yield) as a pale yellow solid. LCMS: 95%, $t_R$=1.56 min, m/z=433.1 [M+H]⁺. ¹H NMR (500 MHz, DMSO-d₆), δ 9.79 (s, 1H), 8.36 (s, 1H), 8.26 (s, 1H), 7.87 (d, J=8.9 Hz, 1H), 7.67 (s, 1H), 7.24 (d, J=8.9 Hz, 1H), 7.14 (t, J=73.7 Hz, 1H), 5.99 (s, 1H), 4.14 (d, J=12.9 Hz, 1H), 3.97 (d, J=12.9

Hz, 1H), 2.67-2.55 (m, 1H), 2.58 (s, 3H), 0.83-0.77 (m, 2H), 0.77-0.65 (m, 2H). m.p.=233-235° C.

Example 20

7-(Cyclopropylamino)-5-((4-(difluoromethoxy)-3-((methylsulfonyl)methyl)phenyl)amino)pyrazolo[1,5-a]pyrimidine-3-carbonitrile (Cpd 20)

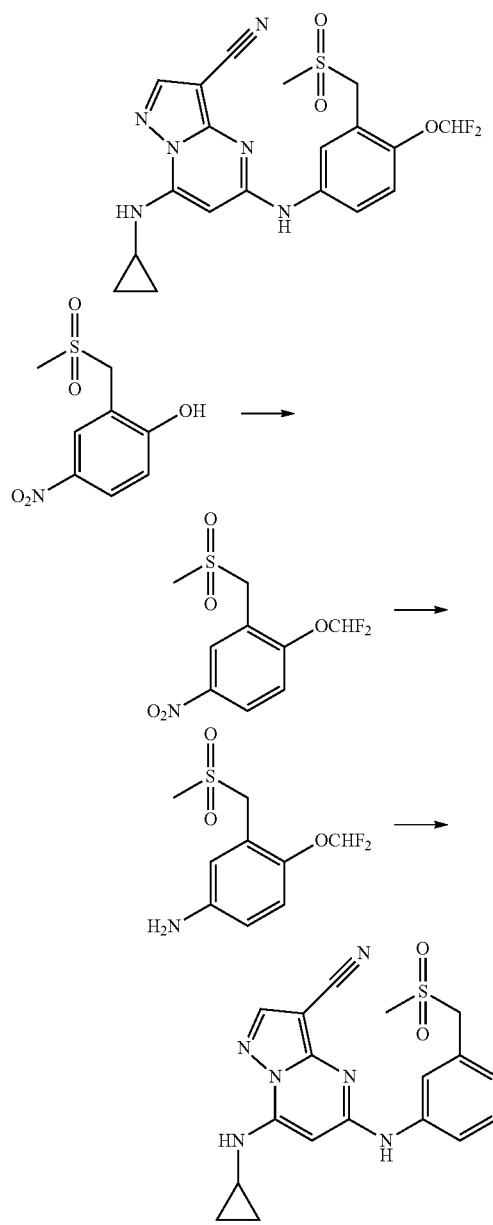

Step 1

1-(Difluoromethoxy)-2-(methylsulfonylmethyl)-4-nitrobenzene

To a stirred suspension of potassium carbonate (269 mg, 1.95 mmol) in N,N-dimethylformamide (900 µL) was added a mixture of 2-(methylsulfonylmethyl)-4-nitrophenol (300 mg, 1.30 mmol) and sodium chlorodifluoroacetate (397 mg, 2.60 mmol) as a solution in N,N-dimethylformamide (750 µL) dropwise over 30 min at 95° C. The reaction mixture was stirred at 95° C. for 15 min. The mixture was diluted with water (5 mL). The precipitate was collected and washed with water (2 mL) to give the title compound (310 mg, 1.10 mmol, 85%) as a white solid. LCMS: 98%, $t_R$=1.192 min, m/z=280 [M−H]⁻.

Step 2

4-(Difluoromethoxy)-3-(methylsulfonylmethyl)aniline

To a stirred mixture of 1-(difluoromethoxy)-2-(methylsulfonylmethyl)-4-nitrobenzene (380 mg, 1.35 mmol) and iron powder (378 mg, 6.77 mmol) in methanol (4 mL) was added saturated aqueous ammonium chloride solution (1.21 mL) and the reaction mixture was stirred at 80° C. for 1 h. The mixture was diluted with ethyl acetate (20 mL) and filtered through a pad of Celite. The filtrate was washed with saturated sodium bicarbonate solution (1×10 mL). The aqueous layer was extracted with ethyl acetate (1×10 mL). The combined organic layers were washed with brine (1×10 mL), dried over magnesium sulfate and evaporated to give the title compound (314 mg, 1.25 mmol, 93%) as a tan solid. LCMS: 99%, $t_R$=0.358 min, m/z=252 [M+H]⁺.

Step 3

7-(Cyclopropylamino)-5-[4-(difluoromethoxy)-3-(methylsulfonylmethyl)anilino]pyrazolo[1,5-a]pyrimidine-3-carbonitrile A mixture of 5-chloro-7-(cyclopropylamino)pyrazolo[1,5-a]pyrimidine-3-carbonitrile (243 mg, 1.04 mmol), 4-(difluoromethoxy)-3-(methylsulfonylmethyl)aniline (314 mg, 1.25 mmol), 2,2'-bis(diphenylphosphino)-1,1'-binaphthalene (BINAP, 65 mg, 0.10 mmol), tris(dibenzylideneacetone)dipalladium(0) (46 mg, 0.05 mmol) and cesium carbonate (779 mg, 2.39 mmol) in N-methyl-2-pyrrolidinone (5 mL) was stirred at 150° C. for 2.5 h. The reaction mixture was diluted with water (75 mL). The precipitate was collected, washed with water (15 mL) and dried in air. The crude product was purified by silica gel column chromatography eluting with chloroform. The product was triturated with ethanol (3 mL) and with water (3 mL) to give the title compound (90 mg, 0.201 mmol, 19%) as a white crystalline solid. LCMS: 100%, $t_R$=1.604 min, m/z=449.1 [M+H]⁺. ¹H NMR (500 MHz, DMSO-$d_6$) δ 9.82 (s, 1H), 8.36 (s, 1H), 8.27 (s, 1H), 7.96 (dd, J=9.0, 2.7 Hz, 1H), 7.69 (d, J=2.8 Hz, 1H), 7.26 (d, J=9.1 Hz, 1H), 7.10 (t, J=74.5 Hz, 1H), 6.00 (s, 1H), 4.49 (s, 2H), 3.03 (s, 3H), 2.66-2.58 (m, 1H), 0.86-0.78 (m, 2H), 0.76-0.68 (m, 2H). m.p.>260° C.

Example 21

(±)-7-(Cyclopropylamino)-5-((4-(methyl(2-(methylamino)ethyl)amino)-3-((methylsulfinyl)methyl)phenyl)amino)pyrazolo[1,5-a]pyrimidine-3-carbonitrile mono trifluoroacetic acid salt (Cpd 21)

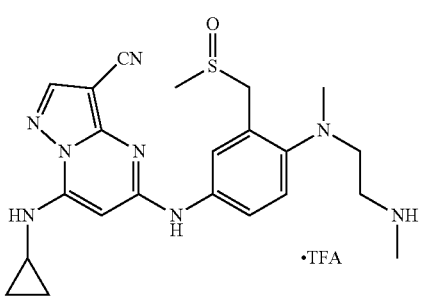 [SMILES: CNCCN(C)c1ccc(Nc2cc(NC3CC3)n3ncc(C#N)c3n2)cc1CS(C)=O]

This compound was prepared using the same general method as described in Example 7.

ES+, m/z 453.0 [M+1]; $^1$H NMR (500 MHz, DMSO-d$_6$), δ 9.70 (s, 1H), 8.35 (s, 1H), 8.27 (brs, 2H), 8.21 (s, 1H), 7.82 (dd, J=8.5, 2.5 Hz, 1H), 7.65 (d, J=2.5 Hz, 1H), 7.32 (d, J=8.5 Hz, 1H), 5.99 (s, 1H), 4.26 (d, J=14.5 Hz, 1H), 4.21 (d, J=14.5 Hz, 1H), 3.22-3.18 (m, 1H), 3.16-3.14 (m, 1H), 3.03-2.99 (m, 2H), 2.72 (s, 3H), 2.60 (m, 1H), 2.59 (s, 3H), 0.82-0.80 (m, 2H), 0.74-0.72 (m, 2H).

Example 22

5-((4-((R)-3-Aminopyrrolidin-1-yl)-3-(((R,S)-methylsulfinyl)methyl)phenyl)amino)-7-(cyclopropylamino)pyrazolo[1,5-a]pyrimidine-3-carbonitrile mono trifluoroacetic acid salt (Cpd 22)

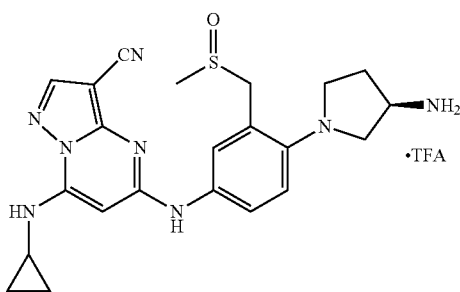 [SMILES: CS(=O)Cc1cc(Nc2cc(NC3CC3)n3ncc(C#N)c3n2)ccc1N1CC[C@@H](N)C1]

This compound was prepared using the same general method as described in Example 7.

ES+, m/z 451.4 [M+1]; $^1$H NMR (500 MHz, DMSO-d$_6$), δ 9.65 (s, 1H), 8.33 (s, 1H), 8.17 (s, 1H), 7.99 (brs, 3H), 7.83 (d, J=8.5 Hz, 0.5H), 7.79 (d, J=8.5 Hz, 0.5H), 7.55 (d, J=2.5 Hz, 0.5H), 7.51 (d, J=2.5 Hz, 0.5H), 7.25 (d, J=8.5 Hz, 1H), 5.99 (s, 0.5H), 5.98 (s, 0.5H), 4.24-4.02 (m, 2H), 3.87 (brs, 1H), 3.30-3.27 (m, 2H), 3.07-3.04 (m, 1H), 2.94-2.88 (m, 1H), 2.60 (m, 1H), 2.59 (s, 3H), 2.33-2.30 (m, 1H), 1.90-1.88 (m, 1H), 0.82-0.80 (m, 2H), 0.73-0.71 (m, 2H).

Example 23

5-((4-((S)-3-Aminopyrrolidin-1-yl)-3-(((R,S)-methylsulfinyl)methyl)phenyl)amino)-7-(cyclopropylamino)pyrazolo[1,5-a]pyrimidine-3-carbonitrile mono trifluoroacetic acid salt (Cpd 23)

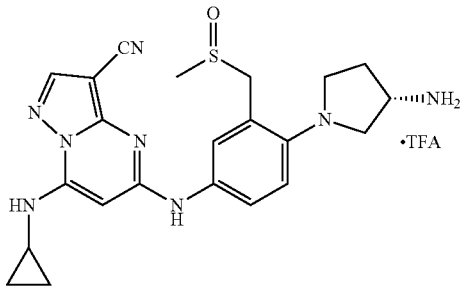 [SMILES: CS(=O)Cc1cc(Nc2cc(NC3CC3)n3ncc(C#N)c3n2)ccc1N1CC[C@H](N)C1]

This compound was prepared using the same general method as described in Example 7. ES+, m/z 451.3 [M+1]; $^1$H NMR (500 MHz, DMSO-d$_6$), δ 9.65 (s, 1H), 8.33 (s, 1H), 8.17 (s, 1H), 7.99 (brs, 3H), 7.83 (d, J=8.5 Hz, 0.5H), 7.79 (d, J=8.5 Hz, 0.5H), 7.55 (d, J=2.0 Hz, 0.5H), 7.51 (d, J=2.0 Hz, 0.5H), 7.25 (d, J=8.5 Hz, 1H), 5.99 (s, 0.5H), 5.98 (s, 0.5H), 4.24-4.08 (m, 2H), 3.87 (brs, 1H), 3.30-3.27 (m, 2H), 3.07-3.04 (m, 1H), 2.95-2.88 (m, 1H), 2.59 (s, 3H), 2.58 (m, 1H), 2.33-2.30 (m, 1H), 1.90-1.88 (m, 1H), 0.82-0.80 (m, 2H), 0.73-0.71 (m, 2H).

Example 24

5-((4-((R)-3-Aminopiperidin-1-yl)-3-(((R,S)-methylsulfinyl)methyl)phenyl)amino)-7-(cyclopropylamino)pyrazolo[1,5-a]pyrimidine-3-carbonitrile mono trifluoroacetic acid salt (Cpd 24)

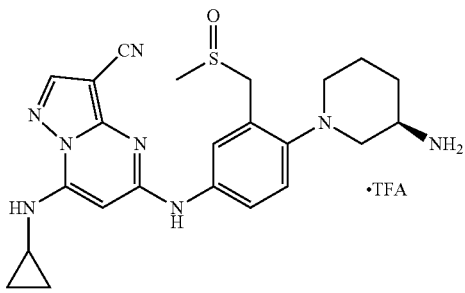 [SMILES: CS(=O)Cc1cc(Nc2cc(NC3CC3)n3ncc(C#N)c3n2)ccc1N1CCC[C@@H](N)C1]

This compound was prepared using the same general method as described in Example 7. ES+, m/z 465.5 [M+1]; $^1$H NMR (500 MHz, DMSO-d$_6$), δ 9.68 (s, 1H), 8.34 (s, 1H), 8.19 (s, 1H), 7.90 (brs, 3H), 7.84 (d, J=8.5, Hz, 0.5H), 7.79 (d, J=8.5, Hz, 0.5H), 7.59 (d, J=2.5 Hz, 0.5H), 7.56 (d, J=2.5 Hz, 0.5H), 7.25 (d, J=8.5 Hz, 0.5H), 7.23 (d, J=8.5 Hz, 0.5H), 5.99 (s, 0.5H), 5.98 (s, 0.5H), 4.21-4.02 (m, 2H), 3.13-3.09 (m, 1H), 2.77 (m, 3H), 2.59 (s, 3H), 2.58 (m, 1H), 2.55 (m, 1H), 1.88 (m, 2H), 1.63 (m, 2H), 0.82-0.80 (m, 2H), 0.73-0.70 (m, 2H).

Example 25

5-((4-((S)-3-Aminopiperidin-1-yl)-3-(((R,S)-methylsulfinyl)methyl)phenyl)amino)-7-(cyclopropylamino)pyrazolo[1,5-a]pyrimidine-3-carbonitrile mono trifluoroacetic acid salt (Cpd 25)

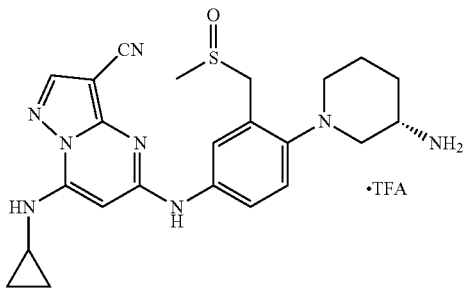 [SMILES: CS(=O)Cc1cc(Nc2cc(NC3CC3)n3ncc(C#N)c3n2)ccc1N1CCC[C@H](N)C1]

This compound was prepared using the same general method as described in Example 7.

ES+, m/z 465.5 [M+1]; $^1$H NMR (500 MHz, DMSO-d$_6$), δ 9.68 (s, 1H), 8.34 (s, 1H), 8.20 (s, 1H), 7.90 (brs, 3H), 7.84 (d, J=8.5 Hz, 0.5H), 7.79 (d, J=8.5 Hz, 0.5H), 7.59 (d, J=2.5

Hz, 0.5H), 7.56 (d, J=2.5 Hz, 0.5H), 7.25 (d, J=8.5 Hz, 0.5H), 7.23 (d, J=8.5 Hz, 0.5H), 5.99 (s, 0.5H), 5.98 (s, 0.5H), 4.21-4.03 (m, 2H), 3.13-3.09 (m, 1H), 2.77 (m, 3H), 2.59 (s, 3H), 2.58 (m, 1H), 2.55 (m, 1H), 1.88 (m, 2H), 1.63 (m, 2H), 0.82-0.80 (m, 2H), 0.73-0.70 (m, 2H).

Example 26

5-((4-(2-aminoethoxy)-3-((methylsulfonyl)methyl)phenyl)amino)-7-(cyclopropylamino)pyrazolo[1,5-a]pyrimidine-3-carbonitrile hydrochloric acid salt (Cpd 26)

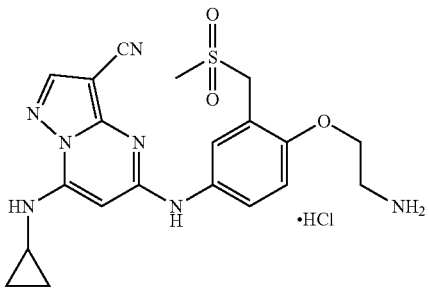 [SMILES: CS(=O)(=O)Cc1cc(Nc2cc(NC3CC3)n3ncc(C#N)c3n2)ccc1OCCN ; Cl]

Starting from 2-((methylsulfonyl)methyl)-4-nitrophenol, described in Example 18, this compound was prepared using the same general method as described in Example 31, with the exception that the final step was carried out with HCl in 1,4-dioxane. (59% yield) white foamy solid. LCMS: 96.7%, $t_R$=1.099 min, m/z=442.2 [M+H]$^+$. $^1$H NMR (500 MHz, DMSO-$d_6$) δ 9.66 (s, 1H), 8.33 (s, 1H), 8.21-8.10 (m, 4H), 7.95-7.85 (m, 1H), 7.49 (d, J=2.7 Hz, 1H), 7.11 (d, J=9.0 Hz, 1H), 5.98 (s, 1H), 4.61 (s, 2H), 4.22 (t, J=4.9 Hz, 2H), 3.29-3.20 (m, 2H), 2.94 (s, 3H), 2.62-2.55 (m, 1H), 0.86-0.76 (m, 2H), 0.74-0.66 (m, 2H). m.p.=238-240° C.

Example 27

(±)-7-(cyclopropylamino)-5-((4-(3-hydroxyazetidin-1-yl)-3-((methylsulfinyl)methyl)phenyl)amino)pyrazolo[1,5-a]pyrimidine-3-carbonitrile (Cpd 27)

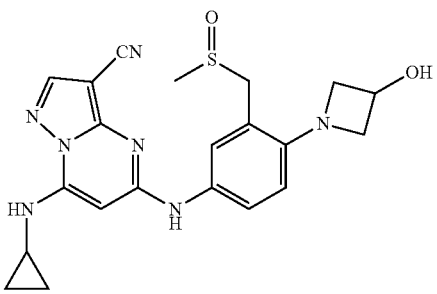 [SMILES: CS(=O)Cc1cc(Nc2cc(NC3CC3)n3ncc(C#N)c3n2)ccc1N1CC(O)C1]

This compound was prepared using the same general method as described in Example 7.

ES+, m/z 438.3 [M+1]; $^1$H NMR (500 MHz, DMSO-$d_6$), δ 9.41 (s, 1H), 8.29 (s, 1H), 8.04 (s, 1H), 7.56 (d, J=7.5 Hz, 1H), 7.38 (d, J=2.5 Hz, 1H), 6.59 (d, J=9.0 Hz, 1H), 5.91 (s, 1H), 5.51 (d, J=6.5 Hz, 1H), 4.51-4.48 (m, 1H), 4.15-4.09 (m, 2H), 3.98 (d, J=13.5 Hz, 1H), 3.88 (d, J=13.5 Hz, 1H), 3.63-3.56 (m, 2H), 2.60 (s, 3H), 2.58 (m, 1H), 0.80-0.78 (m, 2H), 0.70-0.69 (m, 2H).

Example 28

(±)-5-((4-((1-aminocyclopropyl)methoxy)-3-((methylsulfinyl)methyl)phenyl)amino)-7-(cyclopropylamino)pyrazolo[1,5-a]pyrimidine-3-carbonitrile mono trifluoroacetic acid salt (Cpd 28)

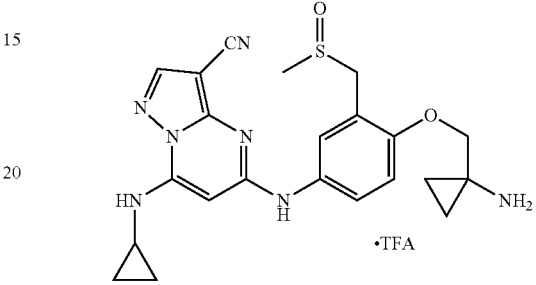

(±)-tert-Butyl (1-((2-((methylsulfinyl)methyl)-4-nitrophenoxy)methyl)cyclopropyl)carbamate

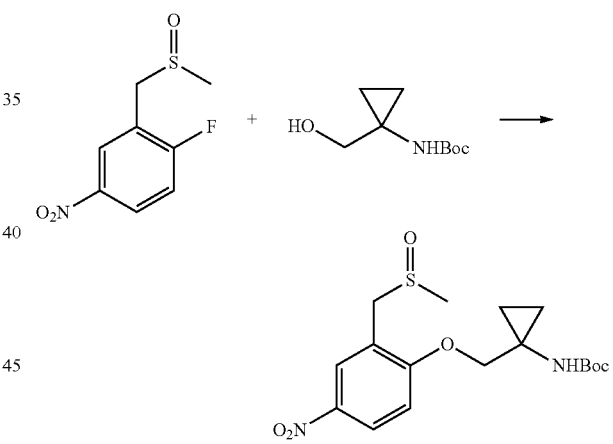

To a solution of tert-butyl (1-(hydroxymethyl)cyclopropyl)carbamate (235 mg, 1.25 mmol) in dry dioxane (10 mL) under Argon atmosphere, was added potassium tert-butoxide solid (148 mg, 1.32 mmol, 1.05 eq.). The reaction mixture was stirred at r.t. for 15 minutes and then was cooled with an ice bath, followed by addition of a solution of 1-fluoro-2-((methylsulfinyl)methyl)-4-nitrobenzene (248 mg, 1.14 mmol) in 2.0 mL of dioxane. After the reaction was stirred at 0° C.-r.t for 1.5 h, ethyl acetate (50 mL) was added. The resulting mixture was washed with water (20 mL×2), brine, dried (Na$_2$SO$_4$) and concentrated. The crude material was purified on a silica gel column (eluting with 100% EtOAc) to give the desired product as a light yellow solid (280 mg, 58.2% yield). The nitro group was reduced to (±)-tert-butyl (1-((4-amino-2-((methylsulfinyl)methyl)phenoxy)methyl) cyclopropyl)carbamate as described for (±)-4-Fluoro-3-((methylsulfinyl)methyl)aniline in Example 5 and used in the next step.

(±)-5-((4-((1-aminocyclopropyl)methoxy)-3-((methylsulfinyl)methyl)phenyl)amino)-7-(cyclopropylamino)pyrazolo[1,5-a]pyrimidine-3-carbonitrile mono trifluoroacetic acid salt This compound was prepared in two steps from (±)-tert-butyl (1-((4-amino-2-((methylsulfinyl)methyl)phenoxy)methyl)cyclopropyl)carbamate and tert-butyl (5-chloro-3-cyanopyrazolo[1,5-a]pyrimidin-7-yl)(cyclopropyl)carbamate as described in Example 7.

ES+, m/z 452.4 [M+1]; $^1$H NMR (500 MHz, DMSO-d$_6$), δ 9.55 (s, 1H), 8.36 (brs, 3H), 8.31 (s, 1H), 8.12 (s, 1H), 7.75 (dd, J=9.0, 2.5 Hz, 1H), 7.50 (d, J=2.5 Hz, 1H), 7.04 (d, J=9.0 Hz, 1H), 5.94 (s, 1H), 4.27 (d, J=13.0 Hz, 1H), 4.15 (d, J=13.0 Hz, 1H), 4.11 (s, 2H), 2.57 (s, 3H), 2.56 (m, 1H), 1.06-1.04 (m, 2H), 0.97-0.94 (m, 2H), 0.82-0.80 (m, 2H), 0.72-0.70 (m, 2H).

Example 29

(S)-5-((4-(3-aminopyrrolidin-1-yl)-3-((methylsulfonyl)methyl)phenyl)amino)-7-(cyclopropylamino)pyrazolo[1,5-a]pyrimidine-3-carbonitrile mono trifluoroacetic acid salt (Cpd 29)

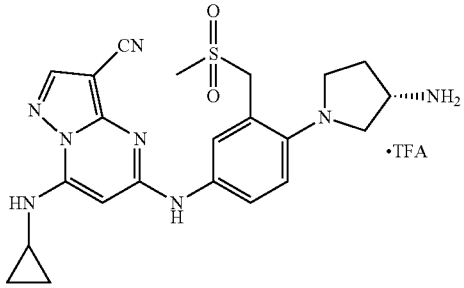 [SMILES: CS(=O)(=O)Cc1cc(Nc2cc(NC3CC3)n3ncc(C#N)c3n2)ccc1N1CC[C@H](N)C1]

This compound was prepared using the same general method as described in Example 7.

Prepared as mono TFA salt. ES+, m/z 467.4 [M+1]; $^1$H NMR (500 MHz, DMSO-d$_6$), δ 9.68 (s, 1H), 8.33 (s, 1H), 8.15 (s, 1H), 7.95 (m, 4H), 7.58 (d, J=2.5 Hz, 1H), 7.34 (d, J=9.0 Hz, 1H), 6.01 (s, 1H), 4.69 (d, J=13.5 Hz, 1H), 4.55 (d, J=13.5 Hz, 1H), 3.88 (brs, 1H), 3.28-3.25 (m, 2H), 3.07-3.05 (m, 1H), 2.99 (s, 3H), 2.91-2.88 (m, 1H), 2.61 (m, 1H), 2.36-2.31 (m, 1H), 1.89-1.87 (m, 1H), 0.82-0.80 (m, 2H), 0.73-0.71 (m, 2H).

Example 30

(±)-5-((4-(2-amino-2-methylpropoxy)-3-((methylsulfinyl)methyl)phenyl)amino)-7-(cyclopropylamino)pyrazolo[1,5-a]pyrimidine-3-carbonitrile mono trifluoroacetic acid salt (Cpd 30)

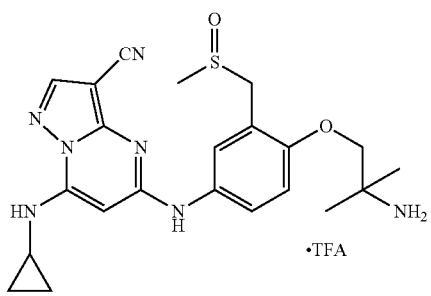 [SMILES: CS(=O)Cc1cc(Nc2cc(NC3CC3)n3ncc(C#N)c3n2)ccc1OCC(C)(C)N]

(±)-tert-Butyl (2-methyl-1-(2-((methylsulfinyl)methyl)-4-nitrophenoxy)propan-2-yl)carbamate

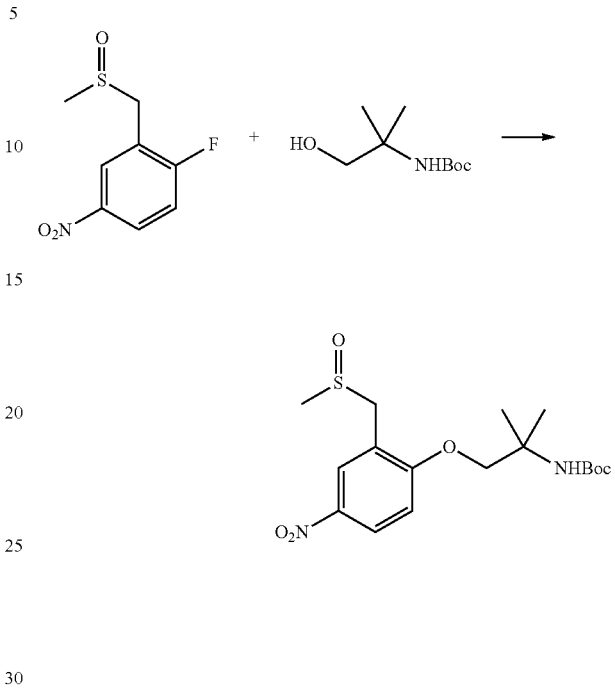

To a solution of tert-butyl (1-hydroxy-2-methylpropan-2-yl)carbamate (285 mg, 1.50 mmol) in dry dioxane (12 mL) under Argon atmosphere, was added potassium tert-butoxide solid (180 mg, 1.60 mmol, 1.05 eq.). The reaction mixture was stirred at r.t. for 20 minutes and then was cooled with an ice bath, followed by addition of a solution of 1-fluoro-2-((methylsulfinyl)methyl)-4-nitrobenzene (248 mg, 1.14 mmol) in 3.0 mL of dioxane. After the reaction was stirred at r.t over night, ethyl acetate (80 mL) was added. The resulting mixture was washed with water (30 mL×2), brine, dried (Na$_2$SO$_4$) and concentrated. The crude material was purified on a silica gel column (eluting with 100% EtOAc) to give the desired product as a light yellow solid (375 mg, 61% yield). The nitro group was reduced to (±)-tert-butyl (1-(4-amino-2-((methylsulfinyl)methyl)phenoxy)-2-methylpropan-2-yl)carbamate as described for (±)-4-fluoro-3-((methylsulfinyl)methyl)aniline in Example 5 and used in the next step.

(±)-5-((4-(2-amino-2-methylpropoxy)-3-((methylsulfinyl)methyl)phenyl)amino)-7-(cyclopropylamino)pyrazolo[1,5-a]pyrimidine-3-carbonitrile mono trifluoroacetic acid salt This compound was prepared in two steps from (±)-tert-butyl (1-(4-amino-2-((methylsulfinyl)methyl)phenoxy)-2-methylpropan-2-yl)carbamate and tert-butyl (5-chloro-3-cyanopyrazolo[1,5-a]pyrimidin-7-yl)(cyclopropyl)carbamate as described in Example 7. ES+, m/z 453.9 [M+1]; $^1$H NMR (500 MHz, DMSO-d$_6$), δ 9.56 (s, 1H), 8.31 (s, 1H), 8.12 (s, 1H), 8.01 (m, 3H), 7.75 (dd, J=2.5, 9.0 Hz, 1H), 7.50 (d, J=2.5 Hz, 1H), 7.08 (d, J=9.0 Hz, 1H), 5.94 (s, 1H), 4.27 (d, J=13.0 Hz, 1H), 4.17 (d, J=13.0 Hz, 1H), 3.99 (s, 2H), 2.57 (s, 3H), 2.56 (m, 1H), 1.38 (s, 3H), 1.37 (s, 3H), 0.83-0.80 (m, 2H), 0.73-0.70 (m, 2H).

Example 31

(±)-5-((4-(2-aminoethoxy)-3-((methylsulfinyl)methyl)phenyl)amino)-7-(cyclopropylamino)pyrazolo[1,5-a]pyrimidine-3-carbonitrile (Cpd 31)

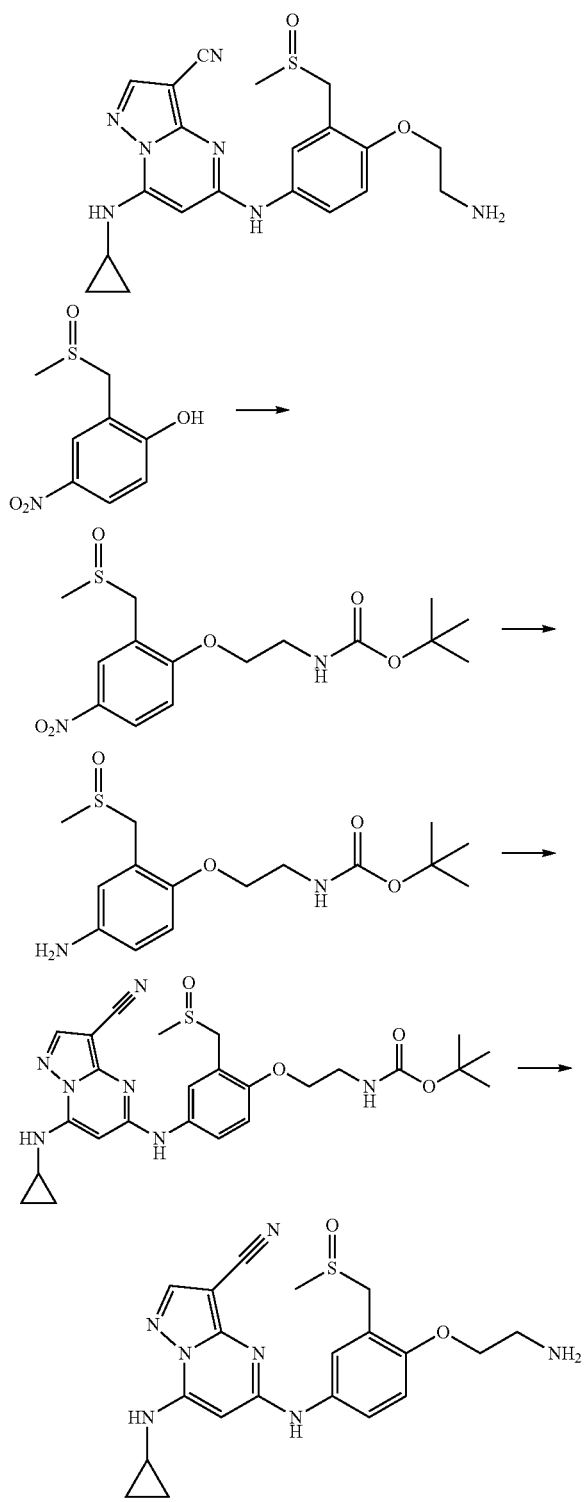

Step 1

(±)-tert-Butyl (2-(2-((methylsulfinyl)methyl)-4-nitrophenoxy)ethyl)carbamate

To a stirred mixture of 2-((methylsulfinyl)methyl)-4-nitrophenol (400 mg, 1.86 mmol), tert-butyl N-(2-hydroxyethyl)carbamate (329 mg, 2.05 mmol) and triphenylphosphine (634 mg, 2.42 mmol) in tetrahydrofuran (4 mL) was added diethyl azodicarboxylate (40 wt. % in toluene, 1.053 g, 2.42 mmol) at 0° C. The reaction mixture was stirred at room temperature for 2 h. To the reaction mixture was added triphenylphosphine (634 mg, 2.42 mmol) at room temperature. To the reaction mixture was added diethyl azodicarboxylate (40 wt. % in toluene, 1.053 g, 2.42 mmol) at 0° C. The reaction mixture was stirred at room temperature for 16 h. The mixture was diluted with ethyl acetate (100 mL) and washed with water (1×30 mL). The organic layer was dried over sodium sulfate and evaporated. The residue was purified by gradient silica gel column chromatography eluting with chloroform:methanol (100:0495:5) to give the title compound (495 mg, 1.38 mmol, 74%) as a yellow crystalline solid. LCMS: 100%, $t_R$=1.297 min, m/z=259 [M+H-Boc]$^+$.

Step 2

(±)-tert-Butyl (2-(4-amino-2-((methylsulfinyl)methyl)phenoxy)ethyl)carbamate

To a stirred mixture of (±)-tert-butyl (2-(2-((methylsulfinyl)methyl)-4-nitrophenoxy)ethyl)carbamate (485 mg, 1.35 mmol) and iron powder (378 mg, 6.77 mmol) in methanol (5 mL) was added saturated aqueous ammonium chloride solution (1.21 mL). The reaction mixture was stirred at 80° C. for 2 h. The reaction mixture was diluted with ethyl acetate (20 mL) and filtered through a pad of Celite. The filtrate was washed with saturated sodium bicarbonate solution (1×10 mL). The aqueous layer was extracted with ethyl acetate (1×10 mL). The combined organic layers were washed with brine (1×10 mL), dried over magnesium sulfate and evaporated to give the title compound (426 mg, 1.30 mmol, 96%) as a tan solid. LCMS: 92%, $t_R$=0.766 min, m/z=229 [M+H-Boc]$^+$.

Step 3

(±)-tert-Butyl (2-(4-((3-cyano-7-(cyclopropylamino)pyrazolo[1,5-a]pyrimidin-5-yl)amino)-2-((methylsulfinyl)methyl)phenoxy)ethyl)carbamate A mixture of 5-chloro-7-(cyclopropylamino)pyrazolo[1,5-a]pyrimidine-3-carbonitrile (244 mg, 1.05 mmol), (±)-tert-Butyl (2-(4-amino-2-((methylsulfinyl)methyl)phenoxy)ethyl)carbamate (413 mg, 1.26 mmol), 2,2'-bis(diphenylphosphino)-1,1'-binaphthalene (BINAP, 65 mg, 0.11 mmol), tris(dibenzylideneacetone)dipalladium(0) (48 mg, 0.05 mmol) and cesium carbonate (787 mg, 2.42 mmol) in N-methyl-2-pyrrolidinone (5 mL) was stirred at 120° C. for 2.5 h. The reaction mixture was diluted with water (100 mL). The precipitate was collected, washed with water (20 mL) and dried in air. The crude product was purified by gradient silica gel column chromatography eluting with chloroform:methanol (100:0→98:2) to give the title compound (257 mg, 0.49 mmol, 47%) as a white crystalline solid. LCMS: 96%, $t_R$=1.545 min, m/z=526 [M+H]$^+$.

Step 4

(±)-5-((4-(2-aminoethoxy)-3-((methylsulfinyl)methyl)phenyl)amino)-7-(cyclopropylamino)pyrazolo[1,5-a]pyrimidine-3-carbonitrile To a stirred solution of (±)-tert-butyl (2-(4-((3-cyano-7-(cyclopropylamino)pyrazolo[1,5-c]pyrimidin-5-yl)amino)-2-((methylsulfinyl)methyl)phenoxy)ethyl)carbamate (130 mg, 0.248 mmol) in dichloromethane (650 μL) was added trifluoroacetic acid (650 μL, 8.49 mmol) at 0° C. The reaction mixture was stirred at room temperature for 1 h. The mixture was evaporated under a nitrogen stream. The residue was dissolved in dichloromethane (1 mL) and evaporated under a nitrogen stream. The residue was triturated with diethyl ether (2 mL). The crude product was taken up in water (4 mL) and the mixture was made basic to pH 14 by addition of 1 N aqueous sodium hydroxide. The aqueous layer was extracted with chloroform (4×2 mL). The combined organic layers were dried over sodium sulfate and evaporated. The residue was triturated with diethyl ether (5 mL) and with acetonitrile (2 mL). The product was triturated with water (2 mL) and dried in air to give the title compound (40 mg, 0.094 mmol, 38%) as a tan solid. LCMS: 97%, $t_R$=0.995 min, m/z=426.1 [M+H]$^+$. $^1$H NMR (300 MHz, DMSO-d$_6$) δ 9.54 (s, 1H), 8.32 (s, 1H), 8.26-8.01 (m, 1H), 7.78-7.63 (m, 1H), 7.47 (d, J=2.7 Hz, 1H), 7.03 (d, J=8.9 Hz, 1H), 5.93 (s, 1H), 4.04 (q, J=12.6 Hz, 2H), 3.95 (t, J=5.5 Hz, 2H), 2.96-2.78 (m, 2H), 2.64-2.55 (m, 1H), 2.50 (s, 3H), 1.95-1.34 (m, 2H), 0.86-0.75 (m, 2H), 0.74-0.63 (m, 2H). m.p.=206-208° C.

Example 32

5-((4-(Azetidin-1-yl)-3-((methylsulfonyl)methyl)phenyl)amino)-7-(cyclopropylamino)pyrazolo[1,5-a]pyrimidine-3-carbonitrile (Cpd 32)

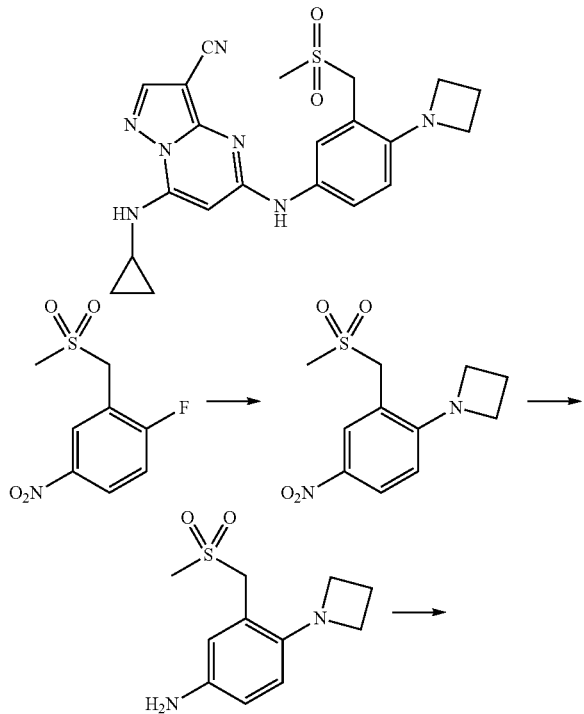

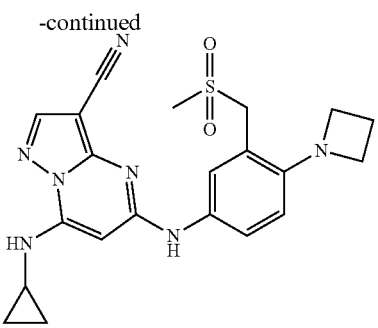

Step 1

1-[2-(Methylsulfonylmethyl)-4-nitrophenyl]azetidine

To a solution of 1-fluoro-2-(methylsulfonylmethyl)-4-nitrobenzene (400 mg, 1.72 mmol) in N,N-dimethylformamide (4 mL) was added azetidine (185 μL, 2.75 mmol) at room temperature. The reaction mixture was stirred at 50° C. for 4 h. To the reaction mixture was added azetidine (90 μL, 1.34 mmol) and the reaction mixture was stirred at 50° C. for 16 h. The reaction mixture was diluted with saturated sodium bicarbonate solution (10 mL) and the precipitate was collected. The solid was washed with water (2 mL) and dried in air to give the title compound (344 mg, 1.27 mmol, 74%) as a yellow crystalline solid. LCMS: 100%, $t_R$=1.140 min, m/z=271 [M+H]$^+$.

Step 2

4-(Azetidin-1-yl)-3-(methylsulfonylmethyl)aniline

To a stirred mixture of 1-[2-(methylsulfonylmethyl)-4-nitrophenyl]azetidine (259 mg, 0.96 mmol) and Raney-Nickel (aqueous slurry, 250 mg) in a mixture of dichloromethane and methanol (1:1, 5 mL) was added hydrazine monohydrate (255 μL, 5.29 mmol) at room temperature. The reaction mixture was heated to reflux for 1 h. The mixture was filtered and washed with water (1×3 mL). The aqueous layer was extracted with dichloromethane (1×3 mL). The combined organic layers were dried over sodium sulfate and evaporated to give the title compound (225 mg, 0.94 mmol, 98%) as a tan solid. LCMS: 98%, $t_R$=1.290 min, m/z=241 [M+H]$^+$.

Step 3

5-[4-(Azetidin-1-yl)-3-(methylsulfonylmethyl)anilino]-7-(cyclopropylamino)pyrazolo[1,5-a]pyrimidine-3-carbonitrile A mixture of 5-chloro-7-(cyclopropylamino)pyrazolo[1,5-a]pyrimidine-3-carbonitrile (182 mg, 0.78 mmol), 4-(azetidin-1-yl)-3-(methylsulfonylmethyl)aniline (225 mg, 0.94 mmol), 2,2'-bis(diphenylphosphino)-1,1'-binaphthalene (BINAP, 50 mg, 0.08 mmol), tris(dibenzylideneacetone)dipalladium(0) (45 mg, 0.05 mmol) and cesium carbonate (585 mg, 1.79 mmol) in N-methyl-2-pyrrolidinone (4 mL) was stirred at 120° C. for 2.5 h. The reaction mixture was diluted with water (20 mL). The precipitate was collected, washed with water, and air dried. The crude product was purified by silica gel column chromatography eluting with chloroform. The product was triturated with diethyl ether (5 mL) to give the title compound (204 mg, 0.47 mmol, 60%) as a tan solid. LCMS: 96%, $t_R$=1.324 min, m/z=438.2 [M+H]$^+$. $^1$H NMR (500 MHz, DMSO-d$_6$) δ 9.45 (s, 1H), 8.30 (s, 1H), 8.10 (d, J=2.0 Hz, 1H), 7.70-7.60 (m, 1H), 7.38 (d, J=2.6 Hz, 1H), 6.60 (d, J=8.9 Hz, 1H), 5.92 (s, 1H), 4.37 (s, 2H), 3.93 (t, J=7.2 Hz, 4H), 3.02 (s, 3H), 2.61-2.55 (m, 1H), 2.26-2.18 (m, 2H), 0.82-0.75 (m, 2H), 0.74-0.65 (m, 2H). m.p.=220-222° C.

Example 33

(±)-7-(Cyclopropylamino)-5-((4-(dimethylamino)-3-((methylsulfinyl)methyl)phenyl)amino)pyrazolo[1,5-a]pyrimidine-3-carbonitrile (Cpd 33)

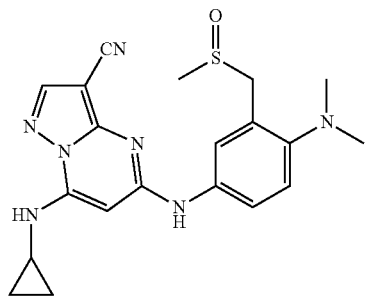 [SMILES: CN(C)c1ccc(Nc2cc(NC3CC3)n3ncc(C#N)c3n2)cc1CS(C)=O]

This compound was prepared using the same general method as described in Example 32. Off-white crystalline solid (59%); LCMS: 99%, $t_R$=1.071 min, m/z=410.2 [M+H]$^+$. $^1$H NMR (500 MHz, DMSO-d$_6$) δ 9.62 (s, 1H), 8.33 (s, 1H), 8.20-8.15 (m, 1H), 7.78 (dd, J=8.6, 2.6 Hz, 1H), 7.56 (d, J=2.6 Hz, 1H), 7.26 (d, J=8.7 Hz, 1H), 5.99 (s, 1H), 4.11 (d, J=12.5 Hz, 1H), 4.07 (d, J=12.5 Hz, 1H), 2.65-2.58 (m, 1H), 2.61 (s, 6H), 2.56 (s, 3H), 0.85-0.78 (m, 2H), 0.75-0.68 (m, 2H). m.p.=229-233° C.

Example 34

7-(Cyclopropylamino)-5-((4-(dimethylamino)-3-((methylsulfonyl)methyl)phenyl)amino)pyrazolo[1,5-a]pyrimidine-3-carbonitrile (Cpd 34)

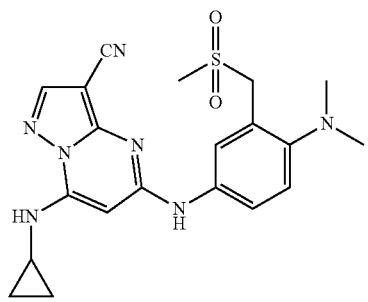 [SMILES: CN(C)c1ccc(Nc2cc(NC3CC3)n3ncc(C#N)c3n2)cc1CS(C)(=O)=O]

This compound was prepared using the same general method as described in Example 32.

Off-white crystalline solid (50%); LCMS: 99%, $t_R$=1.209 min, m/z=422.2 [M+H]$^+$. $^1$H NMR (500 MHz, DMSO-d$_6$) δ 9.68 (s, 1H), 8.34 (s, 1H), 8.22-8.16 (m, 1H), 7.96-7.89 (m, 1H), 7.58 (d, J=2.6 Hz, 1H), 7.33 (d, J=8.8 Hz, 1H), 6.01 (s, 1H), 4.55 (s, 2H), 2.97 (s, 3H), 2.64-2.58 (m, 1H), 2.61 (s, 6H), 0.84-0.78 (m, 2H), 0.74-0.69 (m, 2H). m.p.=243-245° C.

Example 35

(±)-7-(Cyclopropylamino)-5-((3-((methylsulfinyl)methyl)-4-(1H-pyrazol-4-yl)phenyl)amino)pyrazolo[1,5-a]pyrimidine-3-carbonitrile (Cpd 35)

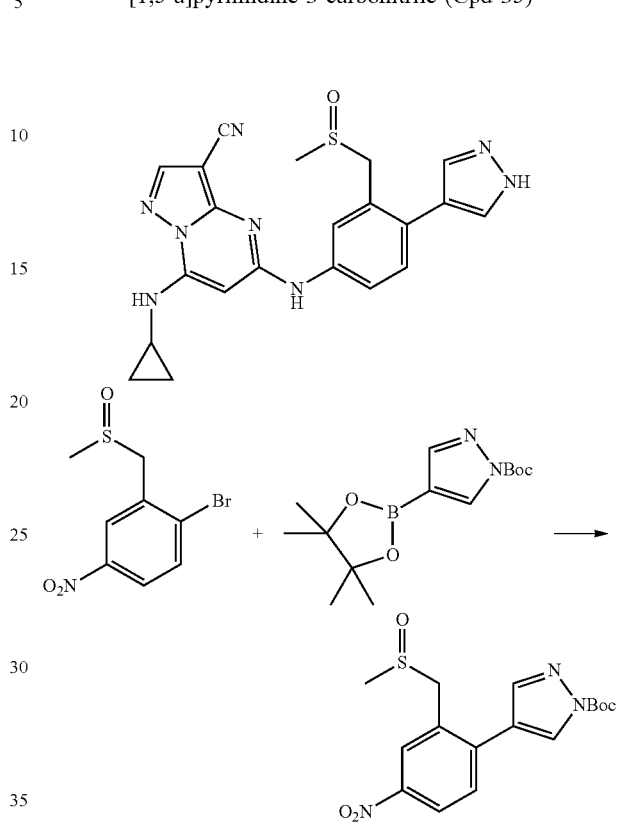

(±)-tert-Butyl 4-(2-((methylsulfinyl)methyl)-4-nitrophenyl)-1H-pyrazole-1-carboxylate To a mixture of 1-bromo-2-((methylsulfinyl)methyl)-4-nitrobenzene (212 mg, 0.763 mmol), tert-butyl 4-(4,4,5,5-tetramethyl-1,3,2-dioxaborolan-2-yl)-1H-pyrazole-1-carboxylate (250 mg, 0.84 mmol, 1.1 eq.), and potassium carbonate (421 mg, 3.05 mmol, 4.0 eq.) in dioxane/water (8 mL/2 mL) under argon, was added PddppfCl$_2$ (56 mg, 0.75 mmol, 0.1 eq.). The resulting reaction mixture was stirred at 100° C. for 16 h. The reaction mixture was cooled to r.t., diluted with EtOAc (100 mL), and the mixture was washed with water (30 mL×2), brine, dried (Na$_2$SO$_4$), and concentrated to get a residue, which was purified on a silica gel column (eluting with EtOAc) to give the desired product as a light yellow solid (205 mg, 73.5% yield). The nitro group was reduced to (±)-tert-butyl 4-(4-amino-2-((methylsulfinyl)methyl)phenyl)-1H-pyrazole-1-carboxylate as described for (±)-4-fluoro-3-((methylsulfinyl)methyl)aniline in Example 5 and used in the next step.

(±)-7-(Cyclopropylamino)-5-((3-((methylsulfinyl)methyl)-4-(1H-pyrazol-4-yl)phenyl)amino)pyrazolo[1,5-a]pyrimidine-3-carbonitrile This compound was prepared in two steps from (±)-tert-butyl 4-(4-amino-2-((methylsulfinyl)methyl)phenyl)-1H-pyrazole-1-carboxylate and tert-butyl (5-chloro-3-cyanopyrazolo[1,5-a]pyrimidin-7-yl)(cyclopropyl)carbamate as described in Example 7.

ES+, m/z 433.8 [M+1]; $^1$H NMR (500 MHz, DMSO-d$_6$), δ 9.12 (s, 1H), 8.68 (s, 1H), 8.64 (s, 1H), 8.07 (s, 1H), 7.16 (d, J=8.5 Hz, 1H), 7.10 (s, 1H), 6.65 (d, J=2.5 Hz, 1H), 6.61 (dd, J=2.5, 8.0 Hz, 1H), 5.33 (s, 2H), 4.05 (d, J=16.5 Hz, 1H), 4.00 (d, J=16.5 Hz, 1H), 2.83 (m, 1H), 2.57 (s, 3H), 0.93-0.91 (m, 2H), 0.81-0.79 (m, 2H).

Example 36

(±)-5-((4-(Cyclopropyl(methyl)amino)-3-((methylsulfinyl)methyl)phenyl)amino)-7-(cyclopropylamino)pyrazolo[1,5-a]pyrimidine-3-carbonitrile (Cpd 36)

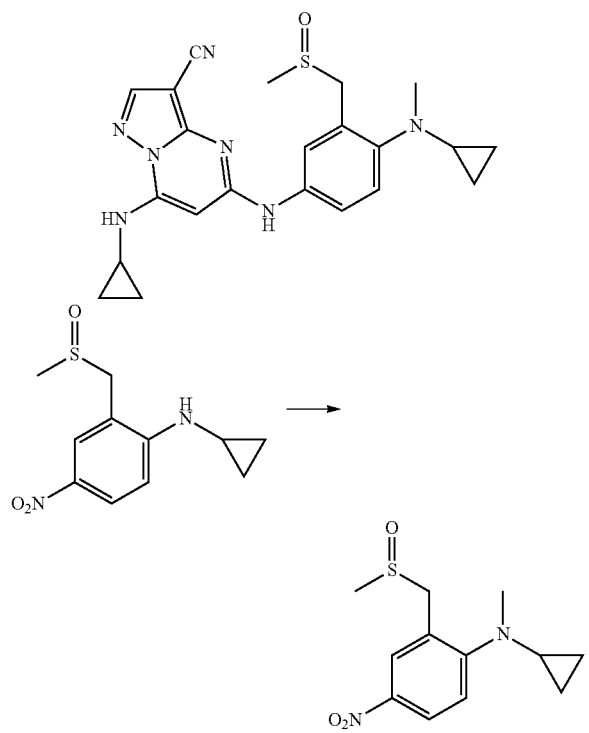

(±)-N-cyclopropyl-N-methyl-2-((methylsulfinyl)methyl)-4-nitroaniline

To a solution of (±)-N-cyclopropyl-2-((methylsulfinyl)methyl)-4-nitroaniline (522 mg, 2.05 mmol) in dry DMF (5 mL) at 0° C. under Argon atmosphere, was added NaH (60% in mineral oil, 86 mg, 1.05 eq.). After 30 minutes, iodomethane (320 mg, 2.26 mmol, 1.1 eq.) was added to the reaction mixture. The reaction was stirred at 0° C.-r.t for 5 h. The reaction mixture was diluted with EtOAc (120 mL), and the mixture was washed with water (40 mL×2), brine, dried (Na$_2$SO$_4$), and concentrated to get crude product, which was purified on a silica gel column (eluting with hexanes/EtOAc 1/1 to 100% EtOAc) to give the desired product as yellow solid (448 mg, 81% yield). The nitro group was reduced to (±)—N$^1$-cyclopropyl-N$^1$-methyl-2-((methylsulfinyl)methyl)benzene-1,4-diamine as described for (±)-4-fluoro-3-((methylsulfinyl)methyl)aniline in Example 5 and used in the next step.

(±)-5-((4-(Cyclopropyl(methyl)amino)-3-((methylsulfinyl)methyl)phenyl)amino)-7-(cyclopropylamino)pyrazolo[1,5-a]pyrimidine-3-carbonitrile This compound was prepared in two steps from (±)—N$^1$-cyclopropyl-N$^1$-methyl-2-((methylsulfinyl)methyl)benzene-1,4-diamine and tert-butyl (5-chloro-3-cyanopyrazolo[1,5-a]pyrimidin-7-yl)(cyclopropyl)carbamate as described in Example 7. ES+, m/z 436.3 [M+1]; $^1$H NMR (500 MHz, DMSO-d$_6$), δ 9.64 (s, 1H), 8.34 (s, 1H), 8.20 (s, 1H), 7.78 (dd, J=2.0, 8.5 Hz, 1H), 7.53 (d, J=2.5 Hz, 1H), 7.41 (d, J=9.0 Hz, 1H), 5.98 (s, 1H), 3.99 (d, J=13.0 Hz, 1H), 3.94 (d, J=13.0 Hz, 1H), 2.66 (s, 3H), 2.60 (m, 1H), 2.53 (s, 3H), 2.53 (m, 1H), 0.82-0.80 (m, 2H), 0.72-0.70 (m, 2H), 0.53-0.52 (m, 2H), 0.33-0.31 (m, 2H).

Example 37

(±)-5-((4-(Azetidin-1-yl)-3-((methylsulfinyl)methyl)phenyl)amino)-7-(cyclopropylamino)pyrazolo[1,5-a]pyrimidine-3-carbonitrile (Cpd 37)

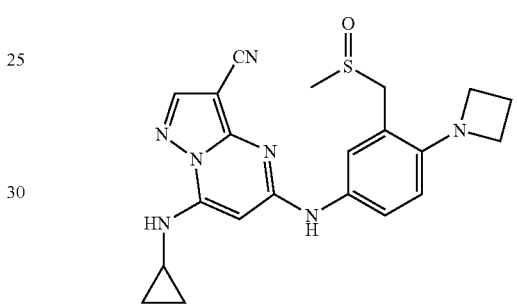

This compound was prepared using the same general method as described in Example 32.

Tan solid (36%); LCMS: 98%, t$_R$=1.664 min, m/z=422.4 [M+H]$^+$. $^1$H NMR (300 MHz, DMSO-d$_6$) δ 9.44 (s, 1H), 8.30 (s, 1H), 8.18-8.05 (m, 1H), 7.63-7.52 (m, 1H), 7.43-7.29 (m, 1H), 6.56 (dd, J=8.7 Hz, 1H), 5.91 (s, 1H), 4.05-3.79 (m, 6H), 2.64-2.55 (m, 1H), 2.60 (s, 3H), 2.30-2.14 (m, 2H), 0.85-0.74 (m, 2H), 0.74-0.63 (m, 2H). m.p.=204-207° C.

Example 38

(±)-5-((4-(1-(Aminomethyl)cyclopropyl)-3-((methylsulfinyl)methyl)phenyl)amino)-7-(cyclopropylamino)pyrazolo[1,5-a]pyrimidine-3-carbonitrile (Cpd 38)

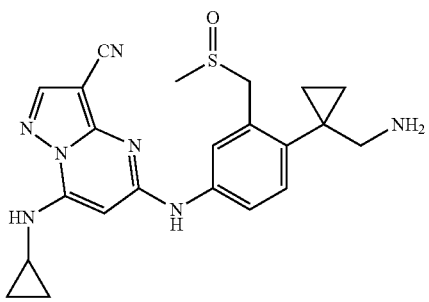 [SMILES: CS(=O)Cc1cc(Nc2cc(NC3CC3)n3ncc(C#N)c3n2)ccc1C1(CN)CC1]

Ethyl 2-cyano-2-(2-((methylthio)methyl)-4-nitrophenyl)acetate 1-(2-((Methylthio)methyl)-4-nitrophenyl)cyclopropane-1-carbonitrile

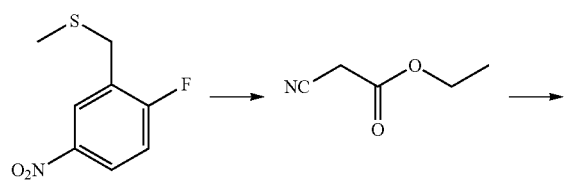

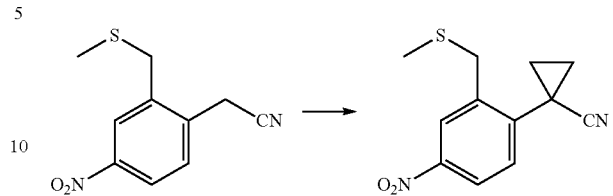

To a mixture of 2-(2-((methylthio)methyl)-4-nitrophenyl)acetonitrile (3.72 g, 16.76 mmol), 1,2-dibromoethane (6.3 g, 33.5 mmol, 2.0 eq.), tetrabutylammonium bromide (5.4 g, 16.76 mmol, 1.0 eq.), in DCM (60 mL) under Argon, was added aqueous NaOH (5N, 21.8 mL, 109 mmol, 6.5 eq.). The resulting reaction mixture was stirred at 35° C. for 3 days. The reaction mixture was diluted with DCM (300 mL) and water (100 mL). The organic phase was separated. The aqueous phase was further extracted with DCM (100 mL×2). The combined extracts were washed with brine (50 mL×2), dried ($Na_2SO_4$), and concentrated. The crude product was purified on a silica gel column (eluting with hexanes to 10% EtOAc/hexanes) to give the product as a reddish solid (2.32 g, 55.8% yield).

To a solution of (2-fluoro-5-nitrobenzyl)(methyl)sulfane (4.53 g, 22.5 mmol), ethyl 2-cyanoacetate (5.08 g, 45.02 mmol, 2.0 eq.) in dry DMF (20 mL), was added $K_2CO_3$ (6.21 g, 45.0 mmol, 2.0 eq.). The resulting mixture was heated at 100° C. under Argon for 3 h. After cooling down to r.t., the reaction mixture was acidified with aqueous 2N HCl (about 48 mL) to pH 3-4. The aqueous mixture was extracted with EtOAc (100 mL×2). The organic extractions were combined and washed with water (50 mL×2), brine, dried ($Na_2SO_4$), and concentrated. The crude product was purified on a silica gel column (eluting with hexanes to 10% EtOAc/hexanes) to give the product as a light yellow oil (5.88 g, 89% yield).

tert-Butyl ((1-(2-((methylthio)methyl)-4-nitrophenyl)cyclopropyl)methyl)carbamate

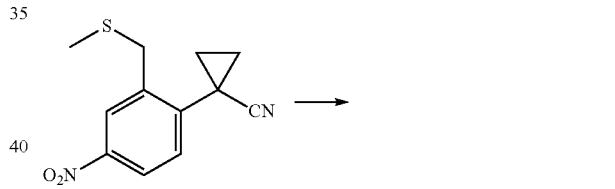

2-(2-((Methylthio)methyl)-4-nitrophenyl)acetonitrile

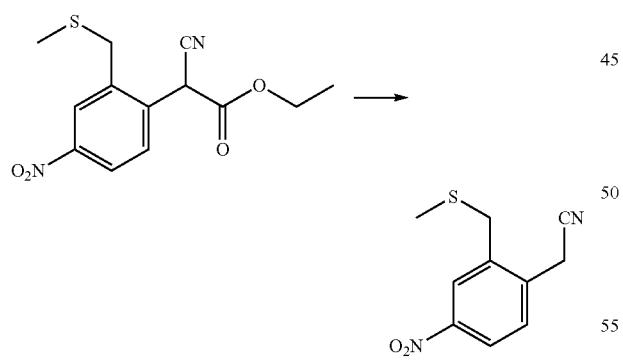

A mixture of ethyl 2-cyano-2-(2-((methylthio)methyl)-4-nitrophenyl)acetate (5.88 g, 20 mmol) in dioxane (100 mL) and aqueous 6N HCl (50 mL) was heated at 100° C. for 5 h. The reaction mixture was cooled down to r.t., extracted with $Et_2O$ (100 mL×3). The combined organic extracts were washed with brine (100 mL×2), dried ($Na_2SO_4$), and concentrated. The crude residue was purified on a silica gel column (eluting with hexanes to 10% EtOAc/hexanes) to give the product as a light yellow solid (4.15 g, 93% yield).

To a solution of 1-(2-((methylthio)methyl)-4-nitrophenyl)cyclopropane-1-carbonitrile (435 mg, 1.754 mmol) in dry THF (10 mL) under Argon, was added borane in THF (1M, 7.0 mL, 4.0 eq.). The resulting reaction mixture was refluxed for 4 h. After cooling down to r.t., the reaction mixture was quenched by addition of ice water (10 mL) in portions. The resulting mixture was adjusted to pH to 10 by addition of 2 N aqueous NaOH. To this basic aqueous mixture, was added ($Boc)_2O$ (573 mg, 2.63 mmol, 1.5 eq.). The reaction was then stirred at r.t. for 3 h. The reaction mixture was extracted with EtOAc (50 mL×2). The combined extracts were washed with brine, dried ($Na_2SO_4$), and concentrated. The crude product was purified on a silica gel column [eluting with hexanes/EtOAc (10/1)] to get the title compound as a light yellow oily product (390 mg, 63.2% yield in two steps).

(±)-tert-Butyl ((1-(2-((methylsulfinyl)methyl)-4-nitrophenyl)cyclopropyl)methyl)carbamate

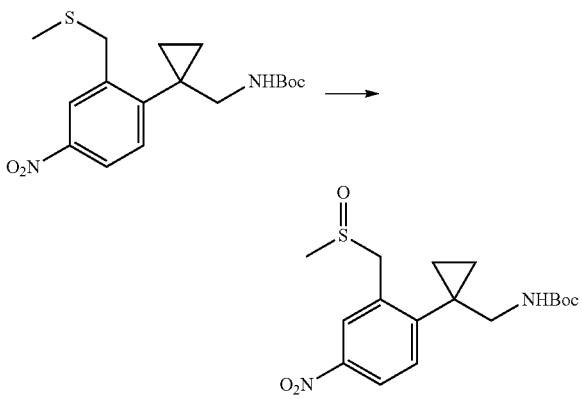

To a solution of tert-butyl ((1-(2-((methylthio)methyl)-4-nitrophenyl)cyclopropyl)methyl)carbamate (380 mg, 1.08 mmol) in DCM (10 mL) at 0° C., was added MCPBA (77%, 254 mg, 1.05 eq.). The reaction mixture was stirred at 0° C. to r.t. for 3.5 h. The mixture was diluted with DCM (50 mL), washed with 1N of NaOH aqueous solution (10 mL), brine (10 mL), dried (Na$_2$SO$_4$), and concentrated. The residue was purified on a silica gel column (eluting with hexanes/EtOAc 1/1 to 100% EtOAc) to get the title compound as a white solid (298 mg, 75% yield).

The nitro group was reduced to (±)-tert-butyl ((1-(4-amino-2-((methylsulfinyl)methyl)phenyl)cyclopropyl)methyl)carbamate as described for (±)-4-fluoro-3-((methylsulfinyl)methyl)aniline in Example 5 and used in the next step.

(±)-5-((4-(1-(Aminomethyl)cyclopropyl)-3-((methylsulfinyl)methyl)phenyl)amino)-7-(cyclopropylamino)pyrazolo[1,5-a]pyrimidine-3-carbonitrile This compound was prepared in two steps from (±)-tert-butyl ((1-(4-amino-2-((methylsulfinyl)methyl)phenyl)cyclopropyl)methyl)carbamate and ten-butyl (5-chloro-3-cyanopyrazolo[1,5-a]pyrimidin-7-yl)(cyclopropyl)carbamate and neutralization as described in Example 7. ES+, m/z 436.3 [M+1]; $^1$H NMR (500 MHz, DMSO-d$_6$), δ 9.72 (s, 1H), 8.35 (s, 1H), 8.22 (s, 1H), 7.79 (d, J=7.0 Hz, 1H), 7.62 (d, J=2.5 Hz, 1H), 7.29 (d, J=8.5 Hz, 1H), 6.03 (s, 1H), 4.26 (d, J=13.0 Hz, 1H), 4.17 (d, J=13.0 Hz, 1H), 2.74 (s, 3H), 2.70-2.60 (m, 3H), 0.88-0.86 (m, 2H), 0.82-0.80 (m, 2H), 0.76-0.74 (m, 1H), 0.72-0.70 (m, 2H), 0.64-0.62 (m, 1H).

Example 39

5-((4-(1-(Aminomethyl)cyclopropyl)-3-((methylsulfonyl)methyl)phenyl)amino)-7-(cyclopropylamino)pyrazolo[1,5-a]pyrimidine-3-carbonitrile mono trifluoroacetic acid salt

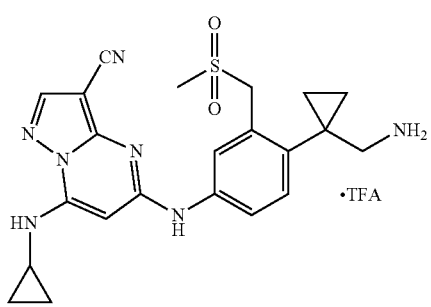 [SMILES: CS(=O)(=O)Cc1cc(Nc2cc(NC3CC3)n3ncc(C#N)c3n2)ccc1C1(CN)CC1]

This compound was prepared using the same general method as described in Example 7. ES+, m/z 452.3 [M+1]; $^1$H NMR (500 MHz, DMSO-d$_6$), δ 9.83 (s, 1H), 8.37 (s, 1H), 8.26 (s, 1H), 8.09 (dd, J=2.0, 8.5 Hz, 1H), 7.71 (brs, 3H), 7.60 (d, J=2.0 Hz, 1H), 7.41 (d, J=8.5 Hz, 1H), 6.05 (s, 1H), 4.70 (s, 2H), 3.40 (m, 2H), 3.23 (s, 3H), 2.62 (m, 1H), 1.08-1.06 (m, 2H), 0.90 (m, 2H), 0.83-0.80 (m, 2H), 0.73-0.71 (m, 2H).

Example 40

(±)-5-((4-(3-Aminoazetidin-1-yl)-3-((methylsulfinyl)methyl)phenyl)amino)-7-(cyclopropylamino)pyrazolo[1,5-a]pyrimidine-3-carbonitrile (Cpd 40)

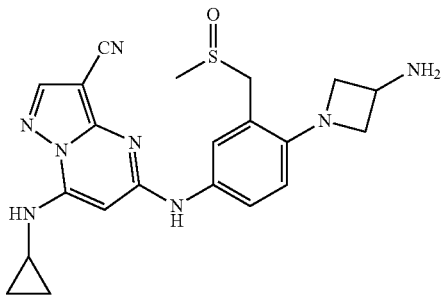 [SMILES: CS(=O)Cc1cc(Nc2cc(NC3CC3)n3ncc(C#N)c3n2)ccc1N1CC(N)C1]

This compound was prepared using the same general method as described in Example 7. ES+, m/z 437.4 [M+1]; $^1$H NMR (500 MHz, DMSO-d$_6$), δ 9.44 (s, 1H), 8.30 (s, 1H), 8.11 (s, 1H), 7.56 (d, J=8.0 Hz, 1H), 7.36 (s, 1H), 6.57 (d, J=9.0 Hz, 1H), 5.91 (s, 1H), 4.10-4.08 (m, 2H), 4.06 (d, J=13.0 Hz, 1H), 3.89 (d, J=13.0 Hz, 1H), 3.73 (m, 1H), 3.50-3.45 (m, 2H), 2.61 (s, 3H), 2.57 (m, 1H), 0.79-0.78 (m, 2H), 0.69 (m, 2H).

Example 41

5-((4-(3-Aminoazetidin-1-yl)-3-((methylsulfonyl)methyl)phenyl)amino)-7-(cyclopropylamino)pyrazolo[1,5-a]pyrimidine-3-carbonitrile (Cpd 41)

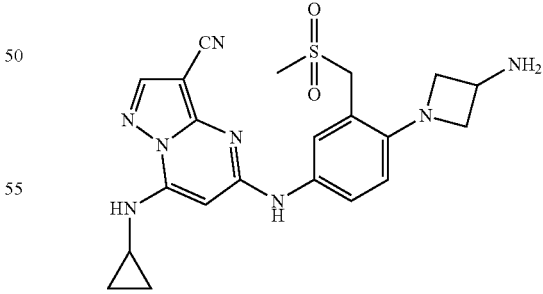

This compound was prepared using the same general method as described in Example 7. ES+, m/z 453.1 [M+1]; $^1$H NMR (500 MHz, DMSO-d$_6$), δ 9.46 (s, 1H), 8.30 (s, 1H), 8.11 (s, 1H), 7.66 (m, 1H), 7.38 (d, J=2.5 Hz, 1H), 6.62 (d, J=9.0 Hz, 1H), 5.92 (s, 1H), 4.37 (s, 2H), 4.13 (m, 2H), 3.72 (m, 1H), 3.51 (m, 2H), 3.01 (s, 3H), 2.57 (m, 1H), 0.80-0.77 (m, 2H), 0.70-0.67 (m, 2H).

Example 42

(±)-5-((4-(3-(Aminomethyl)azetidin-1-yl)-3-((methylsulfinyl)methyl)phenyl)amino)-7-(cyclopropylamino)pyrazolo[1,5-a]pyrimidine-3-carbonitrile (Cpd 42)

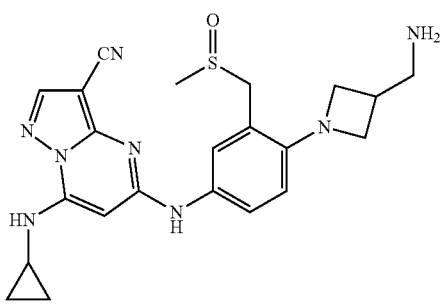 [SMILES: CS(=O)Cc1cc(Nc2cc(NC3CC3)n3ncc(C#N)c3n2)ccc1N1CC(CN)C1]

This compound was prepared using the same general method as described in Example 7. ES+, m/z 451.1 [M+1]; $^1$H NMR (500 MHz, DMSO-$d_6$), δ 9.43 (s, 1H), 8.30 (s, 1H), 8.11 (brs, 1H), 7.55 (brs, 1H), 7.36 (s, 1H), 6.55 (d, J=9.0 Hz, 1H), 5.90 (s, 1H), 4.00-3.96 (m, 2H), 3.95-3.89 (m, 2H), 3.65-3.60 (m, 2H), 2.86-2.84 (m, 2H), 2.58 (s, 3H), 2.61-2.56 (m, 2H), 0.79-0.78 (m, 2H), 0.71-0.69 (m, 2H).

Example 43

5-((4-(3-(Aminomethyl)azetidin-1-yl)-3-((methylsulfonyl)methyl)phenyl)amino)-7-(cyclopropylamino)pyrazolo[1,5-a]pyrimidine-3-carbonitrile (Cpd 43)

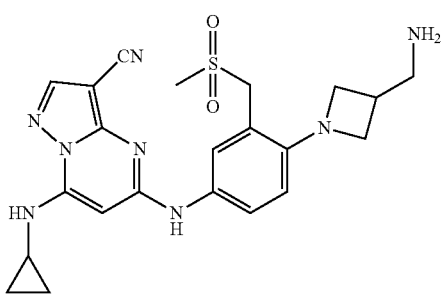 [SMILES: CS(=O)(=O)Cc1cc(Nc2cc(NC3CC3)n3ncc(C#N)c3n2)ccc1N1CC(CN)C1]

This compound was prepared using the same general method as described in Example 7. ES+, m/z 467.5 [M+1]; $^1$HNMR (500 MHz, DMSO-$d_6$), δ 9.45 (s, 1H), 8.30 (s, 1H), 8.11 (brs, 1H), 7.64 (brs, 1H), 7.37 (d, J=2.0 Hz, 1H), 6.58 (d, J=9.0 Hz, 1H), 5.92 (s, 1H), 4.37 (s, 2H), 3.98 (m, 2H), 3.67 (m, 2H), 3.00 (s, 3H), 2.84 (m, 2H), 2.60-2.57 (m, 2H), 0.80-0.77 (m, 2H), 0.70-0.67 (m, 2H).

Example 44

(±)-5-((4-(Azetidin-3-yl(methyl)amino)-3-((methylsulfinyl)methyl)phenyl)amino)-7-(cyclopropylamino)pyrazolo[1,5-a]pyrimidine-3-carbonitrile (Cpd 44)

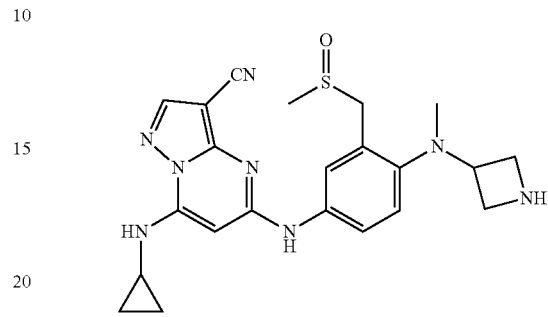

This compound was prepared using the same general method as described in Example 7. ES+, m/z 451.3 [M+1]; $^1$H NMR (500 MHz, DMSO-$d_6$), δ 9.71 (s, 1H), 8.35 (s, 1H), 8.23 (brs, 1H), 7.84 (dd, J=2.0, 8.5 Hz, 1H), 7.62 (d, J=2.5 Hz, 1H), 7.13 (d, J=9.0 Hz, 1H), 5.99 (s, 1H), 4.18 (d, J=12.5 Hz, 1H), 4.15 (d, J=12.5 Hz, 1H), 4.12 (m, 1H), 3.84 (m, 2H), 3.65 (m, 2H), 2.63 (s, 3H), 2.61-2.58 (m, 1H), 2.51 (s, 3H), 0.82-0.79 (m, 2H), 0.72-0.71 (m, 2H).

Example 45

5-((4-(Azetidin-3-yl(methyl)amino)-3-((methylsulfonyl)methyl)phenyl)amino)-7-(cyclopropylamino)pyrazolo[1,5-a]pyrimidine-3-carbonitrile (Cpd 45)

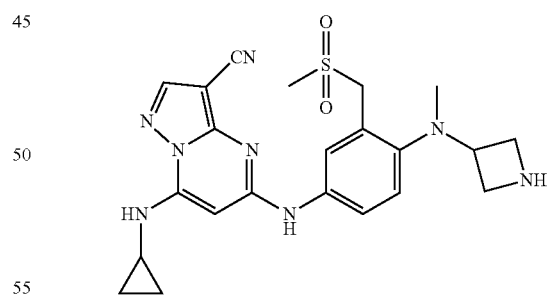

This compound was prepared using the same general method as described in Example 7. ES+, m/z 467.5 [M+1]; $^1$H NMR (500 MHz, DMSO-$d_6$), δ 9.73 (s, 1H), 8.35 (s, 1H), 8.23 (brs, 1H), 7.94 (d, J=7.5 Hz, 1H), 7.64 (d, J=2.5 Hz, 1H), 7.18 (d, J=8.5 Hz, 1H), 6.01 (s, 1H), 4.64 (s, 2H), 4.04 (m, 1H), 3.66 (m, 2H), 3.55 (m, 2H), 3.05 (s, 3H), 2.61 (m, 1H), 2.51 (s, 3H), 0.82-0.79 (m, 2H), 0.72-0.71 (m, 2H).

Example 46

(±)-7-(Cyclopropylamino)-5-((3-((methylsulfinyl)methyl)-4-(pyrrolidin-1-yl)phenyl)amino)pyrazolo[1,5-a]pyrimidine-3-carbonitrile (Cpd 46)

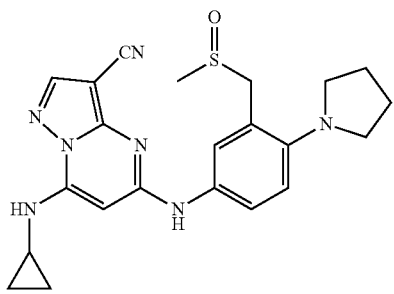 [SMILES: CS(=O)Cc1cc(Nc2cc(NC3CC3)n3ncc(C#N)c3n2)ccc1N1CCCC1]

This compound was prepared using the same general method as described in Example 7. ES+, m/z 436.5 [M+1]; $^1$H NMR (500 MHz, DMSO-$d_6$), δ 9.55 (s, 1H), 8.32 (s, 1H), 8.14 (brs, 1H), 7.67 (d, J=7.0 Hz, 1H), 7.50 (d, J=2.5 Hz, 1H), 7.11 (d, J=8.5 Hz, 1H), 5.96 (s, 1H), 4.10 (d, J=12.5 Hz, 1H), 4.04 (d, J=12.5 Hz, 1H), 3.08-3.05 (m, 4H), 2.59 (m, 1H), 2.56 (s, 3H), 1.88 (m, 4H), 0.81-0.78 (m, 2H), 0.72-0.69 (m, 2H).

Example 47

(±)-6-((4-((2-Aminoethyl)(methyl)amino)-3-((methylsulfinyl)methyl)phenyl)amino)-8-(cyclopropylamino)imidazo[1,2-b]pyridazine-3-carbonitrile mono trifluoroacetic acid salt (Cpd 47)

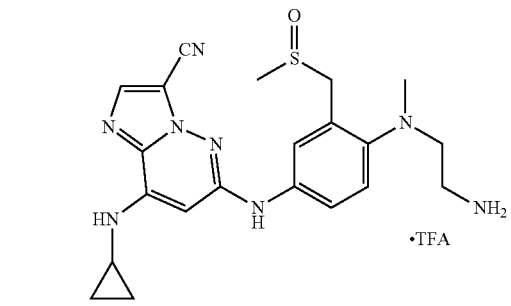

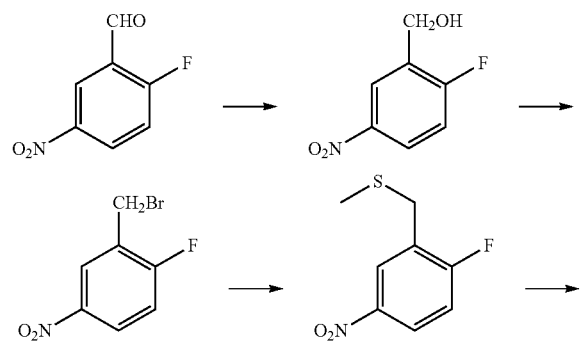

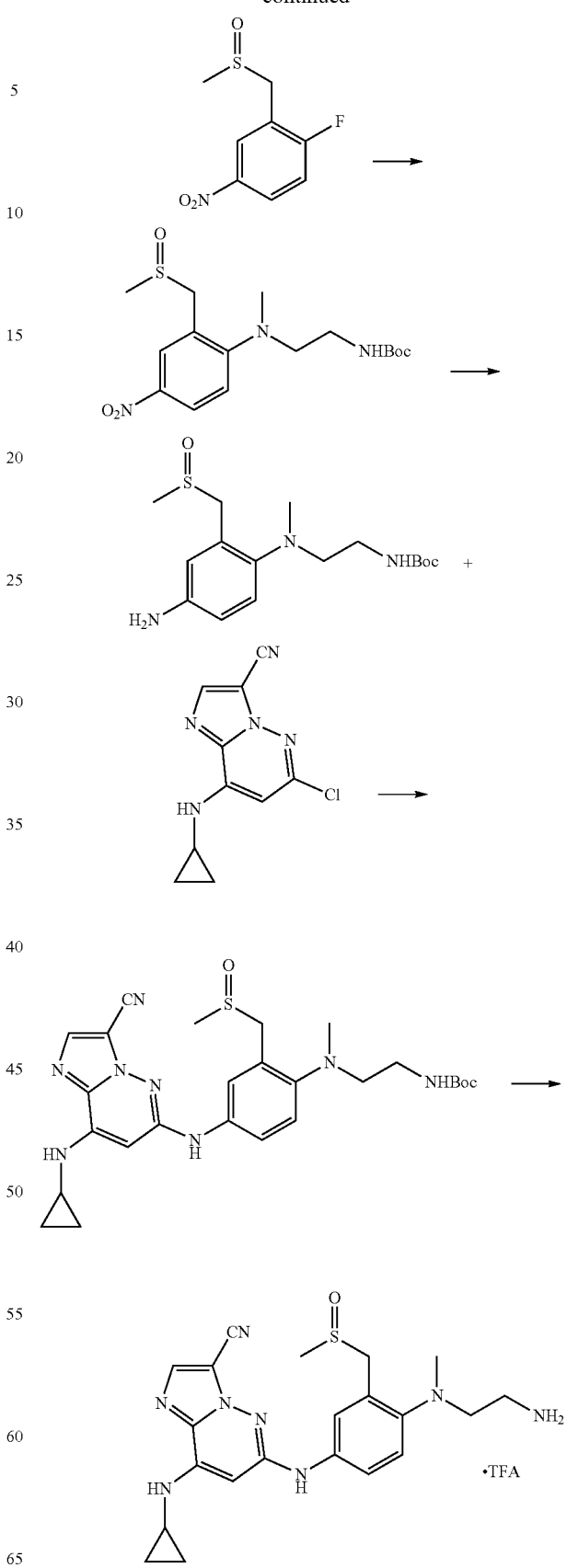

6-Chloro-8-(cyclopropylamino)imidazo[1,2-b]pyridazine-3-carbonitrile

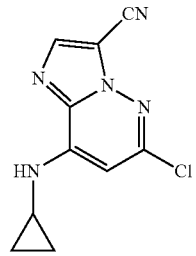

The preparation of 6-chloro-8-(cyclopropyl(4-methoxybenzyl)amino)imidazo[1,2-b]pyridazine-3-carbonitrile [1220631-47-9] has been described in WO2010/042699.

4-Bromo-6-chloropyridazin-3-amine

To a stirred solution of 6-chloropyridazin-3-amine (50 g, 387.1 mmol) in DMF (500 ml) was added NBS (103 g, 581.2 mmol) at room temperature under argon atmosphere. The reaction mixture was maintained at 65° C. for 5 h and the reaction progress was monitored by TLC. The reaction mixture was quenched with water and extracted with ethyl acetate (2×500 mL). The combined extracts were washed with brine, dried over $Na_2SO_4$, and concentrated to give the crude product, which was purified by silica gel column chromatography (eluting with 20% ethyl acetate in pet-ether) to give the title compound 4-bromo-6-chloropyridazin-3-amine (25 g, 31%) as a brown solid. ES+, m/z 210.1 [M+1].

Ethyl 2-chloro-3-oxopropanoate

To a stirred solution of ethyl 2-chloroacetate (150 g, 1.29 mol) and ethyl formate (157 g, 1.29 mol) in THF (1.5 L) was added potassium tert-butoxide (159.22 g, 1.419 mol) at 0° C. under argon atmosphere. The reaction mixture was stirred at room temperature for 16 h. The reaction mixture was filtered and the filter cake was washed with MTBE (500 mL). The combined organic layer was acidified with 1 N HCl and the two layers were separated. Organic layer was dried over $Na_2SO_4$ and concentrated to give ethyl 2-chloro-3-oxopropanoate (180 g, 95%) as a brown liquid. The crude product was taken into the next step without further purification.

Ethyl 6,8-dichloroimidazo[1,2-b]pyridazine-3-carboxylate and ethyl 8-bromo-6-chloroimidazo[1,2-b]pyridazine-3-carboxylate (mixture)

A mixture of 4-bromo-6-chloropyridazin-3-amine (55 g, 264.4 mmol) and ethyl 2-chloro-3-oxopropanoate (139 g, 925.4 mmol) was heated for 5 h at 95° C. The reaction was monitored by TLC. The reaction mixture was quenched with water and extracted with ethyl acetate (3×500 mL). The combined organic layer was washed with water (50 mL), brine (50 mL), dried over $Na_2SO_4$, and concentrated to give a crude product, which was passed through a silica gel column (eluting with ethyl acetate-petroleum ether 10:90 to 30:70) to afford a mixture of ethyl 6,8-dichloroimidazo[1,2-b]pyridazine-3-carboxylate and ethyl 8-bromo-6-chloroimidazo[1,2-b]pyridazine-3-carboxylate (43 g, 54%) as a dark brown solid. ES+, m/z 260.3 [M+1] and 304.2 [M+1].

6,8-Dichloroimidazo[1,2-b]pyridazine-3-carboxylic acid and 8-bromo-6-chloroimidazo[1,2-b]pyridazine-3-carboxylic acid (mixture)

To a stirred solution of a ethyl 6,8-dichloroimidazo[1,2-b]pyridazine-3-carboxylate and ethyl 8-bromo-6-chloroimidazo[1,2-b]pyridazine-3-carboxylate (43 g, ~165.33 mmol) mixture in THF (516 mL) and water (430 mL) was added $LiOH.H_2O$ (10.41 g, 248 mmol) at 0° C. The reaction mixture was stirred at room temperature for 2 h. The reaction was monitored by TLC. The solvents were removed by rotary evaporation and the residue was acidified with aqueous HCl (1N) to pH 2. The aqueous layer was extracted with ethyl acetate and the organic layer was washed with water (50 mL), brine (50 mL), dried over $Na_2SO_4$, and concentrated to give 6,8-dichloroimidazo[1,2-b]pyridazine-3-carboxylic acid and 8-bromo-6-chloroimidazo[1,2-b]pyridazine-3-carboxylic acid (28 g, 62.2%) as an off-white solid. ES+, m/z 232.2 [M+1] and 276.2 [M+1].

6,8-Dichloroimidazo[1,2-b]pyridazine-3-carboxamide and 8-bromo-6-chloroimidazo[1,2-b]pyridazine-3-carboxamide (mixture)

To a stirred solution of a 6,8-dichloroimidazo[1,2-b]pyridazine-3-carboxylic acid and 8-bromo-6-chloroimidazo[1,2-b]pyridazine-3-carboxylic acid mixture (28 g, ~121.2 mmol) in $CH_2Cl_2$ (20 mL) were added DMF (catalytic amount) followed by oxalyl chloride (61.52 g, 484.8 mmol) at 0° C. The reaction mixture was stirred for 1 h at 40° C. The solvent was evaporated completely below 35° C. to afford acid chloride, which was re-dissolved in 1,4-dioxane and cooled to 0° C., prior to the addition of ammonia in THF (280 mL). The reaction mixture was stirred at room temperature for 2 h. The mixture was concentrated to remove most of the solvent and the residue was diluted with water. The solid thus precipitated was filtered, dried, and purified on a silica gel column (eluting with 1% MeOH in $CH_2Cl_2$) to get 6,8-dichloroimidazo[1,2-b]pyridazine-3-carboxamide and 8-bromo-6-chloroimidazo[1,2-b]pyridazine-3-carboxamide (17 g, 60%) as a brown solid. ES+, m/z 231.2 [M+1] and 275.2 [M+1].

6,8-Dichloroimidazo[1,2-b]pyridazine-3-carbonitrile and 8-bromo-6-chloroimidazo[1,2-b]pyridazine-3-carbonitrile (mixture)

A mixture of 6,8-dichloroimidazo[1,2-b]pyridazine-3-carboxamide and 8-bromo-6-chloroimidazo[1,2-b]pyridazine-3-carboxamide (17 g, ~73.9 mmol) was suspended in $POCl_3$ and heated the mixture at 100° C. for 4 h. The reaction was monitored by TLC. Upon completion of the reaction, the excess reagent was removed in-vacuo. The residue was basified with saturated sodium bicarbonate solution and extracted with $CH_2Cl_2$ (2×200 mL). The combined organic layer was dried over $Na_2SO_4$ and evaporated to afford 6,8-dichloroimidazo[1,2-b]pyridazine-3-carbonitrile and 8-bromo-6-chloroimidazo[1,2-b]pyridazine-3-carbonitrile (15 g, 80%) as a dark brown solid. The crude product was taken into next step without further purification. ES+, m/z 213.2 [M+1] and 257 [M+1].

6-Chloro-8-(cyclopropyl(4-methoxybenzyl)amino)imidazo[1,2-b]pyridazine-3-carbonitrile To a stirred solution of 6,8-dichloroimidazo[1,2-b]pyridazine-3-carbonitrile and 8-bromo-6-chloroimidazo[1, 2-b]pyridazine-3-carbonitrile (15 g, 71.09 mmol) in THF (20 mL) was added DIPEA (14 mL, 78.19 mmol) at room temperature under argon atmosphere, prior to the addition of N-(4-methoxybenzyl)cyclopropanamine (13.99 g, 78.19 mmol) at room temperature. The reaction mixture was stirred for 4 h at 65° C. The reaction mixture was quenched with water and extracted with ethyl acetate (2×200 mL). The combined extracts were washed with brine, dried over $Na_2SO_4$, concentrated to give the crude product, which was purified on a silica gel column (eluting with 20% ethyl acetate: pet ether) to get the title compound 6-chloro-8-(cyclopropyl(4-methoxybenzyl)amino)imidazo[1,2-b]pyridazine-3-carbonitrile (18 g, 71.1%) as a pale yellow solid. ES+, m/z 354.4 [M+1].

6-Chloro-8-(cyclopropylamino)imidazo[1,2-b]pyridazine-3-carbonitrile

To a stirred solution of 6-chloro-8-(cyclopropyl(4-methoxybenzyl)amino)imidazo[1,2-b]pyridazine-3-carbonitrile (20 g, 56.6 mmol) in $CH_2Cl_2$ (150 mL), TFA was added (38.7 g, 339.0 mmol) at 0° C. The reaction mixture was stirred at room temperature for 12 h. The reaction mixture was concentrated and quenched with sat.NaHCO$_3$ and extracted with $CH_2Cl_2$ (2×200 mL). The combined extracts were washed with brine, dried over $Na_2SO_4$, concentrated to give the crude product, which was purified on a silica gel column (eluting with 40% ethyl acetate:pet-ether) to give the title compound 6-chloro-8-(cyclopropylamino)imidazo[1,2-b]pyridazine-3-carbonitrile as an off-white solid (8.0 g, 60.3%). ES+, m/z 234.2 [M+1]. $^1$H NMR (400 MHz, CDCl$_3$), δ 7.94 (s, 1H), 6.52 (s, 1H), 6.26 (brs, 1H), 2.67 (m, 1H), 1.01-0.96 (m, 2H), 0.77-0.73 (m, 2H).
Step 1

(2-Fluoro-5-nitrophenyl)methanol

To a stirred solution of 2-fluoro-5-nitrobenzaldehyde (30 g, 177.5 mmol) in methanol (350 mL) NaBH$_4$ (8.1 g, 213.01 mmol) was added portion wise at 0° C. The reaction mixture was allowed warm to room temperature and stirred for 1 h. After completion of the reaction as indicated by TLC, the solvents were removed by rotary evaporation. The residue was diluted with ice-cold water (100 mL) and the aqueous layer was extracted with EtOAc (3×150 mL), washed with brine, dried over anhydrous Na$_2$SO$_4$, filtered and concentrated under reduced pressure to afford (2-fluoro-5-nitrophenyl)methanol (30.3 g, yield: 99.8%, LC-MS: 96.7%) as an off-white solid. ES+, m/z 172.3 [M+1].
Step 2

2-(Bromomethyl)-1-fluoro-4-nitrobenzene

To a stirred solution of (2-fluoro-5-nitrophenyl)methanol (30 g, 175.43 mmol), PPh$_3$ (68.9 g, 263.15 mmol) in dry dichloromethane (800 ml), NBS (62.37 g, 350.87 mmol) was added in portions at 0° C. under argon atmosphere. The reaction mixture was stirred for 1.5 h at 0° C. The reaction mixture was diluted with dichloromethane (150 mL), washed with water (2×100 mL), brine (2×100 mL), dried Na$_2$SO$_4$ and concentrated. The crude product was purified on a silica gel column, eluting with ethyl acetate in pet-ether (2:98) to afford 2-(bromomethyl)-1-fluoro-4-nitrobenzene (33 g, yield: 80.7%, LC-MS: 97.6%) as an off-white solid. ES+, m/z 236.2 [M+1].

Step 3

(2-Fluoro-5-nitrobenzyl)(methyl)sulfane

To a stirred suspension of 2-(bromomethyl)-1-fluoro-4-nitrobenzene (33 g, 141.02 mmol) in methanol (470 ml), NaSMe (10.8 g, 155.12 mmol) was added portion wise at 0° C. The reaction mixture was allowed to warm to room temperature and stirred for 16 h. The solvents were removed by rotary evaporation, and the residue was dissolved in EtOAc (500 mL), washed with water (2×100 mL) and brine (2×100 mL), dried over anhydrous Na$_2$SO$_4$, filtered and concentrated under reduced pressure. The crude product was purified on a silica gel column, eluting with ethyl acetate in pet ether (2:98) to afford (2-fluoro-5-nitrobenzyl)(methyl)sulfane (24.1 g, yield: 85.0%, LC-MS: 98.8%) as a yellow oil. ES+, m/z 202.3 [M+1].
Step 4

(±)-1-Fluoro-2-(methylsulfinylmethyl)-4-nitrobenzene

To a stirred solution of (2-fluoro-5-nitrobenzyl)(methyl)sulfane (10 g, 49.75 mmol) in dichloromethane (230 mL) cooling with an ice bath, was added mCPBA (9.44 g, 54.72 mmol). The reaction mixture was allowed to warm to room temperature and stirred for 16 h. The reaction mixture was diluted with dichloromethane (100 mL), washed with NaHCO$_3$ (2×200 mL), brine (2×50 mL), dried over anhydrous Na$_2$SO$_4$, filtered and concentrated under reduced pressure. The crude product was purified on a silica gel column, eluting with MeOH in CH$_2$Cl$_2$ (5:95) to afford 1-fluoro-2-(methylsulfinylmethyl)-4-nitrobenzene (8.8 g, yield: 81.6%, LC-MS: 98.5%) as an off-white solid. ES+, m/z 218.1 [M+1].
Step 5 (also described in Example 7)

(±)-tert-Butyl 2-(methyl(2-(methylsulfinylmethyl)-4-nitrophenyl)amino)ethylcarbamate To a stirred solution of 1-fluoro-2-(methylsulfinylmethyl)-4-nitrobenzene (7 g, 32.25 mmol) in dry DMF (60 mL) at 0° C. were added tert-butyl 2-(methylamino)ethylcarbamate (6.7 g, 38.709 mmol) and K$_2$CO$_3$ (6.67 g, 48.37 mmol) and reaction mixture was stirred at 95° C. for 16 h. The reaction mixture was cooled to room temperature, diluted with cold water (50 mL) and extracted with EtOAc (2×50 mL). The combined organic layer was washed with brine (2×50 mL), dried over anhydrous Na$_2$SO$_4$, filtered and concentrated under reduced pressure to afford (±)-tert-butyl 2-(methyl(2-(methylsulfinylmethyl)-4-nitrophenyl)amino) ethylcarbamate (12 g, yield: 100%, LC-MS: 86%) as a brown liquid. ES+, m/z 372.2 [M+1].
Step 6 (also described in Example 7)

(±)-tert-Butyl 2-((4-amino-2-((methylsulfinyl)methyl)phenyl)(methyl)amino)ethyl)carbamate To a stirred solution of (±)-tert-butyl 2-(methyl(2-(methylsulfinylmethyl)-4-nitrophenyl)amino)ethylcarbamate (12 g, 32.34 mmol) in 70% aqueous ethanol at room temperature were added NH$_4$Cl (8.6 g, 161.72 mmol), Fe (9 g, 161.72 mmol) and stirred at 90° C. for 5 h. The reaction mixture was cooled to room temperature and filtered through celite pad. The filtrate was evaporated to get crude compound. The crude product was purified on a silica gel column (eluting with MeOH:CH$_2$Cl$_2$, 3:97) to afford tert-butyl 2-((4-amino- 2-(methylsulfinylmethyl)phenyl)(methyl)amino)ethylcarbamate (9.5 g, yield: 86.2%, LC-MS: 94%) as a brown solid. ES+, m/z 342.2 [M+1].

Step 7

(±)-tert-Butyl 2-((4-(3-cyano-8-(cyclopropylamino) imidazo[1,2-b]pyridazin-6-ylamino)-2-(methylsulfinylmethyl)phenyl)(methyl)amino)ethylcarbamate To a stirred solution of (±)-tert-butyl 2-((4-amino-2-(methylsulfinylmethyl)phenyl) (methyl)amino) ethylcarbamate (0.643 g, 1.88 mmol) in toluene (15 mL) at room temperature were added 6-chloro-8-(cyclopropylamino)imidazo[1,2-b]pyridazine-3-carbonitrile (0.4 g, 1.716 mmol), Cs₂CO₃ (1.1 g, 3.43 mmol), tBuXPhos (0.145 g, 0.34 mmol), Pd(OAc)₂ (0.115 g, 0.171 mmol). The reaction mixture was degassed with argon for 5 min and stirred at 130° C. under microwave for 2 h. The reaction mixture was extracted with EtOAc (3×100 mL). The organic layer was washed with water, brine, dried over anhydrous Na₂SO₄, filtered and concentrated under reduced pressure. The crude product was purified on a silica gel column (eluting with MeOH:CH₂Cl₂, 2:98) to give (±)-tert-butyl 2-((4-(3-cyano-8-(cyclopropylamino)imidazo[1,2-b]pyridazin-6-ylamino)-2-(methylsulfinylmethyl)phenyl)(methyl)amino)ethylcarbamate (0.25 g, yield: 39.6%, LC-MS: 92.1%) as a brown solid. ES+, m/z 539.3 [M+1].

Step 8

(±)-6-((4-((2-Aminoethyl)(methyl)amino)-3-((methylsulfinyl)methyl)phenyl)amino)-8-(cyclopropylamino)imidazo[1,2-b]pyridazine-3-carbonitrile mono trifluoroacetic acid salt To a stirred suspension of (±)-tert-butyl 2-((4-(3-cyano-8-(cyclopropylamino)imidazo[1,2-b]pyridazin-6-ylamino)-2-(methylsulfinylmethyl)phenyl)(methyl)amino)ethylcarbamate (200 mg 0.371 mmol) in dichloromethane (10 mL) was added TFA (4 mL) at 0° C. The reaction mixture was stirred at room temperature for 5 h. The reaction mixture was concentrated under reduced pressure. The crude product was purified by prep-HPLC (Mobile phase: 0.1% TFA in H₂O: ACN, Column: KROMOSIL-C18 (150*25), 10 u, Gradient: (T % B): 0/10, 6.3/55, 6.4/98, 8/98, 8.1/10, 10/10, Flow Rate: 25 ml/min, Diluent: ACN+H₂O+MeOH+THF) to get (±)-6-(4-((2-aminoethyl)(methyl)amino)-3-(methylsulfinylmethyl)phenylamino)-8-(cyclopropylamino)imidazo[1,2-b]pyridazine-3-carbonitrile (90 mg, as TFA salt, yield: 56%, HPLC-99.7%) as a pale brown solid. ES+, m/z 439.2 [M-TFA+H], ¹H NMR (400 MHz, DMSO-d₆), δ 9.37 (s, 1H), 8.12 (s, 1H), 7.85 (s, 1H), 7.76-7.67 (m, 5H), 7.28 (d, J=8.8 Hz, 1H), 6.23 (s, 1H), 4.61 (d, J=12.4 Hz, 1H), 4.14 (d, J=12.8 Hz, 1H), 3.16-3.03 (m, 2H), 2.97-2.85 (m, 2H), 2.70 (s, 3H) 2.55 (s, 3H), 0.82-0.78 (m, 2H), 0.67-0.64 (m, 2H). m.p.=91-94° C.

Example 48

6-((4-((2-aminoethyl)(methyl)amino)-3-((methylsulfonyl)methyl)phenyl)amino)-8-(cyclopropylamino) imidazo[1,2-b]pyridazine-3-carbonitrile mono trifluoroacetic acid salt (Cpd 48)

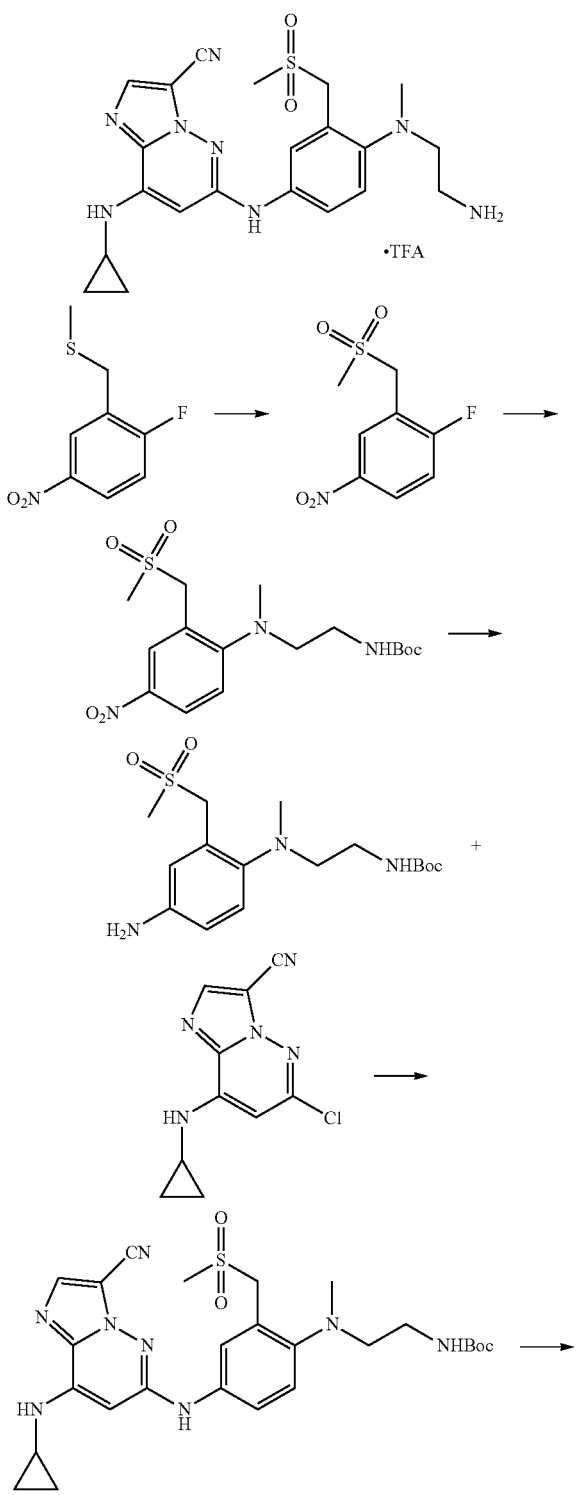

-continued

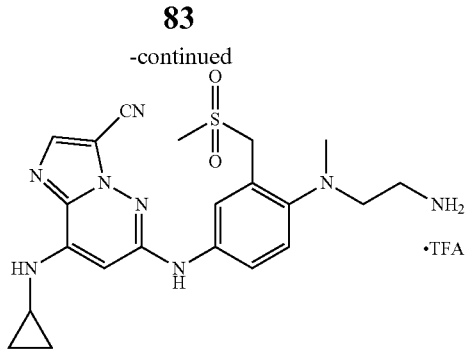

Step 1

1-Fluoro-2-(methylsulfonylmethyl)-4-nitrobenzene

To a stirred solution of (2-Fluoro-5-nitrobenzyl)(methyl)sulfane (10 g, 49.75 mmol) in dichloromethane (230 ml), mCPBA (235.74 g, 149.25 mmol) was added in portions at 0° C. The reaction mixture was allowed to warm to room temperature and stirred for 16 h. The reaction mixture was diluted with dichloromethane (100 mL), washed with NaHCO$_3$ (2×200 mL), brine (2×50 mL), dried over anhydrous Na$_2$SO$_4$, filtered and concentrated under reduced pressure. The crude product was purified on a silica gel column (eluting with MeOH: dichloromethane, 5:95) to afford 1-fluoro-2-(methylsulfonylmethyl)-4-nitrobenzene (11.7 g, yield: 100%, LC-MS: 97.4%) as an off white solid. ES−, m/z 232.0 [M−1].

Step 2 tert-Butyl 2-(methyl(2-(methylsulfonylmethyl)-4-nitrophenyl)amino)ethylcarbamate To a stirred solution of 1-fluoro-2-(methylsulfonylmethyl)-4-nitrobenzene (7 g, 30.05 mmol) in dry DMF (50 mL) at 0° C. were added tert-butyl 2-(methylamino)ethylcarbamate (6.27 g, 36.05 mmol) and K$_2$CO$_3$ (6.21 g, 45.06 mmol), and the reaction mixture was stirred at 95° C. for 16 h. The reaction mixture was cooled to room temperature, diluted with cold water (50 mL), extracted with EtOAc (2×50 mL). The combined organic layer was washed with brine (50 mL), dried over anhydrous Na$_2$SO$_4$, filtered and concentrated under reduced pressure to afford tert-butyl 2-(methyl(2-(methylsulfonylmethyl)-4-nitrophenyl)amino) ethylcarbamate (11.7 g, yield: 94%, LC-MS: 92.39%), as a brown liquid. ES+, m/z 388.2 [M+1].

Step 3 tert-Butyl 2-((4-amino-2-(methylsulfonylmethyl) phenyl) (methyl)amino)ethylcarbamate To a stirred solution of tert-butyl 2-(methyl(2-(methylsulfonylmethyl)-4-nitrophenyl)amino)ethylcarbamate (11.7 g, 30.23 mmol) in 70% aqueous ethanol (146 mL) at room temperature were added NH$_4$Cl (8.1 g, 151.16 mmol), Fe powder (8.5 g, 151.16 mmol) and the reaction mixture was stirred at 90° C. for 5 h. The reaction mixture was cooled to room temperature and filtered through celite pad, and the filtrate was concentrated under reduced pressure. The crude product was purified on a silica gel column (eluting with MeOH:dichloromethane 3:97) to afford tert-butyl 2-((4-amino-2-(methylsulfonylmethyl)phenyl) (methyl)amino) ethylcarbamate (9.2 g, 85.2%, LC-MS: 93%) as a brown semi solid. ES+, m/z 358.2 [M+1].

Step 4 tert-Butyl 2-((4-(3-cyano-8-(cyclopropylamino)imidazo[1,2-b]pyridazin-6-ylamino)-2-(methylsulfonylmethyl)phenyl)(methyl)amino)ethylcarbamate To a stirred solution of tert-butyl 2-((4-amino-2-(methylsulfonylmethyl)phenyl)(methyl)amino) ethylcarbamate (0.3 g, 1.287 mmol) in toluene (15 ml) at room temperature were added 6-chloro-8-(cyclopropylamino)imidazo[1,2-b]pyridazine-3-carbonitrile (0.504 g, 1.416 mmol), Cs$_2$CO$_3$ (0.84 g, 2.575 mmol), tBuXPhos (0.108 g, 0.2575 mmol), and Pd(OAc)$_2$ (0.086 g, 0.128 mmol). The reaction mass was degassed with argon for 5 min and stirred at 130° C. under microwave for 2 h. The reaction mixture was extracted with EtOAc (3×100 mL). The organic layer was washed with water, brine, dried over anhydrous Na$_2$SO$_4$, filtered and concentrated under reduced pressure. The crude product was purified on a silica gel column (eluting with MeOH:CH$_2$Cl$_2$, 2:98) to afford tert-butyl 2-((4-(3-cyano-8-(cyclopropylamino)imidazo[1,2-b]pyridazin-6-ylamino)-2-(methylsulfonylmethyl)phenyl)(methyl)amino)ethylcarbamate (0.2 g, 28%, LC-MS: 92.1%) as a brown solid. ES+, m/z 555.3 [M+1].

Step 4

6-(4-((2-Aminoethyl)(methyl)amino)-3-(methylsulfonylmethyl)phenylamino)-8-(cyclopropylamino) imidazo[1,2-b]pyridazine-3-carbonitrile mono trifluoroacetic acid salt To a stirred suspension of tert-butyl 2-((4-(3-cyano-8-(cyclopropylamino)imidazo[1,2-b]pyridazin-6-ylamino)-2-(methylsulfonylmethyl)phenyl)(methyl)amino)ethylcarbamate (200 mg) in CH$_2$Cl$_2$ (15 mL) was added TFA (5 mL) at 0° C. The reaction mixture was stirred at room temperature for 5 h. The reaction mixture was concentrated under reduced pressure to obtain a brown gummy solid. The crude was washed with ethyl acetate, diethyl ether, and purified by prep-HPLC (Mobile phase: 0.1% TFA in H$_2$O:ACN, Column: KROMOSIL-C18 (150*25), 10 u, Gradient: (T % B): 0/10, 6/55, 7/55, 7.1/98, 9/98, 9.1/10, 11/10, Flow Rate: 25 ml/min, Diluent: ACN+H$_2$O+MeOH+THF) to afford 6-(4-((2-aminoethyl)(methyl)amino)-3-(methylsulfonylmethyl) phenylamino)-8-(cyclopropylamino)imidazo[1,2-b] pyridazine-3-carbonitrile (120 mg as a TFA salt, yield: 79.7%, LC-MS: 95.5%, HPLC: 97.87%) as an off white solid. ES+, m/z 455.2 [M-TFA+H]; [C$_{21}$H$_{26}$N$_8$O$_2$S] $^1$H NMR (500 MHz, DMSO-d$_6$), δ 9.38 (s, 1H), 8.12 (s, 1H), 7.98-7.97 (m, 1H), 7.85 (s, 1H), 7.57-7.56 (m, 4H), 7.33 (d, J=8.8 Hz, 1H), 6.25 (s, 1H), 4.62 (s, 2H), 3.09-3.07 (m, 5H), 2.97-2.94 (m, 2H), 2.55-2.43 (m, 4H), 0.81-0.79 (m, 2H), 0.66-0.65 (m, 2H). m.p.=121-124° C.

Example 49

(±)-2-((4-((2-aminoethyl)(methyl)amino)-3-((methylsulfinyl)methyl)phenyl)amino)-3-((methylsulfinyl)methyl)phenyl)amino)-4-(cyclopropylamino)imidazo[2,1-f][1,2,4]triazine-7-carbonitrile mono trifluoroacetic acid salt (Cpd 49)

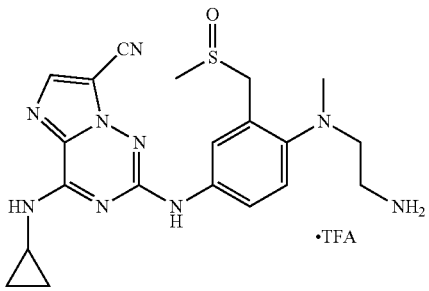 [SMILES: CN(CCN)c1ccc(Nc2nc(NC3CC3)c3ncc(C#N)n3n2)cc1CS(C)=O]

2-Chloro-4-(cyclopropylamino)imidazo[2,1-f][1,2,4]triazine-7-carbonitrile

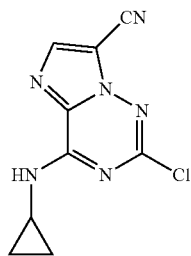 [SMILES: N#Cc1cnc2c(NC3CC3)nc(Cl)nn12]

The preparation of 2-chloro-4-(cyclopropyl(4-methoxybenzyl)amino)imidazo[2,1-f][1,2,4]triazine-7-carbonitrile has been described in US2015/0065465.

Ethyl 1-amino-1H-imidazole-2-carboxylate

To a stirred suspension of ammonium chloride (228 g, 4.28 mol) in MTBE (2.4 L), aq. $NH_3$ (1.2 L) was added at −20° C., prior to the addition of 11-14% sodium hypochlorite (3.5 L, 4.79 mol) at the same temperature over a period of 30 min. The reaction mixture was stirred at the same temperature for 1 h, after which the MTBE layer was separated and washed with brine solution. MTBE layer was dried over $Na_2SO_4$ and kept in the refrigerator and used immediately.

In an another flask NaH (20 g, 513.9 mmol) was suspended in DMF (600 mL) at −10° C., to which a solution of ethyl 1H-imidazole-2-carboxylate (60 g, 428.2 mmol) in DMF (150 mL) was added slowly. The reaction mixture was stirred at room temperature for 1.5 h and cooled to −20° C., prior to the drop-wise addition of the chloramine solution in MTBE. The reaction was stirred at −10° C. for 1 h and at room temperature for 2 h. The reaction was monitored by TLC. After completion of the reaction, the reaction mixture was cooled to 0° C. and quenched with 1 L of 10% $Na_2S_2O_3$ solution. Organic layer was separated; and the aqueous layer was extracted with EtOAc. The combined organic layer was washed with brine (500 mL), dried over $Na_2SO_4$, filtered and evaporated to get crude ethyl 1-amino-1H-imidazole-2-carboxylate as a solution in DMF, which was used in the next step as such. A small portion of the solution was dried in vacuo to remove DMF and the product was characterized by $^1$H-NMR and LC-MS. ES+, m/z 156.3 [M+1].

Ethyl 1-(ethoxycarbonylamino)-1H-imidazole-2-carboxylate

To a stirred solution of ethyl 1-amino-1H-imidazole-2-carboxylate in $CH_2Cl_2$ (750 mL), cooled to 10-15° C., were added pyridine (30 mL) followed by ethyl chloroformate (25 mL) and the reaction mixture was stirred at 10-15° C. for 1.5 h. Additional portions of pyridine (15 mL) and ethyl chloroformate (15 mL) were again added at 10-15° C. The reaction mixture was stirred for another ~1.5 h at 10-15° C. The reaction was monitored by TLC. The reaction mixture was concentrated under reduced pressure. The crude compound was diluted with EtOAc (1 L) and washed with 10% citric acid solution (180 mL). The citric acid solution was back extracted with EtOAc (3×1 L). The combined organic layer was washed with brine solution (2×80 mL), dried over $Na_2SO_4$ and concentrated to get a brown syrup, which was triturated with hexane and diethyl ether, and solid thus formed was collected by filtration and dried to afford ethyl 1-(ethoxycarbonylamino)-1H-imidazole-2-carboxylate (36 g, 61%). ES+, m/z 228.3 [M+1].

Imidazo[1,2-f][1,2,4]triazine-2,4-diol

A stirred solution of ethyl 1-(ethoxycarbonylamino)-1H-imidazole-2-carboxylate (36.0 g, 158.59 mmol, 1.0 eq.) in IPA (300 mL) was cooled to −50° C. and purged with ammonia gas for 30-60 min. The reaction mixture was transferred to autoclave, and heated at 120° C. for 20 h while maintaining the pressure at 8-10 kg/m$^2$. After 20 h, the reaction was cooled to room temperature and concentrated to get crude compound. The crude compound was suspended in minimal amount of methanol (360 mL) and stirred for 10 min, filtered and dried under vacuum to afford imidazo[1,2-f][1,2,4]triazine-2,4-diol (19 g, 77%) as an off-white solid. ES+, m/z 153.2 [M+1].

7-Bromoimidazo[1,2-f][1,2,4]triazine-2,4-diol

A stirred solution of imidazo[1,2-f][1,2,4]triazine-2,4-diol (19.0 g, 125.01 mmol) in water (850 mL) was cooled to 10-15° C. To this suspension was added portion-wise added NBS (7.7 g, 202.81 mmol). After completion of addition, the resulting mixture was stirred at room temperature for 1 h. The reaction was monitored by LC-MS. The reaction mixture was diluted with water and extracted with $CH_2Cl_2$ (3×200 mL). The $CH_2Cl_2$ extract was discarded and the aqueous layer was concentrated to dryness to afford crude product. The residue was suspended in methanol and stirred for 30 min. The resulting solid was collected by filtration and dried completely under high vacuum to afford 7-bromoimidazo[1,2-f][1,2,4]triazine-2,4-diol (22 g, 76.5%) as an off-white solid. ES+, m/z 231.1 [M+1].

7-Bromo-2,4-dichloroimidazo[1,2-f][1,2,4]triazine $POCl_3$ (236 mL, 2565 mmol, 25 eq) was added to a mixture of 7-bromoimidazo[1,2-f][1,2,4]triazine-2,4-diol (22.0 g, 95.65 mmol), TEA.HCl (26.33 g, 191.3 mmol) in a 2 L sealed tube. The reaction mixture was heated at 110° C. for 24 h. The reaction mixture was cooled to room temperature and concentrated to dryness to give residue. The residue was azeotroped with toluene (3×200 mL). The residue was cooled to 0° C. and slowly basified with saturated NaHCO₃ solution, and extracted with EtOAc (3×500 mL). The organic layer was washed with brine solution, dried over Na₂SO₄, filtered and concentrated to dryness to furnish 7-bromo-2,4-dichloroimidazo[1,2-f][1,2,4]triazine (32.5 g, crude) as a black solid, which was used in the next step without further purification. ES+, m/z 267.1 [M+1].

7-Bromo-2-chloro-N-cyclopropyl-N-(4-methoxybenzyl)imidazo[1,2-f][1,2,4]triazin-4-amine To a stirred solution of 7-bromo-2,4-dichloroimidazo[1,2-f][1,2,4]triazine (crude) (32.5 g, 122.18 mmol) and N-(4-methoxybenzyl)cyclopropanamine (25.96 g, 152.72 mmol) in THF (150 mL), DIPEA (15 mL) was added drop wise at room temperature and the reaction mixture was heated at 70° C. for 4 h. After completion, the reaction mixture was evaporated to give a crude compound, which was diluted with ethyl acetate and washed with water. The organic layer was separated, washed with brine, dried over Na₂SO₄ and concentrated to get the crude product, which was purified on a silica gel column (eluting with 5-10% ethyl acetate in pet ether) to give the title compound 7-bromo-2-chloro-N-cyclopropyl-N-(4-methoxybenzyl)imidazo[1,2-f][1,2,4]triazin-4-amine (34.5 g, 88.5%) as a white solid. ES+, m/z 408.2 [M+1].

2-Chloro-4-(cyclopropyl(4-methoxybenzyl)amino)imidazo[1,2-f][1,2,4]triazine-7-carbonitrile A mixture of 7-bromo-2-chloro-N-cyclopropyl-N-(4-methoxybenzyl)imidazo[1,2-f][1,2,4]triazin-4-amine (34.5 g, 84.76 mmol, 1.0 eq.) and CuCN (24.0 g, 268.7 mmol, 3.17 eq.) in NMP (700 mL) was stirred at room temperature for 10-15 min, then heated at 135-140° C. for 24 h. The reaction mixture was cooled to room temperature and diluted with ethyl acetate, filtered through celite-pad and washed with ethyl acetate. The filtrate was washed with water and brine solution. The organic layer was dried over Na₂SO₄, and concentrated to get crude compound, which was purified on a silica gel column (eluting with 10-15% of ethyl acetate and pet ether) to afford 2-chloro-4-(cyclopropyl(4-methoxybenzyl)amino)imidazo[1,2-f][1,2,4]triazine-7-carbonitrile (17.4 g, 58%) as an off-white solid. ES+, m/z 355.4 [M+1].

Chloro-4-(cyclopropylamino)imidazo[1,2-f][1,2,4]triazine-7-carbonitrile

To a stirred solution 2-chloro-4-(cyclopropyl(4-methoxybenzyl)amino)imidazo[1,2-f][1,2,4]triazine-7-carbonitrile (17.46 g, 49.32 mmol) in DCM (140 mL) was added TFA (84.35 g, 739.83 mmol) drop wise at 0° C. The reaction mixture was stirred for 16 h at room temperature. The reaction mixture was evaporated and the residual solution was diluted with ice cold water (100 mL) and the resulting solid was filtered. The residue was dissolved in ethyl acetate, the organic layer was washed with NaHCO₃ solution, brine and dried over Na₂SO₄, concentrated to give the crude compound, which was stirred with ethyl acetate (60 mL) for 30 min and filtered, and dried under vacuum to afford 2-chloro-4-(cyclopropylamino)imidazo[1,2-f][1,2,4]triazine-7-carbonitrile (6.0 g, 34.5%) as a white solid. ES+, m/z 235.2 [M+1]. ¹H NMR (400 MHz, CDCl₃), δ 7.94 (s, 1H), 6.87 (brs, 1H), 3.16 (m, 1H), 1.08-1.03 (m, 2H), 0.81-0.77 (m, 2H).

Step 1

(±)-tert-Butyl 2-((4-(7-cyano-4-(cyclopropylamino)imidazo[1,2-f][1,2,4]triazin-2-ylamino)-2-(methylsulfinyl)methyl)phenyl)(methyl)amino)ethylcarbamate This compound was prepared using the same general method as described in Example 47, step 7.

To a stirred solution of (±)-tert-butyl 2-((4-amino-2-(methylsulfinylmethyl)phenyl)(methyl)amino) ethylcarbamate (0.48 g, 1.41 mmol) in toluene (15 ml) at room temperature were added 2-chloro-4-(cyclopropylamino)imidazo[1,2-f][1,2,4]triazine-7-carbonitrile (0.3 g, 1.282 mmol), Cs₂CO₃ (0.836 g, 2.564 mmol), tBuXPhos (0.108 g, 0.256 mmol), and Pd(OAc)₂ (0.086 g, 0.128 mmol). The reaction mixture was degassed with argon for 5 min and stirred at 130° C. under microwaves for 2 h. The reaction mixture was extracted with EtOAc (3×50 mL). The organic layer was washed with water, brine, dried over anhydrous Na₂SO₄, filtered and concentrated under reduced pressure. The crude product was purified on a silica gel column (eluting with MeOH:CH₂Cl₂, 3:98) to give (±)-tert-butyl 2-((4-(7-cyano-4-(cyclopropylamino)imidazo[1,2-f][1,2,4]triazin-2-ylamino)-2-(methylsulfinylmethyl) phenyl) (methyl)amino)ethylcarbamate (0.14 g, yield: 29%, LC-MS: 93%) as a brown solid. ES+, m/z 540.3 [M+1].

Step 2

(±)-2-(4-((2-Aminoethyl)(methyl)amino)-3-(methylsulfinylmethyl)phenylamino)-4-(cyclopropylamino)imidazo[1,2-f][1,2,4]triazine-7-carbonitrile To a stirred suspension of (±)-tert-butyl 2-((4-(7-cyano-4-(cyclopropylamino)imidazo[1,2-f][1,2,4]triazin-2-ylamino)-2-(methylsulfinylmethyl)phenyl)(methyl)amino) ethylcarbamate (0.14 g, 0.259 mmol) in dichloromethane (10 mL) was added TFA (4 mL) at 0° C. The reaction mixture was stirred at room temperature for 3 h. The reaction mixture was concentrated under reduced pressure to obtain gummy solid. The crude product was dissolved in 5 mL of methanol/EtOAc (1/10), and was evaporated again to dryness. Compound was further lyophilized to furnish (±)-2-(4-((2-aminoethyl)(methyl)amino)-3-(methylsulfinylmethyl)phenylamino)-4-(cyclopropylamino)imidazo[1,2-f][1,2,4]triazine-7-carbonitrile (120 mg as a TFA salt, yield: 70%, LC-MS-97%) as a pale brown solid. ES+, m/z 440.2 [M-TFA+H]; [C₂₀H₂₅N₉OS] ¹H NMR (400 MHz, DMSO-d₆), δ 9.49 (s, 1H), 9.18 (d, J=4.4 Hz, 1H), 8.17 (s, 1H), 7.81 (s, 1H), 7.31 (dd, J=2.4 Hz, 2.4 Hz, 1H), 7.64 (bs, 3H), 7.26 (d, J=8.4 Hz, 1H), 4.61 (d, J=12.8 Hz, 1H), 4.12 (d, J=12.8 Hz, 1H), 3.15-3.12 (m, 3H), 2.93-2.85 (m, 2H), 2.70 (s, 3H) 2.54 (s, 3H), 0.82-0.81 (m, 4H). m.p.=93-97° C.

Example 50

2-((4-((2-aminoethyl)(methyl)amino)-3-((methylsulfonyl)methyl)phenyl)amino)-4-(cyclopropylamino)imidazo[2,1-f][1,2,4]triazine-7-carbonitrile mono trifluoroacetic acid salt (Cpd 50)

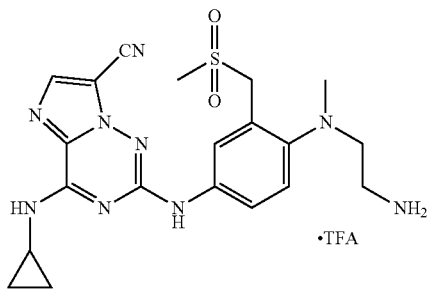 [SMILES: CN(CCN)c1ccc(Nc2nc(NC3CC3)c3ncc(C#N)n3n2)cc1CS(C)(=O)=O]

Step 1 tert-Butyl 2-((4-(7-cyano-4-(cyclopropylamino)imidazo[1,2-f][1,2,4]triazin-2-ylamino)-2-(methylsulfonylmethyl)phenyl)(methyl)amino)ethylcarbamate This compound was prepared using the same general method as described in Example 48, step 4.

To a stirred solution of tert-butyl 2-((4-amino-2-(methylsulfonylmethyl)phenyl) (methyl)amino) ethylcarbamate (0.42 g, 1.175 mmol) in toluene (10 ml) at room temperature were added 2-chloro-4-(cyclopropylamino)imidazo[1,2-f][1,2,4]triazine-7-carbonitrile (0.25 g, 1.06 mmol), CsCO$_3$ (0.69 g, 2.136 mmol), tBuXPhos (0.045 g, 0.106 mmol), and Pd(OAc)$_2$ (0.071 g, 0.106 mmol). The reaction mass was degassed with argon for 10 min and stirred at 130° C. under microwave for 2 h. The reaction mixture was extracted with EtOAc (3×50 mL). The organic layer was washed with water, brine, dried over anhydrous Na$_2$SO$_4$, filtered and concentrated under reduced pressure. The crude product was purified on a silica gel column (eluting with MeOH:CH$_2$Cl$_2$, 3:98) to provide tert-butyl 2-((4-(7-cyano-4-(cyclopropylamino)imidazo[1,2-f][1,2,4]triazin-2-ylamino)-2-(methylsulfonylmethyl)phenyl)(methyl)amino)ethylcarbamate (0.18 g, yield: 47%, LC-MS-95.9%) as a pale yellow solid. ES+, m/z 556.3 [M+1].

Step 2

2-((4-((2-aminoethyl)(methyl)amino)-3-((methylsulfonyl)methyl)phenyl)amino)-4-(cyclopropylamino)imidazo[2,1-f][1,2,4]triazine-7-carbonitrile mono trifluoroacetic acid salt To a stirred solution of tert-butyl 2-((4-(7-cyano-4-(cyclopropylamino)imidazo[1,2-f][1,2,4]triazin-2-ylamino)-2-(methylsulfonylmethyl)phenyl)(methyl)amino)ethylcarbamate (180 mg, 0.324 mmol) in CH$_2$Cl$_2$ (10 mL) was added TFA (4 mL) at 0° C. The reaction mixture was stirred at room temperature for 3 h. The reaction mixture was concentrated under reduced pressure to obtain pale yellow solid. The compound was lyophilized to afford 2-(4-((2-aminoethyl)(methyl)amino)-3-(methylsulfonylmethyl)phenylamino)-4-(cyclopropylamino)imidazo[1,2-f][1,2,4]triazine-7-carbonitrile (120 mg, as a TFA salt, yield: 87%, LC-MS: 97.1%) as an off-white solid. ES+, m/z 456.2 [M-TFA+H]; [C$_{20}$H$_{25}$N$_9$O$_2$S] $^1$H NMR (400 MHz, DMSO-d$_6$), δ 9.52 (s, 1H), 9.18 (d, J=4.4 Hz, 1H), 8.17 (s, 1H), 7.90 (dd, J=8.8 Hz, 8.8 Hz, 1H), 7.79 (d, J=2.0 Hz, 1H), 7.57 (bs, 3H), 7.31 (d, J=9.2 Hz, 1H), 4.60 (s, 2H), 3.17-3.13 (m, 3H), 3.06 (s, 3H), 2.96-2.93 (m, 2H), 2.54 (s, 3H), 0.83-0.80 (m, 4H). m.p.=113-117° C.

Example 51

(±)-2-((4-((2-aminoethyl)(methyl)amino)-3-((methylsulfinyl)methyl)phenyl)amino)-4-(cyclopropylamino)pyrazolo[1,5-a][1,3,5]triazine-8-carbonitrile mono trifluoroacetic acid salt (Cpd 51)

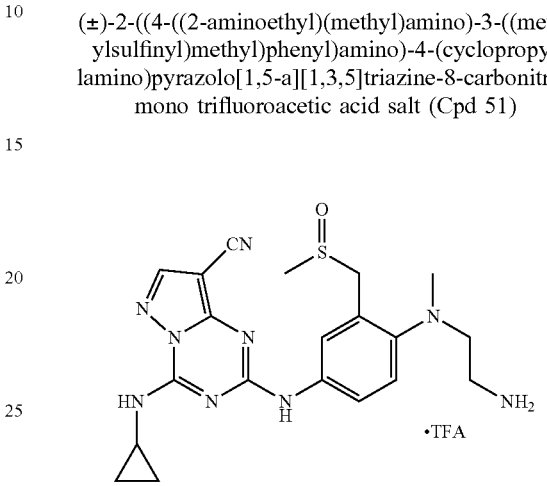

2-Chloro-4-(cyclopropylamino)pyrazolo[1,5-a][1,3,5]triazine-8-carbonitrile

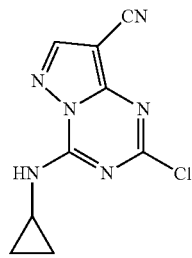 [SMILES: N#Cc1cnn2c(NC3CC3)nc(Cl)nc12]

This compound was prepared using a modification of the procedure described by Nie, et al, *BOMCL*, 2007, 17, 15, p. 4191.

Ethyl ((4-cyano-1H-pyrazol-5-yl)carbamothioyl)carbamate

To a stirred solution of 5-amino-1H-pyrazole-4-carbonitrile (50 g, 462.5 mmol) in ethyl acetate (1 L) was added ethoxycarbonyl isothiocyanate (66.7 g, 508.7 mmol) at room temperature under argon atmosphere. The reaction mass was heated for 2 h at 70° C. The solid was filtered and dried under vacuum to provide ethyl ((4-cyano-1H-pyrazol-5-yl)carbamothioyl)carbamate (80 g, 72.2%) as a yellow solid. This compound was taken into next step without further purification. ES+, m/z 240.3 [M+1].

4-Hydroxy-2-mercaptopyrazolo[1,5-a][1, 3, 5]triazine-8-carbonitrile

This compound [948575-58-4] was originally prepared by Nie, et al, *BOMCL*, 2007, 17, 15, p. 4191.

A suspension of ethyl ((4-cyano-1H-pyrazol-5-yl)carbamothioyl)carbamate (100 g, 462.5 mmol) in 2 N NaOH solution (1.0 L) was stirred at room temperature for 2 h. The solid was filtered and dried under vacuum to afford 4-hydroxy-2-mercaptopyrazolo[1,5-a][1,3,5]triazine-8-carbonitrile (80 g, 90%) as a pale yellow solid. The compound was taken to the next step without further purification. ES−, m/z 192.0 [M−1].

4-Hydroxy-2-(methylthio)pyrazolo[1,5-a][1,3,5]triazine-8-carbonitrile

To a stirred solution of 4-hydroxy-2-mercaptopyrazolo[1,5-a][1,3,5]triazine-8-carbonitrile (80 g, 414.5 mmol) in ethanol (1200 mL) was added 2 N NaOH solution (1.0 L) slowly at 0° C., prior to the addition of methyl iodide (117.71 g, 829 mmol) at 0° C. and the reaction mixture was stirred at room temperature for 2 h. The reaction mixture was acidified with aqueous HCl (5 N) to pH 2. The resulting solid was collected by filtration, washed with water, dried under vacuum to afford 4-hydroxy-2-(methylthio)pyrazolo[1,5-a][1,3,5]triazine-8-carbonitrile (62 g, 72%) as a pale yellow solid. This compound was taken to the next step without further purification. ES+, m/z 208.3 [M+1].

4-(Cyclopropylamino)-2-(methylthio)pyrazolo[1,5-a][1, 3, 5]triazine-8-carbonitrile To a stirred solution of 4-hydroxy-2-(methylthio)pyrazolo[1,5-a][1,3,5]triazine-8-carbonitrile (22 g, 106.0 mmol) in $POCl_3$ (20 mL) was added N,N-dimethylaniline (13.5 mL, 106.0 mmol) at room temperature under argon atmosphere. The reaction mixture was stirred at 115° C. for 4 h. $POCl_3$ was completely distilled under reduced pressure and further co-distilled twice with $CH_2Cl_2$. The crude compound was re-dissolved in $CH_2Cl_2$ (200 mL) and cooled to 0° C., prior to the addition of cyclopropyl amine (42.29 g, 742.0 mmol) at 0° C. The reaction mixture was stirred for 1 h at room temperature. The reaction mixture was quenched with water and extracted with $CH_2Cl_2$ (2×200 mL). The combined organic layer was dried over $Na_2SO_4$ and evaporated to get a green gummy solid (35 g), which was triturated with n-pentane to afford pure 4-(cyclopropylamino)-2-(methylthio)pyrazolo[1,5-a][1,3,5]triazine-8-carbonitrile (22 g, 84%) as a light green solid. ES+, m/z 247.3 [M+1].

4-(Cyclopropylamino)-2-(methylsulfonyl)pyrazolo[1,5-a][1,3,5]triazine-8-carbonitrile To a stirred solution of 4-(cyclopropylamino)-2-(methylthio)pyrazolo[1,5-a][1,3,5]triazine-8-carbonitrile (35 g, 142.0 mmol) in dichloroethane (770 mL) was added mCPBA (110.4 g, 640 mmol) at 0° C. The reaction mixture was stirred at rt for 6 h. The reaction mixture was quenched with 10% sodium sulfite solution and extracted with $CH_2Cl_2$ (3×200 mL). The combined extracts were washed with brine, saturated $NaHCO_3$ and dried over $Na_2SO_4$ and concentrated to provide the crude product, which was then purified on a silica gel column (eluting with 20-25% EtOAc in pet-ether) to get the title compound 4-(cyclopropylamino)-2-(methylsulfonyl)pyrazolo[1,5-a][1,3,5]triazine-8-carbonitrile (8.0 g) as a beige solid. ES+, m/z 279.3 [M+1].

2-Chloro-4-(cyclopropylamino)pyrazolo[1,5-a][1,3,5]triazine-8-carbonitrile 4-(Cyclopropylamino)-2-(methylsulfonyl)pyrazolo[1,5-a][1,3,5]triazine-8-carbonitrile (20 g, 71.9 mmol) was suspended in phenyl phosphonic dichloride (140 mL). Reaction mixture was heated for 6 h at 160° C. The reaction mixture was quenched with ice-cold water and extracted with ethyl acetate (3×100 mL). The combined organic layer was washed with sat. $NaHCO_3$ and dried over $Na_2SO_4$ and concentrated under vacuum. The crude product was purified by column chromatography using 100-200 mesh silica gel and desired product was eluted in 10-15% EtOAc in pet-ether to get the title compound 2-chloro-4-(cyclopropylamino)pyrazolo[1,5-a][1,3,5]triazine-8-carbonitrile (7.1 g, 42.5%) as an off-white solid. ES+, m/z 235.2 [M+1]. $^1H$ NMR (400 MHz, $CDCl_3$), δ 8.17 (s, 1H), 6.91 (brs, 1H), 3.11 (m, 1H), 1.10-1.05 (m, 2H), 0.86-0.82 (m, 2H).

Step 1

(±)-tert-Butyl 2-((4-(8-cyano-4-(cyclopropylamino)pyrazolo[1,5-a][1, 3, 5]triazin-2-ylamino)-2-(methylsulfinylmethyl)phenyl)(methyl)amino)ethylcarbamate To a stirred solution of (±)-tert-butyl 2-((4-amino-2-(methylsulfinylmethyl)phenyl)(methyl)amino)ethylcarbamate (0.48 g, 1.41 mmol) in toluene (15 ml) at room temperature were added 2-chloro-4-(cyclopropylamino)pyrazolo[1,5-a][1,3,5]triazine-8-carbonitrile (0.3 g, 1.282 mmol), $Cs_2CO_3$ (0.836 g, 2.564 mmol), tBuXPhos (0.108 g, 0.256 mmol), and $Pd(OAc)_2$ (0.086 g, 0.128 mmol). The reaction mass was degassed with argon for 5 min and stirred at 130° C. under microwave for 2 h. The reaction mixture was extracted with EtOAc (3×50 mL). The organic layer was washed with water, brine, dried over anhydrous $Na_2SO_4$, filtered and concentrated under reduced pressure. The crude product was purified on a silica gel column (eluting with MeOH:$CH_2Cl_2$, 3:98) to get (±)-tert-butyl 2-((4-(8-cyano-4-(cyclopropylamino)pyrazolo[1,5-a][1,3,5]triazin-2-ylamino)-2-(methylsulfinylmethyl)phenyl)(methyl)amino)ethylcarbamate (0.13 g, yield: 27%, LC-MS-83%) as a brown solid.

Step 2

(±)-2-(4-((2-Aminoethyl)(methyl)amino)-3-(methylsulfinylmethyl)phenylamino)-4-(cyclopropylamino)pyrazolo[1,5-a][1,3,5]triazine-8-carbonitrile mono trifluoroacetic acid salt To a stirred suspension of (±)-tert-butyl 2-((4-(8-cyano-4-(cyclopropylamino)pyrazolo[1,5-a][1,3,5]triazin-2-ylamino)-2-(methylsulfinylmethyl)phenyl)(methyl)amino)ethylcarbamate (0.13 g, 0.241 mmol) in dichloromethane (10 mL) was added TFA (3 mL) at 0° C. The reaction mixture was stirred at room temperature for 3 h. The reaction mixture was concentrated under reduced pressure to obtain gummy solid. The crude was dissolved in 5 mL of methanol/EtOAc (1/10) and the resulting solution was evaporated again to dryness. The crude product was purified by prep-HPLC (Mobile phase: 0.1% TFA in $H_2O$: ACN, Column: KROMOSIL-C18 (150*25), 10 u, Gradient: (T % B): 0/10, 6.3/55, 6.4/98, 8/98, 8.1/10, 10/10, Flow Rate: 25 ml/min, Diluent: ACN+H₂O+MeOH+THF) to get (±)-2-(4-((2-aminoethyl)(methyl)amino)-3-(methylsulfinylmethyl)phenylamino)-4-(cyclopropylamino)pyrazolo[1,5-a][1,3,5]triazine-8-carbonitrile (90 mg as a TFA salt, yield: 90%, LC-MS-98%) as a pale brown solid. ES+, m/z 440.2 [M-TFA+H]: [C₂₀H₂₅N₉OS] ¹H NMR (400 MHz, DMSO-d₆), δ 10.05 (bs, 1H), 9.15 (bs, 1H), 8.38 (s, 1H), 7.83 (m, 2H), 7.66 (bs, 3H), 7.29 (d, J=8.8 Hz, 1H), 4.27 (d, J=12.8 Hz, 1H), 4.16 (d, J=12.8 Hz, 1H), 3.16-3.00 (m, 3H), 2.95-2.86 (m, 2H), 2.70 (s, 3H), 2.55 (s, 3H), 0.82-0.81 (m, 4H). m.p.=78-82° C.

Example 52

2-((4-((2-aminoethyl)(methyl)amino)-3-((methylsulfonyl)methyl)phenyl)amino)-4-(cyclopropylamino)pyrazolo[1,5-a][1,3,5]triazine-8-carbonitrile mono trifluoroacetic acid salt (Cpd 52)

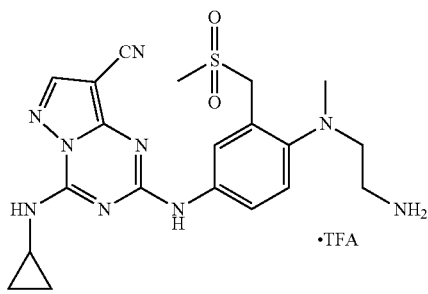 [SMILES: CN(CCN)c1ccc(Nc2nc(NC3CC3)n3ncc(C#N)c3n2)cc1CS(C)(=O)=O]

Step 1 tert-Butyl 2-((4-(8-cyano-4-(cyclopropylamino)pyrazolo[1,5-a][1, 3, 5]triazin-2-ylamino)-2-(methylsulfonylmethyl)phenyl)(methyl)amino)ethylcarbamate To a stirred solution of tert-butyl 2-((4-amino-2-(methylsulfonylmethyl)phenyl)(methyl)amino)ethylcarbamate (0.336 g, 0.940 mmol) in toluene (15 ml) at room temperature were added 2-chloro-4-(cyclopropylamino)pyrazolo[1,5-a][1,3,5]triazine-8-carbonitrile (0.20 g, 0.854 mmol), Cs₂CO₃ (0.55 g, 1.709 mmol), tBuXPhos (0.073 g, 0.170 mmol), and Pd(OAc)₂ (0.058 g, 0.085 mmol). The reaction mass was degassed with argon for 10 min and stirred at 130° C. under microwave for 2 h. The reaction mixture was extracted with EtOAc (3×50 mL). The organic layer was washed with water (2×20 mL), brine (2×25 mL), dried over anhydrous Na₂SO₄, filtered and concentrated under reduced pressure. The crude product was purified on a silica gel column (eluting with MeOH:CH₂Cl₂, 3:98) to get tert-butyl 2-((4-(8-cyano-4-(cyclopropylamino)pyrazolo[1,5-a][1,3,5]triazin-2-ylamino)-2-(methylsulfonylmethyl)phenyl)(methyl)amino)ethylcarbamate (0.15 g, yield: 48%, LC-MS-98%) as a white solid. ES+, m/z 556.3 [M+1].

Step 2

2-(4-((2-Aminoethyl)(methyl)amino)-3-(methylsulfonylmethyl)phenylamino)-4-(cyclopropylamino)pyrazolo[1,5-a][1,3,5]triazine-8-carbonitrile mono trifluoroacetic acid salt To a stirred solution of tert-butyl 2-((4-(8-cyano-4-(cyclopropylamino)pyrazolo[1,5-a][1,3,5]triazin-2-ylamino)-2-(methylsulfonylmethyl)phenyl)(methyl)amino)ethylcarbamate (150 mg, 0.270 mmol) in CH₂Cl₂ (10 mL) was added TFA (4 mL) at 0° C. The reaction mixture was stirred at room temperature for 4 h. The reaction mixture was concentrated under reduced pressure to obtain an off-white solid. The crude compound was dissolved in 5 mL of ethyl acetate/diethyl ether and the resulting solution was concentrated under reduced pressure. Finally the compound was lyophilized to afford 2-(4-((2-aminoethyl)(methyl)amino)-3-(methylsulfonylmethyl)phenylamino)-4-(cyclopropylamino)pyrazolo[1,5-a][1,3,5]triazine-8-carbonitrile mono trifluoroacetic acid salt (100 mg, 81%, LC-MS-96.7%) as an off-white solid. ES+, m/z 456.2 [M-TFA+H]: [C₂₀H₂₅N₉O₂S] ¹H NMR (400 MHz, DMSO-d₆), δ 10.05 (bs, 1H), 9.15 (bs, 1H), 8.38 (s, 1H), 7.88 (d, J=8.8 Hz, 2H), 7.57 (bs, 3H), 7.34 (d, J=9.2 Hz, 1H), 4.62 (s, 2H), 3.07 (bs, 6H), 2.97-2.89 (m, 2H), 2.54 (s, 3H), 0.82-0.81 (m, 4H). m.p.=55-59° C.

Example 53

(±)-7-(cyclopropylamino)-5-((3-((methylsulfinyl)methyl)-4-(1,2,5,6-tetrahydropyridin-3-yl)phenyl)amino)pyrazolo[1,5-a]pyrimidine-3-carbonitrile mono trifluoroacetic acid salt (Cpd 53)

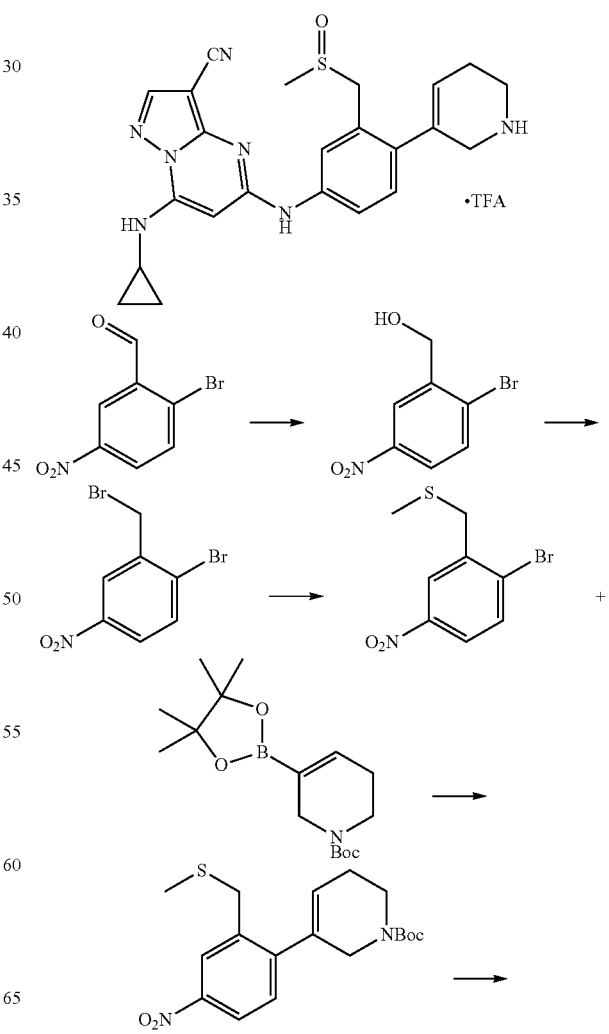

-continued

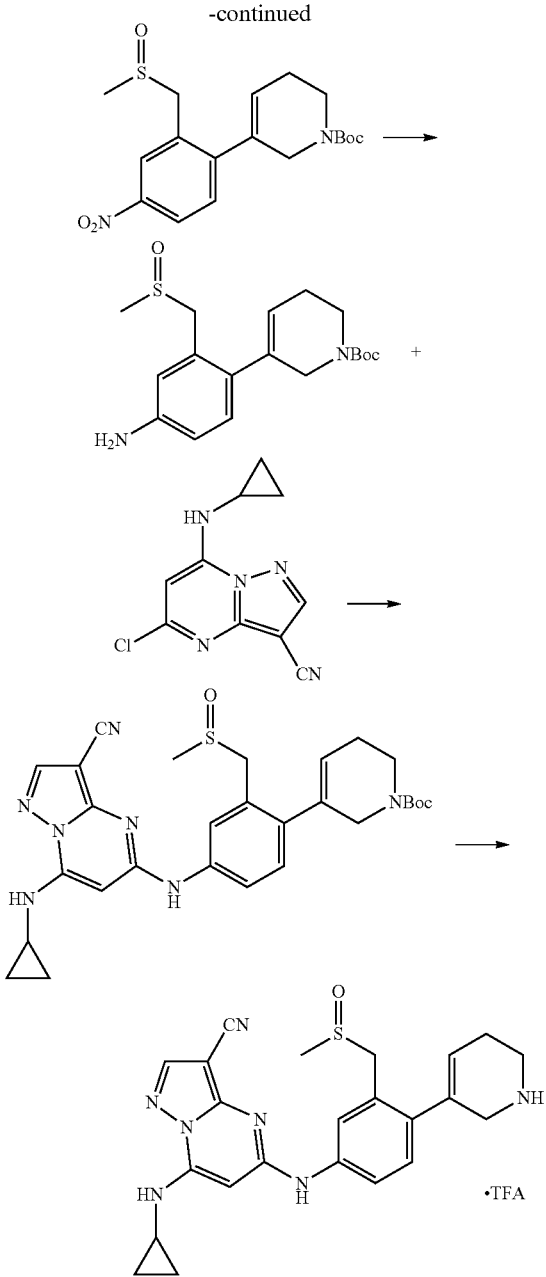

Step 1

(2-Bromo-5-nitrophenyl)methanol

To a stirred solution of 2-bromo-5-nitrobenzaldehyde (10 g, 43.47 mmol) in methanol (150 mL), NaBH$_4$ (1.93 g, 52.17 mmol) was added portion-wise at 0° C. The reaction mixture was allowed to warm to room temperature and stirred for 1 h. After completion of the reaction as indicated by TLC, the solvents were removed by rotary evaporation. The residue was diluted with ice-cold water (100 mL) and the aqueous layer was extracted with EtOAc (3×150 mL). The combined organic layer was washed with brine, dried over anhydrous Na$_2$SO$_4$, filtered and concentrated under reduced pressure to afford (2-bromo-5-nitrophenyl)methanol (9 g, 90%, LC-MS 92%) as an off-white solid. ES+, m/z 232.2 [M+1].

Step 2

1-Bromo-2-(bromomethyl)-4-nitrobenzene

To a stirred solution of (2-bromo-5-nitrophenyl)methanol (9 g, 38.7 mmol), PPh$_3$ (15.2 g, 58.18 mmol) in dry dichloromethane (100 mL), NBS (13.8 g, 77.58 mmol) was added in portions at 0° C. under argon atmosphere. The reaction mixture was stirred for 1.5 h at 0° C. The reaction mixture was diluted with dichloromethane (100 mL), washed with water, brine, dried over Na$_2$SO$_4$ and concentrated. The crude product was purified on a silica gel column, eluting with ethyl acetate in pet-ether (3:97) to afford 1-bromo-2-(bromomethyl)-4-nitrobenzene (11 g, 96%, LC-MS 92.9%) as an off-white solid. $^1$H NMR (400 MHz, CDCl$_3$), δ 8.33 (d, J=2.4 Hz 1H), 8.03 (dd, J=8.8, 3.2 Hz, 1H), 7.78 (d, J=8.8 Hz 1H), 4.63 (s, 2H).

Step 3

(2-Bromo-5-nitrobenzyl)(methyl)sulfane

To a stirred suspension of 1-bromo-2-(bromomethyl)-4-nitrobenzene (12.5 g, 42.80 mmol) in methanol (150 mL), NaSMe (3.3 g, 47.089 mmol) was added portion wise at 0° C. The reaction mixture was allowed to warm to room temperature and stirred for 16 h. The solvents were removed by rotary evaporation, and the residue was dissolved in EtOAc (500 mL). The resulting organic solution was washed with water, brine, dried over anhydrous Na$_2$SO$_4$, filtered and concentrated under reduced pressure. The crude product was purified on a silica gel column, eluting with ethyl acetate in pet ether (3:97) to afford (2-bromo-5-nitrobenzyl)(methyl)sulfane (10.3 g, 92%, LC-MS 94.4%) as a brown solid. ES+, m/z 262.0 [M+1].

Step 4 tert-Butyl 3-(2-(methylthiomethyl)-4-nitrophenyl)-5,6-dihydropyridine-1 (2H)-carboxylate tert-butyl 3-(4,4,5,5-tetramethyl-1,3,2-dioxaborolan-2-yl)-5,6-dihydropyridine-1(2H)-carboxylate (7.07 g, 22.90 mmol), Cs$_2$CO$_3$ (12.44 g, 38.16 mmol) and Pd$_2$(dppf)DCM (0.836 g, 1.14 mmol) were added sequentially to a solution of (2-bromo-5-nitrobenzyl)(methyl)sulfane (5 g, 19.08 mmol) in a mixture of 1,4-dioxane/H$_2$O (100:10 mL, 10:1) at room temperature under argon atmosphere. The reaction mixture was refluxed for overnight. The reaction mixture was cooled to RT and diluted with EtOAc. The resulting organic layer was washed with water, brine, dried over anhydrous Na$_2$SO$_4$ and concentrated under reduced pressure to obtain the crude product. The crude product was purified by column chromatography (silica gel, eluent EtOAc-petroleum ether 30:70) to afford tert-butyl 3-(2-(methylthiomethyl)-4-nitrophenyl)-5,6-dihydropyridine-1(2H)-carboxylate (5 g, 72%, LC-MS 90.3%) as an off-white solid. ES−, m/z 363.1 [M−1].

Step 5

(±)-tert-Butyl 3-(2-(methylsulfinylmethyl)-4-nitrophenyl)-5,6-dihydropyridine-1(2H)-carboxylate To a stirred solution of tert-butyl 3-(2-(methylthiomethyl)-4-nitrophenyl)-5,6-dihydropyridine-1(2H)-carboxylate (5 g, 13.73 mmol) in dichloromethane (70 ml) was added mCPBA (2.60 g, 15.10 mmol) portion-wise at 0° C. The reaction mixture was allowed to warm to room temperature and stirred for 16 h. The reaction mixture was diluted with dichloromethane (100 mL), the organic layer was washed with aqueous NaHCO$_3$, brine, dried over anhydrous Na$_2$SO$_4$, filtered and concentrated under reduced pressure. The crude product was purified on a silica gel column eluting with MeOH in CH$_2$Cl$_2$ (5:95) to afford (±)-tert-butyl 3-(2-(methylsulfinylmethyl)-4-nitrophenyl)-5,6-dihydropyridine-1(2H)-carboxylate (5.2 g, 99%, LC-MS 87%) as an off-white solid. ES+, m/z 381.1 [M+1].

Step 6

(±)-tert-Butyl 3-(4-amino-2-(methylsulfinylmethyl)phenyl)-5,6-dihydropyridine-1(2H)-carboxylate To a stirred solution of (±)-tert-butyl 3-(2-(methylsulfinylmethyl)-4-nitrophenyl)-5,6-dihydropyridine-1(2H)-carboxylate (2.5 g, 6.578 mmol) in 70% aqueous ethanol at room temperature were added NH$_4$Cl (1.75 g, 32.89 mmol) and Fe (1.8 g, 32.89 mmol) and the reaction mixture was stirred at 90° C. for 5 h. The reaction mixture was cooled to room temperature and filtered through celite pad. The filtrate was evaporated to get crude compound. The crude product was purified on a silica gel column eluting with MeOH: CH$_2$Cl$_2$, (3:97) to afford (±)-tert-butyl 3-(4-amino-2-(methylsulfinylmethyl)phenyl)-5,6-dihydropyridine-1(2H)-carboxylate (2.2 g, 95%, LC-MS 95%) as a brown solid. ES+, m/z 351.2 [M+1].

Step 7

(±)-tert-Butyl 3-(4-(3-cyano-7-(cyclopropylamino)pyrazolo[1,5-a]pyrimidin-5-ylamino)-2-(methylsulfinylmethyl)phenyl)-5,6-dihydropyridine-1(2H)-carboxylate To a stirred solution of (±)-tert-butyl 3-(4-amino-2-(methylsulfinylmethyl)phenyl)-5,6-dihydropyridine-1(2H)-carboxylate (0.250 g, 0.714 mmol) in toluene (15 ml) at room temperature were added 5-chloro-7-(cyclopropylamino) pyrazolo[1,5-a]pyrimidine-3-carbonitrile (0.214 g, 0.64 mmol), Cs$_2$CO$_3$ (0.465 g, 1.42 mmol), BINAP (0.044 g, 0.07 mmol), Pd$_2$(dba)$_3$ (0.064 g, 0.07 mmol). The reaction mass was degassed with argon for 5 min and stirred at 135° C. under microwaves for 2 h. The reaction mixture was extracted with EtOAc (3×100 mL). The organic layer was washed with water, brine, dried over anhydrous Na$_2$SO$_4$, filtered and concentrated under reduced pressure. The crude product was purified on a silica gel column (eluting with MeOH:CH$_2$Cl$_2$, 2:98) to give (±)-tert-butyl 3-(4-(3-cyano-7-(cyclopropylamino)pyrazolo[1,5-a]pyrimidin-5-ylamino)-2-(methylsulfinylmethyl)phenyl)-5,6-dihydropyridine-1(2H)-carboxylate (0.18 g, 46%, HPLC 95%) as a pale yellow solid. ES+, m/z 548.3 [M+1].

Step 8

(±)-7-(Cyclopropylamino)-5-(3-(methylsulfinylmethyl)-4-(1,2,5,6-tetrahydropyridin-3-yl)phenylamino)pyrazolo[1,5-a]pyrimidine-3-carbonitrile To a stirred suspension of (±)-tert-butyl 3-(4-(3-cyano-7-(cyclopropylamino)pyrazolo[1,5-a]pyrimidin-5-ylamino)-2-(methylsulfinylmethyl)phenyl)-5,6-dihydropyridine-1(2H)-carboxylate (0.18 g 0.278 mmol) in dichloromethane (10 mL) was added TFA (3 mL) at 0° C. The reaction mixture was stirred at room temperature for 5 h. The reaction mixture was concentrated under reduced pressure. The crude product was purified by prep-HPLC (Mobile phase: 0.1% TFA in H$_2$O: MeOH, Column: KROMOSIL-C18 (150*25), 10 u, Gradient: (T % B): 0/35, 8/70, 8.1/98, 10/98, 10.1/35, 12/35, Flow Rate: 25 ml/min, Diluent:ACN+H$_2$O+MeOH+THF) to give (±)-7-(cyclopropylamino)-5-(3-(methylsulfinylmethyl)-4-(1,2,5,6-tetrahydropyridin-3-yl)phenylamino)pyrazolo[1,5-a]pyrimidine-3-carbonitrile (100 mg, as TFA salt, 71%, HPLC 99%) as an off-white solid. ES+, m/z 448.2 [M-TFA+1]$^+$; [C$_{23}$H$_{25}$N$_7$OS]; $^1$H NMR (400 MHz, DMSO-d$_6$): δ 9.82 (s, 1H), 8.98 (br s, 2H), 8.28 (s, 1H), 7.85 (dd, J=10.8, 6.8 Hz, 1H), 7.67 (d, J=2.0 Hz, 1H), 7.20 (d, J=8.4 Hz, 1H), 6.02 (s, 1H), 5.82 (s, 1H), 4.13 (d, J=12.8 Hz, 1H), 3.98 (d, J=10.0 Hz, 1H), 3.82 (d, J=16.4 Hz, 1H), 3.71 (d, J=16.4 Hz, 1H), 3.26 (br s, 2H), 2.64-2.60 (m, 4H), 2.44 (br s, 2H), 0.85-0.78 (m, 2H), 0.74-0.70 (m, 2H). m.p.=126-130° C.

Example 54

(±)-5-((4-Cyclopropyl-3-((methylsulfinyl)methyl)phenyl)amino)-7-(pyridin-2-ylamino)pyrazolo[1,5-a]pyrimidine-3-carbonitrile (Cpd 54)

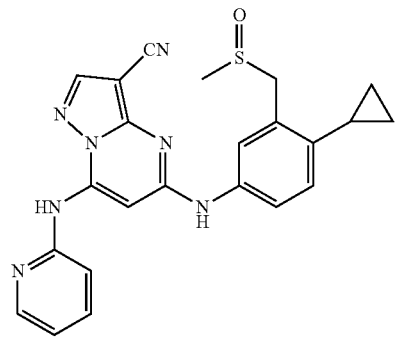 [SMILES: CS(=O)Cc1cc(Nc2cc(Nc3ccccn3)n3ncc(C#N)c3n2)ccc1C1CC1]

Step 1

5-Chloro-7-(pyridin-2-ylamino)pyrazolo[1,5-a]pyrimidine-3-carbonitrile

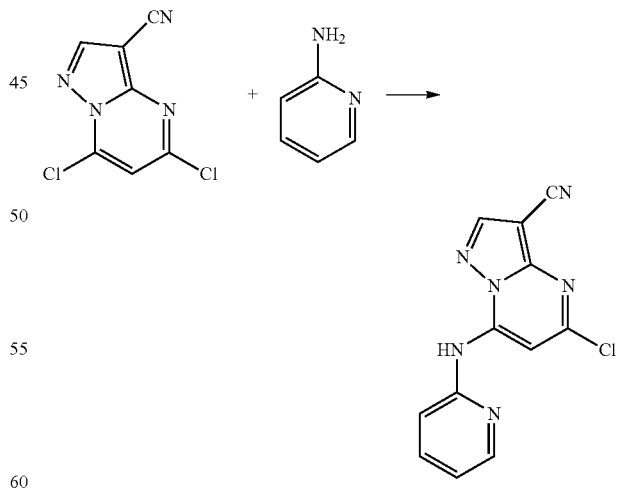

A mixture of 5,7-dichloropyrazolo[1,5-a]pyrimidine-3-carbonitrile (350 mg, 1.64 mmol), pyridin-2-amine (185 mg, 1.97 mmol, 1.2 eq.) and Et$_3$N 9 0.35 mL, 2.46 mmol, 1.5 eq.) in NMP (3 mL) was heated at 60° C. overnight. The reaction mixture was diluted with EtOAc (100 mL), washed with water (50 mL×2), dried (Na$_2$SO$_4$), and concentrated. The residue was purified on a silica gel column (eluting with hexanes/EtOAc 2/1) to get the title compound as a solid (330 mg, 74% yield).

Step 2

(±)-5-((4-Cyclopropyl-3-((methylsulfinyl)methyl)phenyl)amino)-7-(pyridin-2-ylamino)pyrazolo[1,5-a]pyrimidine-3-carbonitrile This compound was prepared from 5-chloro-7-(pyridin-2-ylamino)pyrazolo[1,5-a]pyrimidine-3-carbonitrile and (±)-4-cyclopropyl-3-((methylsulfinyl)methyl)aniline (described in Example 13) using the general procedure described in Example 1. ES+, m/z 444.8 [M+1]; $^1$H NMR (500 MHz, DMSO-d$_6$), δ 10.25 (s, 1H), 9.93 (s, 1H), 8.49 (s, 1H), 8.41 (m, 1H), 7.82 (m, 1H), 7.78 (s, 1H), 7.77 (m, 1H), 7.63 (d, J=2.5 Hz, 1H), 7.60 (d, J=8.5 Hz, 1H), 7.13 (m, 1H), 7.03 (d, J=8.5 Hz, 1H), 5.75 (s, 1H), 4.29 (d, J=12.5 Hz, 1H), 4.17 (d, J=13.0 Hz, 1H), 2.63 (s, 3H), 2.06 (m, 1H), 0.94-0.91 (m, 2H), 0.68-0.63 (m, 2H).

Example 55

(±)-5-((4-Cyclopropyl-3-((methylsulfinyl)methyl)phenyl)amino)-7-(pyridin-3-ylamino)pyrazolo[1,5-a]pyrimidine-3-carbonitrile (Cpd 55)

Using the procedures described above for Example 54 and substituting pyridin-3-amine for pyridin-2-amine, (±)-5-((4-cyclopropyl-3-((methylsulfinyl)methyl)phenyl)amino)-7-(pyridin-3-ylamino)pyrazolo[1,5-a]pyrimidine-3-carbonitrile was prepared from 5-chloro-7-(pyridin-3-ylamino)pyrazolo[1,5-a]pyrimidine-3-carbonitrile and (±)-4-cyclopropyl-3-((methylsulfinyl)methyl)aniline. ES+, m/z 444.8 [M+1]; $^1$H NMR (500 MHz, DMSO-d$_6$), δ 10.0 (s, 1H), 9.61 (s, 1H), 8.70 (d, J=2.5 Hz, 1H), 8.49 (s, 1H), 8.48 (m, 1H), 7.91-7.88 (m, 1H), 7.71 (d, J=8.5 Hz, 1H), 7.53 (m, 1H), 7.49 (d, J=2.0 Hz, 1H), 7.00 (d, J=8.5 Hz, 1H), 6.00 (s, 1H), 4.27 (d, J=12.5 Hz, 1H), 4.14 (d, J=13.0 Hz, 1H), 2.61 (s, 3H), 2.03 (m, 1H), 0.92-0.89 (m, 2H), 0.66-0.61 (m, 2H).

Example 56

(±)-7-((6-Aminopyridin-3-yl)amino)-5-((4-cyclopropyl-3-((methylsulfinyl)methyl)phenyl)amino)pyrazolo[1,5-a]pyrimidine-3-carbonitrile (Cpd 56)

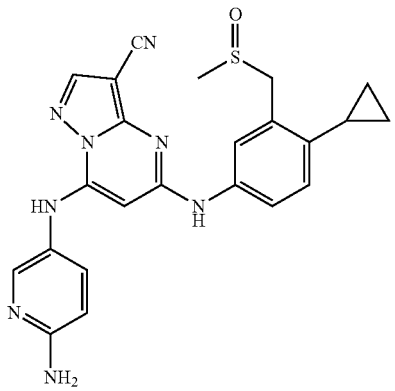 [SMILES: CS(=O)Cc1cc(Nc2cc(Nc3ccc(N)nc3)n3ncc(C#N)c3n2)ccc1C1CC1]

Step 1 tert-Butyl (5-((5-chloro-3-cyanopyrazolo[1,5-a]pyrimidin-7-yl)amino)pyridin-2-yl)carbamate

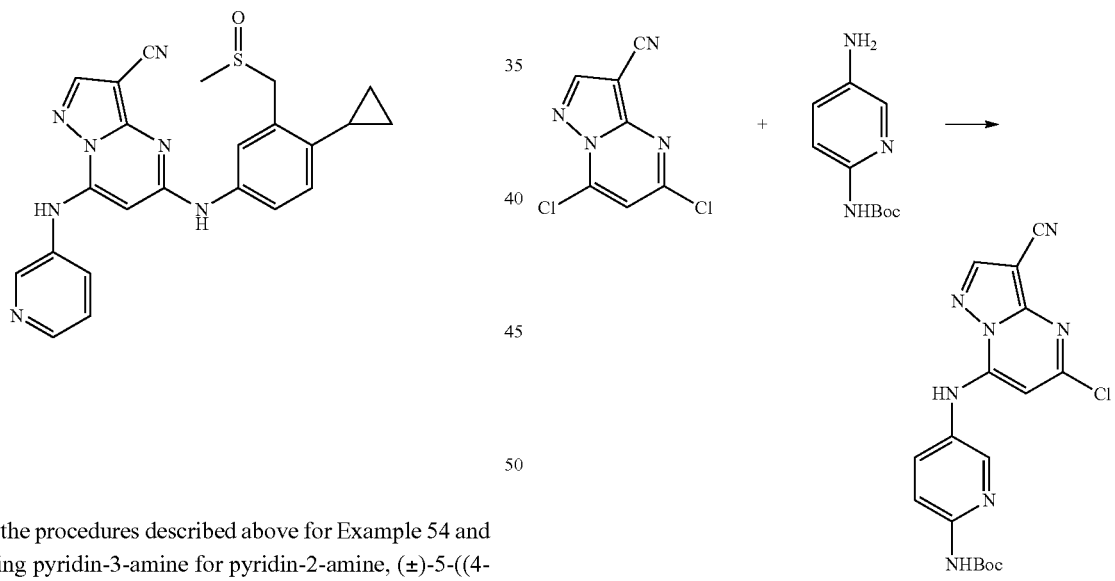

To a solution of 5,7-dichloropyrazolo[1,5-a]pyrimidine-3-carbonitrile (240 mg, 1.126 mmol) in NMP (3 mL) at 0° C., was added tert-butyl (5-aminopyridin-2-yl)carbamate 238 mg, 1.139 mml). The resulting reaction mixture was stirred at 0° C. to r.t overnight. The reaction mixture was diluted with EtOAc (60 mL), washed with water (30 mL×2), dried (Na$_2$SO$_4$), and concentrated. The residue was purified on a silica gel column (eluting with hexanes/EtOAc 2/1) to give tert-butyl (5-((5-chloro-3-cyanopyrazolo[1,5-a]pyrimidin-7-yl)amino)pyridin-2-yl)carbamate as a yellow solid (360 mg, 83% yield).

Step 2

(±)-7-((6-Aminopyridin-3-yl)amino)-5-((4-cyclopropyl-3-((methylsulfinyl)methyl)phenyl)amino)pyrazolo[1,5-a]pyrimidine-3-carbonitrile The compound was prepared as described in Example 54 from tert-butyl (5-((5-chloro-3-cyanopyrazolo[1,5-a]pyrimidin-7-yl)amino)pyridin-2-yl)carbamate and (±)-4-cyclopropyl-3-((methylsulfinyl)methyl)aniline. During the reaction it was observed that the tert-butyl carbamate is cleaved over time, therefore the additional deprotection step with trifluoroacetic acid is unnecessary. ES+, m/z 459.6 [M+1]; $^1$H NMR (500 MHz, DMSO-$d_6$), δ 9.50 (s, 1H), 9.44 (brs, 1H), 8.43 (s, 1H), 7.93 (d, J=2.0 Hz, 1H), 7.67 (d, J=8.5 Hz, 1H), 7.49 (s, 1H), 7.41 (dd, J=2.0, 8.5 Hz, 1H), 6.97 (d, J=9.0 Hz, 1H), 6.54 (d, J=9.0 Hz, 1H), 6.11 (s, 2H), 5.61 (s, 1H), 4.24 (d, J=12.5 Hz, 1H), 4.13 (d, J=12.5 Hz, 1H), 2.60 (s, 3H), 2.02 (m, 1H), 0.92-0.89 (m, 2H), 0.66-0.60 (m, 2H).

Example 57

(±)-7-((5-Aminopyridin-2-yl)amino)-5-((4-cyclopropyl-3-((methylsulfinyl)methyl)phenyl)amino)pyrazolo[1,5-a]pyrimidine-3-carbonitrile (Cpd 57)

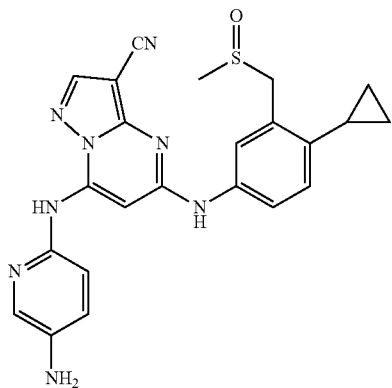

Step 1

5-Chloro-7-((5-nitropyridin-2-yl)amino)pyrazolo[1,5-a]pyrimidine-3-carbonitrile

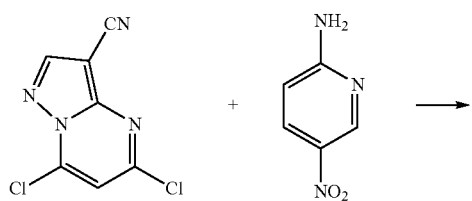

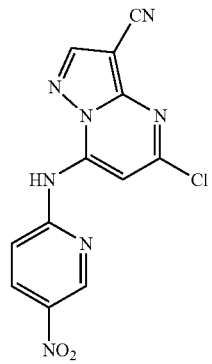

To a solution of 5-nitropyridin-2-amine (209 mg, 1.5 mmol) in dry NMP (2 mL), at 0° C. under Argon, was added NaH (60% in mineral oil, 68 mg, 1.1 eq). After 30 minutes, a solution of 5,7-dichloropyrazolo[1,5-a]pyrimidine-3-carbonitrile (319 mg, 1.5 mmol) in NMP (1 mL) was added with a syringe. The reaction was stirred at 0° C. to r.t overnight. The reaction mixture was mixed with ice water (20 mL). The precipitates that formed were collected by filtration, and was washed with some Et$_2$O, dried in vacuum to give the product as a red brown solid (405 mg, 85.6% yield), which was used directly in the next reaction without further purification.

Step 2

(±)-5-((4-Cyclopropyl-3-((methylsulfinyl)methyl)phenyl)amino)-7-((5-nitropyridin-2-yl)amino)pyrazolo[1,5-a]pyrimidine-3-carbonitrile To a mixture of 5-chloro-7-((5-nitropyridin-2-yl)amino)pyrazolo[1,5-a]pyrimidine-3-carbonitrile (158 mg, 0.5 mmol), (±)-4-cyclopropyl-3-((methylsulfinyl)methyl)aniline (105 mg, 0.50 mmol), Cs$_2$CO$_3$ (245 mg, 0.75 mmol, 1.5 eq.) and BINAP (31 mg, 0.05 mmol, 0.1 eq.) in NMP (5 mL) under Argon atmosphere, was added Pd$_2$(dba)$_3$ (46 mg, 0.05 mmol, 0.1 eq.). The reaction mixture was stirred at 135° C. for 5 hours. The reaction mixture was cooled down to room temperature. The solid were filtered off. The solution was diluted with Et$_2$O (50 mL). The precipitates that formed were collected by filtration. The solid was washed sequentially with Et$_2$O, and EtOAc (5 mL), dried in vacuum to give red brown solid (200 mg, crude yield 80%), which was used in next reaction without further purification.

Step 3

(±)-7-((5-Aminopyridin-2-yl)amino)-5-((4-cyclopropyl-3-((methylsulfinyl)methyl)phenyl)amino)pyrazolo[1,5-a]pyrimidine-3-carbonitrile A mixture of crude (±)-5-((4-cyclopropyl-3-((methylsulfinyl)methyl)phenyl)amino)-7-((5-nitropyridin-2-yl)amino)pyrazolo[1,5-a]pyrimidine-3-carbonitrile (175 mg), 10% Pd/C (50 mg) in methanol (10 mL) was stirred under hydrogen atmosphere (H$_2$ balloon) for 4 h. The catalyst was filtered off. The filtration was concentrated and the residue was purified on prep. TLC (eluting with EtOAc/MeOH 6/1) two times to get the product as a brown solid (37 mg, 21% yield). ES+, m/z 459.8 [M+1]; $^1$H NMR (500 MHz, DMSO-$d_6$), δ 9.81 (brs, 1H), 9.75 (s, 1H), 8.44 (s, 1H), 7.81 (s, 1H), 7.73 (d, J=9.0 Hz, 1H), 7.59 (s, 1H), 7.25 (s, 1H), 7.23 (m, 1H), 7.04 (dd, J=2.5, 8.5 Hz, 1H), 7.01 (d, J=8.5 Hz, 1H), 5.22 (brs, 2H), 4.27 (d, J=12.5 Hz, 1H), 4.16 (d, J=13.0 Hz, 1H), 2.62 (s, 3H), 2.04 (m, 1H), 0.93-0.91 (m, 2H), 0.66-0.63 (m, 2H).

Example 58

(±)-5-((4-((R,S)-1-Aminoethyl)-3-((methylsulfinyl)methyl)phenyl)amino)-7-(cyclopropylamino)pyrazolo[1,5-a]pyrimidine-3-carbonitrile mono trifluoroacetic acid salt (Cpd 58)

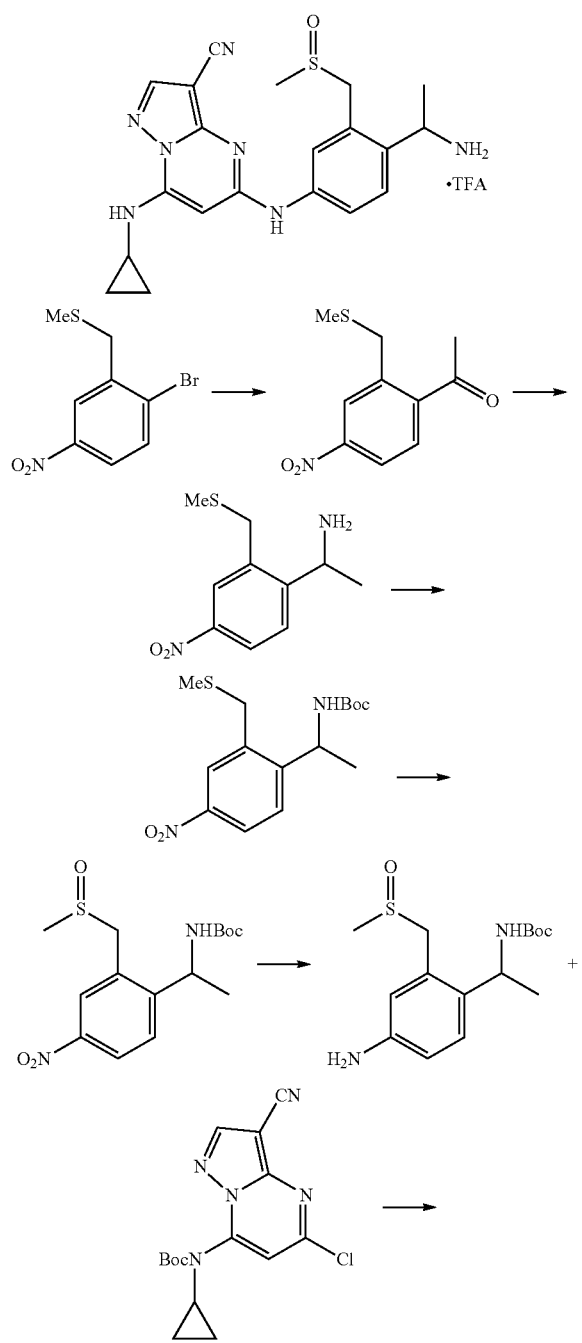

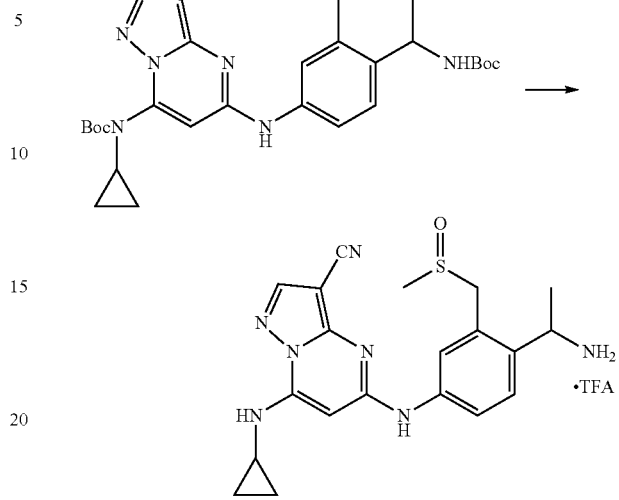

Step 1

1-(2-((Methylthio)methyl)-4-nitrophenyl)ethan-1-one

To a stirred solution of (2-bromo-5-nitrobenzyl)(methyl)sulfane (2.7 g, 10.29 mmol) in DMF (25 mL) at room temperature were added tributyl(1-ethoxyvinyl)stannane (4.09 g, 11.33 mmol) and Pd(PPh$_3$)$_4$ (1.2 g, 1.03 mmol). The reaction mass was degassed with argon for 5 minutes and stirred under reflux for 16 h. The reaction mixture was cooled to 0° C. and quenched with drop-wise addition of 1 M HCl (10 ml) and stirred at room temperature for 2 h. The reaction mixture was diluted with water and extracted with ethyl acetate (3×30 mL). The combined organic layer was dried over Na$_2$SO$_4$ and concentrated under reduced pressure to get crude compound. The crude compound was purified by column chromatography over silica gel (100-200 mesh), eluting with ethyl acetate:pet-ether (15:85) to get 1-(2-((methylthio)methyl)-4-nitrophenyl)ethan-1-one (2 g, 86.9%, LC-MS 96.01%) as a brown solid. ES+, m/z 226.1 [M+1].

Step 2

(R,S)-1-(2-((Methylthio)methyl)-4-nitrophenyl)ethan-1-amine

To a stirred solution 1-(2-((methylthio)methyl)-4-nitrophenyl)ethan-1-one (2 g, 8.88 mmol) in 2 M NH$_3$ in ethanol (22.2 ml), was added Ti(Oi-Pr)$_4$ (5 g, 17.77 mmol) at 0° C. The reaction mixture was stirred at 60° C. for 24 h. The reaction mixture was cooled to 0° C., prior to the portion-wise addition of NaBH$_4$ (0.657 g, 17.76 mmol). The reaction mass was stirred at room temperature for 6 h. The solvent was rotary evaporated and the residue was quenched with NH$_4$Cl solution (100 mL), filtered through celite pad and the aqueous layer was extracted with ethyl acetate (3×50 mL). The combined organic layer was washed with 1 N HCl (50 mL) and basified with 2 M NaOH (30 mL). The aqueous layer was extracted with ethyl acetate (3×50 mL), dried over Na$_2$SO$_4$ and concentrated to get (R,S)-1-(2-((methylthio)methyl)-4-nitrophenyl)ethan-1-amine (1.5 g, 75%, LC-MS 82.06%) as a brown solid. ES+, m/z 227.1 [M+1].

Step 3 tert-Butyl (R,S)-1-(2-((methylthio)methyl)-4-nitrophenyl)ethyl)carbamate

To a stirred solution of (R,S)-1-(2-((methylthio)methyl)-4-nitrophenyl)ethan-1-amine (1.5 g, 6.637 mmol) in CH$_2$Cl$_2$ (15 mL) at 0° C. was added Boc anhydride (1.73 g, 7.96 mmol). The reaction mixture was stirred at room temperature for 16 h. The reaction mixture was diluted with CH$_2$Cl$_2$ (10 mL), washed with water (15 mL), brine (15 mL), dried over Na$_2$SO$_4$, and concentrated under vacuum to provide tert-butyl (R,S)-(1-(2-((methylthio)methyl)-4-nitrophenyl)ethyl)carbamate (1.7 g, 78.7%, LC-MS 95.82%) as a brown liquid. ES+, m/z 327.1 [M+1].

Step 4

(±)-tert-Butyl ((1R,S)-1-(2-((methylsulfinyl)methyl)-4-nitrophenyl)ethyl)carbamate To a stirred solution of tert-butyl (R,S)-(1-(2-((methylthio)methyl)-4-nitrophenyl)ethyl)carbamate (1.7 g, 5.21 mmol) in CH$_2$Cl$_2$ (20 mL) at 0° C., was added mCPBA (0.99 g, 5.73 mmol) in portions. The reaction mixture was stirred for 16 h at room temperature. The reaction mixture was diluted with CH$_2$Cl$_2$ (15 mL) and washed with NaHCO$_3$ (25 mL). The organic layer was dried over Na$_2$SO$_4$ and concentrated under reduced pressure to obtain a brown solid. The crude product was purified by silica gel column chromatography (eluent methanol:CH$_2$Cl$_2$ 5:95) to furnish (±)-tert-butyl ((1R,S)-1-(2-((methylsulfinyl)methyl)-4-nitrophenyl)ethyl)carbamate (1.5 g, 84.2%, LC-MS 99.48%) as an off-white solid. ES+, m/z 343.1 [M−1].

Step 5

(±)-tert-Butyl ((1R,S)-1-(4-amino-2-((methylsulfinyl)methyl)phenyl)ethyl)carbamate To a stirred suspension of (±)-tert-butyl ((1R,S)-1-(2-((methylsulfinyl)methyl)-4-nitrophenyl)ethyl)carbamate (1.5 g, 4.38 mmol) in 70% aqueous ethanol (23 mL) at room temperature were added NH$_4$Cl (1.16 g, 21.92 mmol) and Fe powder (1.21 g, 21.92 mmol). The reaction mixture was heated at 80° C. for 2 h. The reaction mixture was filtered through celite pad and washed with methanol: CH$_2$Cl$_2$ (5:95, 20 mL). The filtrate was concentrated under reduced pressure to give a brown solid which was washed with n-pentane and dried to get (±)-tert-butyl ((1R,S)-1-(4-amino-2-((methylsulfinyl)methyl)phenyl)ethyl)carbamate (1.2 g, 88.2%, LC-MS 98.4%) as an off-white solid. ES+, m/z 313.2 [M+1].

Step 6

(±)-tert-Butyl (5-((4-((R,S)-1-((tert-butoxycarbonyl)amino)ethyl)-3-((methylsulfinyl)methyl)phenyl)amino)-3-cyanopyrazolo[1,5-a]pyrimidin-7-yl)(cyclopropyl)carbamate To a stirred suspension of (±)-tert-butyl ((1R,S)-1-(4-amino-2-((methylsulfinyl)methyl)phenyl)ethyl)carbamate (0.4 g, 1.282 mmol) in dry NMP (10 mL) at room temperature were added tert-butyl 5-chloro-3-cyanopyrazolo[1,5-a]pyrimidin-7-yl(cyclopropyl)carbamate (0.429 g, 1.282 mmol), Cs$_2$CO$_3$ (0.836 g, 2.56 mmol), BINAP (0.08 g, 0.128 mmol), Pd$_2$(dba)$_3$ (0.118 g, 0.128 mmol). The reaction mixture was de-gassed with argon for 5 minutes. The reaction mixture was stirred for 2 h at 130° C. in microwave. The reaction mixture was cooled to room temperature and diluted with water (15 mL), and extracted with methanol: CH$_2$Cl$_2$ (5:95, 3×15 mL). The combined organic layer was dried over Na$_2$SO$_4$ and concentrated under reduced pressure to give a dark brown semi-solid. The crude product was purified by silica gel column chromatography (eluting with methanol: CH$_2$Cl$_2$ 3:97) to furnish (±)-tert-butyl (5-((4-((R,S)-1-((tert-butoxycarbonyl)amino)ethyl)-3-((methylsulfinyl)methyl)phenyl)amino)-3-cyanopyrazolo[1,5-a]pyrimidin-7-yl)(cyclopropyl)carbamate (0.14 g, 17.9%, LC-MS 99.2%) as a brown solid. ES+, m/z 610.1 [M+1].

Step 7

(±)-5-((4-((R,S)-1-Aminoethyl)-3-((methylsulfinyl)methyl)phenyl)amino)-7-(cyclopropylamino)pyrazolo[1,5-a]pyrimidine-3-carbonitrile mono trifluoroacetic acid salt To a stirred suspension of (±)-tert-butyl (5-((4-((R,S)-1-((tert-butoxycarbonyl)amino)ethyl)-3-((methylsulfinyl)methyl)phenyl)amino)-3-cyanopyrazolo[1,5-a]pyrimidin-7-yl)(cyclopropyl)carbamate (0.14 g, 0.229 mmol) in CH$_2$Cl$_2$ (5 mL) at 0° C., TFA (2 mL) was added drop-wise. The reaction mixture was allowed to warm to room temperature and stirred for 2 h. The reaction mixture was concentrated under reduced pressure to get brown gummy solid which was co-distilled with ethyl acetate (2×5 mL) and washed with di ethyl ether (2×5 mL) and dried to give (±)-5-((4-((R,S)-1-Aminoethyl)-3-((methylsulfinyl)methyl)phenyl)amino)-7-(cyclopropylamino)pyrazolo[1,5-a]pyrimidine-3-carbonitrile mono trifluoroacetic acid salt (100 mg, yield: 100%, LC-MS: 93.3%, HPLC: 95.3%) as an off white solid. ES+, m/z: 410.1[M-TFA+H]$^+$; [C$_{20}$H$_{23}$N$_7$OS]; $^1$H NMR (500 MHz, CD$_3$OD): δ 8.15 (d, J=2.5 Hz, 0.5H), 8.12 (d, J=1.0 Hz, 1H), 8.09 (d, J=2.5 Hz, 0.5H), 7.88 (dd, J=8.5, 2.2 Hz, 0.5H), 7.71 (dd, J=8.7, 2.2 Hz, 0.5H), 7.63-7.58 (m, 1H), 6.01 (s, 1H), 4.85-4.80 (m, 1H), 4.34-4.31 (m, 1H), 3.95-3.92 (m, 0.5H), 3.32-3.30 (m, 0.5H), 2.84 (s, 1H), 2.68-2.65 (m, 2H), 2.64 (s, 1H), 1.71-1.66 (m, 3H), 1.42 (s, 1H), 0.94-0.91 (m, 2H), 0.75-0.74 (m, 2H). m.p.=161-165° C.

Example 59

(±)-5-((4-(1-Aminocyclopropyl)-3-((methylsulfinyl)methyl)phenyl)amino)-7-(cyclopropylamino)pyrazolo[1,5-a]pyrimidine-3-carbonitrile mono trifluoroacetic acid salt (Cpd 59)

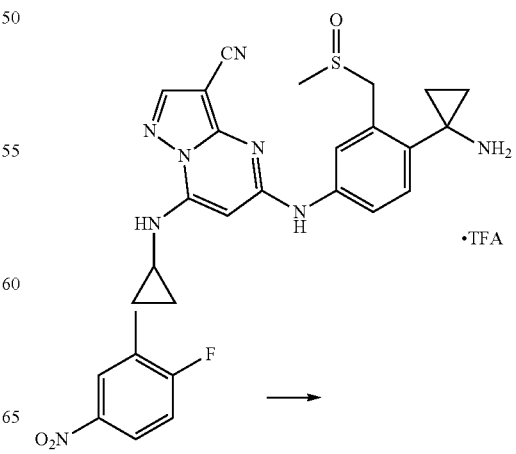

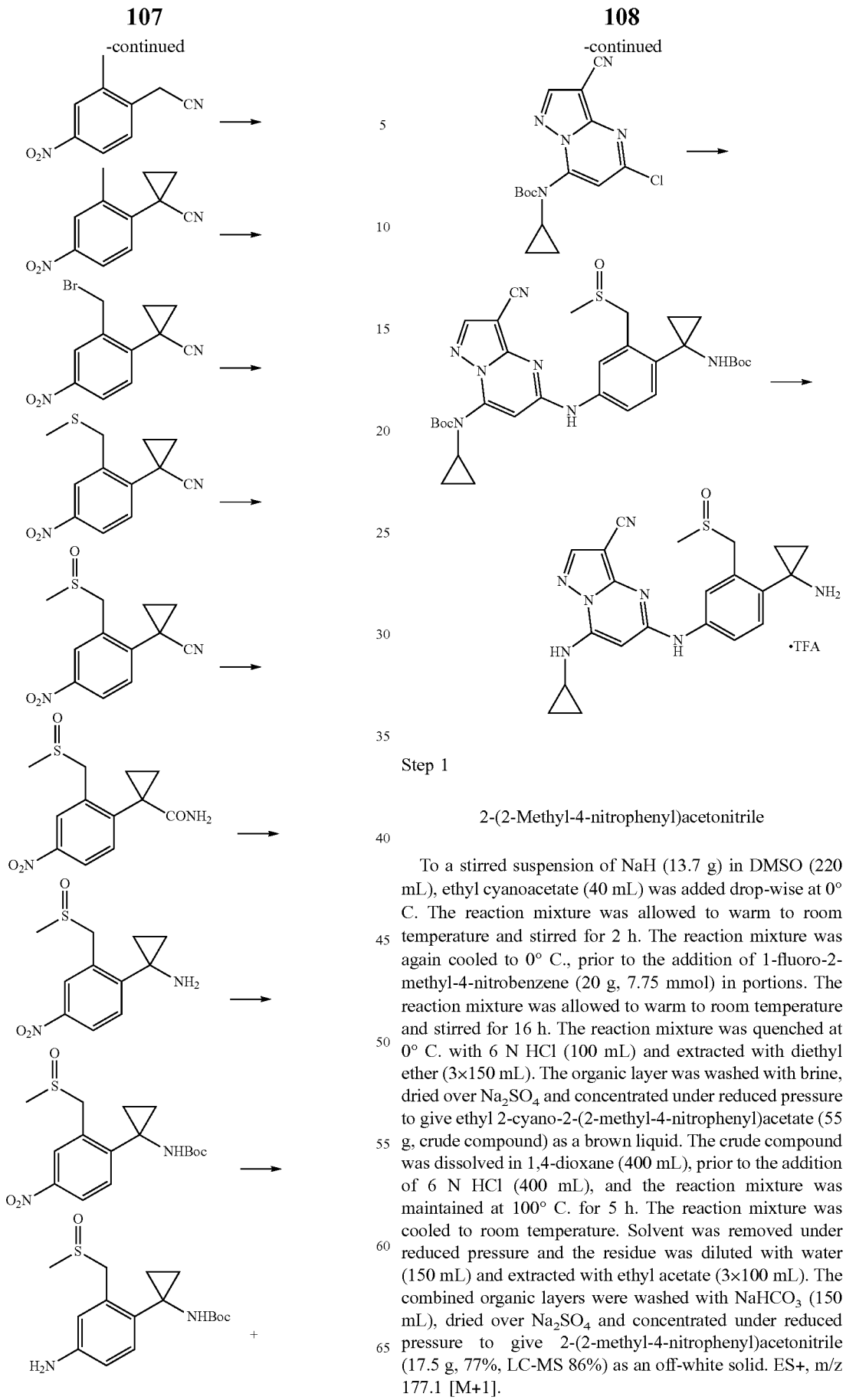

Step 1

2-(2-Methyl-4-nitrophenyl)acetonitrile

To a stirred suspension of NaH (13.7 g) in DMSO (220 mL), ethyl cyanoacetate (40 mL) was added drop-wise at 0° C. The reaction mixture was allowed to warm to room temperature and stirred for 2 h. The reaction mixture was again cooled to 0° C., prior to the addition of 1-fluoro-2-methyl-4-nitrobenzene (20 g, 7.75 mmol) in portions. The reaction mixture was allowed to warm to room temperature and stirred for 16 h. The reaction mixture was quenched at 0° C. with 6 N HCl (100 mL) and extracted with diethyl ether (3×150 mL). The organic layer was washed with brine, dried over $Na_2SO_4$ and concentrated under reduced pressure to give ethyl 2-cyano-2-(2-methyl-4-nitrophenyl)acetate (55 g, crude compound) as a brown liquid. The crude compound was dissolved in 1,4-dioxane (400 mL), prior to the addition of 6 N HCl (400 mL), and the reaction mixture was maintained at 100° C. for 5 h. The reaction mixture was cooled to room temperature. Solvent was removed under reduced pressure and the residue was diluted with water (150 mL) and extracted with ethyl acetate (3×100 mL). The combined organic layers were washed with $NaHCO_3$ (150 mL), dried over $Na_2SO_4$ and concentrated under reduced pressure to give 2-(2-methyl-4-nitrophenyl)acetonitrile (17.5 g, 77%, LC-MS 86%) as an off-white solid. ES+, m/z 177.1 [M+1].

Step 2

1-(2-Methyl-4-nitrophenyl)cyclopropane-1-carbonitrile

To a solution of 2-(2-methyl-4-nitrophenyl)acetonitrile (17.5 g, 99.43 mmol) in acetonitrile (175 mL) at 0° C. were added 1,2-dibromoethane (55.76 g, 298.2 mmol), tetraethyl ammonium chloride (16.5 g, 99.43 mmol), and 50% NaOH solution (17.5 mL). The reaction mixture was maintained at 80° C. for 2 h. The reaction mixture was cooled to room temperature and the solvent was removed under reduced pressure to give crude compound. The crude compound was diluted with water (2×100 mL) and extracted with ethyl acetate (3×200 mL). The combined organic layer was washed with brine, dried over $Na_2SO_4$ and concentrated under reduced pressure to give crude compound. The crude product was purified by silica gel column chromatography (eluting with ethyl acetate: pet-ether 30:70) to get 1-(2-methyl-4-nitrophenyl)cyclopropane-1-carbonitrile (8.3 g, 41.3%, LC-MS 99%) as a pale yellow solid. ES+, m/z 203.1 [M+1].

Step 3

1-(2-(Bromomethyl)-4-nitrophenyl)cyclopropane-1-carbonitrile

To a solution of 1-(2-methyl-4-nitrophenyl)cyclopropane-1-carbonitrile (8.3 g, 41.08 mmol) in 1,2-dichloroethane (80 mL), at 0° C. were added NBS (10.97 g, 61.63 mmol), and AIBN (1.34 g, 8.21 mmol). The reaction mixture was refluxed for 16 h. The reaction mixture was cooled to room temperature and the solvent was removed under reduced pressure to get crude compound. The crude compound was diluted with water (200 mL) and extracted with ethyl acetate (3×200 mL). The combined organic layer was washed with brine, dried over $Na_2SO_4$ and concentrated under reduced pressure to yield brown oily liquid which was washed with n-pentane (3×150 mL), to get 1-(2-(bromomethyl)-4-nitrophenyl)cyclopropane-1-carbonitrile (12 g, 100%, LC-MS 85.57%) as a yellow solid. ES+, m/z 280.9 [M+1]. This compound was directly used in the next reaction without further purification.

Step 4

1-(2-((Methylthio)methyl)-4-nitrophenyl)cyclopropane-1-carbonitrile

To a solution of 1-(2-(bromomethyl)-4-nitrophenyl)cyclopropane-1-carbonitrile (12 g, 42.85 mmol) in methanol (120 mL), at 0° C., was added $NaSCH_3$ (3.3 g, 47.14 mmol) in portions. The reaction mixture was allowed to warm to room temperature and stirred for 16 h. The solvent was removed under reduced pressure to give crude product. The crude compound was diluted with ice-cold water (200 mL), and the resulting brown solid was collected by filtration and dried under vacuum to furnish 1-(2-(methylthiomethyl)-4-nitrophenyl)cyclopropane-1-carbonitrile (9.3 g, 87.5%, LC-MS 70.8%) as a brown solid. $^1$H NMR (400 MHz, $CDCl_3$), δ 8.38 (d, J=2.4 Hz 1H), 8.11 (dd, J=14.4, 2.4 Hz, 1H), 7.51 (dd, J=14.4, 2.4 Hz 1H), 4.08 (s, 2H), 2.19 (s, 3H), 1.86-1.79 (m, 2H), 1.52-1.48 (m, 2H).

Step 5

(±)-1-(2-((Methylsulfinyl)methyl)-4-nitrophenyl)cyclopropane-1-carbonitrile

To a stirred solution of 1-(2-(methylthiomethyl)-4-nitrophenyl)cyclopropane-1-carbonitrile (9 g, 36.29 mmol) in $CH_2Cl_2$ (90 mL) at 0° C., was added mCPBA (6.8 g, 39.9 mmol) in portions. The reaction mixture was allowed to warm to room temperature and stirred for 16 h. The reaction mixture was diluted with $CH_2Cl_2$ (30 mL) and washed with $NaHCO_3$ (2×150 mL), dried over $Na_2SO_4$ and concentrated under reduced pressure to give a brown liquid. The crude product was purified by silica gel column chromatography, eluting with methanol:$CH_2Cl_2$ (3:97) to get (±)-1-(2-((methylsulfinyl)methyl)-4-nitrophenyl)cyclopropane-1-carbonitrile (7 g, 73.0%, LC-MS 89%) as a yellow solid. ES+, m/z 265.0 [M+1].

Step 6

(±)-1-(2-((Methylsulfinyl)methyl)-4-nitrophenyl)cyclopropane-1-carboxamide

To a stirred solution of (±)-1-(2-((methylsulfinyl)methyl)-4-nitrophenyl)cyclopropane-1-carbonitrile (7 g, 26.51 mmol) in DMSO (70 mL) at 0° C., were added 30% aq $H_2O_2$ (7 mL, 265.15 mmol) and $K_2CO_3$ (7.31 g, 53.03 mmol). The reaction mixture was allowed to warm to room temperature and stirred for 3 h. The reaction mixture was diluted with ice-cold water (20 mL) and stirred for 1 h. Solid thus formed was collected by filtration, washed with excess water and dried in vacuum to get (±)-1-(2-((methylsulfinyl)methyl)-4-nitrophenyl)cyclopropane-1-carboxamide (3.4 g, yield: 45.5%, LC-MS: 94%) as an off-white solid. ES+, m/z 283.0 [M+1].

Step 7

(±)-1-(2-((Methylsulfinyl)methyl)-4-nitrophenyl)cyclopropan-1-amine

To a solution of (±)-1-(2-((methylsulfinyl)methyl)-4-nitrophenyl)cyclopropane-1-carboxamide (3.4 g, 12.05 mmol) in t-butanol (70 mL) at room temperature were added sodium hypochlorite (8.97 g, 12.05 mmol) and 3 N NaOH (1.35 g, 33.75 mmol). The reaction mixture was stirred for 16 h at room temperature. The reaction mixture was distilled under reduced pressure to get a solid. The solid product was dissolved in methanol: $CH_2Cl_2$ (5:95) and filtered. The filtrate was evaporated under reduced pressure to give crude product which was purified by silica gel column chromatography (methanol: $CH_2Cl_2$ 5:95) to furnish (±)-1-(2-((methylsulfinyl)methyl)-4-nitrophenyl)cyclopropan-1-amine (1.6 g, 52.2%, LC-MS 95%) as a brown solid. ES+, m/z 255.0 [M+1].

Step 8

(±)-tert-Butyl (1-(2-((methylsulfinyl)methyl)-4-nitrophenyl)cyclopropyl)carbamate To a solution of (±)-1-(2-((methylsulfinyl)methyl)-4-nitrophenyl)cyclopropan-1-amine (0.5 g, 1.968 mmol) in $CH_2Cl_2$ (10 mL) at 0° C. were added $(Boc)_2O$ (1.07 g, 4.921 mmol) and TEA (0.259 g, 2.55 mmol). The reaction mixture was allowed warm to room temperature and stirred for 16 h. The solvent was removed by distillation under reduced pressure. The crude compound was purified by silica gel column chromatography, eluting with methanol: $CH_2Cl_2$ (3:97) to give (±)-tert-butyl 1-(2-(methylsulfinylmethyl)-4-nitrophenyl)cyclopropylcarbamate (0.53 g, 76.0%, LC-MS 96.3%) as a brown solid. $^1$H NMR (400 MHz, $CDCl_3$), δ 8.20 (d, J=2.4 Hz 1H), 8.15 (dd, J=8.4, 2.4 Hz, 1H), 7.88 (brd, J=8.0 Hz, 1H), 4.48 (brm, 1H), 4.34 (d, J=13.2 Hz, 1H), 2.75 (s, 3H), 1.37 (s, 9H), 1.26 (m, 2H), 1.22-1.18 (m, 1H), 1.11-1.08 (m, 1H).

Step 9

(±)-tert-Butyl (1-(4-amino-2-((methylsulfinyl) methyl)phenyl)cyclopropyl)carbamate To a stirred solution of (±)-tert-butyl 1-(2-(methylsulfinylmethyl)-4-nitrophenyl)cyclopropylcarbamate (0.53 g, 1.497 mmol) in ethanol (10 mL) was added 10% Pd/C (0.2 g) at room temperature. The reaction mixture was stirred at room temperature for 16 h under $H_2$ (bladder pressure). The reaction mixture was filtered through celite-pad and the filtrate was evaporated under reduced pressure to give solid. The solid was washed with n-pentane (30 mL) and dried under vacuum to provide (±)-tert-butyl (1-(4-amino-2-((methylsulfinyl)methyl)phenyl)cyclopropyl)carbamate (0.33 g, 68.0%, LC-MS 90.7%) as an off-white solid. ES+, m/z 325.1 [M+1].

Step 10

(±)-tert-Butyl (5-((4-(1-((tert-butoxycarbonyl) amino)cyclopropyl)-3-((methylsulfinyl)methyl)phenyl)amino)-3-cyanopyrazolo[1,5-a]pyrimidin-7-yl) (cyclopropyl)carbamate To a solution (±)-tert-butyl (1-(4-amino-2-((methylsulfinyl)methyl)phenyl)cyclopropyl)carbamate (0.33 g, 1.01 mmol) in dry NMP (5 mL) at room temperature were added tert-butyl 5-chloro-3-cyanopyrazolo[1,5-a]pyrimidin-7-yl (cyclopropyl)carbamate (0.34 g, 1.01 mmol), $Cs_2CO_3$ (0.664 g, 2.03 mmol), $Pd_2(dba)_3$ (0.093 g, 0.101 mmol), and BINAP (0.064 g, 0.101 mmol). The reaction mixture was degassed with argon for 5 minutes and heated at 90° C. for 2 h under microwaves. The reaction mixture was cooled to room temperature, diluted with water (15 mL), and extracted with ethyl acetate (3×15 mL). The combined organic layer was dried over $Na_2SO_4$ and the solvent was evaporated under reduced pressure to give a brown solid. The crude compound was purified by GRACE flash chromatography, eluting with methanol: $CH_2Cl_2$ (16:84) to give (±)-tert-butyl (5-((4-(1-((tert-butoxycarbonyl)amino)cyclopropyl)-3-((methylsulfinyl)methyl)phenyl)amino)-3-cyanopyrazolo[1,5-a]pyrimidin-7-yl)(cyclopropyl)carbamate (0.15 g, 23.7%, LC-MS 92.59%) as a brown solid. ES+, m/z 622.0 [M+1].

Step 11

(±)-5-((4-(1-Aminocyclopropyl)-3-((methylsulfinyl) methyl)phenyl)amino)-7-(cyclopropylamino)pyrazolo[1,5-a]pyrimidine-3-carbonitrile mono trifluoroacetic acid salt To a solution of (±)-tert-butyl (5-((4-(1-((tert-butoxycarbonyl)amino)cyclopropyl)-3-((methylsulfinyl)methyl)phenyl)amino)-3-cyanopyrazolo[1,5-a]pyrimidin-7-yl)(cyclopropyl)carbamate (0.15 g, 0.241 mmol) in $CH_2Cl_2$ (5 mL), at 0° C., TFA (2 mL) was added drop-wise. The reaction mixture was allowed to warm to room temperature and stirred for 3 h. The reaction mixture was distilled under reduced pressure to get an oily compound. The crude product was co-distilled with ethyl acetate (10 mL) and washed with diethyl ether (5 mL), dried in vacuum to afford (±)-5-((4-(1-Aminocyclopropyl)-3-((methylsulfinyl) methyl)phenyl)amino)-7-(cyclopropylamino)pyrazolo[1,5-a]pyrimidine-3-carbonitrile mono trifluoroacetic acid salt (0.104 g, 97.2%, LC-MS 98.73%, HPLC 99.55%) as an off-white solid. ES+, m/z 422.0 [M-TFA+H]$^+$ [$C_{21}H_{23}N_7OS$]; $^1H$ NMR (400 MHz, DMSO-$d_6$), δ 9.91 (s, 1H), 8.39-8.33 (m, 4H), 7.87 (dd, J=8.6 Hz, 2.2 Hz, 1H), 7.19 (d, J=2.4 Hz, 1H), 7.52 (d, J=8.4 Hz, 1H), 7.01-6.31 (bs, 3H), 6.02 (s, 1H), 4.58 (d, J=13.6 Hz, 1H), 4.32 (d, J=13.6 Hz, 1H), 2.83 (s, 3H), 2.63-2.60 (m, 1H), 1.50-1.33 (m, 2H), 1.22-1.10 (m, 2H), 0.85-0.82 (m, 2H), 0.75-0.73 (m, 2H). m.p.=185-189° C.

Example 60

(±)-(E)-5-((4-(4-aminobut-2-en-2-yl)-3-((methylsulfinyl)methyl)phenyl)amino)-7-(cyclopropylamino)pyrazolo[1,5-a]pyrimidine-3-carbonitrile mono trifluoroacetic acid salt (Cpd 60)

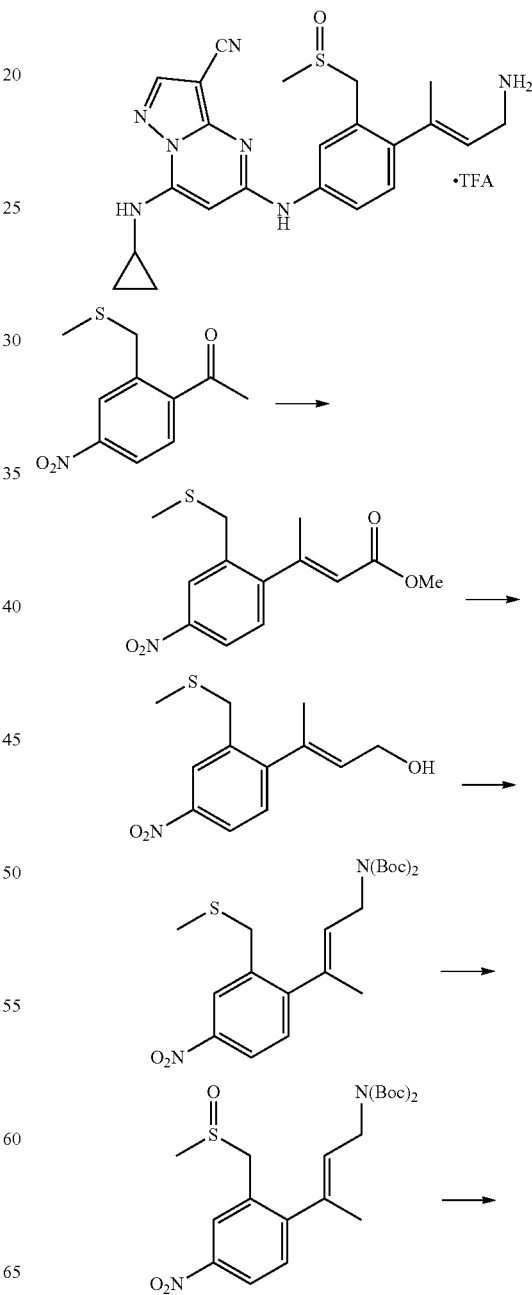

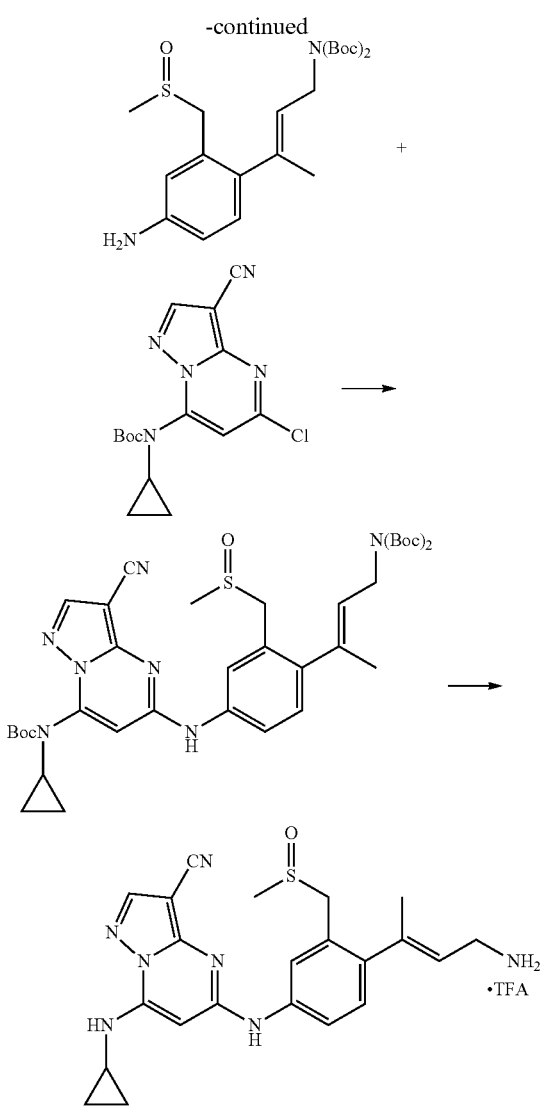

Step 1

Methyl (E,Z)-3-(2-((methylthio)methyl)-4-nitrophenyl)but-2-enoate

To a stirred suspension of sodium hydride (1.28 g, 53.33 mmol) in dry THF (20 mL) was drop wise added triethyl phosphonoacetate (10.3 g, 46.21 mmol) at 0° C. under argon atmosphere. After 30 minutes of stirring, 1-(2-((methylthio)methyl)-4-nitrophenyl)ethan-1-one (8 g, 35.55 mmol) was added to the reaction mixture, which was then allowed to warm to room temperature and stirred for 16 h. Reaction mixture was diluted with saturated aqueous ammonium chloride solution (20 mL). The aqueous phase was extracted with ethyl acetate (4×50 mL) and the combined organic phase was washed with brine, dried over $Na_2SO_4$, and concentrated to give the crude product. This crude compound was purified by silica gel column chromatography (eluting with EtOAc: pet-ether 10:90) to afford methyl (E,Z)-3-(2-((methylthio)methyl)-4-nitrophenyl)but-2-enoate (6 g, yield: 60%, LC-MS 43% & 52% of isomeric m/z). ES+, m/z 282.1 [M+1].

Step 2

(E)-3-(2-((Methylthio)methyl)-4-nitrophenyl)but-2-en-1-ol

To a stirred solution of (E & Z)-methyl 3-(2-(methylthiomethyl)-4-nitrophenyl)but-2-enoate (6 g, 21.35 mmol) in dry THF (60 ml), DIBAL in hexane (1 M, 42.70 mL) was added in portions at −78° C. under argon atmosphere. The reaction mixture was stirred at room temperature for 6 h. The reaction mixture was diluted with aqueous ammonium chloride solution (20 mL) and washed with brine (2×100 mL), dried over $Na_2SO_4$ and concentrated. The crude compound was purified by GRACE flash chromatography (eluted in EtOAc: pet-ether (0-30%)) to afford (Z)-3-(2-((methylthio)methyl)-4-nitrophenyl)but-2-en-1-ol (2.2 g, 40%, LC-MS 92%) as a pale yellow oil and (E)-3-(2-((methylthio)methyl)-4-nitrophenyl)but-2-en-1-ol (2.8 g, 97.6%) as a pale yellow oil. $^1$H NMR (500 MHz, $CDCl_3$), δ 8.20 (d, J=2.5 Hz 1H), 8.06 (dd, J=8.5, 2.5 Hz, 1H), 7.27 (d, J=8.5 Hz, 1H), 5.64 (m, 1H), 4.38 (d, J=6.5 Hz, 2H), 3.75 (s, 2H), 2.06 (s, 3H), 2.04 (s, 3H), 1.52 (brs, 1H). NOE confirms E vs. Z geometry. ES+, m/z 254.0 [M+1].

Step 3 tert-butyl N-((E)-3-(2-((methylthio)methyl)-4-nitrophenyl)but-2-en-1-yl)-N-[(2-methylpropan-2-yl)oxycarbonyl]carbamate To a stirred solution of (E)-3-(2-((methylthio)methyl)-4-nitrophenyl)but-2-en-1-ol (2.2 g, 8.69 mmol) in THF (25 ml) at 0° C., were added triphenylphosphine (3.41 g, 13.04 mmol), di-tert-butyl iminodicarbonate (2.83 g, 13.04 mmol) and DIAD (6.0 g, 13.04 mmol). The reaction mixture was allowed to warm to room temperature and stirred for 16 h. The reaction mixture was concentrated under vacuum. The residue was dissolved in EtOAc (50 mL) and the resulting organic layer was washed with water (2×100 mL) and brine, dried over anhydrous $Na_2SO_4$, filtered and concentrated under reduced pressure. The crude compound was purified by GRACE flash chromatography (eluting with ethyl acetate: pet ether 0-10%) to afford tert-butyl N-((E)-3-(2-((methylthio)methyl)-4-nitrophenyl)but-2-en-1-yl)-N-[(2-methylpropan-2-yl)oxycarbonyl]carbamate (2 g, 50%, LC-MS-89%) as a light yellow liquid. ES+, m/z 475.0 [M+Na].

Step 4

(±)-tert-Butyl N-((E)-3-(2-((methylsulfinyl)methyl)-4-nitrophenyl)but-2-en-1-yl)-N-[(2-methylpropan-2-yl)oxycarbonyl]carbamate To a stirred solution of tert-butyl (E)-3-(2-((methylthio)methyl)-4-nitrophenyl)but-2-en-1-yl)-N-[(2-methylpropan-2-yl)oxycarbonyl]carbamate (2 g, 4.42 mmol) in dichloromethane (25 mL), mCPBA (0.839 g, 4.86 mmol) was added portion-wise at 0° C. The reaction mixture was allowed to warm to room temperature and stirred for 5 h. The reaction mixture was diluted with dichloromethane (100 mL), washed with $NaHCO_3$ and brine, dried over anhydrous $Na_2SO_4$, filtered and concentrated to afford the crude product, which was purified by silica gel column chromatography (eluting with MeOH:$CH_2Cl_2$, 5:95) to afford (±)-tert-butyl N-((E)-3-(2-((methylsulfinyl)methyl)-4-nitrophenyl)but-2-en-1-yl)-N-[(2-methylpropan-2-yl)oxycarbonyl]carbamate (1.5 g, 72%, LC-MS: 96% as a yellow liquid. ES+, m/z 491.0 [M+Na].

Step 5

(±)-tert-Butyl N-((E)-3-(4-amino-2-((methylsulfinyl)methyl)phenyl)but-2-en-1-yl)-N-[(2-methylpropan-2-yl)oxycarbonyl]carbamate To a solution of (±)-tert-butyl N-((E)-3-(2-((methylsulfinyl)methyl)-4-nitrophenyl)but-2-en-1-yl)-N-[(2-methylpropan-2-yl)oxycarbonyl]carbamate (1 g, 2.13 mmol) in ethanol (50 mL) was added 10% Pd/C (0.2 g). The reaction mixture was stirred at room temperature for 4 h under hydrogen (balloon). The reaction mixture was filtered through celite pad and the filtrate was evaporated to give the title compound (±)-tert-butyl N-((E)-3-(4-amino-2-((methylsulfinyl)methyl)phenyl)but-2-en-1-yl)-N-[(2-methylpropan-2-yl)oxycarbonyl]carbamate (0.6 g, 64%, LC-MS-95%) as a pale yellow liquid. ES+, m/z 339.1 [M-Boc+1].

Step 6

(±)-tert-Butyl (E)-(5-((4-(4-bis-((tert-butoxycarbonyl)amino)but-2-en-2-yl)-3-((methylsulfinyl)methyl)phenyl)amino)-3-cyanopyrazolo[1,5-a]pyrimidin-7-yl)(cyclopropyl)carbamate To a stirred solution of (±)-tert-butyl N-((E)-3-(4-amino-2-((methylsulfinyl)methyl)phenyl)but-2-en-1-yl)-N-[(2-methylpropan-2-yl)oxycarbonyl]carbamate (0.4 g, 0.913 mmol) in toluene (15 ml) at room temperature were added tert-butyl 5-chloro-3-cyanopyrazolo[1,5-a]pyrimidin-7-yl(cyclopropyl)carbamate (0.366 g, 1.09 mmol), $Cs_2CO_3$ (595 g, 1.826 mmol), BINAP (0.056 g, 0.091 mmol), and $Pd_2(dba)_3$ (0.083 g, 0.091 mmol). The reaction mass was degassed with argon for 5 min and stirred at 135° C. under microwaves for 2 h. The reaction mixture was extracted with EtOAc (3×100 mL). The organic layer was washed with water, brine, dried over anhydrous $Na_2SO_4$, filtered and concentrated under reduced pressure. The crude product was purified on GRACE flash chromatography, eluting with MeOH:$CH_2Cl_2$ (5:95) to get (±)-tert-butyl (E)-(5-((4-(4-bis-((tert-butoxycarbonyl)amino)but-2-en-2-yl)-3-((methylsulfinyl)methyl)phenyl)amino)-3-cyanopyrazolo[1,5-a]pyrimidin-7-yl)(cyclopropyl)carbamate (0.13 g, 19%, LC-MS 98%) as an off-white solid. ES+, m/z 636.1 [M-Boc+1].

Step 7

(±)-(E)-5-((4-(4-aminobut-2-en-2-yl)-3-((methylsulfinyl)methyl)phenyl)amino)-7-(cyclopropylamino)pyrazolo[1,5-a]pyrimidine-3-carbonitrile mono trifluoroacetic acid salt To a stirred solution of (±)-tert-butyl (E)-(5-((4-(4-bis-((tert-butoxycarbonyl)amino)but-2-en-2-yl)-3-((methylsulfinyl)methyl)phenyl)amino)-3-cyanopyrazolo[1,5-a]pyrimidin-7-yl)(cyclopropyl)carbamate (0.13 g, 0.176 mmol) in dichloromethane (10 mL) was added TFA (3 mL) at 0° C. The reaction mixture was stirred at room temperature for 5 h. The reaction mixture was concentrated under reduced pressure. The crude product was purified by prep HPLC (Mobile phase: 0.1% TFA in $H_2O$: ACN, Column: KROMOSIL-C18 (150*25), 10 u, Gradient: (T % B): 0/10, 6.3/55, 6.4/98, 8/98, 8.1/10, 10/10, flow rate: 25 ml/min, Diluent: ACN+$H_2O$+MeOH+THF) to get (±)-(E)-5-((4-(4-aminobut-2-en-2-yl)-3-((methylsulfinyl)methyl)phenyl)amino)-7-(cyclopropylamino)pyrazolo[1,5-a]pyrimidine-3-carbonitrile mono trifluoroacetic acid salt (65 mg, 85%, LC-MS 98.65%) as a white solid. ES+, m/z 436.1 [M-TFA+H]+; [$C_{22}H_{25}N_7OS$]; 1H NMR (500 MHz, DMSO-$d_6$), δ 9.78 (s, 1H), 8.36 (s, 1H), 8.27 (s, 1H), 7.85-7.83 (m, 4H), 7.62 (d, J=2.5 Hz, 1H), 7.15 (d, J=8.5 Hz, 1H), 6.02 (s, 1H), 5.34 (t, J=7.0 Hz, 1H), 4.08 (d, J=13.0 Hz, 1H), 3.99 (d, J=13.0 Hz, 1H), 3.62-3.50 (m, 4H), 2.63-2.58 (m, 4H), 1.99 (s, 3H), 0.84-0.80 (m, 2H), 0.73-0.71 (m, 2H). m.p.=249-253° C.

Example 61

(±)-7-(Cyclopropylamino)-5-((3-((methylsulfinyl)methyl)-4-((R,S)-piperidin-3-yl)phenyl)amino)pyrazolo[1,5-a]pyrimidine-3-carbonitrile mono trifluoroacetic acid salt (Cpd 61)

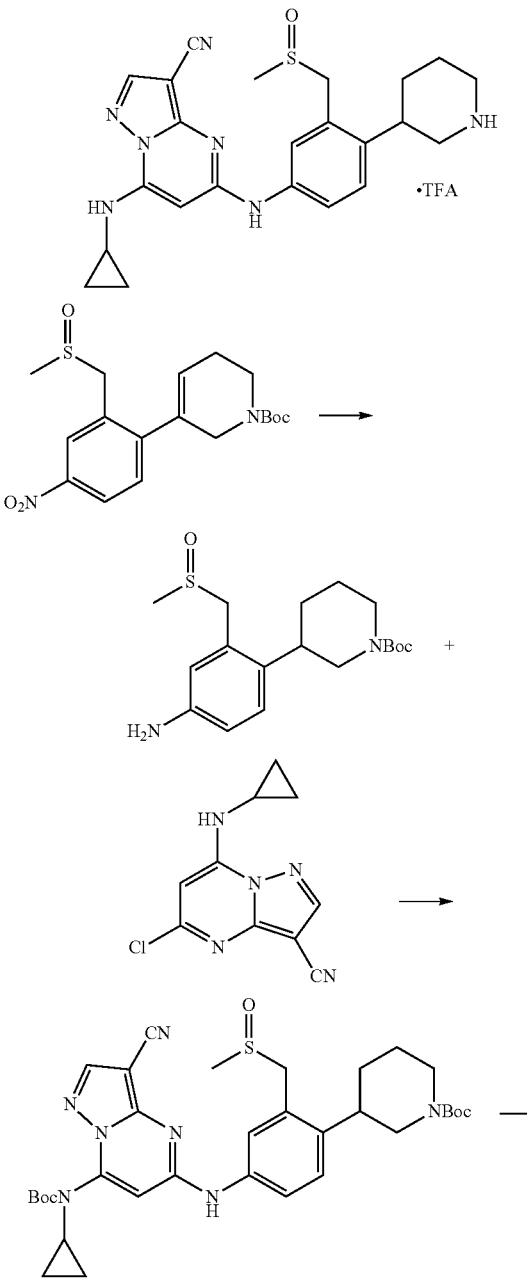

-continued

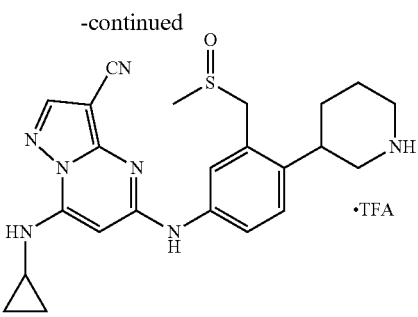

Step 1

(±)-tert-Butyl 3-(4-amino-2-((methylsulfinyl)methyl)phenyl)piperidine-1-carboxylate To a stirred solution of (±)-tert-butyl 5-(2-((methylsulfinyl)methyl)-4-nitrophenyl)-3,6-dihydropyridine-1(2H)-carboxylate (1.5 g, 3.94 mmol) (see Example 53, Step 5) in ethyl acetate was added 10% Pd—C (250 mg) in Parr shaker, stirred at room temperature for 12 h. The reaction mixture was filtered through celite pad. The filtrate was evaporated to get crude compound. The crude product was purified on a silica gel column eluting with MeOH:CH$_2$Cl$_2$, (4:96) to afford (±)-tert-butyl 3-(4-amino-2-(methylsulfinylmethyl)phenyl)piperidine-1-carboxylate (1.2 g, 86%, LC-MS 71%) as an off white solid. ES+, m/z 353.2 [M+1].

Step 2

(±)-tert-Butyl 3-(4-((7-((tert-butoxycarbonyl)(cyclopropyl)amino)-3-cyanopyrazolo[1,5-a]pyrimidin-5-yl)amino)-2-((methylsulfinyl)methyl)phenyl)piperidine-1-carboxylate To a stirred solution of (±)-tert-butyl 3-(4-amino-2-(methylsulfinylmethyl)phenyl)piperidine-1-carboxylate (0.250 g, 0.710 mmol) in toluene (15 ml) at room temperature were added 5-chloro-7-(cyclopropylamino)pyrazolo[1,5-a]pyrimidine-3-carbonitrile (0.260 g, 0.78 mmol), Cs$_2$CO$_3$ (0.462 g, 1.42 mmol), BINAP (0.044 g, 0.07 mmol), Pd$_2$(dba)$_3$ (0.064 g, 0.07 mmol). The reaction mass was degassed with argon for 5 min and stirred at 135° C. under microwave for 2 h. The reaction mixture was extracted with EtOAc (3×100 mL). The organic layer was washed with water, brine, dried over anhydrous Na$_2$SO$_4$, filtered and concentrated under reduced pressure. The crude product was purified on a silica gel column (eluting with MeOH:CH$_2$Cl$_2$, 2:98) to give (±)-tert-butyl 3-(4-((7-((tert-butoxycarbonyl)(cyclopropyl)amino)-3-cyanopyrazolo[1,5-a]pyrimidin-5-yl)amino)-2-((methylsulfinyl)methyl)phenyl)piperidine-1-carboxylate (0.20 g, 43%, LC-MS 82%) as a yellow solid. ES+, m/z 650.3 [M+1].

Step 3

(±)-7-(Cyclopropylamino)-5-((3-((methylsulfinyl)methyl)-4-((R,S)-piperidin-3-yl)phenyl)amino)pyrazolo[1,5-a]pyrimidine-3-carbonitrile mono trifluoroacetic acid salt To a stirred suspension of (±)-tert-butyl 3-(4-(7-(tert-butoxycarbonyl(cyclopropyl)amino)-3-cyanopyrazolo[1,5-a]pyrimidin-5-ylamino)-2-(methylsulfinylmethyl)phenyl)piperidine-1-carboxylate (0.2 g 0.308 mmol) in dichloromethane (15 mL) was added TFA (4 mL) at 0° C. The reaction mixture was stirred at room temperature for 4 h. The reaction mixture was concentrated under reduced pressure. The crude product was purified by prep-HPLC (Mobile phase: 0.1% TFA in H$_2$O: MeOH, Column: KROMOSIL-C18 (150*25), 10 u, Gradient: (T % B): 0/35, 8/70, 8.1/98, 10/98, 10.1/35, 12/35, Flow Rate: 25 ml/min, Diluent: ACN+H$_2$O+MeOH+THF) to give (±)-7-(cyclopropylamino)-5-(3-(methylsulfinylmethyl)-4-(piperidin-3-yl)phenylamino) pyrazolo[1,5-a]pyrimidine-3-carbonitrile mono trifluoroacetic acid salt (120 mg, as TFA salt, 86%, HPLC-97%) as a pale yellow solid. ES+, m/z 450.2 [M-TFA+H]$^+$; [C$_{23}$H$_{27}$N$_7$OS]; 1H NMR (400 MHz, DMSO-d$_6$), δ 9.74 (s, 1H), 8.73 (br s, 1H), 8.43-8.35 (m, 2H), 8.25 (s, 1H), 7.86-7.84 (m, 1H), 7.58 (d, J=2.0 Hz, 1H), 7.40 (dd, J=10.8 Hz, 6.4 Hz, 1H), 5.99 (s, 1H), 4.23-4.18 (m, 1H), 4.10-4.02 (m, 1H), 3.38-3.32 (m, 3H), 3.01-2.90 (m, 2H), 2.61 (d, J=11.2 Hz, 4H), 1.89-1.76 (m, 4H), 0.84-0.79 (m, 2H), 0.77-0.72 (m, 2H). m.p.=55-59° C.

Example 62

(±)-7-(Cyclopropylamino)-5-((4-(2,5-dihydro-1H-pyrrol-3-yl)-3-((methylsulfinyl)methyl)phenyl)amino)pyrazolo[1,5-a]pyrimidine-3-carbonitrile mono trifluoroacetic acid salt (Cpd 62)

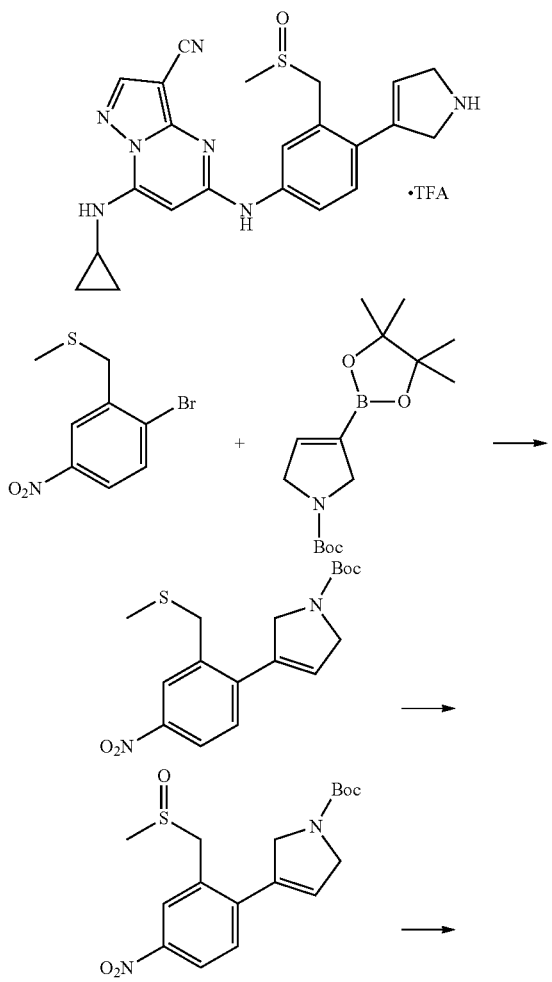

-continued

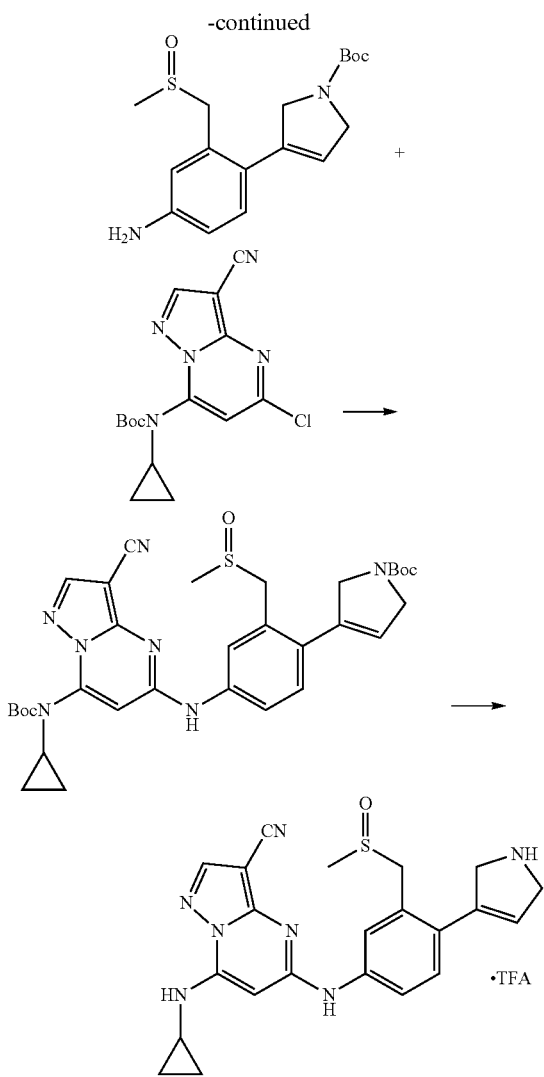

Step I (±)-tert-Butyl 3-(2-(methylthiomethyl)-4-nitrophenyl)-2,5-dihydro-1H-pyrrole-1-carboxylate To a stirred solution of (±)-tert-butyl 3-(4,4,5,5-tetramethyl-1,3,2-dioxaborolan-2-yl)-2,5-dihydro-1H-pyrrole-1-carboxylate (0.753 g, 2.874 mmol) in 1,4-dioxane (10 mL) were added (2-bromo-5-nitrobenzyl)(methyl)sulfane (0.85 g, 2.87 mmol) (sse Example 53, step 3), Pd(dppf)Cl$_2$.DCM (0.128 g, 0.172 mmol), Cs$_2$CO$_3$ (1.9 g, 5.748 mmol), and H$_2$O (3 mL) at room temperature. The reaction mixture was degassed with argon for 5 minutes and maintained at 90° C. for 16 h. 1,4-dioxane was removed under reduced pressure to give a brown residue. The crude compound was purified by GRACE flash chromatography using ethyl acetate in pet-ether (10:90) as eluent to get (±)-tert-butyl 3-(2-(methylthiomethyl)-4-nitrophenyl)-2,5-dihydro-1H-pyrrole-1-carboxylate (0.87 g, 86.5%, LC-MS 97.4%) as a yellow liquid. ES+, m/z 349.0 [M−1].

Step 2

(±)-tert-Butyl 3-(2-(methylsulfinylmethyl)-4-nitrophenyl)-2,5-dihydro-1H-pyrrole-1-carboxylate To a stirred solution of (±)-tert-butyl 3-(2-(methylthiomethyl)-4-nitrophenyl)-2,5-dihydro-1H-pyrrole-1-carboxylate (0.87 g, 2.485 mmol) in CH$_2$Cl$_2$ (10 mL), mCPBA (0.472 g, 2.734 mmol) was added in portions at 0° C. The reaction mass was allowed warm to room temperature and stirred for 16 h. The reaction mass diluted with CH$_2$Cl$_2$ (20 mL), washed with NaHCO$_3$ and brine, dried over Na$_2$SO$_4$ and concentrated to afford the crude product, which was purified on a silica gel column (eluting with methanol in CH$_2$Cl$_2$ 5:95) to furnish (±)-tert-butyl 3-(2-(methylsulfinylmethyl)-4-nitrophenyl)-2,5-dihydro-1H-pyrrole-1-carboxylate (0.67 g, 81.5%, LC-MS 98.52%) as an off white solid. ES+, m/z 267.0 [M-Boc+1].

Step 3

(±)-tert-Butyl 3-(4-amino-2-(methylsulfinylmethyl)phenyl)-2,5-dihydro-1H-pyrrole-1-carboxylate To a stirred solution of (±)-tert-butyl 3-(2-(methylsulfinylmethyl)-4-nitrophenyl)-2,5-dihydro-1H-pyrrole-1-carboxylate (0.3 g, 0.8196 mmol) in 70% aqueous ethanol (5 mL) at room temperature were added NH$_4$Cl (0.219 g, 4.098 mmol) and Fe powder (0.229 g, 4.0983 mmol). The reaction mixture was stirred at 90° C. for 5 h. The reaction mixture was cooled to room temperature and filtered through celite pad. The filtrate was evaporated to get a crude compound. The crude compound was washed with n-pentane (2×5 mL) and obtained (±)-tert-butyl 3-(4-amino-2-(methylsulfinylmethyl)phenyl)-2,5-dihydro-1H-pyrrole-1-carboxylate (0.2 g, 72.7%, LC-MS 89.6%) as an off white solid. ES+, m/z 237.1 [M-Boc+1].

Step 4

(±)-tert-Butyl 3-(4-(7-(tert-butoxycarbonyl(cyclopropyl)amino)-3-cyanopyrazolo[1,5-a]pyrimidin-5-ylamino)-2-(methylsulfinylmethyl)phenyl)-2,5-dihydro-1H-pyrrole-1-carboxylate To a stirred solution of (±)-tert-butyl 3-(4-amino-2-(methylsulfinylmethyl)phenyl)-2,5-dihydro-1H-pyrrole-1-carboxylate (0.2 g, 0.59 mmol) in NMP (5 mL) at room temperature were added tert-butyl 5-chloro-3-cyanopyrazolo[1,5-a]pyrimidin-7-yl(cyclopropyl)carbamate (0.199 g, 0.595 mmol), Cs$_2$CO$_3$ (0.388 g, 1.190 mmol), Pd$_2$(dba)$_3$ (0.055 g, 0.059 mmol), and BINAP (0.037 g, 0.0592 mmol). The reaction mass was degassed with argon for 5 min and stirred at 130° C. under microwave for 2 h. The reaction mixture was diluted with water (10 mL) and extracted with ethyl acetate (3×15 mL). The organic layer was washed with water, brine, dried over anhydrous Na$_2$SO$_4$, filtered and concentrated under reduced pressure. The crude product was purified by GRACE flash chromatography (eluting with MeOH:CH$_2$Cl$_2$, 16:84) to get (±)-tert-butyl 3-(4-(7-(tert-butoxycarbonyl(cyclopropyl)amino)-3-cyanopyrazolo[1,5-a]pyrimidin-5-ylamino)-2-(methylsulfinylmethyl)phenyl)-2,5-dihydro-1H-pyrrole-1-carboxylate (0.06 g, 15.9%, LC-MS 99.5%) as an off white solid. ES+, m/z 634.0 [M+1].

Step 5

(±)-7-(Cyclopropylamino)-5-((4-(2,5-dihydro-1H-pyrrol-3-yl)-3-((methylsulfinyl)methyl)phenyl)amino)pyrazolo[1,5-a]pyrimidine-3-carbonitrile mono trifluoroacetic acid salt To a stirred solution of (±)-tert-butyl 3-(4-(7-(tert-butoxycarbonyl(cyclopropyl)amino)-3-cyanopyrazolo[1,5-a]pyrimidin-5-ylamino)-2-(methylsulfinylmethyl)phenyl)-2,5-dihydro-1H-pyrrole-1-carboxylate (0.05 g, 0.0789 mmol) in CH$_2$Cl$_2$ (5 mL) at 0° C., TFA (2.5 mL) was added drop wise.

The reaction mixture was allowed to warm to room temperature and stirred for 6 h. The reaction mixture was concentrated under reduced pressure to get brown gummy solid which was co-distilled with ethyl acetate (2×5 mL) and washed with diethyl ether (2×5 mL) to get (±)-7-(cyclopropylamino)-5-(4-(2,5-dihydro-1H-pyrrol-3-yl)-3-(methylsulfinylmethyl)phenylamino) pyrazolo[1,5-a]pyrimidine-3-carbonitrile (0.036 g as a TFA salt, yield 95%, LC-MS 97.3%, HPLC 97.95%) as an off-white solid. ES+m/z 434.0 [M-TFA+H]$^+$. $C_{22}H_{23}N_7OS$; $^1$H NMR (500 MHz, DMSO-d$_6$), δ 9.88 (s, 1H), 9.24 (br s, 2H), 8.38 (s, 1H), 8.32 (s, 1H), 7.94 (dd, J=8.50, 2.0 Hz, 1H), 7.71-7.68 (m, 1H), 7.34 (d, J=8.5 Hz, 1H), 6.04-6.03 (m, 2H), 4.32-4.15 (m, 5H), 4.09-4.06 (m, 1H), 2.64-2.60 (m, 4H), 0.83-0.82 (m, 2H), 0.73-0.72 (m, 2H). m.p.=147-151° C.

Example 63

(±)-7-(Cyclopropylamino)-5-((3-((methylsulfinyl)methyl)-4-((R,S)-pyrrolidin-3-yl)phenyl)amino)pyrazolo[1,5-a]pyrimidine-3-carbonitrile mono trifluoroacetic acid salt (Cpd 63)

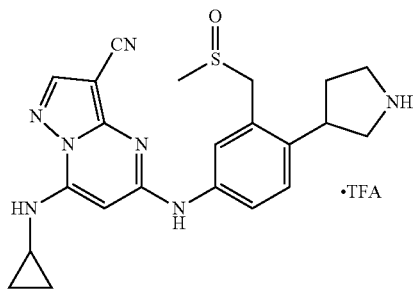 [SMILES: CS(=O)Cc1cc(Nc2cc(NC3CC3)n3ncc(C#N)c3n2)ccc1C1CCNC1]

This compound was prepared from (±)-tert-butyl 3-(4-amino-2-((methylsulfinyl)methyl)phenyl)pyrrolidine-1-carboxylate using the procedure as described in Example 62.

(±)-tert-Butyl (3R,S)-3-(4-amino-2-((methylsulfinyl)methyl)phenyl)pyrrolidine-1-carboxylate

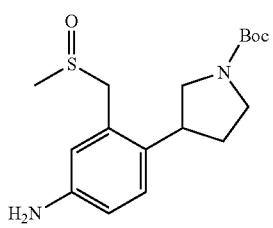

To a stirred solution of (±)-tert-butyl 3-(2-(methylsulfinylmethyl)-4-nitrophenyl)-2,5-dihydro-1H-pyrrole-1-carboxylate (0.35 g, 0.95 mmol) in ethanol (20 mL) was added 10% Pd/C (0.15 g) at room temperature. The reaction mixture was stirred for 16 h at room temperature under H$_2$ (60 psi) in a Parr shaker. The reaction mixture was filtered through celite pad. The filtrate was evaporated under reduced pressure to afford the crude product, which was in turn purified on a silica gel column (eluting with methanol:CH$_2$Cl$_2$ 5:95) to get (±)-tert-butyl (3R, S)-3-(4-amino-2-((methylsulfinyl)methyl)phenyl)pyrrolidine-1-carboxylate (0.17 g, 52.6%, LC-MS 75.93%) as a yellow solid. ES+, m/z 239.0 [M-Boc+1].

(±)-7-(Cyclopropylamino)-5-((3-((methylsulfinyl)methyl)-4-((R,S)-pyrrolidin-3-yl)phenyl)amino)pyrazolo[1,5-a]pyrimidine-3-carbonitrile mono trifluoroacetic acid salt (90%, LC-MS 96.7%, HPLC 97.6%) Off white solid. ES+, m/z 436.0 [M-TFA+H]$^+$. $C_{22}H_{25}N_7OS$; $^1$H NMR (500 MHz, DMSO-d$_6$), δ 9.75 (s, 1H), 8.84-8.75 (m, 2H), 8.36 (s, 1H), 8.27 (s, 1H), 7.94-7.91 (m, 1H), 7.54-7.52 (m, 1H), 7.47 (dd, J=8.5 Hz, 3.0 Hz, 1H), 6.00 (s, 1H), 4.34 (d, J=10.4 Hz, 0.5H), 4.01 (d, J=10.4 Hz, 0.5H), 3.54 (m, 1H), 3.45 (m, 1H), 3.36 (m, 1H), 3.32 (m, 1H), 3.22 (m, 1H), 3.10 (m, 1H), 2.64-2.60 (m, 4H), 2.49 (m, 1H), 1.95 (m, 1H), 0.82-0.81 (m, 2H), 0.72-0.70 (m, 2H). m.p.=173-177° C.

Example 64

(±)-5-((4-(R,S)-4-Aminobutan-2-yl)-3-((methylsulfinyl)methyl)phenyl)amino)-7-(cyclopropylamino)pyrazolo[1,5-a]pyrimidine-3-carbonitrile mono trifluoroacetic acid salt

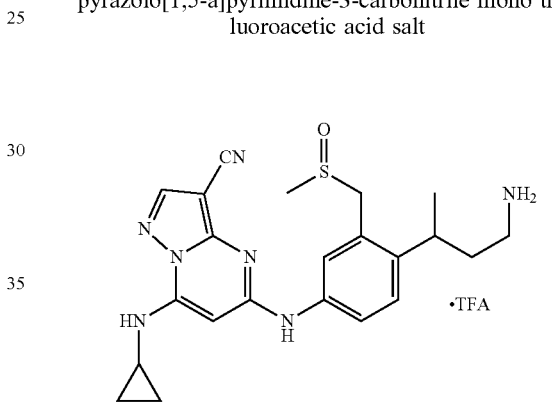

This compound was prepared from (±)-tert-butyl N-((E,Z)-3-(2-((methylsulfinyl)methyl)-4-nitrophenyl)but-2-en-1-yl)-N-[(2-methylpropan-2-yl)oxycarbonyl]carbamate using the procedure described in Example 60.

(±)-tert-Butyl N-((3R,S)-3-(4-amino-2-((methylsulfinyl)methyl)phenyl)butyl)-N-[(2-methylpropan-2-yl)oxycarbonyl]carbamate

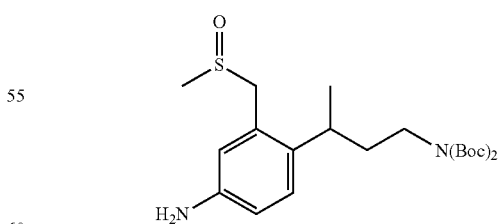

To a solution of (±)-tert-butyl N-((E,Z)-3-(2-((methylsulfinyl)methyl)-4-nitrophenyl)but-2-en-1-yl)-N-[(2-methylpropan-2-yl)oxycarbonyl]carbamate (2 g, 4.27 mmol) in ethanol (50 mL) was added 10% Pd/C (0.6 g) in a Parr shaker. The reaction mixture was stirred at room temperature for 48 h under hydrogen (70 psi). The reaction mixture was filtered through celite pad and the filtrate was evaporated to give a crude product, which was in turn was purified GRACE flash chromatography, eluting with MeOH:CH$_2$Cl$_2$, (5:95) to afford (±)-tert-butyl N-((3R,S)-3-(4-amino-2-((methylsulfinyl)methyl)phenyl)butyl)-N-[(2-methylpropan-2-yl)oxycarbonyl]carbamate (600 mg, 31%, LC-MS 90%) as a yellow liquid. ES+, m/z 341.1 [M-Boc+1].)

(±)-5-((4-((R,S)-4-Aminobutan-2-yl)-3-((methylsulfinyl)methyl)phenyl)amino)-7-(cyclopropylamino)pyrazolo[1,5-a]pyrimidine-3-carbonitrile mono trifluoroacetic acid salt Purified by Prep HPLC (Mobile phase: 0.1% TFA in H$_2$O: ACN, Column: KROMOSIL-C18 (150*25), 10 u, Gradient: (T % B): 0/10, 6.3/55, 6.4/98, 8/98, 8.1/10, 10/10, Flow Rate: 25 ml/min, Diluent: ACN+H$_2$O+MeOH+THF (60 mg, 60%, LC-MS 98%); Off white solid. ES+, m/z 438.0 [M-TFA+H]$^+$; [C$_{22}$H$_{27}$N$_7$OS] $^1$H NMR (400 MHz, DMSO-d$_6$), δ 9.71 (d, J=3.6 Hz, 1H), 8.35 (s, 1H), 8.24 (s, 1H), 7.90-7.81 (m, 1H), 7.61-7.51 (m, 4H), 7.31 (d, J=8.4 Hz, 1H), 6.02 (s, 1H), 4.29-4.00 (m, 2H), 3.18-3.10 (m, 1H), 2.75-2.66 (m, 6H), 1.96-1.79 (m, 2H), 1.17-1.12 (m, 3H), 0.84-0.81 (m, 2H), 0.77-0.72 (m, 2H). m.p.=119-123° C.

Example 65

(±)-5-((4-(((1-Aminocyclopropyl)methyl)(methyl)amino)-3-((methylsulfinyl)methyl)phenyl)amino)-7-(cyclopropylamino)pyrazolo[1,5-a]pyrimidine-3-carbonitrile mono trifluoroacetic acid salt (Cpd 65)

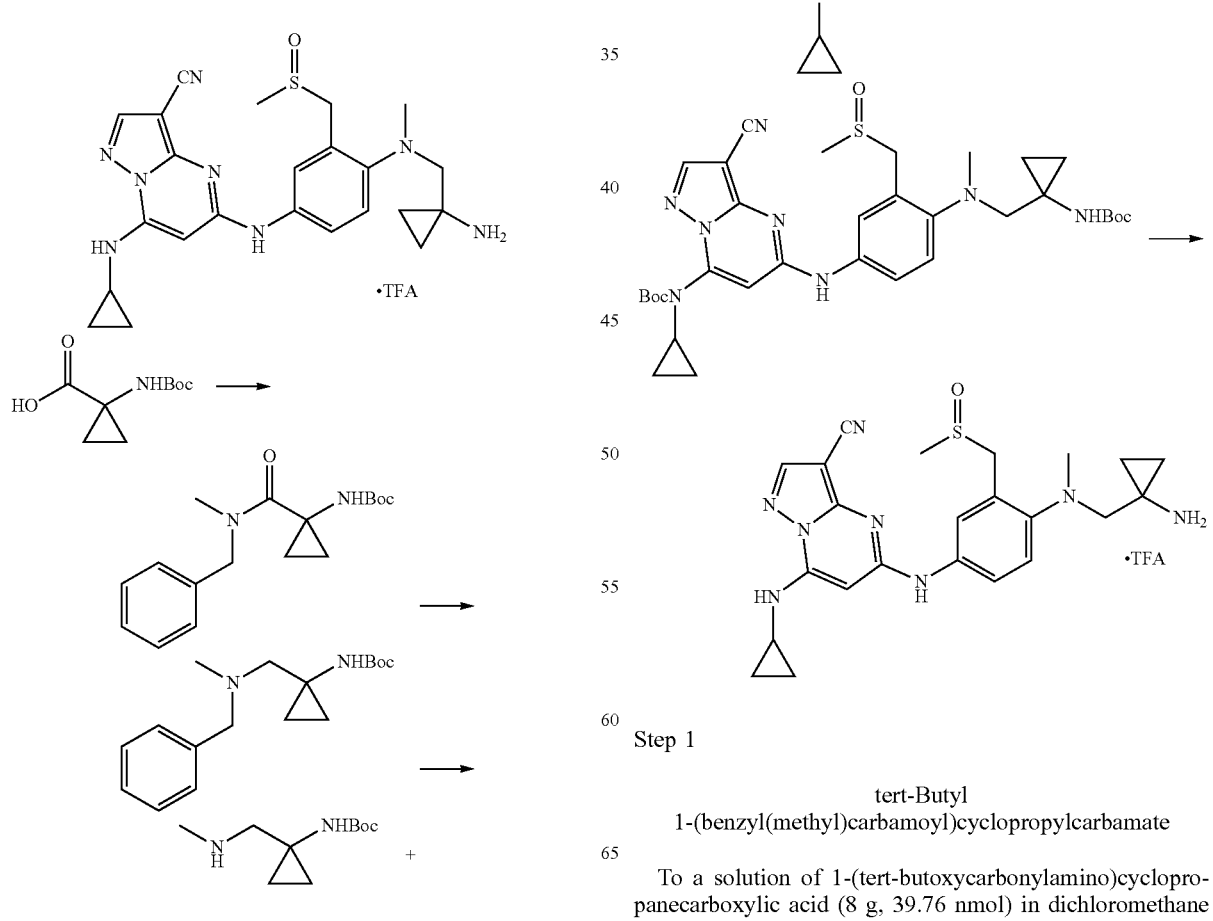

Step 1 tert-Butyl 1-(benzyl(methyl)carbamoyl)cyclopropylcarbamate

To a solution of 1-(tert-butoxycarbonylamino)cyclopropanecarboxylic acid (8 g, 39.76 nmol) in dichloromethane (80 mL) were added HOBt (8 g, 59.6 mmol), EDCI (11.5 g, 59.642 mmol), DPEA (13.6 ml, 47.71 mmol) and N-methyl-N-benzylamine (6.1 ml, 47.71 mmol). The reaction mixture was stirred at room temperature for 12 h. The reaction mixture was diluted with ethyl acetate (100 mL), and washed with brine, dried over $Na_2SO_4$, and concentrated. The crude product was purified on a silica gel column (eluting with pet ether: ethyl acetate 17:83) to give the title compound tert-butyl 1-(benzyl(methyl)carbamoyl)cyclopropylcarbamate (10 g, 83%, LC-MS 98%) as a colorless liquid. ES+, m/z 305.1 [M+1].

Step 2 tert-Butyl 1-((benzyl(methyl)amino)methyl)cyclopropylcarbamate

To a stirred solution of tert-butyl 1-(benzyl(methyl)carbamoyl)cyclopropylcarbamate (9.8 g, 32.23 mmol) in dry THF (80 ml) borane dimethylsulfide complex in THF (2M) was added in portions at 0° C. under argon. The reaction mixture was stirred at 80° C. for 6 h. The reaction mixture was diluted with methanol (30 mL) and refluxed at 70° C. for 2 h. The reaction mixture was concentrated under vacuum and diluted with EtOAc (20 mL). The resulting organic layer was washed with water, brine, dried ($Na_2SO_4$), and concentrated. The crude product was purified on a silica gel column (eluting with EtOAc: pet-ether, 30:70) to afford tert-butyl 1-((benzyl(methyl)amino)methyl)cyclopropylcarbamate (4.5 g, 48%, LC-MS 96%) as a colorless liquid. ES+, m/z 291.1 [M+1].

Step 3 tert-Butyl 1-((methylamino)methyl)cyclopropylcarbamate

To a solution of tert-butyl 1-((benzyl(methyl)amino)methyl)cyclopropylcarbamate (4.5 g, 15.51 mmol) in ethanol (50 mL) was added 10% Pd/C (0.5 g) in a Parr shaker bottle. The reaction mixture was stirred at room temperature for 16 h under hydrogen (60 psi). The reaction mixture was filtered through celite pad and the filtrate was evaporated to give the title compound tert-butyl 1-((methylamino)methyl)cyclopropylcarbamate (3.0 g, 96%) as a pale yellow oil. $^1$H NMR (500 MHz, $CDCl_3$), δ 5.21 (brs, 1H), 2.67 (brs, 2H), 2.45 (s, 3H), 1.98 (s, 1H), 1.44 (brs, 9H), 0.80 (m, 2H), 0.69 (m, 2H).

Step 4

(±)-tert-Butyl 1-((methyl(2-((methylsulfinyl) methyl)-4-nitrophenyl)amino)methyl) cyclopropylcarbamate To a stirred solution of tert-butyl 1-((methylamino) methyl)cyclopropylcarbamate (1 g, 5.0 mmol) in dry DMF (30 ml) at 0° C. were added 1-fluoro-2-(methylsulfinylmethyl)-4-nitrobenzene (1.07 g, 5.0 mmol) and $K_2CO_3$ (1.03 g, 7.5 mmol) and the reaction mixture was stirred at 95° C. for 16 h. The reaction mixture was cooled to room temperature, diluted with cold water (50 mL) and extracted with EtOAc (2×50 mL). The combined organic layer was washed with brine, dried over anhydrous $Na_2SO_4$, filtered and concentrated under reduced pressure to afford (±)-tert-butyl 1-((methyl(2-((methylsulfinyl)methyl)-4-nitrophenyl) amino)methyl) cyclopropylcarbamate (900 mg, 45%, LC-MS 97%) as a brown solid. ES+, m/z 398.0 [M+1].

Step 5

(±)-tert-Butyl (1-(((4-amino-2-((methylsulfinyl) methyl)phenyl)(methyl)amino)methyl)cyclopropyl) carbamate To a stirred solution of (±)-tert-butyl 1-((methyl(2-(methylsulfinylmethyl)-4-nitrophenyl)amino) methyl)cyclopropylcarbamate (0.9 g, 2.26 mmol) in 70% aqueous ethanol at room temperature were added $NH_4Cl$ (0.60 g, 11.33 mmol), Fe powder (0.62 g, 11.33 mmol) and stirred at 90° C. for 5 h. The reaction mixture was cooled to room temperature and filtered through celite pad. The filtrate was evaporated and the resulting crude compound was purified by column chromatography (silica gel, eluted with MeOH:$CH_2Cl_2$, 5:95) to afford (±)-tert-butyl 1-(((4-amino-2-(methylsulfinylmethyl)phenyl) (methyl)amino)methyl) cyclopropylcarbamate (0.75 g, 90%, LC-MS 97%) as a brown solid. ES+, m/z 368.1 [M+1].

Step 6

(±)-tert-Butyl (5-((4-(((1-((tert-butoxycarbonyl) amino)cyclopropyl)methyl)(methyl)amino)-3-((methylsulfinyl)methyl)phenyl)amino)-3-cyanopyrazolo[1,5-a]pyrimidin-7-yl)(cyclopropyl)carbamate To a stirred solution of (±)-tert-butyl 1-(((4-amino-2-(methylsulfinylmethyl)phenyl) (methyl)amino)methyl)cyclopropylcarbamate (0.3 g, 0.81 mmol) in NMP (15 ml) at room temperature were added tert-butyl 5-chloro-3-cyanopyrazolo[1,5-a]pyrimidin-7-yl(cyclopropyl)carbamate (0.3 g, 0.899 mmol), $Cs_2CO_3$ (0.53 g, 1.634 mmol), BINAP (0.05 g, 0.08 mmol), and $Pd_2(dba)_3$ (0.074 g, 0.08 mmol). The reaction mass was degassed with argon for 5 min and stirred at 135° C. under microwaves for 2 h. The reaction mixture was extracted with EtOAc (3×100 mL). The organic layer was washed with water, brine, dried over anhydrous $Na_2SO_4$, filtered and concentrated under reduced pressure. The crude product was purified by GRACE flash chromatography (eluent MeOH:$CH_2Cl_2$, 17:83) to afford (±)-tert-butyl (5-((4-(((1-((tert-butoxycarbonyl)amino)cyclopropyl) methyl)(methyl)amino)-3-((methylsulfinyl)methyl)phenyl) amino)-3-cyanopyrazolo[1,5-a]pyrimidin-7-yl) (cyclopropyl)carbamate (0.18 g, 33%, LC-MS 85%) as a brown solid. ES+, m/z 665.0 [M+1].

Step 7

(±)-5-((4-(((1-Aminocyclopropyl)methyl)(methyl) amino)-3-((methylsulfinyl)methyl)phenyl)amino)-7-(cyclopropylamino)pyrazolo[1,5-a]pyrimidine-3-carbonitrile mono trifluoroacetic acid salt To a stirred suspension of (±)-tert-butyl (5-((4-(((1-((tert-butoxycarbonyl)amino)cyclopropyl)methyl)(methyl) amino)-3-((methylsulfinyl)methyl)phenyl)amino)-3-cyanopyrazolo[1,5-a]pyrimidin-7-yl)(cyclopropyl)carbamate (0.18 g, 0.271 mmol) in dichloromethane (10 mL) was added TFA (3 mL) at 0° C. The reaction mixture was stirred at room temperature for 3 h. The reaction mixture was concentrated under reduced pressure. The crude product was purified by prep HPLC (Mobile phase: 0.1% TFA in $H_2O$: ACN, Column: KROMOSIL-C18 (150*25), 10 u, Gradient: (T % B): 0/20, 6.5/52, 6.6/98, 8/98, 8.1/20, 10/20, Flow Rate: 25 ml/min, Diluent: ACN+$H_2O$+MeOH+THF) to get (±)-5-((4-(((1-aminocyclopropyl)methyl)(methyl)amino)-3-((methylsulfinyl)methyl)phenyl)amino)-7-(cyclopropylamino)pyrazolo[1,5-a]pyrimidine-3-carbonitrile mono trifluoroacetic acid salt (90 mg, 75%, LC-MS 97%) as an off-white solid. ES+, m/z 465.0 [M-TFA+H]$^+$; [$C_{23}H_{28}N_8OS$]; 1H NMR (400 MHz, DMSO-$d_6$), δ 9.70 (s, 1H), 8.35 (s, 1H), 8.24 (d, J=0.8 Hz, 1H), 8.09 (s, 3H), 7.79 (dd, J=9.2 Hz, 5.2 Hz, 1H), 7.63 (d, J=2.0 Hz, 1H), 7.27 (d, J=6.8 Hz, 1H), 5.98 (s, 1H), 4.28 (dd, J=15.0 Hz, 10.0 Hz, 2H), 3.08 (q, 2H), 2.71 (s, 3H), 2.61 (s, 3H), 0.97-0.90 (m, 2H), 0.89-0.79 (m, 6H). m.p.=126-130° C.

Example 66

5-((4-(((1-aminocyclopropyl)methyl)(methyl) amino)-3-((methylsulfonyl)methyl)phenyl)amino)-7-(cyclopropylamino)pyrazolo[1,5-a]pyrimidine-3-carbonitrile mono trifluoroacetic acid salt (Cpd 66)

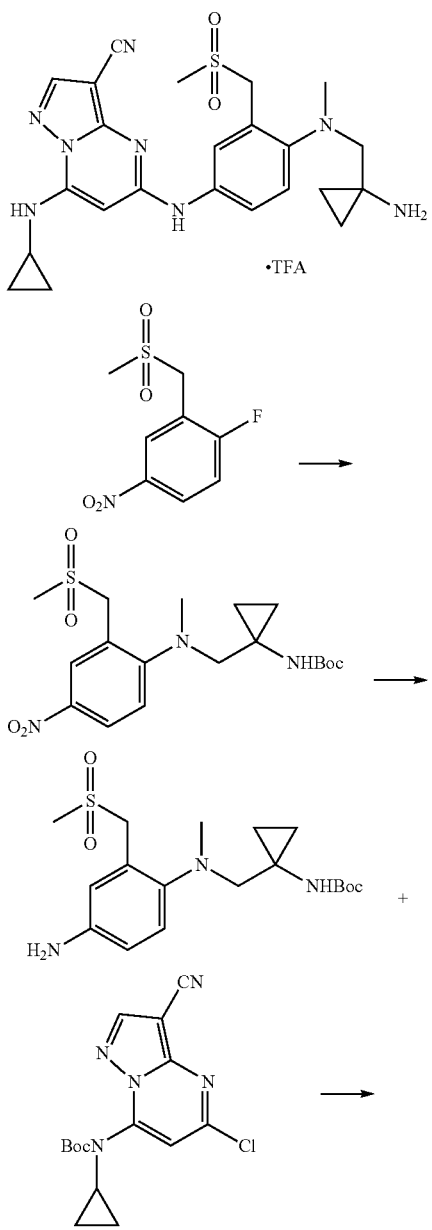

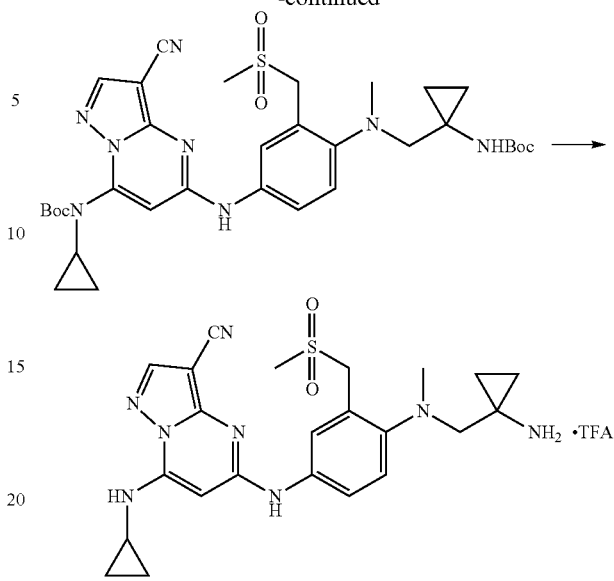

Step 1 tert-Butyl (1-((methyl(2-((methylsulfonyl)methyl)-4-nitrophenyl)amino)methyl)cyclopropyl)carbamate To a stirred solution of tert-butyl 1-((methylamino) methyl)cyclopropylcarbamate (0.9 g, 4.5 mmol) in dry DMF (20 ml) at 0° C. were added 1-fluoro-2-(methylsulfonylmethyl)-4-nitrobenzene (1.15 g, 4.95 mmol) and $K_2CO_3$ (1.24 g, 9.0 mmol) and the reaction mixture was stirred at 95° C. for 16 h. The reaction mixture was cooled to room temperature, diluted with cold water (50 mL) and extracted with EtOAc (2×50 mL). The combined organic layer was washed with brine (2×50 mL), dried over anhydrous $Na_2SO_4$, filtered and concentrated under reduced pressure to afford tert-butyl 1-((methyl(2-(methylsulfonylmethyl)-4-nitrophenyl)amino)methyl) cyclopropylcarbamate (1.2 g, 66%, LC-MS 96%) as an off-white solid. ES+, m/z 414.0 [M+1].

Step 2 tert-butyl (1-(((4-amino-2-((methylsulfonyl)methyl) phenyl)(methyl)amino)methyl)cyclopropyl)carbamate To a stirred solution of tert-butyl 1-((methyl(2-(methylsulfonylmethyl)-4-nitrophenyl) amino)methyl) cyclopropylcarbamate (1.1 g, 2.66 mmol) in 70% aqueous ethanol at room temperature were added $NH_4Cl$ (0.71 g, 13.33 mmol) and Fe powder (0.744 g, 13.33 mmol) and the reaction mixture was stirred at 90° C. for 5 h. The reaction mixture was cooled to room temperature and filtered through celite pad and the filtrate was evaporated. The crude compound was purified by column chromatography (silica gel, eluting with MeOH:$CH_2Cl_2$, 5:95) to afford tert-butyl 1-(((4-amino-2-(methylsulfonylmethyl)phenyl)(methyl)amino)methyl) cyclopropylcarbamate (0.90 g, 89%, LC-MS 97%) as an off-white solid. ES+, m/z 384.1 [M+1].

Step 3 tert-Butyl (5-((4-(((1-((tert-butoxycarbonyl)amino) cyclopropyl)methyl)(methyl)amino)-3-((methylsulfonyl)methyl)phenyl)amino)-3-cyanopyrazolo[1,5-a] pyrimidin-7-yl)(cyclopropyl)carbamate To a solution of tert-butyl 1-(((4-amino-2-(methylsulfonylmethyl)phenyl)(methyl)amino)methyl) cyclopropylcarbamate (0.3 g, 0.78 mmol) in NMP (10 ml) at room temperature were added tert-butyl 5-chloro-3-cyanopyrazolo[1,5-a]pyrimidin-7-yl(cyclopropyl)carbamate (0.287 g, 0.86 mmol), Cs$_2$CO$_3$ (0.508 g, 1.56 mmol), BINAP (0.048 g, 0.07 mmol), and Pd$_2$(dba)$_3$ (0.071 g, 0.078 mmol). The reaction mass was degassed with argon for 5 min and stirred at 135° C. under microwave for 2 h. The reaction mixture was extracted with EtOAc (2×50 mL). The organic layer was washed with water, brine, dried over anhydrous Na$_2$SO$_4$, filtered and concentrated under reduced pressure. The crude product was purified by GRACE chromatography (eluent MeOH:CH$_2$Cl$_2$, 5:95) to afford tert-butyl (5-((4-(((1-((tert-butoxycarbonyl)amino)cyclopropyl)methyl)(methyl) amino)-3-((methylsulfonyl)methyl)phenyl)amino)-3-cyanopyrazolo[1,5-a]pyrimidin-7-yl)(cyclopropyl)carbamate (0.15 g, 28%, LC-MS 90%) as an off white solid. ES+, m/z 681.0 [M+1].

Step 4

5-((4-(((1-Aminocyclopropyl)methyl)(methyl) amino)-3-((methylsulfonyl)methyl)phenyl)amino)-7-(cyclopropylamino)pyrazolo[1,5-a]pyrimidine-3-carbonitrile mono trifloroacetic acid salt To a stirred suspension of tert-butyl (5-((4-(((1-((tert-butoxycarbonyl)amino)cyclopropyl)methyl)(methyl) amino)-3-((methylsulfonyl)methyl)phenyl)amino)-3-cyanopyrazolo[1,5-a]pyrimidin-7-yl)(cyclopropyl)carbamate (0.15 g, 0.22 mmol) in dichloromethane (10 mL) was added TFA (2 mL) at 0° C. The reaction mixture was stirred at room temperature for 3 h. The reaction mixture was concentrated under reduced pressure. The crude product was purified by prep-HPLC (Mobile phase: 0.1% TFA in H$_2$O: ACN, Column: KROMOSIL-C18 (150*25), 10 u, Gradient: (T % B): 0/20, 6.5/52, 6.6/98, 8/98, 8.1/20, 10/20, Flow Rate: 25 ml/min, Diluent: ACN+H$_2$O+MeOH+THF) to furnish 5-((4-(((1-aminocyclopropyl)methyl)(methyl)amino)-3-((methylsulfonyl)methyl)phenyl)amino)-7-(cyclopropylamino)pyrazolo[1,5-a]pyrimidine-3-carbonitrile mono trifluoroacetic acid salt (80 mg, 80%, LC-MS 99%) as an off-white solid. ES+, m/z 481.0 [M-TFA+H]$^+$; [C$_{23}$H$_{28}$N$_8$OS]; $^1$H NMR (500 MHz, DMSO-d$_6$), δ 9.73 (s, 1H), 8.35 (s, 1H), 8.25 (s, 1H), 8.00-7.96 (m, 4H), 7.59 (d, J=2.5 Hz, 1H), 7.27 (d, J=9.0 Hz, 1H), 6.0 (s, 1H), 4.71 (s, 2H), 3.08 (s, 3H), 3.01 (s, 2H), 2.61-2.60 (m, 4H), 0.97-0.96 (m, 2H), 0.81-0.78 (m, 4H), 0.72-0.70 (m, 2H). m.p.=185-189° C.

Example 67

(±)-5-((4-((2-Amino-2-methylpropyl)(methyl) amino)-3-((methylsulfinyl)methyl)phenyl)amino)-7-(cyclopropylamino)pyrazolo[1,5-a]pyrimidine-3-carbonitrile mono trifluoroacetic acid salt (Cpd 67)

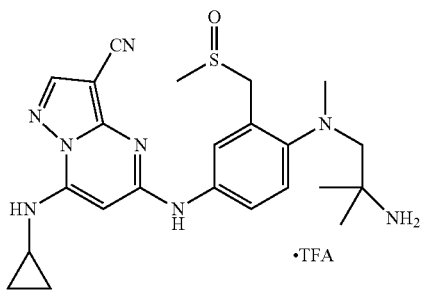

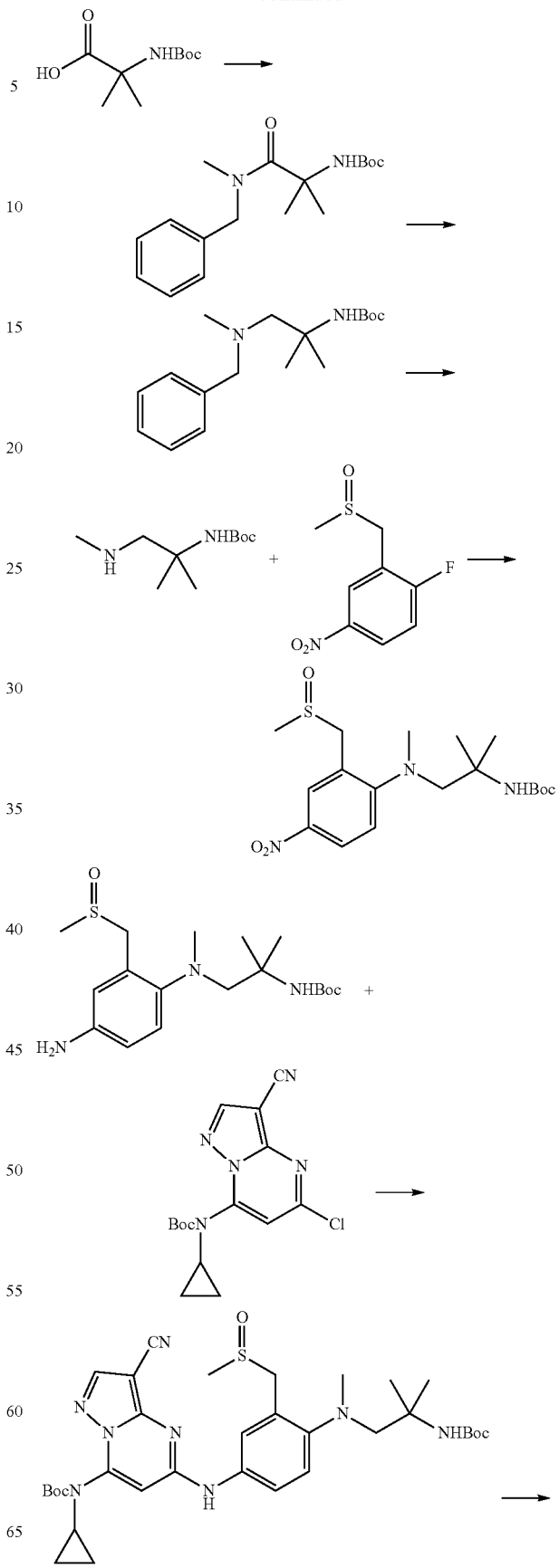

-continued

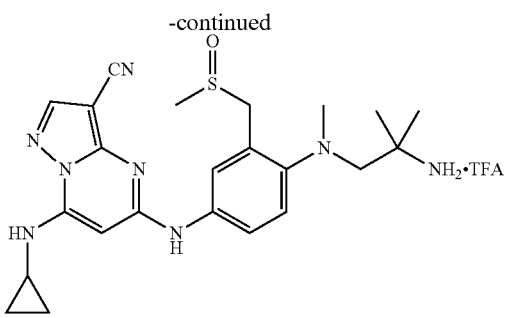

Step 1 tert-Butyl 1-(benzyl(methyl)amino)-2-methyl-1-oxopropan-2-ylcarbamate

To a solution of 2-(tert-butoxycarbonylamino)-2-methylpropanoic acid (15 g, 73.89 mmol) in CH₂Cl₂ (80 mL) were added HOBt (14.9 g, 110.8 mmol), EDCI (21.2 g, 110.83 mmol), DPEA (25.7 ml, 147.71 mmol) and N-methyl-N-benzylamine (11.4 mL). The reaction mixture was stirred at room temperature for 12 h. The reaction mixture was diluted with ethyl acetate (100 mL), the organic layer was washed with brine, dried over Na₂SO₄, and concentrated to give the crude product, which in turn purified on a silica gel column (eluting with pet ether: ethyl acetate 17:83%) to give the title compound tert-butyl 1-(benzyl(methyl)amino)-2-methyl-1-oxopropan-2-ylcarbamate (13 g, 57%, LC-MS 98%) as a colorless liquid. ES+, m/z 307.0 [M+1].

Step 2 tert-Butyl 1-(benzyl(methyl)amino)-2-methylpropan-2-ylcarbamate

To a stirred solution of tert-butyl 1-(benzyl(methyl)amino)-2-methyl-1-oxopropan-2-ylcarbamate (13 g, 42.6 mmol) in dry THF (120 mL), borane dimethylsulfide complex in THF (2M) (42.6 mL, 85.2 mmol) was added in portions at 0° C. under argon. The reaction mixture was stirred at 80° C. for 6 h. The reaction mixture was diluted with methanol (50 ml) and refluxed at 70° C. for 2 h. The reaction mixture was concentrated under vacuum and diluted with EtOAc (20 mL); the organic layer was washed with water, brine, dried over Na₂SO₄, and concentrated. The crude product was purified on a silica gel column (eluting with EtOAc: pet-ether (40:60), to afford tert-butyl 1-(benzyl(methyl)amino)-2-methylpropan-2-ylcarbamate (2.5 g, 20%, LC-MS 97%) as a colorless liquid. ES+, m/z 293.1 [M+1].

Step 3 tert-Butyl 2-methyl-1-(methylamino)propan-2-ylcarbamate

To a solution of tert-butyl 1-(benzyl(methyl)amino)-2-methylpropan-2-ylcarbamate (2.5 g, 8.53 mmol) in ethanol (40 mL) was added 10% Pd/C (0.4 g) in a Parr shaker bottle and shaken the mixture under hydrogen (60 psi) at room temperature for 16 h. The reaction mixture was filtered through celite pad and the filtrate was evaporated to provide the title compound tert-butyl 2-methyl-1-(methylamino)propan-2-ylcarbamate (1.3 g, 76%) as a colorless liquid. ¹H NMR (400 MHz, CDCl₃), δ 5.01 (brs, 1H), 2.59 (brs, 2H), 2.46 (s, 3H), 1.44 (brs, 9H), 1.29 (s, 6H).

Step 4

(±)-tert-Butyl 2-methyl-1-(methyl(2-(methylsulfinylmethyl)-4-nitrophenyl)amino)propan-2-ylcarbamate

To a stirred solution of tert-butyl 2-methyl-1-(methylamino)propan-2-ylcarbamate (1.3 g, 6.43 mmol) in dry DMF (25 mL) at room temperature were added (±)-1-fluoro-2-(methylsulfinylmethyl)-4-nitrobenzene (1.53 g, 7.07 mmol) and K₂CO₃ (1.77 g, 12.86 mmol). The reaction mixture was stirred at 95° C. for 48 h. The reaction mixture was cooled to room temperature, diluted with cold water (50 mL) and extracted with EtOAc (2×50 mL). The combined organic layer was washed with brine, dried over anhydrous Na₂SO₄, filtered and concentrated under reduced pressure to afford (±)-tert-butyl 2-methyl-1-(methyl(2-(methylsulfinylmethyl)-4-nitrophenyl)amino)propan-2-ylcarbamate (600 mg, 23%, LC-MS 95%) as a colorless liquid. ES+, m/z 400.0 [M+1].

Step 5

(±)-tert-Butyl 1-((4-amino-2-(methylsulfinylmethyl)phenyl)(methyl)amino)-2-methylpropan-2-ylcarbamate

To a stirred solution of (±)-tert-butyl 2-methyl-1-(methyl(2-(methylsulfinylmethyl)-4-nitrophenyl)amino)propan-2-ylcarbamate (0.6 g, 1.50 mmol) in 70% aqueous ethanol (20 mL), at room temperature were added NH₄Cl (0.40 g, 7.51 mmol) and Fe powder (0.41 g, 7.51 mmol). The reaction mixture was stirred at 90° C. for 5 h. The reaction mixture was cooled to room temperature and filtered through celite pad. The filtrate was evaporated to afford crude compound. The crude compound was purified by column chromatography (silica gel, eluting with MeOH:CH₂Cl₂, 5:95) to afford (±)-tert-butyl 1-((4-amino-2-(methylsulfinylmethyl)phenyl)(methyl)amino)-2-methylpropan-2-ylcarbamate (0.35 g, 63%, LC-MS 87%) as an off white solid. ES+, m/z 370.1 [M+1].

Step 6

(±)-tert-Butyl (5-((4-((2-((tert-butoxycarbonyl)amino)-2-methylpropyl)(methyl)amino)-3-((methylsulfinyl)methyl)phenyl)amino)-3-cyanopyrazolo[1,5-a]pyrimidin-7-yl)(cyclopropyl)carbamate

To a stirred solution (±)-tert-butyl 1-((4-amino-2-(methylsulfinylmethyl)phenyl)(methyl)amino)-2-methylpropan-2-ylcarbamate (0.35 g, 0.94 mmol) in NMP (15 mL) at room temperature were added tert-butyl 5-chloro-3-cyanopyrazolo[1,5-a]pyrimidin-7-yl(cyclopropyl)carbamate (0.34 g, 1.04 mmol), Cs₂CO₃ (0.612 g, 1.88 mmol), BINAP (0.058 g, 0.09 mmol), and Pd₂(dba)₃ (0.082 g, 0.09 mmol). The reaction mass was degassed with argon for 5 min and stirred at 135° C. under microwaves for 2 h. The reaction mixture was cooled to RT and extracted with EtOAc (3×100 mL). The organic layer was washed with water, brine, dried over anhydrous Na₂SO₄, filtered and concentrated under reduced pressure. The crude compound was purified by GRACE flash chromatography (eluent MeOH:CH₂Cl₂, 17:83) to get (±)-tert-butyl (5-((4-((2-((tert-butoxycarbonyl)amino)-2-methylpropyl)(methyl)amino)-3-((methylsulfinyl)methyl)phenyl)amino)-3-cyanopyrazolo[1,5-a]pyrimidin-7-yl)(cyclopropyl)carbamate (0.15 g, 23%, LC-MS 90%) as an off-white solid. ES+, m/z 667.0 [M+1].

Step 7

(±)-5-((4-((2-Amino-2-methylpropyl)(methyl) amino)-3-((methylsulfinyl)methyl)phenyl)amino)-7-(cyclopropylamino)pyrazolo[1,5-a]pyrimidine-3-carbonitrile mono trifluoroacetic acid salt To a stirred suspension of (±)-tert-butyl (5-((4-((2-((tert-butoxycarbonyl)amino)-2-methylpropyl)(methyl)amino)-3-((methylsulfinyl)methyl)phenyl)amino)-3-cyanopyrazolo[1,5-a]pyrimidin-7-yl)(cyclopropyl)carbamate (0.15 g, 0.22 mmol) in dichloromethane (10 mL) was added TFA (3 mL) at 0° C. The reaction mixture was stirred at room temperature for 3 h. The reaction mixture was concentrated under reduced pressure. The crude product was purified by Prep HPLC (Mobile phase: 0.1% TFA in $H_2O$: ACN, Column: KROMOSIL-C18 (150*25), 10 u, Gradient: (T % B): 0/20, 6.5/52, 6.6/98, 8/98, 8.1/20, 10/20, Flow Rate: 25 ml/min, Diluent: ACN+$H_2O$+MeOH+THF) to furnish (±)-5-((4-((2-Amino-2-methylpropyl)(methyl)amino)-3-((methylsulfinyl)methyl)phenyl)amino)-7-(cyclopropylamino)pyrazolo[1,5-a]pyrimidine-3-carbonitrile mono trifluoroacetic acid salt (100 mg, as a TFA salt, 47%, LC-MS: 99%) as an off white solid. ES+, m/z 467.0 [M-TFA+H]$^+$; [$C_{23}H_{30}N_8OS$]; $^1H$ NMR (500 MHz, DMSO-$d_6$), δ 9.70 (s, 1H), 8.35 (s, 1H), 8.25 (s, 2H), 7.82 (dd, J=8.8 Hz, 5.2 Hz, 1H), 7.69 (br s, 2H), 7.64 (d, J=2.0 Hz, 1H), 7.38 (d, J=7.2 Hz, 1H), 5.97 (s, 1H), 4.35 (d, J=10.0 Hz, 1H), 4.25 (d, J=10.4 Hz, 1H), 3.32 (d, J=11.6 Hz, 1H), 3.05 (d, J=11.6 Hz, 1H), 2.80 (s, 3H), 2.65-2.59 (m, 4H), 1.24 (s, 3H), 1.11 (s, 3H), 0.82-0.80 (m, 2H), 0.77-0.72 (m, 2H). m.p.=141-145° C.

Example 68

(±)-7-((5-Aminopyridin-2-yl)amino)-5-((4-((S)-3-aminopyrrolidin-1-yl)-3-((methylsulfinyl)methyl) phenyl)amino)pyrazolo[1,5-a]pyrimidine-3-carbonitrile (Cpd 68)

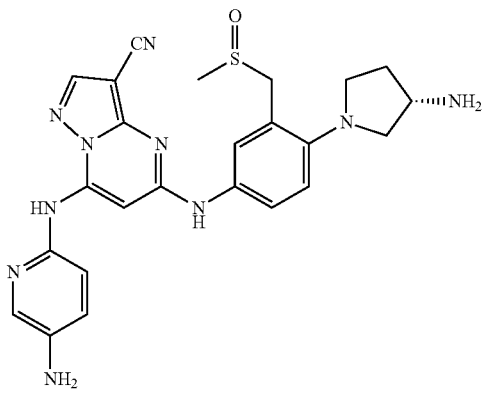 [SMILES: CS(=O)Cc1cc(Nc2cc(Nc3ccc(N)cn3)n3ncc(C#N)c3n2)ccc1N1CC[C@H](N)C1]

This compound was prepared using the same general method as described in Example 57, substituting (±)-tert-butyl ((3S)-1-(4-amino-2-((methylsulfinyl)methyl)phenyl) pyrrolidin-3-yl)carbamate for (±)-4-cyclopropyl-3-((methylsulfinyl)methyl)aniline. ES+, m/z 503.4 [M+1]; $^1H$ NMR (500 MHz, DMSO-$d_6$), δ 9.66 (brs, 1H), 8.42 (s, 1H), 7.80 (d, J=2.5 Hz, 1H), 7.76 (brs, 1H), 7.53 (brs, 1H), 7.24 (d, J=8.5 Hz, 1H), 7.22 (s, 1H), 7.11 (d, J=9.0 Hz, 1H), 7.05 (dd, J=2.5, 8.5 Hz, 1H), 5.21 (s, 2H), 4.14-4.04 (m, 2H), 3.56 (m, 1H), 3.28-3.22 (m, 2H), 3.10-3.00 (m, 1H), 2.87-2.84 (m, 1H), 2.57 (s, 3H), 2.18-2.11 (m, 1H), 1.67-1.63 (m, 1H).

Example 69

(±)-5-((4-Cyclopropyl-3-((methylsulfinyl)methyl) phenyl)amino)-7-((5-(((dimethylamino)methyl)pyridin-2-yl)amino)pyrazolo[1,5-a]pyrimidine-3-carbonitrile (Cpd 69)

-continued

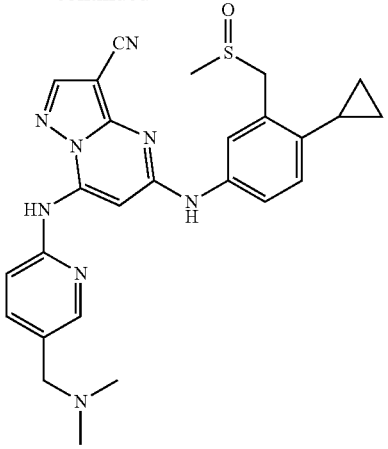

Step 1

5-Chloro-7-((5-formylpyridin-2-yl)amino)pyrazolo[1,5-a]pyrimidine-3-carbonitrile To a solution of 6-aminonicotinaldehyde (257 mg, 2.1 mmol) in dry DMF (5 mL) at 0° C. under argon was added NaH (60% in mineral oil, 90 mg, 1.1 eq). After 30 minutes, 5,7-dichloropyrazolo[1,5-a]pyrimidine-3-carbonitrile (425 mg, 2.0 mmol) was added. The reaction was stirred at 0° C. to r.t overnight. The reaction was quenched by addition of 1.0 mL of water. The solvents were removed by rotovap and the residue was purified on a silica gel column (eluting with DCM/EtOAc 3/1 to 2/1) to give the title compound as a yellow solid (343 mg, 57.5% yield).

Step 2

(±)-5-((4-Cyclopropyl-3-((methylsulfinyl)methyl)phenyl)amino)-7-((5-formylpyridin-2-yl)amino)pyrazolo[1,5-a]pyrimidine-3-carbonitrile To a mixture of 5-chloro-7-((5-formylpyridin-2-yl)amino)pyrazolo[1,5-a]pyrimidine-3-carbonitrile (330 mg, 1.1 mmol), (±)-4-cyclopropyl-3-((methylsulfinyl)methyl)aniline (230 mg, 1.1 mmol), $Cs_2CO_3$ (540 mg, 1.65 mmol, 1.5 eq.) and BINAP (69 mg, 0.11 mmol, 0.1 eq.) in NMP (6 mL) under Argon atmosphere, was added $Pd_2(dba)_3$ (100 mg, 0.11 mmol, 0.1 eq.). The reaction mixture was stirred at 135° C. for 5 hours. The reaction mixture was cooled down to room temperature. The solid were filtered off. The solution was concentrated in reduced pressure to remove most of NMP. The residue was purified on a silica gel column (eluting with 100% DCM to DCM/MeOH 10/1) to provide the title compound as a yellow solid (358 mg, 69% yield).

Step 3

(±)-5-((4-Cyclopropyl-3-((methylsulfinyl)methyl)phenyl)amino)-7-((5-((dimethylamino)methyl)pyridin-2-yl)amino)pyrazolo[1,5-a]pyrimidine-3-carbonitrile To a mixture of (±)-5-((4-cyclopropyl-3-((methylsulfinyl)methyl)phenyl)amino)-7-((5-formylpyridin-2-yl)amino)pyrazolo[1,5-a]pyrimidine-3-carbonitrile (73 mg, 0.155 mmol), dimethylamine hydrochloride (25.3 mg, 0.31 mmol, 2.0 eq.), trimethylamine (0.05 mL), in 5% (v/v) HAc/DMF (3.0 mL) at r.t., was added sodium triacetoxyborohydride (83 mg, 0.39 mmol, 2.5 eq.). The reaction was stirred at r.t. for 3 h. LCMS indicated the completion of reaction. The reaction was quenched by addition of water (1.0 mL). The volatiles were mostly removed by rotovap under reduced pressure. The residue was dissolved in EtOAc/MeOH (10/1, 100 mL), washed with 10% aqueous $K_2CO_3$ (20 mL), brine, dried ($Na_2SO_4$) and concentrated. The crude product was purified on a prep. TLC (DCM/MeOH 5/1) to give the title compound as a yellow solid (48 mg, 61% yield). ES+, m/z 501.4 [M+1]; $^1$H NMR (500 MHz, DMSO-$d_6$), δ 10.25 (s, 1H), 9.92 (s, 1H), 8.49 (s, 1H), 8.27 (s, 1H), 7.77-7.71 (m, 3H), 7.62 (s, 1H), 7.55 (d, J=8.5 Hz, 1H), 7.03 (d, J=8.5 Hz, 1H), 4.30 (d, J=12.5 Hz, 1H), 4.17 (d, J=12.5 Hz, 1H), 3.40 (s, 2H), 2.63 (s, 3H), 2.16 (s, 6H), 2.06 (m, 1H), 0.93-0.91 (m, 2H), 0.67-0.63 (m, 2H).

Example 70

(±)-7-((5-(aminomethyl)pyridin-2-yl)amino)-5-((4-cyclopropyl-3-((methylsulfinyl)methyl)phenyl)amino)pyrazolo[1,5-a]pyrimidine-3-carbonitrile (Cpd 70)

Compound 70 can be prepared according to the procedure described in Example 69 with 4-cyclopropyl-3-((methylsulfinyl)methyl)aniline and tert-butyl ((6-((5-chloro-3-cyanopyrazolo[1,5-a]pyrimidin-7-yl)amino)pyridin-3-yl)methyl)carbamate.

Example 71

(±)-5-((4-chloro-3-((methylsulfinyl)methyl)phenyl)amino)-7-((5-((dimethylamino)methyl)pyridin-2-yl)amino)pyrazolo[1,5-a]pyrimidine-3-carbonitrile (Cpd 71)

Compound 71 can be prepared according to the procedure described in Example 69 with 4-chloro-3-((methylsulfonyl)methyl)aniline.

Example 72

(±)-7-((5-((dimethylamino)methyl)pyridin-2-yl)amino)-5-((3-((methylsulfinyl)methyl)-4-(pyrrolidin-1-yl)phenyl)amino)pyrazolo[1,5-a]pyrimidine-3-carbonitrile (Cpd 72)

Compound 72 can be prepared according to the procedure described in Example 69 with 3-((methylsulfonyl)methyl)-4-(pyrrolidin-1-yl)aniline.

Example 73

(R,S)-5-((4-(4-aminobutan-2-yl)-3-((methylsulfonyl)methyl)phenyl)amino)-7-(cyclopropylamino)pyrazolo[1,5-a]pyrimidine-3-carbonitrile mono trifluoroacetic acid salt (Cpd 73)

Compound 73 can be prepared according to the procedure described in Examples 60 and 64 with tert-butyl N-((3R,S)-3-(4-amino-2-((methylsulfonyl)methyl)phenyl)butyl)-N-[(2-methylpropan-2-yl)oxycarbonyl]carbamate.

Example 74

(±)-5-((4-(2-aminocyclopropyl)-3-((methylsulfinyl)methyl)phenyl)amino)-7-(cyclopropylamino)pyrazolo[1,5-a]pyrimidine-3-carbonitrile mono trifluoroacetic acid salt (Cpd 74)

Compound 74 can be prepared according to the procedure described in Example 59 with tert-butyl (2-(4-amino-2-((methylsulfinyl)methyl)phenyl)cyclopropyl)carbamate.

Example 75

(±)-5-((4-(2-(aminomethyl)cyclopropyl)-3-((methylsulfinyl)methyl)phenyl)amino)-7-(cyclopropylamino)pyrazolo[1,5-a]pyrimidine-3-carbonitrile mono trifluoroacetic acid salt (Cpd 75)

Compound 75 can be prepared according to the procedure described in Example 59 with tert-butyl ((2-(4-amino-2-((methylsulfinyl)methyl)phenyl)cyclopropyl)methyl)carbamate.

Example 76

(±)-5-((4-(2-(2-aminoethyl)cyclopropyl)-3-((methylsulfinyl)methyl)phenyl)amino)-7-(cyclopropylamino)pyrazolo[1,5-a]pyrimidine-3-carbonitrile mono trifluoroacetic acid salt (Cpd 76)

Compound 76 can be prepared according to the procedure described in Example 59 with tert-butyl (2-(2-(4-amino-2-((methylsulfinyl)methyl)phenyl)cyclopropyl)ethyl)carbamate.

Example 77

(±)-2-amino-N-(4-((3-cyano-7-(cyclopropylamino)pyrazolo[1,5-a]pyrimidin-5-yl)amino)-2-((methylsulfinyl)methyl)phenyl)-N-methylacetamide mono trifluoroacetic acid salt (Cpd 77)

Compound 77 can be prepared according to the procedure described in Example 7 with tert-butyl (2-((4-amino-2-((methylsulfinyl)methyl)phenyl)(methyl)amino)-2-oxoethyl)carbamate.

Example 78

7-(cyclopropylamino)-5-((4-fluoro-3-((methylsulfonyl)methyl)phenyl)amino)pyrazolo[1,5-a]pyrimidine-3-carbonitrile (Cpd 78)

Compound 78 can be prepared according to the procedure described in Example 2 with 4-fluoro-3-((methylsulfonyl)methyl)aniline.

Example 79

5-((4-cyclopropyl-3-((methylsulfonyl)methyl)phenyl)amino)-7-(cyclopropylamino)pyrazolo[1,5-a]pyrimidine-3-carbonitrile (Cpd 79)

Compound 79 can be prepared according to the procedure described in Example 13 with 4-cyclopropyl-3-((methylsulfonyl)methyl)aniline.

Example 80

7-(cyclopropylamino)-5-((3-((methylsulfonyl)methyl)-4-(piperazin-1-yl)phenyl)amino)pyrazolo[1,5-a]pyrimidine-3-carbonitrile mono trifluoroacetic acid salt (Cpd 80)

Compound 80 can be prepared according to the procedure described in Example 7 with tert-butyl 4-(4-amino-2-((methylsulfonyl)methyl)phenyl)piperazine-1-carboxylate.

Example 81

5-((4-(aminomethyl)-3-((methylsulfonyl)methyl)phenyl)amino)-7-(cyclopropylamino)pyrazolo[1,5-a]pyrimidine-3-carbonitrile mono trifluoroacetic acid salt (Cpd 81)

Compound 81 can be prepared according to the procedure described in Example 7 with tert-butyl (4-amino-2-((methylsulfonyl)methyl)benzyl)carbamate.

Example 82

7-(cyclopropylamino)-5-((4-((cyclopropylmethyl)(methyl)amino)-3-((methylsulfonyl)methyl)phenyl)amino)pyrazolo[1,5-a]pyrimidine-3-carbonitrile (Cpd 82)

Compound 82 can be prepared according to the procedure described in Example 32 with $N^1$-(cyclopropylmethyl)-M-methyl-2-((methylsulfonyl)methyl)benzene-1,4-diamine.

Example 83

7-(cyclopropylamino)-5-((4-(methyl(2-(methylamino)ethyl)amino)-3-((methylsulfonyl)methyl)phenyl)amino)pyrazolo[1,5-a]pyrimidine-3-carbonitrile mono trifluoroacetic acid salt (Cpd 83)

Compound 83 can be prepared according to the procedure described in Example 7 with tert-butyl (2-((4-amino-2-((methylsulfinyl)methyl)phenyl)(methyl)amino)ethyl)(methyl)carbamate.

Example 84

(R)-5-((4-(3-aminopyrrolidin-1-yl)-3-((methylsulfonyl)methyl)phenyl)amino)-7-(cyclopropylamino)pyrazolo[1,5-a]pyrimidine-3-carbonitrile mono trifluoroacetic acid salt (Cpd 84)

Compound 84 can be prepared according to the procedure described in Example 7 with tert-butyl (R)-(1-(4-amino-2-((methylsulfonyl)methyl)phenyl)pyrrolidin-3-yl)carbamate.

Example 85

(R)-5-((4-(3-aminopiperidin-1-yl)-3-((methylsulfonyl)methyl)phenyl)amino)-7-(cyclopropylamino)pyrazolo[1,5-a]pyrimidine-3-carbonitrile mono trifluoroacetic acid salt (Cpd 85)

Compound 85 can be prepared according to the procedure described in Example 7 with tert-butyl (R)-(1-(4-amino-2-((methylsulfonyl)methyl)phenyl)piperidin-3-yl)carbamate.

Example 86

(S)-5-((4-(3-aminopiperidin-1-yl)-3-((methylsulfonyl)methyl)phenyl)amino)-7-(cyclopropylamino)pyrazolo[1,5-a]pyrimidine-3-carbonitrile mono trifluoroacetic acid salt (Cpd 86)

Compound 86 can be prepared according to the procedure described in Example 7 with tert-butyl (S)-(1-(4-amino-2-((methylsulfonyl)methyl)phenyl)piperidin-3-yl)carbamate.

Example 87

7-(cyclopropylamino)-5-((4-(3-hydroxyazetidin-1-yl)-3-((methylsulfonyl)methyl)phenyl)amino)pyrazolo[1,5-a]pyrimidine-3-carbonitrile (Cpd 87)

Compound 87 can be prepared according to the procedure described in Example 32 with azetidin-3-ol.

Example 88

5-((4-((1-aminocyclopropyl)methoxy)-3-((methylsulfonyl)methyl)phenyl)amino)-7-(cyclopropylamino)pyrazolo[1,5-a]pyrimidine-3-carbonitrile mono trifluoroacetic acid salt (Cpd 88)

Compound 88 can be prepared according to the procedure described in Example 28 with tert-butyl (1-((4-amino-2-((methylsulfonyl)methyl)phenoxy)methyl)cyclopropyl)carbamate.

Example 89

5-((4-(2-amino-2-methylpropoxy)-3-((methylsulfonyl)methyl)phenyl)amino)-7-(cyclopropylamino)pyrazolo[1,5-a]pyrimidine-3-carbonitrile mono trifluoroacetic acid salt (Cpd 89)

Compound 89 can be prepared according to the procedure described in Example 30 with tert-butyl (1-(4-amino-2-((methylsulfonyl)methyl)phenoxy)-2-methylpropan-2-yl)carbamate

Example 90

7-(cyclopropylamino)-5-((3-((methylsulfonyl)methyl)-4-(1H-pyrazol-4-yl)phenyl)amino)pyrazolo[1,5-a]pyrimidine-3-carbonitrile (Cpd 90)

Compound 90 can be prepared according to the procedure described in Example 35 with 3-((methylsulfonyl)methyl)-4-(1H-pyrazol-4-yl)aniline.

Example 91

5-((4-(cyclopropyl(methyl)amino)-3-((methylsulfonyl)methyl)phenyl)amino)-7-(cyclopropylamino)pyrazolo[1,5-a]pyrimidine-3-carbonitrile (Cpd 91)

Compound 91 can be prepared according to the procedure described in Example 36 with $N^1$-cyclopropyl-M-methyl-2-((methylsulfonyl)methyl)benzene-1,4-diamine.

Example 92

7-(cyclopropylamino)-5-((3-((methylsulfonyl)methyl)-4-(pyrrolidin-1-yl)phenyl)amino)pyrazolo[1,5-a]pyrimidine-3-carbonitrile (Cpd 92)

Compound 92 can be prepared according to the procedure described in Example 32 with 3-((methylsulfonyl)methyl)-4-(pyrrolidin-1-yl)aniline.

Example 93

7-(cyclopropylamino)-5-((3-((methylsulfonyl)methyl)-4-(1,2,5,6-tetrahydropyridin-3-yl)phenyl)amino)pyrazolo[1,5-a]pyrimidine-3-carbonitrile mono trifluoroacetic acid salt (Cpd 93)

Compound 93 can be prepared according to the procedure described in Example 53 with tert-butyl 5-(4-amino-2-((methylsulfonyl)methyl)phenyl)-3,6-dihydropyridine-1(2H)-carboxylate.

Example 94

5-((4-cyclopropyl-3-((methylsulfonyl)methyl)phenyl)amino)-7-(pyridin-2-ylamino)pyrazolo[1,5-a]pyrimidine-3-carbonitrile (Cpd 94)

Compound 94 can be prepared according to the procedure described in Example 54 with 4-cyclopropyl-3-((methylsulfonyl)methyl)aniline.

Example 95

5-((4-cyclopropyl-3-((methylsulfonyl)methyl)phenyl)amino)-7-(pyridin-3-ylamino)pyrazolo[1,5-a]pyrimidine-3-carbonitrile (Cpd 95)

Compound 95 can be prepared according to the procedure described in Example 55 with 4-cyclopropyl-3-((methylsulfonyl)methyl)aniline.

Example 96

7-((6-aminopyridin-3-yl)amino)-5-((4-cyclopropyl-3-((methylsulfonyl)methyl)phenyl)amino)pyrazolo[1,5-a]pyrimidine-3-carbonitrile (Cpd 96)

Compound 96 can be prepared according to the procedure described in Example 56 with 4-cyclopropyl-3-((methylsulfonyl)methyl)aniline.

Example 97

7-((5-aminopyridin-2-yl)amino)-5-((4-cyclopropyl-3-((methylsulfonyl)methyl)phenyl)amino)pyrazolo[1,5-a]pyrimidine-3-carbonitrile (Cpd 97)

Compound 97 can be prepared according to the procedure described in Example 57 with 4-cyclopropyl-3-((methylsulfonyl)methyl)aniline.

Example 98

(R,S)-5-((4-(1-aminoethyl)-3-((methylsulfonyl)methyl)phenyl)amino)-7-(cyclopropylamino)pyrazolo[1,5-a]pyrimidine-3-carbonitrile mono trifluoroacetic acid salt (Cpd 98)

Compound 98 can be prepared according to the procedure described in Example 58 with tert-butyl (R,S)-(1-(4-amino-2-((methylsulfonyl)methyl)phenyl)ethyl)carbamate.

Example 99

5-((4-(1-aminocyclopropyl)-3-((methylsulfonyl)methyl)phenyl)amino)-7-(cyclopropylamino)pyrazolo[1,5-a]pyrimidine-3-carbonitrile mono trifluoroacetic acid salt (Cpd 99)

Compound 99 can be prepared according to the procedure described in Example 59 with tert-butyl (1-(4-amino-2-((methylsulfonyl)methyl)phenyl)cyclopropyl)carbamate.

Example 100

(E)-5-((4-(4-aminobut-2-en-2-yl)-3-((methylsulfonyl)methyl)phenyl)amino)-7-(cyclopropylamino)pyrazolo[1,5-a]pyrimidine-3-carbonitrile mono trifluoroacetic acid salt (Cpd 100)

Compound 100 can be prepared according to the procedure described in Example 60 with tert-butyl N-((E)-3-(4-amino-2-((methylsulfonyl)methyl)phenyl)but-2-en-1-yl)-AN-[(2-methylpropan-2-yl)oxycarbonyl]carbamate.

Example 101

(R,S)-7-(cyclopropylamino)-5-((3-((methylsulfonyl)methyl)-4-(piperidin-3-yl)phenyl)amino)pyrazolo[1,5-a]pyrimidine-3-carbonitrile mono trifluoroacetic acid salt (Cpd 101)

Compound 101 can be prepared according to the procedure described in Example 61 with tert-butyl 3-(4-amino-2-((methylsulfonyl)methyl)phenyl)piperidine-1-carboxylate.

Example 102

7-(cyclopropylamino)-5-((4-(2,5-dihydro-1H-pyrrol-3-yl)-3-((methylsulfonyl)methyl)phenyl)amino)pyrazolo[1,5-a]pyrimidine-3-carbonitrile mono trifluoroacetic acid salt (Cpd 102)

Compound 102 can be prepared according to the procedure described in Example 62 with tert-butyl 3-(4-amino-2-((methylsulfonyl)methyl)phenyl)-2,5-dihydro-1H-pyrrole-1-carboxylate.

Example 103

(R,S)-7-(cyclopropylamino)-5-((3-((methylsulfonyl)methyl)-4-(pyrrolidin-3-yl)phenyl)amino)pyrazolo[1,5-a]pyrimidine-3-carbonitrile mono trifluoroacetic acid salt (Cpd 103)

Compound 103 can be prepared according to the procedure described in Example 63 with tert-butyl (R,S)-3-(4-amino-2-((methylsulfonyl)methyl)phenyl)pyrrolidine-1-carboxylate.

Example 104

5-((4-((2-amino-2-methylpropyl)(methyl)amino)-3-((methylsulfonyl)methyl)phenyl)amino)-7-(cyclopropylamino)pyrazolo[1,5-a]pyrimidine-3-carbonitrile mono trifluoroacetic acid salt (Cpd 104)

Compound 104 can be prepared according to the procedure described in Example 67 with tert-butyl (1-((4-amino-2-((methylsulfonyl)methyl)phenyl)(methyl)amino)-2-methylpropan-2-yl)carbamate.

Example 105

(S)-7-((5-aminopyridin-2-yl)amino)-5-((4-(3-aminopyrrolidin-1-yl)-3-((methylsulfonyl)methyl)phenyl)amino)pyrazolo[1,5-a]pyrimidine-3-carbonitrile (Cpd 105)

Compound 105 can be prepared according to the procedure described in Example 68 with tert-butyl (S)-(1-(4-amino-2-((methylsulfonyl)methyl)phenyl)pyrrolidin-3-yl)carbamate.

Example 106

5-((4-cyclopropyl-3-((methylsulfonyl)methyl)phenyl)amino)-7-((5-((dimethylamino)methyl)pyridin-2-yl)amino)pyrazolo[1,5-a]pyrimidine-3-carbonitrile (Cpd 106)

Compound 106 can be prepared according to the procedure described in Example 69 with 4-cyclopropyl-3-((methylsulfonyl)methyl)aniline.

Example 107

7-((5-(aminomethyl)pyridin-2-yl)amino)-5-((4-cyclopropyl-3-((methylsulfonyl)methyl)phenyl)amino)pyrazolo[1,5-a]pyrimidine-3-carbonitrile (Cpd 107)

Compound 107 can be prepared according to the procedure described in Example 69 with 4-cyclopropyl-3-((methylsulfonyl)methyl)aniline and tert-butyl ((6-((5-chloro-3-cyanopyrazolo[1,5-a]pyrimidin-7-yl)amino)pyridin-3-yl)methyl)carbamate.

Example 108

5-((4-chloro-3-((methylsulfonyl)methyl)phenyl)amino)-7-((5-((dimethylamino)methyl)pyridin-2-yl)amino)pyrazolo[1,5-a]pyrimidine-3-carbonitrile (Cpd 108)

Compound 108 can be prepared according to the procedure described in Example 69 with 4-chloro-3-((methylsulfonyl)methyl)aniline.

Example 109

7-((5-((dimethylamino)methyl)pyridin-2-yl)amino)-5-((3-((methylsulfonyl)methyl)-4-(pyrrolidin-1-yl)phenyl)amino)pyrazolo[1,5-a]pyrimidine-3-carbonitrile (Cpd 109)

Compound 109 can be prepared according to the procedure described in Example 69 with 3-((methylsulfonyl)methyl)-4-(pyrrolidin-1-yl)aniline.

Example 110

5-((4-(2-aminocyclopropyl)-3-((methylsulfonyl)methyl)phenyl)amino)-7-(cyclopropylamino)pyrazolo[1,5-a]pyrimidine-3-carbonitrile mono trifluoroacetic acid salt (Cpd 110)

Compound 110 can be prepared according to the procedure described in Example Example 59 with tert-butyl (2-(4-amino-2-((methylsulfonyl)methyl)phenyl)cyclopropyl)carbamate.

Example 111

5-((4-(2-(aminomethyl)cyclopropyl)-3-((methylsulfonyl)methyl)phenyl)amino)-7-(cyclopropylamino)pyrazolo[1,5-a]pyrimidine-3-carbonitrile mono trifluoroacetic acid salt (Cpd 111)

Compound 111 can be prepared according to the procedure described in Example 59 with tert-butyl ((2-(4-amino-2-((methylsulfonyl)methyl)phenyl)cyclopropyl)methyl)carbamate.

Example 112

5-((4-(2-(2-aminoethyl)cyclopropyl)-3-((methylsulfonyl)methyl)phenyl)amino)-7-(cyclopropylamino)pyrazolo[1,5-a]pyrimidine-3-carbonitrile mono trifluoroacetic acid salt (Cpd 112)

Compound 112 can be prepared according to the procedure described in Example 59 with tert-butyl (2-(2-(4-amino-2-((methylsulfonyl)methyl)phenyl)cyclopropyl)ethyl)carbamate.

Example 113

2-amino-N-(4-((3-cyano-7-(cyclopropylamino)pyrazolo[1,5-a]pyrimidin-5-yl)amino)-2-((methylsulfonyl)methyl)phenyl)-N-methylacetamide mono trifluoroacetic acid salt (Cpd 113)

Compound 113 can be prepared according to the procedure described in Example 7 with tert-butyl (2-((4-amino-2-((methylsulfonyl)methyl)phenyl)(methyl)amino)-2-oxoethyl)carbamate.

CK2 Protein Kinase Inhibition Assay

A coupled PK (pyruvate kinase)/LDH (lactate dehydrogenase) assay was used to measure compounds' ability to inhibit purified CK2α enzyme.

The ADP product of kinase CK2a is the cofactor for PK. Phospho(enol)pyruvate (PEP) PEP is metabolized by pyruvate kinase to yield pyruvate, which is the substrate for LDH.

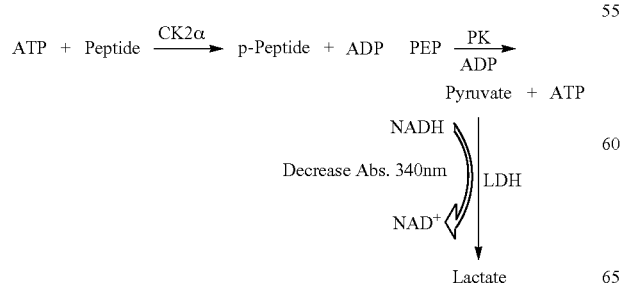

Serially diluted compounds were pre-incubated for 10 min at 37° C. with and 1.5 mM RRRDDDSDDD peptide substrate, 6 U/ml PK and 10 U/ml LDH (purchased from Sigma-Aldrich), 100 μM ATP, 1.2 mM NADH, 4 mM PEP in the reaction buffer (50 mM Tris (pH 8.25), 0.1 M NaCl, 10 mM magnesium acetate). The reaction was initiated by the addition of an equal volume of purified CK2 enzyme (final concentration 25 nM) diluted in the reaction buffer. Absorbance at 340 nm was measured overtime (for 30 min) at 37° C.; as NADH was converted to NAD+ the absorbance decreases. Absorbance decrease rate (per min) was plotted against the compound concentration and Ki is determined by GraphPad Prism using Morrison equation. All data points were performed in triplicate and each compound was tested in at least two separate experiments.

The results of this assay are set forth in Table 1 below. To this end, K, values of less than 2.5 nM are labelled as "+++", from 2.5 nM to 10 nM are labelled as "++", and greater than 10 nM are labelled as "+".

TABLE 1

| Example | $K_i$ (nM) |
| --- | --- |
| 1 | +++ |
| 2 | +++ |
| 3 | +++ |
| 4 | ++ |
| 5 | ++ |
| 6 | ++ |
| 7 | +++ |
| 8 | +++ |
| 9 | +++ |
| 10 | +++ |
| 11 | +++ |
| 12 | ++ |
| 13 | +++ |
| 14 | ++ |
| 15 | ++ |
| 16 | +++ |
| 17 | +++ |
| 18 | +++ |
| 19 | +++ |
| 20 | +++ |
| 21 | +++ |
| 22 | +++ |
| 23 | +++ |
| 24 | +++ |
| 25 | +++ |
| 26 | ++ |
| 27 | +++ |
| 28 | ++ |
| 29 | +++ |
| 30 | ++ |
| 31 | +++ |
| 32 | +++ |
| 33 | +++ |
| 34 | +++ |
| 35 | + |
| 36 | +++ |
| 37 | +++ |
| 38 | ++ |
| 39 | +++ |
| 40 | +++ |
| 41 | ++ |
| 42 | +++ |
| 43 | +++ |
| 44 | ++ |
| 45 | ++ |
| 46 | +++ |
| 47 | ++ |
| 48 | ++ |
| 49 | ++ |
| 50 | ++ |
| 51 | +++ |
| 52 | ++ |
| 53 | ++ |

TABLE 1-continued

| Example | $K_i$ (nM) |
|---|---|
| 54 | +++ |
| 55 | +++ |
| 56 | +++ |
| 57 | +++ |
| 58 | ++ |
| 59 | ++ |
| 60 | +++ |
| 61 | ++ |
| 62 | ++ |
| 63 | ++ |
| 64 | ++ |
| 65 | +++ |
| 66 | +++ |
| 67 | +++ |
| 68 | +++ |
| 69 | +++ |

Combination of CK2 Inhibitor and Other Anti-Cancer Drugs in a Cancer Cell Panel

Cells were plated in 96-well plates and treated for 72 hours with a serially diluted CK2 inhibitor or anti-cancer drug or their combination. The suspension cell lines were treated right after plating, while the adherent cells were allowed to attach overnight prior to the start of the treatment.

Cell viability was determined by adding resazurin to cell cultures and measuring fluorescence with a plate reader. Relative cell viability was calculated by dividing the cell viability signal from a test sample by that of a non-treated control. Reduction in relative cell viability after treatment with a combination of the CK2 inhibitor and anti-cancer drug was compared to that observed after treatment with each agent by itself (CK2 inhibitor or the anti-cancer drug). Bliss Independence and Highest Single Agent models were used to determine if there is synergy, additivity or antagonism between the CK2 inhibitor and an anti-cancer drug.

The following anti-cancer drugs were assessed in combination studies with the compound of Example 3:
  DNA damaging agents: 5-FU, fludarabine, gemcitabine, cisplatin and doxorubicin
  Kinase inhibitors: trametinib, erlotinib and sunitinib
  Tubulin inhibitor and stabilizer: vinblastine and paclitaxel
  mTOR inhibitor: rapamycin
  Proteasome inhibitor: bortezomib

TABLE 2

| Cancer | Cell Line | Example 3 IC$_{50}$ (nM) | 5FU | Fludarabine | Gemcitabine | Cisplatin | Doxorubicin | Trametinib | Erlotinib | Sunitinib | Vinblastine | Paclitaxel | Rapamycin | Bortezomib |
|---|---|---|---|---|---|---|---|---|---|---|---|---|---|---|
| Prostate | PC3 | 112 | ? | ? | + | + | + | ? | - | ? | ? | ? | ? | + |
| | LnCap | 420 | + | +++ | ++ | ++ | ++ | ++ | +++ | + | + | + | ++ | ++ |
| Ovarian | SKOV-3 | 1379 | ? | ++ | ? | ? | + | ++ | ++ | - | + | + | +++ | +++ |
| | OVCAR-3 | 42 | ? | ++ | ++ | ++ | ++ | ++ | ++ | ++ | ++ | ? | ++ | ++ |
| | A2780 | 527 | ++ | + | +++ | ++++ | + | ++ | ++ | +++ | ? | ? | ? | ++ |
| | Caov-3 | 50 | + | ? | ? | ? | ? | ++ | ? | ++ | ? | + | ++ | ++ |
| Pancreatic | Mia-Paca-2 | 253 | ? | ? | ++ | + | ++ | + | +++ | ++ | ? | ? | ++ | +++ |
| | Panc-1 | 539 | ? | + | +++ | + | + | +++ | ++ | ++ | + | ? | +++ | +++ |
| | BxPC3 | 3597 | + | ? | +++ | ? | ? | ++++ | +++ | +++ | +++ | +++ | +++ | - |
| Colon | HCT116 | 356 | ++ | ? | + | ? | ? | +++ | ? | +++ | ? | ? | ? | + |
| | HT29 | 197 | + | + | + | ++ | ++ | +++ | + | ++ | + | + | ++ | +++ |
| | Colo205 | 1116 | ? | + | ? | ++ | + | ++++ | ? | +++ | ++++ | +++ | +++ | + |
| | LoVo | 170 | + | + | + | + | + | +++ | + | +++ | +++ | +++ | +++ | +++ |
| | DLD-1 | 572 | + | + | + | + | ++ | +++ | ? | +++ | ? | ++ | + | ++ |
| NSCLC | H1299 | 246 | + | ? | + | + | ++ | +++ | + | +++ | ? | ? | ? | ++ |
| | A549 | 1669 | +++ | + | ++++ | ++++ | +++ | ++++ | ? | +++ | ++ | ++ | +++ | +++ |
| | H460 | 350 | + | + | ++ | ++ | ++ | ++++ | +++ | +++ | ++++ | +++ | +++ | ++ |
| | H1975 | 387 | -- | ? | ++ | ++ | ++ | +++ | ? | +++ | + | ++ | ++ | + |
| | H23 | 575 | + | ? | ++ | + | ++ | ++++ | + | ++ | + | ++ | + | ++ |
| | H2122 | 227 | + | + | + | + | + | ++ | ++++ | ++ | ? | ? | ? | + |
| Breast | SkBr-3 | 228 | + | ? | ++ | ? | ? | ++ | + | ++ | ? | ? | + | +++ |
| | MDA-MB-453 | 148 | + | + | ++ | ++ | ++ | +++ | ? | +++ | ? | ++ | ++ | ++ |
| | MDA-MB-231 | 567 | + | ++ | ++ | + | + | +++ | + | +++ | ++ | ++ | ++ | +++ |
| | MDA-MB-157 | 447 | + | + | ++ | + | + | +++ | ? | +++ | ? | ? | + | + |
| | BT-20 | 98 | ? | ? | ++ | ? | ? | +++ | ? | ++ | ++ | ++ | ++ | ++ |
| | BT-474 | 338 | + | + | + | + | + | +++ | + | +++ | ++ | ++ | ++ | + |
| | ZR-75-1 | 323 | + | + | + | + | + | +++ | + | +++ | ++ | ++ | ++ | ++ |
| | T47D | 861 | + | + | + | ? | ? | ++ | + | ? | + | ? | ? | - |
| | MCF7 | 1822 | ++ | + | + | + | + | ++ | +++ | ++ | +++ | ? | ? | - |
| Renal | 786-O | 2616 | +++ | ++ | +++ | + | +++ | +++ | ++ | +++ | +++ | ? | ++ | +++ |
| | ACHN | 409 | + | + | + | + | + | ? | - - | ++ | + | + | + | + |
| | Caki-1 | 171 | + | + | + | + | + | +++ | + | +++ | ++ | ? | + | + |
| | Caki-2 | 669 | ? | ? | ++ | + | ++ | +++ | + | ++ | + | ? | + | +++ |
| Melanoma | A375 | 218 | ? | + | ++ | ++ | ++ | +++ | + | ++ | ? | ++ | ++ | +++ |
| | SK-MEL-3 | 429 | + | + | + | + | + | +++ | + | +++ | ? | + | ? | +++ |
| | SK-MEL-24 | 1414 | ? | + | + | + | + | +++ | + | +++ | + | + | + | ++ |
| | WM-115 | 286 | + | + | + | + | + | ? | + | ++ | + | + | ++ | + |
| | MeWO | 263 | - | ? | ++ | ++ | ++ | +++ | ? | +++ | + | ? | + | ++ |
| multiple myeloma | U266 | >10,000 | + | + | ++ | ++ | ++ | ++ | ? | ++ | + | + | + | + |
| | RPMI8226 | 233 | + | + | + | + | + | +++ | ? | ++ | + | + | ++++ | +++ |
| Glioblastoma | U87MG | 1119 | + | ? | ++ | + | + | ? | + | ++ | + | + | ? | ++ |
| Burkitt's | Ramos | 312 | ++ | ++ | ++ | + | ++ | ? | ++ | ++++ | ++ | - | + | ++ |
| | Raji | 249 | + | ? | + | ? | ? | + | ? | ++ | + | ? | + | + |
| Lymphoma | Daudi | 217 | ? | ? | + | + | + | ? | ++ | ++ | + | ++ | + | ++ |
| | NAMALWA | 206 | ++ | ++ | ++ | + | ++ | ? | + | + | + | + | + | + |

TABLE 2-continued

| Cancer | Cell Line | Example 3 IC$_{50}$ (nM) | 5FU | Fludarabine | Gemcitabine | Cisplatin | Doxorubicin | Trametinib | Erlotinib | Sunitinib | Vinblastine | Paclitaxel | Rapamycin | Bortezomib |
|---|---|---|---|---|---|---|---|---|---|---|---|---|---|---|
| Leukemia | K562 | 463 | ~ | ~ | + | ~ | + | + | +++ | +++ | + | + | ++ | + |
| | HL60 | 261 | + | +++ | ++ | + | ++ | ++ | ++ | ++ | ++ | ++ | ~ | + |
| | EOL-1 | 138 | + | + | ++++ | ++ | ++ | ++ | + | ++ | ~ | - - | ++ | ++ |
| | MOLT4 | 420 | ++ | + | +++ | ++ | +++ | + | ++ | + | - | | + | ++ |

+ + + + Strong synergy relative to each agent alone (CI < 0.4 by Bliss Independence Model)
+ + + Synergy relative to each agent alone (CI = 0.4-0.74 by Bliss Independence Model)
+ + Slight synergy relative to each agent alone (CI = 0.75-0.9 by Bliss Independence Model)
+ Additive relative to each agent alone (CI = 0.9-1 by Bliss Independence Model and <0.9 by Highest Single Agent Model)
~ Combination had same activity as the highest agent alone
- Slightly antagonistic relative to each agent alone (CI = 1.1-1.2 by Highest Single Agent Model)
- - Antagonistic relative to each agent alone (CI = 1.2-1.49 by Highest Single Agent Model)
- - - Strongly antagonistic relative to each agent alone (CI > 1.49 by Highest Single Agent Model)

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

The invention claimed is:

1. A compound according to Formula (I):

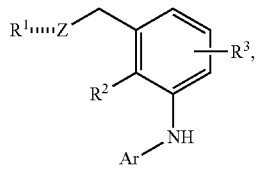

or a stereoisomer, a tautomer or a pharmaceutically acceptable salt thereof, wherein:
⸺ is —, ▶ or ⫶⫶⫶⫶;
Z is S(O) or S(O)$_2$;
$R^1$ is OH or alkyl;
$R^2$ is H;
$R^3$ groups each independently are H, halogen, CN, OR$^5$, (C$_1$-C$_8$)alkyl, (C$_2$-C$_8$)alkenyl, (C$_2$-C$_8$)alkynyl, NHR$^5$, NR$^5$R$^5$, [(C$_1$-C$_8$)alkylene]NHR$^5$, [(C$_1$-C$_8$)alkylene]NR$^5$R$^5$, N(C$_1$-C$_8$)alkyl[(C$_1$-C$_8$)alkylene]NHR$^5$, N(C$_1$-C$_8$)alkyl[(C$_1$-C$_8$)alkylene]NR$^5$R$^5$, cycloalkyl, heterocyclyl, aryl or heteroaryl;
$R^5$ is H, (C$_1$-C$_8$)alkyl, (C$_1$-C$_8$)haloalkyl, cycloalkyl, [(C$_1$-C$_8$)alkylene]cycloalkyl, or R$^5$ and R$^5$ taken together with the nitrogen atom to which they are attached form a heterocyclyl;
Ar is

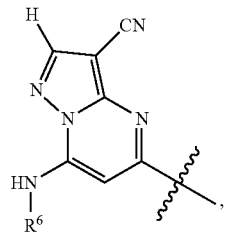

wherein
$R^6$ is H, alkyl, cycloalkyl, heterocyclyl, aryl, heteroaryl; and
wherein any alkyl, alkenyl, alkynyl, haloalkyl, alkylene, cycloalkyl, heterocyclyl, aryl or heteroaryl is optionally substituted with 1, 2 or 3 groups selected from OH, CN, NH$_2$, NO$_2$, halogen, cycloalkyl, -(C$_1$-C$_3$ alkylene)NH$_2$ and -(C$_1$-C$_3$ alkylene)N(C$_1$-C$_3$ alkyl)$_2$.

2. The compound according to claim 1 wherein R$^1$ is methyl.

3. The compound according to claim 1 wherein Z is S(O).

4. The compound according to claim 1 wherein Z is SO$_2$.

5. The compound according to claim 1 wherein R$^3$ is independently H, halogen, OR$^5$, NR$^5$R$^5$, [(C$_1$-C$_8$)alkylene]NR$^5$R$^5$, N(C$_1$-C$_8$)alkyl)[(C$_1$-C$_8$)alkylene]NHR$^5$, N(C$_1$-C$_8$)alkyl)[(C$_1$-C$_8$)alkylene]NR$^5$R$^5$, cycloalkyl or heterocyclyl.

6. The compound according to claim 1 wherein the R$^3$ groups are independently H, Cl, F, CN, NR$^5$R$^5$, [(C$_1$-C$_8$)alkylene]NR$^5$R$^5$, OR$^5$, cycloalkyl or heterocyclyl.

7. The compound according to claim 1 wherein the R$^3$ groups are independently H, Cl, F, CN, NR$^5$R$^5$, [(C$_1$-C$_8$)alkylene]NR$^5$R$^5$, OR$^5$, cyclopropane or piperazine.

8. The compound according to claim 1 wherein R$^5$ is optionally substituted (C$_1$-C$_8$)alkyl or (C$_1$-C$_8$)alkylene cycloalkyl.

9. The compound according to claim 1 wherein R$^5$ is CH$_3$, CHF$_2$, CH$_2$CH$_2$NH$_2$ or methylcyclopropane.

10. The compound according to claim 1 wherein R$^6$ is cycloalkyl.

11. The compound according to claim 1 wherein R$^6$ is cyclopropane.

12. The compound according to claim 1 selected from
(±)-5-((4-chloro-3-((methylsulfinyl)methyl)phenyl)amino)-7-(cyclopropylamino)pyrazolo[1,5-a]pyrimidine-3-carbonitrile,
5-((4-chloro-3-((methylsulfonyl)methyl)phenyl)amino)-7-(cyclopropylamino)pyrazolo[1,5-a]pyrimidine-3-carbonitrile,
(S)(+)-5-((4-chloro-3-((methylsulfinyl)methyl)phenyl)amino)-7-(cyclopropylamino)pyrazolo [1,5-a]pyrimidine-3-carbonitrile,
(R)(−)-5-((4-chloro-3-((methylsulfinyl)methyl)phenyl)amino)-7-(cyclopropylamino)pyrazolo [1,5-a]pyrimidine-3-carbonitrile,
(±)-7-(cyclopropylamino)-5-((4-fluoro-3-((methylsulfinyl)methyl)phenyl)amino)pyrazolo[1,5-a]pyrimidine-3-carbonitrile,
(±)-5-((4-cyano-3-((methylsulfinyl)methyl)phenyl)amino)-7-(cyclopropylamino)pyrazolo[1,5-a]pyrimidine-3-carbonitrile,
(±)-5-((4-((2-aminoethyl)(methyl)amino)-3-((methylsulfinyl)methyl)phenyl)amino)-7-(cyclopropylamino)pyrazolo[1,5-a]pyrimidine-3-carbonitrile mono trifluoroacetic acid salt,
(±)-5-((4-(2-aminoethyl)-3-((methylsulfinyl)methyl)phenyl)amino)-7-(cyclopropylamino)pyrazolo[1,5-a]pyrimidine-3-carbonitrile mono trifluoroacetic acid salt,
5-((4-cyano-3-((methylsulfonyl)methyl)phenyl)amino)-7-(cyclopropylamino)pyrazolo [1,5-a]pyrimidine-3-carbonitrile,
5-((4-((2-aminoethyl)(methyl)amino)-3-((methylsulfonyl)methyl)phenyl)amino)-7-(cyclopropylamino)pyrazolo[1,5-a]pyrimidine-3-carbonitrile mono trifluoroacetic acid salt,
5-((4-(2-aminoethyl)-3-((methylsulfonyl)methyl)phenyl)amino)-7-(cyclopropylamino)pyrazolo[1,5-a]pyrimidine-3-carbonitrile mono trifluoroacetic acid salt,
(±)-5-((4-cyclopropyl-3-((methylsulfinyl)methyl)phenyl)amino)-7-(cyclopropylamino)pyrazolo[1,5-a]pyrimidine-3-carbonitrile,
(±)-7-(cyclopropylamino)-5-((3-((methylsulfinyl)methyl)-4-(piperazin-1-yl)phenyl)amino)pyrazolo[1,5-a]pyrimidine-3-carbonitrile mono trifluoroacetic acid salt, (±)-5-((4-(aminomethyl)-3-((methylsulfinyl)methyl)phenyl)amino)-7-(cyclopropylamino)pyrazolo[1,5-a]pyrimidine-3-carbonitrile mono trifluoroacetic acid salt, (±)-7-(cyclopropylamino)-5-((4-((cyclopropylmethyl)(methyl)amino)-3-((methylsulfinyl)methyl)phenyl)amino)pyrazolo [1,5-a]pyrimidine-3-carbonitrile, (±)-7-(cyclopropylamino)-5-((4-methoxy-3-((methylsulfinyl)methyl)phenyl)amino)pyrazolo [1,5-a]pyrimidine-3-carbonitrile, 7-(cyclopropylamino)-5-((4-methoxy-3-((methylsulfonyl)methyl)phenyl)amino)pyrazolo[1,5-a]pyrimidine-3-carbonitrile, (±)-7-(cyclopropylamino)-5-((4-(difluoromethoxy)-3-((methylsulfinyl)methyl)phenyl)amino)pyrazolo [1,5-a]pyrimidine-3-carbonitrile, 7-(cyclopropylamino)-5-((4-(difluoromethoxy)-3-((methylsulfonyl)methyl)phenyl)amino)pyrazolo [1,5-a]pyrimidine-3-carbonitrile, (±)-7-(cyclopropylamino)-5-((4-(methyl(2-(methylamino)ethyl)amino)-3-((methylsulfinyl)methyl)phenyl)amino)pyrazolo[1,5-a]pyrimidine-3-carbonitrile mono trifluoroacetic acid salt, 5-((4-((R)-3-aminopyrrolidin-1-yl)-3-(((R,S)-methylsulfinyl)methyl)phenyl)amino)-7-(cyclopropylamino)pyrazolo[1,5-a]pyrimidine-3-carbonitrile mono trifluoroacetic acid salt, 5-((4-((S)-3-aminopyrrolidin-1-yl)-3-(((R,S)-methylsulfinyl)methyl)phenyl)amino)-7-(cyclopropylamino)pyrazolo[1,5-a]pyrimidine-3-carbonitrile mono trifluoroacetic acid salt, 5-((4-((R)-3-aminopiperidin-1-yl)-3-(((R,S)-methylsulfinyl)methyl)phenyl)amino)-7-(cyclopropylamino)pyrazolo[1,5-a]pyrimidine-3-carbonitrile mono trifluoroacetic acid salt, 5-((4-((S)-3-aminopiperidin-1-yl)-3-(((R,S)-methylsulfinyl)methyl)phenyl)amino)-7-(cyclopropylamino)pyrazolo[1,5-a]pyrimidine-3-carbonitrile mono trifluoroacetic acid salt, 5-((4-(2-aminoethoxy)-3-((methylsulfonyl)methyl)phenyl)amino)-7-(cyclopropylamino)pyrazolo[1,5-a]pyrimidine-3-carbonitrile hydrochloric acid salt, (±)-7-(cyclopropylamino)-5-((4-(3-hydroxyazetidin-1-yl)-3-((methylsulfinyl)methyl)phenyl)amino)pyrazolo [1,5-a]pyrimidine-3-carbonitrile, (±)-5-((4-((1-aminocyclopropyl)methoxy)-3-((methylsulfinyl)methyl)phenyl)amino)-7-(cyclopropylamino)pyrazolo[1,5-a]pyrimidine-3-carbonitrile mono trifluoroacetic acid salt, (S)-5-((4-(3-aminopyrrolidin-1-yl)-3-((methylsulfonyl)methyl)phenyl)amino)-7-(cyclopropylamino)pyrazolo[1,5-a]pyrimidine-3-carbonitrile mono trifluoroacetic acid salt, (±)-5-((4-(2-amino-2-methylpropoxy)-3-((methylsulfinyl)methyl)phenyl)amino)-7-(cyclopropylamino)pyrazolo[1,5-a]pyrimidine-3-carbonitrile mono trifluoroacetic acid salt, (±)-5-((4-(2-aminoethoxy)-3-((methylsulfinyl)methyl)phenyl)amino)-7-(cyclopropylamino)pyrazolo[1,5-a]pyrimidine-3-carbonitrile, 5-((4-(azetidin-1-yl)-3-((methylsulfonyl)methyl)phenyl)amino)-7-(cyclopropylamino)pyrazolo[1,5-a]pyrimidine-3-carbonitrile, (±)-7-(cyclopropylamino)-5-((4-(dimethylamino)-3-((methylsulfinyl)methyl)phenyl)amino)pyrazolo[1,5-a]pyrimidine-3-carbonitrile, 7-(cyclopropylamino)-5-((4-(dimethylamino)-3-((methylsulfonyl)methyl)phenyl)amino)pyrazolo[1,5-a]pyrimidine-3-carbonitrile, (±)-7-(cyclopropylamino)-5-((3-((methylsulfinyl)methyl)-4-(1H-pyrazol-4-yl)phenyl)amino)pyrazolo[1,5-a]pyrimidine-3-carbonitrile, (±)-5-((4-(cyclopropyl(methyl)amino)-3-((methylsulfinyl)methyl)phenyl)amino)-7-(cyclopropylamino)pyrazolo[1,5-a]pyrimidine-3-carbonitrile, (±)-5-((4-(azetidin-1-yl)-3-((methylsulfinyl)methyl)phenyl)amino)-7-(cyclopropylamino)pyrazolo[1,5-a]pyrimidine-3-carbonitrile, (±)-5-((4-(1-(aminomethyl)cyclopropyl)-3-((methylsulfinyl)methyl)phenyl)amino)-7-(cyclopropylamino)pyrazolo[1,5-a]pyrimidine-3-carbonitrile, 5-((4-(1-(aminomethyl)cyclopropyl)-3-((methylsulfonyl)methyl)phenyl)amino)-7-(cyclopropylamino)pyrazolo[1,5-a]pyrimidine-3-carbonitrile mono trifluoroacetic acid salt, (±)-5-((4-(3-aminoazetidin-1-yl)-3-((methylsulfinyl)methyl)phenyl)amino)-7-(cyclopropylamino)pyrazolo[1,5-a]pyrimidine-3-carbonitrile, 5-((4-(3-aminoazetidin-1-yl)-3-((methylsulfonyl)methyl)phenyl)amino)-7-(cyclopropylamino)pyrazolo[1,5-a]pyrimidine-3-carbonitrile, (±)-5-((4-(3-(aminomethyl)azetidin-1-yl)-3-((methylsulfinyl)methyl)phenyl)amino)-7-(cyclopropylamino)pyrazolo[1,5-a]pyrimidine-3-carbonitrile, 5-((4-(3-(aminomethyl)azetidin-1-yl)-3-((methylsulfonyl)methyl)phenyl)amino)-7-(cyclopropylamino)pyrazolo[1,5-a]pyrimidine-3-carbonitrile, (±)-5-((4-(azetidin-3-yl(methyl)amino)-3-((methylsulfinyl)methyl)phenyl)amino)-7-(cyclopropylamino)pyrazolo[1,5-a]pyrimidine-3-carbonitrile, 5-((4-(azetidin-3-yl(methyl)amino)-3-((methylsulfonyl)methyl)phenyl)amino)-7-(cyclopropylamino)pyrazolo[1,5-a]pyrimidine-3-carbonitrile, (±)-7-(cyclopropylamino)-5-((3-((methylsulfinyl)methyl)-4-(pyrrolidin-1-yl)phenyl)amino)pyrazolo[1,5-a]pyrimidine-3-carbonitrile, (±)-2-((4-((2-aminoethyl)(methyl)amino)-3-((methylsulfinyl)methyl)phenyl)amino)-4-(cyclopropylamino)pyrazolo[1,5-a][1,3,5]triazine-8-carbonitrile mono trifluoroacetic acid salt, 2-((4-((2-aminoethyl)(methyl)amino)-3-((methylsulfonyl)methyl)phenyl)amino)-4-(cyclopropylamino)pyrazolo[1,5-a][1,3,5]triazine-8-carbonitrile mono trifluoroacetic acid salt, (±)-7-(cyclopropylamino)-5-((3-((methylsulfinyl)methyl)-4-(1,2,5,6-tetrahydropyridin-3-yl)phenyl)amino)pyrazolo[1,5-a]pyrimidine-3-carbonitrile mono trifluoroacetic acid salt, (±)-5-((4-cyclopropyl-3-((methylsulfinyl)methyl)phenyl)amino)-7-(pyridin-2-ylamino)pyrazolo [1,5-a]pyrimidine-3-carbonitrile, (±)-5-((4-cyclopropyl-3-((methylsulfinyl)methyl)phenyl)amino)-7-(pyridin-3-ylamino)pyrazolo [1,5-a]pyrimidine-3-carbonitrile, (±)-7-((6-aminopyridin-3-yl)amino)-5-((4-cyclopropyl-3-((methylsulfinyl)methyl)phenyl)amino)pyrazolo[1,5-a]pyrimidine-3-carbonitrile, (±)-7-((5-aminopyridin-2-yl)amino)-5-((4-cyclopropyl-3-((methylsulfinyl)methyl)phenyl)amino)pyrazolo[1,5-a]pyrimidine-3-carbonitrile, (±)-5-((4-((R,S)-1-aminoethyl)-3-((methylsulfinyl) methyl)phenyl)amino)-7-(cyclopropylamino)pyrazolo [1,5-a]pyrimidine-3-carbonitrile mono trifluoroacetic acid salt, (±)-5-((4-(1-aminocyclopropyl)-3-((methylsulfinyl) methyl)phenyl)amino)-7-(cyclopropylamino)pyrazolo [1,5-a]pyrimidine-3-carbonitrile mono trifluoroacetic acid salt, (±)-(E)-5-((4-(4-aminobut-2-en-2-yl)-3-((methylsulfinyl) methyl)phenyl)amino)-7-(cyclopropylamino)pyrazolo [1,5-a]pyrimidine-3-carbonitrile mono trifluoroacetic acid salt, (±)-7-(cyclopropylamino)-5-((3-((methylsulfinyl) methyl)-4-((R,S)-piperidin-3-yl)phenyl)amino)pyrazolo[1,5-a]pyrimidine-3-carbonitrile mono trifluoroacetic acid salt, (±)-7-(cyclopropylamino)-5-((4-(2,5-dihydro-1H-pyrrol-3-yl)-3-((methylsulfinyl)methyl)phenyl)amino)pyrazolo[1,5-a]pyrimidine-3-carbonitrile mono trifluoroacetic acid salt, (±)-7-(cyclopropylamino)-5-((3-((methylsulfinyl) methyl)-4-((R,S)-pyrrolidin-3-yl)phenyl)amino)pyrazolo[1,5-a]pyrimidine-3-carbonitrile mono trifluoroacetic acid salt, (±)-5-((4-((R,S)-4-aminobutan-2-yl)-3-((methylsulfinyl) methyl)phenyl)amino)-7-(cyclopropylamino)pyrazolo [1,5-a]pyrimidine-3-carbonitrile mono trifluoroacetic acid salt, (±)-5-((4-(((1-aminocyclopropyl)methyl)(methyl) amino)-3-((methylsulfinyl)methyl)phenyl)amino)-7-(cyclopropylamino)pyrazolo[1,5-a]pyrimidine-3-carbonitrile mono trifluoroacetic acid salt, 5-((4-(((1-aminocyclopropyl)methyl)(methyl)amino)-3-((methylsulfonyl)methyl)phenyl)amino)-7-(cyclopropylamino)pyrazolo[1,5-a]pyrimidine-3-carbonitrile mono trifluoroacetic acid salt, (±)-5-((4-((2-amino-2-methylpropyl)(methyl)amino)-3-((methylsulfinyl)methyl)phenyl)amino)-7-(cyclopropylamino)pyrazolo[1,5-a]pyrimidine-3-carbonitrile mono trifluoroacetic acid salt, (±)-7-((5-aminopyridin-2-yl)amino)-5-((4-((S)-3-aminopyrrolidin-1-yl)-3-((methylsulfinyl)methyl)phenyl) amino)pyrazolo[1,5-a]pyrimidine-3-carbonitrile, (±)-5-((4-cyclopropyl-3-((methylsulfinyl)methyl)phenyl) amino)-7-((5-((dimethylamino)methyl)pyridin-2-yl) amino)pyrazolo[1,5-a]pyrimidine-3-carbonitrile, (±)-7-((5-(aminomethyl)pyridin-2-yl)amino)-5-((4-cyclopropyl-3-((methylsulfinyl)methyl)phenyl)amino)pyrazolo[1,5-a]pyrimidine-3-carbonitrile, (±)-5-((4-chloro-3-((methylsulfinyl)methyl)phenyl) amino)-7-((5-((dimethylamino)methyl)pyridin-2-yl) amino)pyrazolo[1,5-a]pyrimidine-3-carbonitrile, (±)-7-((5-((dimethylamino)methyl)pyridin-2-yl)amino)-5-((3-((methylsulfinyl)methyl)-4-(pyrrolidin-1-yl)phenyl)amino)pyrazolo[1,5-a]pyrimidine-3-carbonitrile, (R,S)-5-((4-(4-aminobutan-2-yl)-3-((methylsulfonyl) methyl)phenyl)amino)-7-(cyclopropylamino)pyrazolo [1,5-a]pyrimidine-3-carbonitrile mono trifluoroacetic acid salt, (±)-5-((4-(2-aminocyclopropyl)-3-((methylsulfinyl) methyl)phenyl)amino)-7-(cyclopropylamino)pyrazolo [1,5-a]pyrimidine-3-carbonitrile mono trifluoroacetic acid salt, (±)-5-((4-(2-(aminomethyl)cyclopropyl)-3-((methylsulfinyl)methyl)phenyl)amino)-7-(cyclopropylamino)pyrazolo[1,5-a]pyrimidine-3-carbonitrile mono trifluoroacetic acid salt, (±)-5-((4-(2-(2-aminoethyl)cyclopropyl)-3-((methylsulfinyl)methyl)phenyl)amino)-7-(cyclopropylamino)pyrazolo[1,5-a]pyrimidine-3-carbonitrile mono trifluoroacetic acid salt, 7-(cyclopropylamino)-5-((4-fluoro-3-((methylsulfonyl) methyl)phenyl)amino)pyrazolo[1,5-a]pyrimidine-3-carbonitrile, 5-((4-cyclopropyl-3-((methylsulfonyl)methyl)phenyl) amino)-7-(cyclopropylamino)pyrazolo[1,5-a]pyrimidine-3-carbonitrile, 7-(cyclopropylamino)-5-((3-((methylsulfonyl)methyl)-4-(piperazin-1-yl)phenyl)amino)pyrazolo[1,5-a]pyrimidine-3-carbonitrile mono trifluoroacetic acid salt, 5-((4-(aminomethyl)-3-((methylsulfonyl)methyl)phenyl) amino)-7-(cyclopropylamino)pyrazolo[1,5-a]pyrimidine-3-carbonitrile mono trifluoroacetic acid salt, 7-(cyclopropylamino)-5-((4-((cyclopropylmethyl) (methyl)amino)-3-((methylsulfonyl)methyl)phenyl) amino)pyrazolo[1,5-a]pyrimidine-3-carbonitrile, 7-(cyclopropylamino)-5-((4-(methyl(2-(methylamino) ethyl)amino)-3-((methylsulfonyl)methyl)phenyl) amino)pyrazolo[1,5-a]pyrimidine-3-carbonitrile mono trifluoroacetic acid salt, (R)-5-((4-(3-aminopyrrolidin-1-yl)-3-((methylsulfonyl) methyl)phenyl)amino)-7-(cyclopropylamino)pyrazolo [1,5-a]pyrimidine-3-carbonitrile mono trifluoroacetic acid salt, (R)-5-((4-(3-aminopiperidin-1-yl)-3-((methylsulfonyl) methyl)phenyl)amino)-7-(cyclopropylamino)pyrazolo [1,5-a]pyrimidine-3-carbonitrile mono trifluoroacetic acid salt, (S)-5-((4-(3-aminopiperidin-1-yl)-3-((methylsulfonyl) methyl)phenyl)amino)-7-(cyclopropylamino)pyrazolo [1,5-a]pyrimidine-3-carbonitrile mono trifluoroacetic acid salt, 7-(cyclopropylamino)-5-((4-(3-hydroxyazetidin-1-yl)-3-((methylsulfonyl)methyl)phenyl)amino)pyrazolo[1,5-a]pyrimidine-3-carbonitrile, 5-((4-((1-aminocyclopropyl)methoxy)-3-((methylsulfonyl)methyl)phenyl)amino)-7-(cyclopropylamino)pyrazolo[1,5-a]pyrimidine-3-carbonitrile mono trifluoroacetic acid salt, 5-((4-(2-amino-2-methylpropoxy)-3-((methylsulfonyl) methyl)phenyl)amino)-7-(cyclopropylamino)pyrazolo [1,5-a]pyrimidine-3-carbonitrile mono trifluoroacetic acid salt, 7-(cyclopropylamino)-5-((3-((methylsulfonyl)methyl)-4-(1H-pyrazol-4-yl)phenyl)amino)pyrazolo[1,5-a]pyrimidine-3-carbonitrile, 5-((4-(cyclopropyl(methyl)amino)-3-((methylsulfonyl) methyl)phenyl)amino)-7-(cyclopropylamino)pyrazolo [1,5-a]pyrimidine-3-carbonitrile, 7-(cyclopropylamino)-5-((3-((methylsulfonyl)methyl)-4-(pyrrolidin-1-yl)phenyl)amino)pyrazolo[1,5-a]pyrimidine-3-carbonitrile, 7-(cyclopropylamino)-5-((3-((methylsulfonyl)methyl)-4-(1,2,5,6-tetrahydropyridin-3-yl)phenyl)amino)pyrazolo[1,5-a]pyrimidine-3-carbonitrile mono trifluoroacetic acid salt, 5-((4-cyclopropyl-3-((methylsulfonyl)methyl)phenyl) amino)-7-(pyridin-2-ylamino)pyrazolo[1,5-a]pyrimidine-3-carbonitrile, 5-((4-cyclopropyl-3-((methylsulfonyl)methyl)phenyl) amino)-7-(pyridin-3-ylamino)pyrazolo[1,5-a]pyrimidine-3-carbonitrile, 7-((6-aminopyridin-3-yl)amino)-5-((4-cyclopropyl-3-((methylsulfonyl)methyl)phenyl)amino)pyrazolo[1,5-a]pyrimidine-3-carbonitrile, 7-((5-aminopyridin-2-yl)amino)-5-((4-cyclopropyl-3-((methylsulfonyl)methyl)phenyl)amino)pyrazolo[1,5-a]pyrimidine-3-carbonitrile, (R,S)-5-((4-(1-aminoethyl)-3-((methylsulfonyl)methyl)phenyl)amino)-7-(cyclopropylamino)pyrazolo[1,5-a]pyrimidine-3-carbonitrile mono trifluoroacetic acid salt, 5-((4-(1-aminocyclopropyl)-3-((methylsulfonyl)methyl)phenyl)amino)-7-(cyclopropylamino)pyrazolo[1,5-a]pyrimidine-3-carbonitrile mono trifluoroacetic acid salt, (E)-5-((4-(4-aminobut-2-en-2-yl)-3-((methylsulfonyl)methyl)phenyl)amino)-7-(cyclopropylamino)pyrazolo[1,5-a]pyrimidine-3-carbonitrile mono trifluoroacetic acid salt, (R,S)-7-(cyclopropylamino)-5-((3-((methylsulfonyl)methyl)-4-(piperidin-3-yl)phenyl)amino)pyrazolo[1,5-a]pyrimidine-3-carbonitrile mono trifluoroacetic acid salt, 7-(cyclopropylamino)-5-((4-(2,5-dihydro-1H-pyrrol-3-yl)-3-((methylsulfonyl)methyl)phenyl)amino)pyrazolo[1,5-a]pyrimidine-3-carbonitrile mono trifluoroacetic acid salt, (R,S)-7-(cyclopropylamino)-5-((3-((methylsulfonyl)methyl)-4-(pyrrolidin-3-yl)phenyl)amino)pyrazolo[1,5-a]pyrimidine-3-carbonitrile mono trifluoroacetic acid salt, 5-((4-((2-amino-2-methylpropyl)(methyl)amino)-3-((methylsulfonyl)methyl)phenyl)amino)-7-(cyclopropylamino)pyrazolo[1,5-a]pyrimidine-3-carbonitrile mono trifluoroacetic acid salt, (S)-7-((5-aminopyridin-2-yl)amino)-5-((4-(3-aminopyrrolidin-1-yl)-3-((methylsulfonyl)methyl)phenyl)amino)pyrazolo[1,5-a]pyrimidine-3-carbonitrile, 5-((4-cyclopropyl-3-((methylsulfonyl)methyl)phenyl)amino)-7-((5-((dimethylamino)methyl)pyridin-2-yl)amino)pyrazolo[1,5-a]pyrimidine-3-carbonitrile, 7-((5-(aminomethyl)pyridin-2-yl)amino)-5-((4-cyclopropyl-3-((methylsulfonyl)methyl)phenyl)amino)pyrazolo[1,5-a]pyrimidine-3-carbonitrile, 5-((4-chloro-3-((methylsulfonyl)methyl)phenyl)amino)-7-((5-((dimethylamino)methyl)pyridin-2-yl)amino)pyrazolo[1,5-a]pyrimidine-3-carbonitrile, 7-((5-((dimethylamino)methyl)pyridin-2-yl)amino)-5-((3-((methylsulfonyl)methyl)-4-(pyrrolidin-1-yl)phenyl)amino)pyrazolo[1,5-a]pyrimidine-3-carbonitrile, 5-((4-(2-aminocyclopropyl)-3-((methylsulfonyl)methyl)phenyl)amino)-7-(cyclopropylamino)pyrazolo[1,5-a]pyrimidine-3-carbonitrile mono trifluoroacetic acid salt, 5-((4-(2-(aminomethyl)cyclopropyl)-3-((methylsulfonyl)methyl)phenyl)amino)-7-(cyclopropylamino)pyrazolo[1,5-a]pyrimidine-3-carbonitrile mono trifluoroacetic acid salt, and 5-((4-(2-(2-aminoethyl)cyclopropyl)-3-((methylsulfonyl)methyl)phenyl)amino)-7-(cyclopropylamino)pyrazolo[1,5-a]pyrimidine-3-carbonitrile mono trifluoroacetic acid salt, or a stereoisomer, a tautomer or a pharmaceutically acceptable salt thereof.

13. A pharmaceutical composition comprising (i) a therapeutically effective amount of at least one compound according to claim 1 or a stereoisomer, a tautomer or a pharmaceutically acceptable salt thereof; (ii) in combination with a pharmaceutically acceptable carrier, diluent or excipient.

* * * * *